US010508151B2

(12) United States Patent
Zhang et al.

(10) Patent No.: US 10,508,151 B2
(45) Date of Patent: Dec. 17, 2019

(54) ANTI-TRANSFERRIN RECEPTOR ANTIBODIES AND METHODS OF USE

(71) Applicant: Genentech, Inc., South San Francisco, CA (US)

(72) Inventors: Yin Zhang, South San Francisco, CA (US); Joy Yu Zuchero, South San Francisco, CA (US); Jasvinder Atwal, South San Francisco, CA (US); Jessica Couch, South San Francisco, CA (US); Mark S Dennis, South San Francisco, CA (US); James A Ernst, South San Francisco, CA (US); Ryan J Watts, South San Francisco, CA (US); Gregory A Lazar, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 123 days.

(21) Appl. No.: 15/525,832

(22) PCT Filed: Nov. 18, 2015

(86) PCT No.: PCT/US2015/061405
§ 371 (c)(1),
(2) Date: May 10, 2017

(87) PCT Pub. No.: WO2016/081643
PCT Pub. Date: May 26, 2016

(65) Prior Publication Data
US 2018/0134797 A1   May 17, 2018

Related U.S. Application Data

(60) Provisional application No. 62/081,827, filed on Nov. 19, 2014.

(51) Int. Cl.
*C07K 16/28*        (2006.01)
*C07K 16/40*        (2006.01)
*A61K 39/395*       (2006.01)
*A61K 39/00*        (2006.01)

(52) U.S. Cl.
CPC .... *C07K 16/2881* (2013.01); *A61K 39/39558* (2013.01); *C07K 16/283* (2013.01); *C07K 16/40* (2013.01); *A61K 2039/505* (2013.01); *C07K 2317/24* (2013.01); *C07K 2317/31* (2013.01); *C07K 2317/33* (2013.01); *C07K 2317/41* (2013.01); *C07K 2317/52* (2013.01); *C07K 2317/524* (2013.01); *C07K 2317/526* (2013.01); *C07K 2317/55* (2013.01); *C07K 2317/565* (2013.01); *C07K 2317/567* (2013.01); *C07K 2317/71* (2013.01); *C07K 2317/72* (2013.01); *C07K 2317/732* (2013.01); *C07K 2317/90* (2013.01); *C07K 2317/92* (2013.01); *C07K 2317/94* (2013.01)

(58) Field of Classification Search
CPC .. C07K 16/2881; C07K 16/283; C07K 16/40; C07K 2317/94; C07K 2317/92; C07K 2317/90; C07K 2317/732; C07K 2317/72; C07K 2317/71; C07K 2317/52; C07K 2317/41; C07K 2317/33; C07K 2317/31; C07K 2317/24; A61K 2039/505
See application file for complete search history.

(56) References Cited

U.S. PATENT DOCUMENTS

2006/0269989 A1   11/2006   Miyazaki
2009/0041770 A1    2/2009   Chamberlain

FOREIGN PATENT DOCUMENTS

| JP | S63-003262 A    | 1/1988  |
|----|-----------------|---------|
| JP | 2009-515819     | 4/2009  |
| WO | WO 93/10819     | 6/1993  |
| WO | WO 95/02421     | 1/1995  |
| WO | WO 2005/111082  | 11/2005 |
| WO | WO 2007/044323 A2 | 4/2007 |
| WO | 2012075037 A1   | 6/2012  |
| WO | WO 2012/130831 A1 | 10/2012 |
| WO | 2013177062 A2   | 11/2013 |
| WO | 2014189973 A2   | 11/2014 |

OTHER PUBLICATIONS

Yu et al., "Therapeutic bispecific antibodies cross the blood-brain barrier in nonhuman primates" Science Translational Medicine 6(261):1-11 (Nov. 5, 2014)
Yu et al., "Boosting Brain Uptake of a Therapeutic Antibody by Reducing its Affinity for a Transcytosis Target", Science Translational Medicine, AAAS—American Association for the Advancement of Science, vol. 3, No. 84, May 25, 2011, pp. 1-8.
Paul, Steven M., "Therapeutic Antibodies for Brain Disorders", Science Translational Medicine, AAAS—American Association for the Advancement of Science, vol. 3, No. 84, May 25, 2011.
Couch et al., "Addressing Safety Liabilities of TfR Bispecific Antibodies that Cross the Blood-Brain barrier", Science Translational Medicine, AAAS—American Association for the Advancement of Science, vol. 5, No. 183, May 1, 2013, 14 pages.
Sopper et al., "Lymphocyte Subsets and Expression of Differentiation Markers in Blood and Lymphoid Organs of Rhesus Monkeys", Cytometry vol. 29, No. 4, Dec. 1, 1997, pp. 351-362.
Atwal et al. "A Therapeutic Antibody Targeting BACE1 Inhibits Amyloid-[Beta] Production in Vivo", Science Translational Medicine, AAAS—American Association for the Advancement of Science, vol. 3, No. 84, May 25, 2011, 14 pages.
International Search Report and Written Opinion issued in PCT/US2015/061405, dated Mar. 15, 2016, 19 pages.
Bien-Ly et al., "Transferrin receptor (TfR) trafficking determines brain uptake of TfR antibody affinity variants" J. Exp. Med. 211(2):233-244 ( 2014).

(Continued)

*Primary Examiner* — Ruixiang Li
(74) *Attorney, Agent, or Firm* — McNeill Baur PLLC

(57) ABSTRACT

The present invention relates to anti-transferrin receptor antibodies and methods of their use.

40 Claims, 51 Drawing Sheets
Specification includes a Sequence Listing.

(56) References Cited

OTHER PUBLICATIONS

Biocompare: anti-TFRC (transferrin receptor) antibody from antibodies-online, Biocompare.com, (Aug. 1, 2014), http://www.biocompare.com/9776-Antibodies/4144935-anti-Transferrin-Receptor-p90-CD71-TFRC-antibody-APC/ pp. 3 (retrieved from the internet Aug. 4, 2014).

Daniels et al., "The transferrin receptor part 1: Biology and targeting with cytotoxic antibodies for the treatment of cancer," Clinical Immunology 121(2):144-158 (2006).

Daniels et al., "The transferrin receptor and the targeted delivery of therapeutic agents against cancer," Biochimica et Biophysica Acta 1820(3):291-317 (2012).

Excoffen et al., "The Coxsackie B Virus and Adenovirus Receptor Resides in a Distinct Membrane Microdomain," J. Virology 77(4):2559-2567 (2003).

Fundamental Immunology Paul, W. ed., Third edition, New York:Raven Press, p. 242 ( 1993).

Friden et al., "Characterization, receptor mapping and blood-brain barrier transcytosis of antibodies to the human transferrin receptor" J Pharmacol Exp Ther. 278(3):1491-8 (1996).

GenBank Accession No. AAT76192.1, immunoglobulin heavy chain variable region, partial (Mus musculus), pp. 2 (published2005).

GenBank Accession No. AAT76270.1, immunoglobulin light chain variable region, partial (Mus musculus), pp. 1 (published2005).

http://www.genetex.com/CD71-antibody-MEM-75-GTX29179.html, pp. 3 (printed Oct. 1, 2002).

Horejsi et al., "Monoclonal Antibodies against Human Leukocyte Antigens. II. Antibodies against CD45 (T200), CD3 (T3), CD43, CD10 (CALLA), Transferrin Receptor (T9), A Novel Broadly Expressed 18-kDa Antigen (MEM-43) and a Novel Antigen of Restricted Expression (MEM-74)" Folia Biologica (Praha) 34(1):23-34 (1988).

International Search Report and Written Opinion for International Application No. PCT/US2014/038847, pp. 28 (dated Jan. 9, 2015).

Janeway et al., Immunobiology, 3rd edition, 1997, Garland Publishing inc., pp. 3:1-3:11.

LSBio: Anti-CD71/Transferrin Receptor Antibody (clone MEM-75, APC) LS-C46200, pp. 2 (retrieved from the internet Aug 5, 2014).

Manger et al., "A transferrin receptor antibody represents one signal for the induction of IL 2 production by a human T cell line," J Immunol. 136(2):532-538 (1986).

Molecular Probes, Anti-Human Transferring Receptor, Mouse Monoclonal 236-15375 (A-11130), from tools.thermofisher.com/content/sfs/manuals/mp11130.pdf, pp. 2 (Revised Dec. 5, 2001).

Office Action and Search Report for Taiwanese Patent Application No. 103117676, with complete English translation, pp. 24 (dated Dec. 24, 2015).

Poláková et al., "Characterization of a new monoclonal antibody (TR-19) against human transferrin receptor and its application in topographic study," Neoplasma 38(1):21-31 (1991).

Portolano et al., "Lack of promiscuity in autoantigen-specific H and L chain combinations as revealed by human H and L chain 'roulette'" J Immunol 150(3):880-7 (Feb. 1, 1993).

Sade, et al., "A Human Blood-Brain Barrier Transcytosis Assay Reveals Antibody Transcytosis Influenced by pH-Dependent Receptor Binding," PLOS ONE, 9(4): e96340, 11 pages (2014).

Rudikoff et al., "Single amino acid substitution altering antigen-binding specificity" Proc. Natl.Acad. Sci. 79(Immunology):1979-1983 (Mar. 1982).

Taetle et al., "Mechanisms of Growth Inhibition by Anti-Transferrin Receptor Monoclonal Antibodies" J Cancer Res. 46(4 SUPPL Part 1):1759-1763 ( 1986).

White et al., "Combinations of Anti-Transferrin Receptor Monoclonal Antibodies Inhibit Human Tumor Cell Growth in Vitro and in Vivo: Evidence for Synergistic Antiproliferative Effects'" Cancer Research 50:6295-6301 ( 1990).

Characterization of Human- and Cynomolgous Monkey-cross-reactive Anti-TfR Hybridomas that Don't Compete with Tf Binding to TfR

| | | Competes with Apical Domain Binder | huTfR ELISA Binding | Cyno TfR ELISA Binding | Biacore of Hybridoma or Chimeric IgG ||||||| Cy/hu KD Ratio |
|---|---|---|---|---|---|---|---|---|---|---|---|---|
| | | | | | huTfR ||| CynoTfR ||| |
| | | | | | Ka | Kd | KD | Ka | Kd | KD | |
| Class I | 7A4 | +++ | +++ | +++ | 2.11E+06 | 4.34E-04 | 2.06E-10 | 1.06E+06 | 6.63E-04 | 6.27E-10 | 3.04 |
| | 8A2 | +++ | +++ | +++ | 1.22E+06 | 2.17E-04 | 1.79E-10 | 7.91E+05 | 7.15E-04 | 9.04E-10 | 5.06 |
| | 7A4 HC/8A2 LC | +++ | +++ | +++ | 3.01E+06 | 3.35E-04 | 1.12E-10 | 1.32E+06 | 1.22E-03 | 9.25E-10 | 8.29 |
| | 15O2 | +++ | +++ | +++ | | | | | | | |
| | 10D11 | +++ | +++ | +++ | 1.66E+05 | 3.44E-04 | 2.08E-09 | 6.46E+04 | 5.81E-03 | 8.99E-08 | 43.32 |
| | 7B10 | +++ | +++ | +++ | | | | | | | |
| | 15G11 | +++ | +++ | +++ | 8.90E+05 | 8.83E-04 | 9.92E-10 | 1.29E+06 | 3.35E-03 | 2.60E-09 | 2.62 |
| Class II | 13C3 | +++ | +++ | +++ | | | | | | | |
| | 16G5 | +++ | +++ | +++ | | | | | | | |
| | 16G4 | +++ | +++ | +++ | 4.77E+05 | 1.62E-03 | 3.40E-09 | 2.33E+05 | 5.23E-03 | 2.24E-08 | 6.59 |
| Class III | 16F6 | +++ | +++ | +++ | 1.36E+05 | 2.81E-04 | 2.07E-09 | 1.23E+05 | 9.13E-04 | 7.45E-09 | 3.6 |
| | 7G7 | - | +++ | +++ | 1.33E+05 | 6.08E-03 | 4.57E-08 | 4.63E+04 | 1.21E-02 | 2.62E-07 | 5.73E |
| Class IV | 4C2 | - | +++ | ++ | | | | | | | |
| | 1B12 | - | +++ | ++ | 1.36E+05 | 2.76E-04 | 2.03E-09 | 1.34E+05 | 5.80E-03 | 4.34E-08 | 21.35 |
| | 13D4 | - | +++ | ++ | 9.99E+04 | 9.49E-04 | 9.50E-09 | 7.06E+04 | 5.98E-04 | 8.47E-09 | 0.89 |

FIG. 2C

Light Chain Variable Region

|   |   | CDR L1 - Contact |
|---|---|---|
|   | CDR L1 - Chothia | |
|   | CDR L1 - Kabat | |

| Kabat Number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 27a | 27b | 27c | 27d | 28 | 29 | 30 | 31 | 32 | 33 | 34 | 35 | 36 | 37 | 38 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 7A4   | D | I | V | L | T | Q | S | P | A | S | L | A | V | S | L | G | Q | R | A | T | I | S | C | R | A | S | E | S | V | D | S | Y | G | N | S | F | M | H | W | Y | Q | Q |
| 8A2   | D | I | V | L | T | Q | S | P | A | S | L | A | V | S | L | G | Q | R | A | T | I | S | C | R | A | S | E | S | V | D | S | Y | G | N | S | F | M | H | W | Y | Q | Q |
| 15D2  | D | I | V | L | T | Q | S | P | A | S | L | A | V | S | L | G | Q | R | A | T | I | S | C | R | A | S | E | S | V | D | D | Y | G | N | S | F | M | H | W | Y | Q | Q |
| 10D11 | D | I | V | L | T | Q | S | P | A | S | L | A | V | S | L | G | Q | R | A | T | I | S | C | R | A | S | E | S | V | D | S | Y | G | [P] | S | F | M | H | W | Y | Q | Q |
| 7B10  | D | I | V | L | T | Q | S | P | A | S | L | A | V | S | L | G | Q | R | A | T | I | S | C | R | A | S | E | S | V | D | S | Y | G | N | S | F | M | H | W | Y | Q | Q |

|   |   | CDR L2 - Contact |
|---|---|---|
|   | CDR L2 - Chothia | |
|   | CDR L2 - Kabat | |

| Kabat Number | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 7A4   | K | P | G | Q | P | P | K | L | L | I | Y | R | A | S | N | L | E | S | G | I | P | A | R | F | S | G | S | G | S | R | T | D | F | T | L | T | I | N | P | V | E | A |
| 8A2   | K | P | G | Q | P | P | K | L | L | I | Y | R | A | S | N | L | E | S | G | I | P | A | R | F | S | G | S | G | S | R | T | D | F | T | L | T | I | N | P | V | E | A |
| 15D2  | K | P | G | Q | P | P | K | L | L | I | Y | R | A | S | N | L | E | S | G | I | P | A | R | F | S | G | S | G | S | R | T | D | F | T | L | T | I | N | P | V | E | A |
| 10D11 | K | P | G | Q | P | P | K | L | L | I | Y | R | A | S | N | L | E | S | G | I | P | A | R | F | S | G | S | G | S | R | T | D | F | T | L | T | I | N | P | V | E | A |
| 7B10  | K | P | G | Q | P | P | K | L | L | I | Y | R | A | S | N | L | H | S | G | I | P | A | R | F | S | G | S | G | S | R | T | D | F | T | L | T | I | N | P | V | E | A |

|   |   | CDR L3 - Contact |
|---|---|---|
|   | CDR L3 - Chothia | |
|   | CDR L3 - Kabat | |

| Kabat Number | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | |
|---|---|---|---|---|---|---|---|---|---|---|---|---|---|---|---|---|---|---|---|---|---|---|---|---|---|---|---|---|
| 7A4   | D | D | V | A | T | Y | Y | C | C | Q | Q | S | N | E | A | P | F | T | F | G | G | G | T | K | L | E | I | R | SEQ ID NO: 4 |
| 8A2   | D | D | V | A | T | Y | Y | C | C | Q | Q | S | N | E | [G] | P | F | T | F | G | G | G | T | K | L | E | I | [K] | SEQ ID NO: 5 |
| 15D2  | D | D | V | A | T | Y | Y | C | C | Q | Q | S | N | E | [D] | P | F | T | F | G | G | G | T | K | L | E | I | [K] | SEQ ID NO: 5 |
| 10D11 | D | D | V | A | T | Y | Y | C | C | Q | Q | S | N | E | A | P | F | T | F | G | G | G | T | [R] | L | E | I | R | SEQ ID NO: 6 |
| 7B10  | D | D | V | A | T | Y | Y | C | C | Q | [H] | S | N | E | A | P | F | T | F | G | G | G | T | K | L | E | I | R | SEQ ID NO: 4 |

Light Chain Variable Region

| | CDR L1 - Contact | | |
|---|---|---|---|
| | | CDR L1 - Chothia | |
| | | | CDR L1 - Kabat |

| Kabat Number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 15G11 | D | I | Q | M | T | Q | S | P | S | S | L | S | V | S | V | G | E | T | V | T | I | T | C | R | A | S | D | N | L | Y | S | N | L | A | W | Y | Q | Q | K | Q | G | K |
| 16G5  | D | I | Q | L | T | Q | S | P | S | S | L | S | V | S | V | G | E | T | V | T | I | T | C | R | A | S | E | N | I | Y | S | N | L | A | W | Y | Q | Q | K | Q | G | K |
| 13G3  | D | I | Q | M | T | Q | S | P | A | S | L | S | V | S | V | G | E | T | V | T | I | T | C | R | A | S | D | N | I | Y | S | N | L | A | W | Y | Q | Q | K | Q | G | K |
| 16G4  | D | I | Q | M | T | Q | S | P | A | S | L | S | V | S | V | G | E | T | V | T | I | T | C | R | A | S | D | N | I | Y | S | N | L | A | W | Y | Q | Q | K | Q | G | K |

| | CDR L2 - Contact | | |
|---|---|---|---|
| | | CDR L2 - Chothia | |
| | | | CDR L2 - Kabat |

| Kabat Number | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 15G11 | S | P | Q | L | L | V | Y | D | A | T | N | L | A | D | G | V | P | S | R | F | S | G | S | G | S | G | T | Q | Y | S | L | K | I | N | S | L | Q | S | E | D | F | G |
| 16G5  | S | P | Q | L | L | V | Y | D | A | T | D | L | A | D | G | V | P | S | R | F | S | G | S | G | S | G | T | Q | Y | S | L | K | I | N | S | L | Q | S | E | D | F | G |
| 13G3  | S | P | Q | L | L | V | Y | D | A | T | N | L | A | D | G | V | P | S | R | F | G | G | S | G | S | G | T | Q | Y | S | L | K | I | N | S | L | Q | S | E | D | F | G |
| 16G4  | S | P | Q | L | L | V | Y | A | V | T | N | L | A | D | G | V | P | S | R | F | S | G | S | G | S | G | T | Q | Y | S | L | K | I | N | S | L | Q | S | E | D | F | G |

| | CDR L3 - Contact | | |
|---|---|---|---|
| | | CDR L3 - Chothia | |
| | | | CDR L3 - Kabat |

| Kabat Number | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | | |
|---|---|---|---|---|---|---|---|---|---|---|---|---|---|---|---|---|---|---|---|---|---|---|---|---|---|
| 15G11 | T | Y | Y | C | Q | H | F | W | G | T | P | L | T | F | G | A | G | T | K | L | E | L | K | SEQ ID NO: 11 | |
| 16G5  | S | Y | Y | C | Q | H | F | W | G | T | P | L | M | F | G | A | G | T | K | L | E | L | I | SEQ ID NO: 12 | |
| 13G3  | S | Y | Y | C | Q | H | F | W | G | T | P | L | T | F | G | G | G | T | K | L | E | L | K | SEQ ID NO: 13 | |
| 16G4  | S | Y | Y | C | Q | H | F | W | G | T | P | L | T | F | G | A | G | T | K | L | E | L | K | SEQ ID NO: 14 | |

FIG. 3B-1

Heavy Chain Variable Region

| Kabat Number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 15G11 | Q | V | Q | L | Q | Q | P | G | A | E | L | V | K | P | G | A | S | V | K | L | S | C | K | A | S | G | Y | T | F | T | S | Y | W | M | H | W | V | K | Q | R | P | G |
| 16G5  | Q | V | Q | L | Q | Q | P | G | A | E | L | V | K | P | G | A | S | V | K | L | S | C | K | A | S | G | Y | T | F | T | S | Y | W | M | H | W | V | K | Q | R | P | G |
| 13G3  | Q | V | Q | L | Q | Q | P | G | A | E | L | V | R | P | G | A | S | V | K | L | S | C | K | A | S | G | Y | T | F | A | S | Y | W | M | H | W | V | K | Q | R | P | G |
| 16G4  | Q | V | Q | L | Q | Q | P | G | A | E | L | V | K | P | G | A | S | V | K | L | S | C | K | A | S | G | Y | T | F | T | S | Y | W | M | H | W | V | K | Q | R | P | G |

CDR H1 - Contact: 30-35
CDR H1 - Chothia: 26-32
CDR H1 - Kabat: 31-35

| Kabat Number | 43 | 44 | 45 | 46 | 47 | 48 | 49 | 50 | 51 | 52 | 52a | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 82a |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 15G11 | Q | G | L | E | W | I | G | E | I | N | P | T | N | G | R | T | N | Y | I | E | K | F | K | S | K | A | T | L | T | V | D | K | S | S | S | T | A | Y | M | Q | L | S |
| 16G5  | Q | G | L | E | W | I | G | E | I | N | P | T | N | G | R | T | N | Y | N | E | N | F | K | S | K | A | T | L | T | V | D | K | S | S | S | T | A | Y | M | Q | L | S |
| 13G3  | Q | G | L | E | W | I | G | E | I | N | P | I | N | G | R | T | N | Y | N | E | K | F | K | S | K | A | T | L | T | V | D | K | S | S | S | T | A | Y | M | Q | L | S |
| 16G4  | Q | G | L | E | W | I | G | E | I | N | P | S | N | G | R | T | N | Y | N | E | T | F | K | S | K | A | T | L | T | V | D | K | S | S | S | T | A | Y | M | Q | L | S |

CDR H2 - Contact: 47-58
CDR H2 - Chothia: 50-58
CDR H2 - Kabat: 50-65

| Kabat Number | 82b | 82c | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 | |
|---|---|---|---|---|---|---|---|---|---|---|---|---|---|---|---|---|---|---|---|---|---|---|---|---|---|---|---|---|---|---|---|---|---|---|
| 15G11 | S | L | T | S | E | D | S | A | V | Y | Y | C | A | R | G | T | R | A | Y | H | Y | W | G | Q | G | T | S | V | T | V | S | S | | SEQ ID NO: 15 |
| 16G5  | S | L | T | S | E | D | S | A | V | Y | Y | C | A | R | G | T | R | A | Y | H | Y | W | G | Q | G | T | S | V | T | V | S | S | | SEQ ID NO: 16 |
| 13G3  | S | L | T | S | E | D | S | A | V | Y | Y | C | A | R | G | T | R | A | Y | H | F | W | G | Q | G | T | T | V | T | V | S | S | | SEQ ID NO: 17 |
| 16G4  | S | L | T | S | E | D | S | A | V | Y | Y | C | A | R | G | T | R | A | Y | H | Y | W | G | Q | G | T | S | V | T | V | S | S | | SEQ ID NO: 18 |

CDR H3 - Contact: 95-101
CDR H3 - Chothia: 95-102
CDR H3 - Kabat: 95-102

*FIG. 3B-2*

Light Chain Variable Region

```
              Kabat Number  1  2  3  4  5  6  7  8  9 10 11 12 13 14 15 16 17 18 19 20 21 22 23 24 25 26 27 28 29 30 31 32 33 34 35 36 37 38 39 40 41 42
                      16F6 D  V  Q  I  T  Q  S  P  S  Y  L  T  A  S  P  G  E  T  I  T  I  N  C  R  A  S  K  S  I  S  K  Y  L  A  W  Y  Q  E  K  P  G  K
                                                                                                              [CDR L1 - Chothia]
                                                                                                           [CDR L1 - Kabat     ]
                                                                                                                  [CDR L1 - Contact]

Kabat Number 43 44 45 46 47 48 49 50 51 52 53 54 55 56 57 58 59 60 61 62 63 64 65 66 67 68 69 70 71 72 73 74 75 76 77 78 79 80 81 82 83 84
                      16F6 T  N  K  L  I  T  Y  S  G  S  T  L  Q  S  G  I  P  S  R  F  S  G  S  G  S  G  T  D  F  T  L  T  I  S  N  L  E  P  E  D  F  A
                                           [CDR L2 - Contact]
                                              [CDR L2 - Chothia]
                                              [CDR L2 - Kabat  ]

Kabat Number 85 86 87 88 89 90 91 92 93 94 95 96 97 98 99 100 101 102 103 104 105 106 107   SEQ ID NO: 19
                      16F6 M  Y  Y  C  Q  Q  H  N  E  Y  P  W  T  F  G  G  G  T  K  L  E  I  K
                                        [CDR L3 - Contact]
                                          [CDR L3 - Chothia]
                                          [CDR L3 - Kabat  ]
```

*FIG. 3C-1*

Heavy Chain Variable Region

| Kabat Number | 1 2 3 4 5 6 7 8 9 10 11 12 13 14 15 16 17 18 19 20 21 22 23 24 25 26 27 28 29 30 31 32 33 34 35 35a 36 37 38 39 40 41 |
|---|---|
| 16F6 | D V Q L Q E S G P G L V K P S Q S L S L T C T V T G N S I T S E Y A W N W I R Q F P |

CDR H1 - Contact: positions 30-35a
CDR H1 - Chothia: positions 31-35
CDR H1 - Kabat: positions 31-35a

| Kabat Number | 42 43 44 45 46 47 48 49 50 51 52 53 54 55 56 57 58 59 60 61 62 63 64 65 66 67 68 69 70 71 72 73 74 75 76 77 78 79 80 81 82 82a |
|---|---|
| 16F6 | G N K L E W M G Y I S Y S G T T S Y N P S L K S R I S I T R D T S K N Q L F L Q L N |

CDR H2 - Contact: positions 47-58
CDR H2 - Chothia: positions 50-57
CDR H2 - Kabat: positions 50-65

| Kabat Number | 82b 82c 83 84 85 86 87 88 89 90 91 92 93 94 95 96 97 98 99 100 100a 100b 100c 100d 100e 101 102 103 104 105 106 107 108 109 110 111 112 113 |
|---|---|
| 16F6 | S V T T E D T A T Y F C A R Y G Y G N P A T R Y F P D V W G A G T L V T V S S |

CDR H3 - Contact: positions 93-101
CDR H3 - Chothia: positions 96-101
CDR H3 - Kabat: positions 95-102

SEQ ID NO: 20

FIG. 3C-2

Light Chain Variable Region

| Kabat Number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 27a | 27b | 27c | 27d | 28 | 29 | 30 | 31 | 32 | 33 | 34 | 35 | 36 | 37 | 38 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 7G7 | D | I | V | L | T | Q | S | P | A | S | L | A | V | S | L | G | Q | R | A | T | I | S | C | R | A | R | Q | S | V | S | T | S | S | Y | S | F | M | E | W | Y | R | Q |
| 4C2 | D | I | V | L | T | Q | S | P | A | S | L | A | V | S | L | G | Q | R | A | T | I | S | C | R | A | R | Q | S | V | S | T | S | S | Y | S | F | M | E | W | Y | Q | Q |
| 1B12 | Q | I | V | L | T | Q | S | P | A | I | M | S | A | S | L | G | G | K | V | T | M | T | C | T | T | S | S | . | . | . | . | V | P | S | S | Y | F | H | W | Y | Q | Q |
| 13D4 | D | I | Q | M | T | Q | T | T | S | S | L | S | A | S | L | G | D | R | V | T | I | N | C | R | A | G | Q | . | . | . | . | D | I | T | N | Y | L | N | W | F | Q | Q |

CDR L1 - Contact (cols 30-36)
CDR L1 - Chothia (cols 24-34)
CDR L1 - Kabat (cols 24-34)

| Kabat Number | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 7G7 | K | A | G | Q | P | P | K | L | L | I | K | Y | A | S | T | Q | E | S | G | V | P | A | R | F | S | G | S | G | S | G | T | D | F | T | L | N | I | L | P | V | E | E |
| 4C2 | K | P | G | Q | P | P | K | L | L | I | K | Y | A | S | I | Q | E | S | G | V | P | A | R | F | S | G | S | G | S | G | T | D | F | T | L | N | I | L | P | V | E | E |
| 1B12 | K | P | G | S | S | P | K | L | W | I | Y | V | P | S | N | L | A | S | G | V | P | A | R | F | S | G | S | G | S | G | T | S | Y | S | L | T | I | S | S | M | E | A |
| 13D4 | K | P | D | G | T | V | K | L | L | I | Y | Y | T | S | R | L | H | S | G | V | P | S | R | F | S | G | S | G | S | G | T | D | Y | S | L | T | I | T | N | L | E | Q |

CDR L2 - Contact (cols 46-52)
CDR L2 - Chothia (cols 50-56)
CDR L2 - Kabat (cols 50-56)

| Kabat Number | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|---|---|---|---|
| 7G7 | E | D | T | A | T | Y | Y | C | Q | H | E | W | E | I | P | F | T | F | G | S | G | T | K | L | E | I | K |
| 4C2 | E | D | T | A | T | Y | Y | C | Q | H | E | W | E | I | P | F | T | F | G | S | G | T | K | L | E | I | K |
| 1B12 | E | D | A | A | T | Y | Y | C | Q | Q | W | S | S | Q | . | . | H | R | S | P | R | T | K | N | L | I | K |
| 13D4 | E | D | I | A | T | Y | F | C | Q | Q | . | . | G | Q | T | L | P | Y | T | F | G | G | G | T | K | I | K |

CDR L3 - Contact (cols 89-96)
CDR L3 - Chothia (cols 89-97)
CDR L3 - Kabat (cols 89-97)

7G7    SEQ ID NO: 21
4C2    SEQ ID NO: 22
1B12   SEQ ID NO: 23
13D4   SEQ ID NO: 24

Humanization of 15G11 to Generate hu15G11.v5

Light Chain, Kappa: Mouse Antibody Aligned to Human Germlines

| Kabat Number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | | CDR L1 | | | 24 | 25 | 26 | 27 | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|---|---|---|---|
| IGKV1-NL1*01 | D | I | Q | M | T | Q | S | P | S | S | L | S | A | S | V | G | D | R | V | T | I | T | C | | | | | R | A | S | Q | G | I | S | N | L | A | W | Y |
| 15G11 | D | I | Q | M | T | Q | S | P | A | S | L | S | V | S | V | G | E | T | V | T | I | T | C | | | | | R | A | S | D | N | I | Y | S | N | L | A | W | Y |
| hu15G11.v5 | D | I | Q | M | T | Q | S | P | S | S | L | S | A | S | V | G | D | R | V | T | I | T | C | | | | | R | A | S | D | N | I | Y | S | N | L | A | W | Y |

| Kabat Number | 37 | 38 | 39 | 40 | 41 | 42 | 43 | 44 | 45 | 46 | 47 | 48 | 49 | | CDR L2 | | 50 | 51 | 52 | 53 | 54 | 55 | 56 | 57 | 58 | 59 | 60 | 61 | 62 | 63 | 64 | 65 | 66 | 67 | 68 | 69 | 70 | 71 |
|---|---|---|---|---|---|---|---|---|---|---|---|---|---|---|---|---|---|---|---|---|---|---|---|---|---|---|---|---|---|---|---|---|---|---|---|---|---|---|
| IGKV1-NL1*01 | Q | Q | K | P | G | K | A | P | K | L | L | I | Y | | | | A | A | S | R | L | E | S | G | V | P | S | R | F | S | G | S | G | S | G | T | D | Y |
| 15G11 | Q | Q | K | P | G | K | S | P | Q | L | L | V | Y | | | | D | A | T | N | L | A | D | G | V | P | S | R | F | S | G | S | G | S | G | T | Q | Y |
| hu15G11.v5 | Q | Q | K | P | G | K | S | P | K | L | L | I | Y | | | | D | A | T | N | L | A | D | G | V | P | S | R | F | S | G | S | G | S | G | T | D | Y |

| Kabat Number | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | | CDR L3 | | 96 | 97 | 98 | 99 | 100 | 101 | 102 | 103 | 104 | 105 | 106 | 107 | SEQ ID NO: |
|---|---|---|---|---|---|---|---|---|---|---|---|---|---|---|---|---|---|---|---|---|---|---|---|---|---|---|---|---|---|---|---|---|---|---|---|---|---|---|---|---|
| IGKV1-NL1*01 | T | L | T | I | S | S | L | Q | P | E | D | F | A | T | Y | Y | C | Q | Q | Y | Y | S | T | P | | | | Y | T | F | G | Q | G | T | K | L | E | I | K | 103 |
| 15G11 | S | L | K | I | N | S | L | Q | S | E | D | F | G | T | Y | Y | C | Q | H | F | W | G | T | P | | | | F | T | F | G | A | G | T | K | L | E | L | K | 104 |
| hu15G11.v5 | T | L | T | I | S | S | L | Q | P | E | D | F | A | T | Y | Y | C | Q | H | F | W | G | T | P | | | | F | T | F | G | Q | G | T | K | V | E | I | K | 105 |

FIG. 4A-1

Humanization of 15G11 to Generate Hu15G11.v5

Heavy Chain: Mouse Antibody Aligned to Human Germlines

| Kabat Number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV1-3*01 | Q | V | Q | L | V | Q | S | G | A | E | V | K | K | P | G | A | S | V | K | V | S | C | K | A | S | G | Y | T | F | T | S | Y | A | M | H | W | V | R | Q | A | P | G | Q | R |
| 15G11 | Q | V | Q | L | V | Q | P | G | A | E | L | V | K | P | G | A | S | V | K | L | S | C | K | A | S | G | Y | T | F | T | S | Y | W | M | H | W | V | K | Q | R | P | G | Q | G |
| hu15G11.v5 | Q | V | Q | L | V | Q | S | G | A | E | V | K | K | P | G | A | S | V | K | V | S | C | K | A | S | G | Y | T | F | T | S | Y | W | M | H | W | V | R | Q | A | P | G | Q | R |

CDR H1: positions 26–35

| Kabat Number | 45 | 46 | 47 | 48 | 49 | 50 | 51 | 52 | 52a | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | a | b | c | 83 | 84 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV1-3*01 | L | E | W | M | G | W | I | N | A | G | N | G | N | T | K | Y | S | Q | K | F | Q | G | R | V | T | I | T | R | D | T | S | A | S | T | A | Y | M | E | L | S | S | L | R | S |
| 15G11 | L | E | W | I | G | E | I | N | P | . | . | . | T | N | G | R | T | N | Y | I | E | K | F | K | S | K | A | T | F | T | V | D | K | S | S | S | T | A | Y | M | Q | L | S | S | L | T | S |
| hu15G11.v5 | L | E | W | I | G | E | I | N | P | . | . | . | T | N | G | R | T | N | Y | I | E | K | F | K | S | R | V | T | F | T | V | D | K | S | S | S | T | A | Y | M | E | L | S | S | L | R | S |

CDR H2

| Kabat Number | 85 | 86 | 87 | 88 | 89 | 90 | 91 | 92 | 93 | 94 | 95 | 96 | 97 | 98 | 99 | 101 | 102 | 103 | 104 | 105 | 106 | 107 | 108 | 109 | 110 | 111 | 112 | 113 | SEQ ID NO: |
|---|---|---|---|---|---|---|---|---|---|---|---|---|---|---|---|---|---|---|---|---|---|---|---|---|---|---|---|---|---|
| IGHV1-3*01 | E | D | T | A | V | Y | Y | C | A | R | . | . | . | . | . | . | . | . | . | . | . | . | . | . | . | . | . | . | 106 |
| 15G11 | E | D | T | S | A | V | Y | Y | C | A | R | I | G | T | R | A | F | D | V | W | G | Q | G | T | M | V | T | V | S | S | 107 |
| hu15G11.v5 | E | D | T | A | V | Y | Y | C | A | R | I | G | T | R | A | Y | H | Y | . | W | G | Q | G | T | M | V | T | V | S | S | 108 |

CDR H3

FIG. 4A-2

Humanization of 7A4/8A2 to Generate hu7A4.v15

Light Chain, Kappa: Mouse Antibody Aligned to Human Germlines

| Kabat Number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | a | b | c | d | e | f | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGKV4-1*01 | D | I | V | M | T | Q | S | P | D | S | L | A | V | S | L | G | E | R | A | T | I | N | C | K | S | S | Q | S | V | L | Y | S | S | N | N | K | N | Y | L | A | W | Y |
| 8A2/7A4 | D | I | V | M | T | Q | L | Q | S | P | A | S | L | A | V | S | L | G | Q | R | A | T | I | S | C | R | A | S | E | S | V | D | S | . | . | Y | G | N | S | F | M | H | W | Y |
| hu7A4.v15 | D | I | V | M | T | Q | S | P | D | S | L | A | V | S | L | G | E | R | A | T | I | N | C | R | A | S | E | S | V | D | S | . | . | Y | G | N | S | F | M | H | W | Y |

CDR L1: positions 24–34

| Kabat Number | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 |
|---|---|---|---|---|---|---|---|---|---|---|---|---|---|---|---|---|---|---|---|---|---|---|---|---|---|---|---|---|---|---|---|---|---|---|---|
| IGKV4-1*01 | Q | Q | K | P | G | Q | P | P | K | L | L | I | Y | W | A | S | T | R | E | S | G | V | P | D | R | F | S | G | S | G | S | G | T | D | F |
| 8A2/7A4 | Q | Q | K | P | G | Q | P | P | K | L | L | I | Y | R | A | S | N | L | E | S | G | I | P | A | R | F | S | G | S | G | S | R | T | D | F |
| hu7A4.v15 | Q | Q | K | P | G | Q | P | P | K | L | L | I | Y | R | A | S | N | L | E | S | G | V | P | D | R | F | S | G | S | G | S | G | T | D | F |

CDR L2: positions 50–56

| Kabat Number | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | SEQ ID NO: |
|---|---|---|---|---|---|---|---|---|---|---|---|---|---|---|---|---|---|---|---|---|---|---|---|---|---|---|---|---|---|---|---|---|---|---|---|---|---|
| IGKV4-1*01 | T | L | T | I | S | S | L | Q | A | E | D | V | A | V | Y | Y | C | Q | Q | Y | Y | S | T | P | . | Y | T | F | G | Q | G | T | K | L | E | I | K | 109 |
| 8A2/7A4 | T | L | T | I | N | P | V | E | A | D | D | V | A | T | Y | Y | C | Q | Q | S | N | E | G | P | P | F | T | F | G | G | G | T | K | L | E | I | K | 110 |
| hu7A4.v15 | T | L | T | I | S | S | L | Q | A | E | D | V | A | V | Y | Y | C | Q | Q | S | N | E | A | P | P | F | T | F | G | Q | G | T | K | L | E | I | K | 111 |

CDR L3: positions 89–97

FIG. 4B-1

Humanization of 7A4/8A2 to Generate hu7A4.v15

Heavy Chain: Mouse Antibody Aligned to Human Germlines

| Kabat Number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV4-2*02 | Q | V | Q | L | Q | V | S | G | A | E | V | K | K | P | G | A | S | V | K | V | S | C | K | A | S | G | Y | T | F | T | G | Y | Y | M | H | W | V | R | Q | A | P | G | Q | G |
| 8A2/7A4 | Q | V | Q | L | Q | Q | S | G | A | E | L | V | R | P | G | V | S | V | K | I | S | C | K | G | S | G | Y | T | F | T | D | Y | A | M | H | W | V | K | Q | S | H | A | K | S |
| hu7A4.v15 | E | V | Q | L | V | Q | S | G | A | E | V | K | K | P | G | A | S | V | K | V | S | C | K | G | S | G | Y | T | F | T | D | Y | A | M | H | W | V | R | Q | A | P | G | Q | G |

CDR H1: 31-35

| Kabat Number | 45 | 46 | 47 | 48 | 49 | 50 | 51 | 52 | a | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | a | b | c | 83 | 84 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV4-2*02 | L | E | W | M | G | W | I | N | P | N | S | G | G | T | N | Y | A | Q | K | F | Q | G | R | V | T | M | T | R | D | T | S | I | S | T | A | Y | M | E | L | S | R | L | R | S |
| 8A2/7A4 | L | E | W | I | G | Y | F | S | T | . | . | . | G | R | T | N | Y | N | Q | K | F | K | G | K | A | T | M | T | V | D | K | S | I | S | T | A | Y | M | E | L | A | R | L | T | S |
| hu7A4.v15 | L | E | W | M | G | Y | F | S | T | . | . | . | G | R | T | N | Y | N | Q | K | F | K | G | R | V | T | M | T | V | D | T | S | I | S | T | A | Y | M | E | L | S | R | L | R | S |

CDR H2: 50-65

| Kabat Number | 85 | 86 | 87 | 88 | 89 | 90 | 91 | 92 | 93 | 94 | 95 | 96 | 97 | 98 | 99 | 100 | a | B | 101 | 102 | 103 | 104 | 105 | 106 | 107 | 108 | 109 | 110 | 111 | 112 | 113 | SEQ ID NO: |
|---|---|---|---|---|---|---|---|---|---|---|---|---|---|---|---|---|---|---|---|---|---|---|---|---|---|---|---|---|---|---|---|---|
| IGHV4-2*02 | D | D | T | A | V | Y | Y | C | A | R | . | . | . | . | . | . | . | . | M | D | V | W | G | Q | G | T | T | V | T | V | S | S | 112 |
| 8A2/7A4 | E | D | S | A | L | Y | Y | C | A | R | G | L | S | G | N | Y | V | . | M | D | Y | W | G | Q | G | T | S | V | T | V | S | S | 113 |
| hu7A4.v15 | D | D | T | A | V | Y | Y | C | A | R | G | L | S | G | N | Y | V | . | M | D | Y | W | G | Q | G | T | T | V | T | V | S | S | 114 |

CDR H3: 95-102

FIG. 4B-2

Humanization of 7G7 to Generate hu7G7.v1

Light Chain, Kappa: Mouse Antibody Aligned to K4H1

| Kabat Number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | a | b | c | d | e | f | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| K4H1 | D | I | V | M | T | Q | S | P | S | S | L | S | A | V | S | L | G | E | R | A | T | I | N | C | K | S | S | Q | S | V | L | Y | S | S | N | N | K | N | Y | L | A | W |
| 7G7 | D | I | V | L | T | Q | S | P | A | S | L | A | V | S | L | G | Q | R | A | T | I | S | C | R | A | R | Q | S | V | S | T | . | . | S | S | Y | S | F | M | H | W |
| hu7G7.v1 | D | I | V | M | T | Q | S | P | D | S | L | A | V | S | L | G | E | R | A | T | I | N | C | R | A | R | Q | S | V | S | T | . | . | S | S | Y | S | F | M | H | W |

CDR L1 (positions 24–34)

| Kabat Number | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 |
|---|---|---|---|---|---|---|---|---|---|---|---|---|---|---|---|---|---|---|---|---|---|---|---|---|---|---|---|---|---|---|---|---|---|---|---|
| K4H1 | Q | Q | K | P | G | Q | P | P | K | L | L | I | Y | W | A | S | T | R | E | S | G | V | P | D | R | F | S | G | S | G | S | G | T | D | F |
| 7G7 | Q | R | K | A | G | Q | P | P | K | L | L | I | K | Y | A | S | I | Q | . | . | S | G | V | P | A | R | F | S | G | S | G | S | G | T | D | F |
| hu7G7.v1 | Q | Q | K | P | G | Q | P | P | K | L | L | I | K | Y | A | S | I | Q | . | . | S | G | V | P | D | R | F | S | G | S | G | S | G | T | D | F |

CDR L2 (positions 50–56)

| Kabat Number | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | SEQ ID NO: |
|---|---|---|---|---|---|---|---|---|---|---|---|---|---|---|---|---|---|---|---|---|---|---|---|---|---|---|---|---|---|---|---|---|---|---|---|---|---|
| K4H1 | T | L | T | I | S | S | L | Q | A | E | D | V | A | V | Y | Y | C | Q | Q | Y | S | T | P | . | . | . | P | F | G | Q | G | T | K | V | E | I | K | 115 |
| 7G7 | T | L | N | I | L | P | V | E | E | E | D | T | A | T | Y | Y | C | Q | Q | H | T | W | E | I | P | F | T | F | G | G | G | T | K | L | E | I | K | 116 |
| hu7G7.v1 | T | L | T | I | S | S | L | Q | A | E | D | V | A | T | Y | Y | C | Q | Q | H | T | W | E | I | P | F | T | F | G | Q | G | T | K | V | E | I | K | 117 |

CDR L3 (positions 89–97)

FIG. 4C-1

Humanization of 7G7 to Generate hu7G7.v1

Heavy Chain: Mouse Antibody Aligned to K4H1

| Kabat Number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | CDR H1 | | | | | | | | | | | | | | | | |
| KAH1 | E | V | Q | L | V | Q | S | G | A | E | V | K | K | P | G | A | S | V | K | V | S | C | K | A | S | G | Y | T | F | T | S | Y | Y | I | H | W | V | R | Q | A | P | G | Q | G |
| 7G7 | Q | V | Q | L | Q | Q | P | G | S | E | L | V | R | P | G | A | S | V | K | L | S | C | K | A | S | G | Y | T | F | T | S | Y | W | M | H | W | V | K | Q | R | P | G | Q | G |
| hu7G7.v1 | E | V | Q | L | V | Q | S | G | A | E | V | K | K | P | G | A | S | V | K | V | S | C | K | A | S | G | Y | T | F | T | S | Y | W | M | H | W | V | R | Q | A | P | G | Q | G |

| Kabat Number | 45 | 46 | 47 | 48 | 49 | 50 | 51 | 52 | a | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | a | b | c | 83 | 84 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | CDR H2 | | | | | | | | | | | | | | | | | | | | | | | | | | | | | | | | | | | | | |
| KAH1 | L | E | W | I | G | W | I | N | P | . | . | G | S | G | N | T | N | Y | A | Q | K | F | Q | G | R | V | T | I | T | R | D | T | S | T | S | T | A | Y | L | E | L | S | S | L |
| 7G7 | L | E | W | I | G | N | I | Y | P | . | . | G | S | G | S | T | K | Y | D | E | R | F | K | S | K | G | T | L | T | V | D | T | S | S | S | T | A | Y | M | H | L | S | S | L |
| hu7G7.v1 | L | E | W | I | G | N | I | Y | P | . | . | G | S | G | S | T | K | Y | D | E | R | F | K | S | R | V | T | I | T | V | D | T | S | T | S | T | A | Y | L | E | L | S | S | L |

| Kabat Number | 85 | 86 | 87 | 88 | 89 | 90 | 91 | 92 | 93 | 94 | 95 | 96 | 97 | 98 | 99 | 100 | a | B | | c | 101 | 102 | 103 | 104 | 105 | 106 | 107 | 108 | 109 | 110 | 111 | 112 | 113 | SEQ ID NO: |
|---|---|---|---|---|---|---|---|---|---|---|---|---|---|---|---|---|---|---|---|---|---|---|---|---|---|---|---|---|---|---|---|---|---|---|
| | | | | | | | | | | | | | | | | CDR H3 | | | | | | | | | | | | | | | | | | |
| KAH1 | E | D | T | A | V | Y | Y | C | A | R | . | . | . | . | . | . | . | . | | . | F | D | Y | W | G | Q | G | T | L | V | T | V | S | S | 118 |
| 7G7 | E | D | S | A | V | Y | Y | C | T | R | G | G | Y | D | S | R | A | W | | . | F | A | Y | W | G | Q | G | T | L | V | T | V | S | A | 119 |
| hu7G7.v1 | E | D | T | A | V | Y | Y | C | T | R | G | G | Y | D | S | R | A | W | | . | F | A | Y | W | G | Q | G | T | L | V | T | V | S | S | 120 |

FIG. 4C-2

Humanization of 16F6 to Generate hu16F6.v4

Light Chain, Kappa: Mouse Antibody Aligned to Human Germlines

FIG. 4D-1

Humanization of 16F6 to Generate hu16F6.v4

Heavy Chain: Mouse Antibody Aligned to Human Germlines

| Kabat Number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV4-59*01 | Q | V | Q | L | Q | E | S | G | P | G | L | V | K | P | S | E | T | L | S | L | T | C | T | V | S | G | G | S | I | S | S | Y | Y | W | S | W | I | R | Q | P | P | G | K | G |
| 16F6 | D | V | Q | L | Q | E | S | G | P | G | L | V | K | P | S | Q | S | L | S | L | T | C | T | V | T | G | N | S | I | T | S | E | Y | A | W | N | W | I | R | Q | F | P | G | N | K |
| hu16F6.v4 | E | V | Q | L | V | E | S | G | P | G | L | V | K | P | S | Q | T | L | S | L | T | C | T | V | S | G | N | S | I | T | S | E | Y | A | W | N | W | I | R | Q | P | P | G | K | G |

CDR H1

| Kabat Number | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | a | b | c | 83 | 84 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV4-59*01 | L | E | W | I | G | Y | I | Y | Y | S | G | S | T | N | Y | N | P | S | L | K | S | R | V | T | I | S | V | D | T | S | K | N | Q | F | S | L | K | L | S | S | V | T | A |
| 16F6 | L | E | W | M | G | Y | I | S | . | . | . | . | T | T | S | Y | N | P | S | L | K | S | R | I | T | I | T | R | D | T | S | K | N | Q | L | F | L | Q | L | N | S | V | T | T |
| hu16F6.v4 | L | E | W | I | G | Y | I | H | . | . | . | . | T | T | G | Y | N | P | S | L | K | S | R | V | T | I | S | R | D | T | S | K | N | Q | F | S | L | K | L | S | S | V | T | A |

CDR H2

| Kabat Number | 85 | 86 | 87 | 88 | 89 | 90 | 91 | 92 | 93 | 94 | 95 | 96 | 97 | 98 | 99 | 100 | A | B | C | D | E | 101 | 102 | 103 | 104 | 105 | 106 | 107 | 108 | 109 | 110 | 111 | 112 | 113 | SEQ ID NO: |
|---|---|---|---|---|---|---|---|---|---|---|---|---|---|---|---|---|---|---|---|---|---|---|---|---|---|---|---|---|---|---|---|---|---|---|---|
| IGHV4-59*01 | A | D | T | A | V | Y | Y | C | A | R | . | . | . | . | . | . | . | . | . | . | . | . | . | . | . | . | . | . | . | . | . | . | . | . | 124 |
| 16F6 | E | D | T | A | V | Y | F | C | A | F | Y | G | Y | G | N | P | A | F | T | R | Y | M | D | V | W | G | A | G | T | T | V | T | V | S | 125 |
| hu16F6.v4 | A | D | T | A | V | Y | Y | C | A | R | Y | G | Y | G | N | P | A | F | T | R | Y | F | D | V | W | G | Q | G | T | L | V | T | V | S | 126 |

CDR H3

15G11, 7A4 and 16F6 Humanization Variants

| | LC | | HC | | | | | | huTfR | | | CynoTfR | | | Cy/hu Ratio |
|---|---|---|---|---|---|---|---|---|---|---|---|---|---|---|---|
| | 43 | 48 | 48 | 67 | 69 | 71 | 73 | | Ka | Kd | KD | Ka | Kd | KD | |
| mu15G11 | S | V | I | A | L | V | K | | 8.900E+05 | 8.825E-04 | 9.916E-10 | 1.288E+05 | 3.349E-03 | 2.600E-09 | 2.6 |
| hu15G11.v1 | A | L | M | V | I | R | T | | 6.240E+05 | 3.194E-03 | 5.119E-09 | 8.571E+05 | 8.670E-03 | 1.012E-08 | 2.0 |
| hu15G11.v2 | A | L | M | V | I | V | T | | 3.550E+05 | 3.290E-03 | 9.347E-09 | 4.554E+05 | 8.021E-03 | 1.761E-08 | 1.9 |
| hu15G11.v3 | S | V | M | V | I | R | T | | 5.703E+05 | 2.347E-03 | 4.115E-09 | 8.044E+05 | 4.292E-03 | 5.336E-09 | 1.3 |
| hu15G11.v4 | S | V | M | V | I | V | T | | 4.773E+05 | 1.855E-03 | 3.886E-09 | 5.732E+05 | 4.033E-03 | 7.036E-09 | 1.8 |
| hu15G11.v5 | S | V | I | A | L | V | K | | 6.46E+05 | 0.00215 | 3.33E-09 | 5.43E+05 | 0.00641 | 1.18E-08 | 3.5 |

| | LC | | HC | | | huTfR | | | CynoTfR | | | Cy/hu Ratio |
|---|---|---|---|---|---|---|---|---|---|---|---|---|
| | 27d | 58 | 68 | 94 | 24 | 71 | Ka | Kd | KD | Ka | Kd | KD | |
| ch 7A4 | D | I | R | A | G | V | 2.11E+06 | 4.34E-04 | 2.06E-10 | 1.06E+06 | 6.63E-04 | 6.27E-10 | 3.04 |
| ch7A4/8A2 | S | I | R | G | G | V | 3.007E+06 | 3.353E-04 | 1.115E-10 | 1.315E+06 | 1.216E-03 | 9.247E-10 | 8.3 |
| hu7A4.v1 | S | V | G | G | A | R | 1.41E+06 | 3.94E-04 | 2.79E-10 | 9.15E+05 | 1.53E-03 | 1.67E-09 | 6.0 |
| hu7A4.v2 | S | V | G | G | G | R | 1.60E+06 | 3.71E-04 | 2.32E-10 | 9.62E+05 | 1.17E-03 | 1.22E-09 | 5.3 |
| hu7A4.v3 | S | V | G | G | A | V | 6.24E+05 | 3.39E-04 | 5.43E-10 | 3.22E+05 | 9.34E-04 | 2.90E-09 | 5.3 |
| hu7A4.v4 | S | V | G | G | G | V | 4.82E+05 | 2.95E-04 | 6.12E-10 | 2.52E+05 | 9.66E-04 | 3.83E-09 | 6.3 |
| hu7A4.v5 | S | I | G | G | A | R | 1.748E+06 | 6.363 E-04 | 3.640E-10 | 1.461E+06 | 1.757E-03 | 1.203E-09 | 3.3 |
| hu7A4.v6 | S | I | G | G | G | R | 2.845E+06 | 7.396 E-04 | 2.600E-10 | 1.780E+06 | 1.883E-03 | 1.058E-09 | 4.1 |

FIG. 4E-2

| Variant | | | | | | | huTfR Ka | huTfR Kd | huTfR KD | CynoTfR Ka | CynoTfR Kd | CynoTfR KD | Cy/hu Ratio |
|---|---|---|---|---|---|---|---|---|---|---|---|---|---|
| hu7A4.v7 | S | I | | G | A | V | 1.113E+06 | 5.735E-04 | 5.153E-10 | 2.428E+06 | 2.855E-03 | 1.176E-09 | 2.3 |
| hu7A4.v8 | S | I | | G | G | V | 8.326E+05 | 1.077E-03 | 1.294E-09 | 2.768E+05 | 3.411E-03 | 1.232E-08 | 9.5 |
| hu7A4.v9 | S | V | R | G | A | V | 1.930E+06 | 2.304E-04 | 1.194E-10 | 1.280E+06 | 5.477E-04 | 4.279E-10 | 3.6 |
| hu7A4.v10 | S | V | R | G | G | V | 1.684E+06 | 2.407E-04 | 1.429E-10 | 1.115E+06 | 5.632E-04 | 5.051E-10 | 3.5 |
| hu7A4.v11 | S | V | R | G | A | V | 1.487E+06 | 2.323E-04 | 1.562E-10 | 8.049E+05 | 7.588E-04 | 9.427E-10 | 6.0 |
| hu7A4.v12 | S | V | R | G | G | V | 9.159E+05 | 1.833E-04 | 2.001E-10 | 4.587E+05 | 9.580E-04 | 2.089E-09 | 10.4 |
| hu7A4.v13 | S | V | G | A | A | R | 4.51E+05 | 6.14E-04 | 1.36E-09 | 2.13E+05 | 2.42E-03 | 1.14E-08 | 8.3 |
| hu7A4.v14 | S | I | | A | G | R | 6.14E+05 | 7.33E-04 | 1.19E-09 | 2.30E+05 | 3.61E-03 | 1.57E-08 | 13.2 |
| hu7A4.v15 | S | V | R | A | G | V | 6.73E+05 | 3.77E-04 | 5.61E-10 | 2.90E+05 | 2.26E-03 | 7.80E-09 | 13.9 |

| | LC 43 | LC 44 | HC 71 | HC 78 | huTfR Ka | huTfR Kd | huTfR KD | CynoTfR Ka | CynoTfR Kd | CynoTfR KD | Cy/hu Ratio |
|---|---|---|---|---|---|---|---|---|---|---|---|
| mu16F6 | T | N | R | L | 1.36E+05 | 2.81E-04 | 2.07E-09 | 1.23E+05 | 9.13E-04 | 7.45E-09 | 3.6 |
| hu16F6.v1 | A | P | V | F | 4.10E+04 | 7.67E-04 | 1.87E-08 | 4.64E+04 | 0.009242 | 1.99E-07 | 10.7 |
| hu16F6.v2 | A | P | R | L | 4.62E+04 | 1.97E-04 | 4.25E-09 | 4.38E+04 | 0.002981 | 6.81E-08 | 16.0 |
| hu16F6.v3 | T | N | V | F | 7.86E+04 | 3.23E-04 | 4.11E-09 | 7.26E+04 | 0.002503 | 3.45E-08 | 8.4 |
| hu16F6.v4 | T | N | R | L | 8.99E+04 | 7.94E-05 | 8.84E-10 | 8.30E+04 | 9.13E-04 | 1.10E-08 | 12.5 |

Antibody binding in the (open, dashed line) presence or (filled, solid line) absence of 6.3 µM holo-Tf hu7A4.v15 - Square
hu15G11.v5 - Diamond
hu7G7.v1 - Triangle
Tf Competing Antibody - Circle

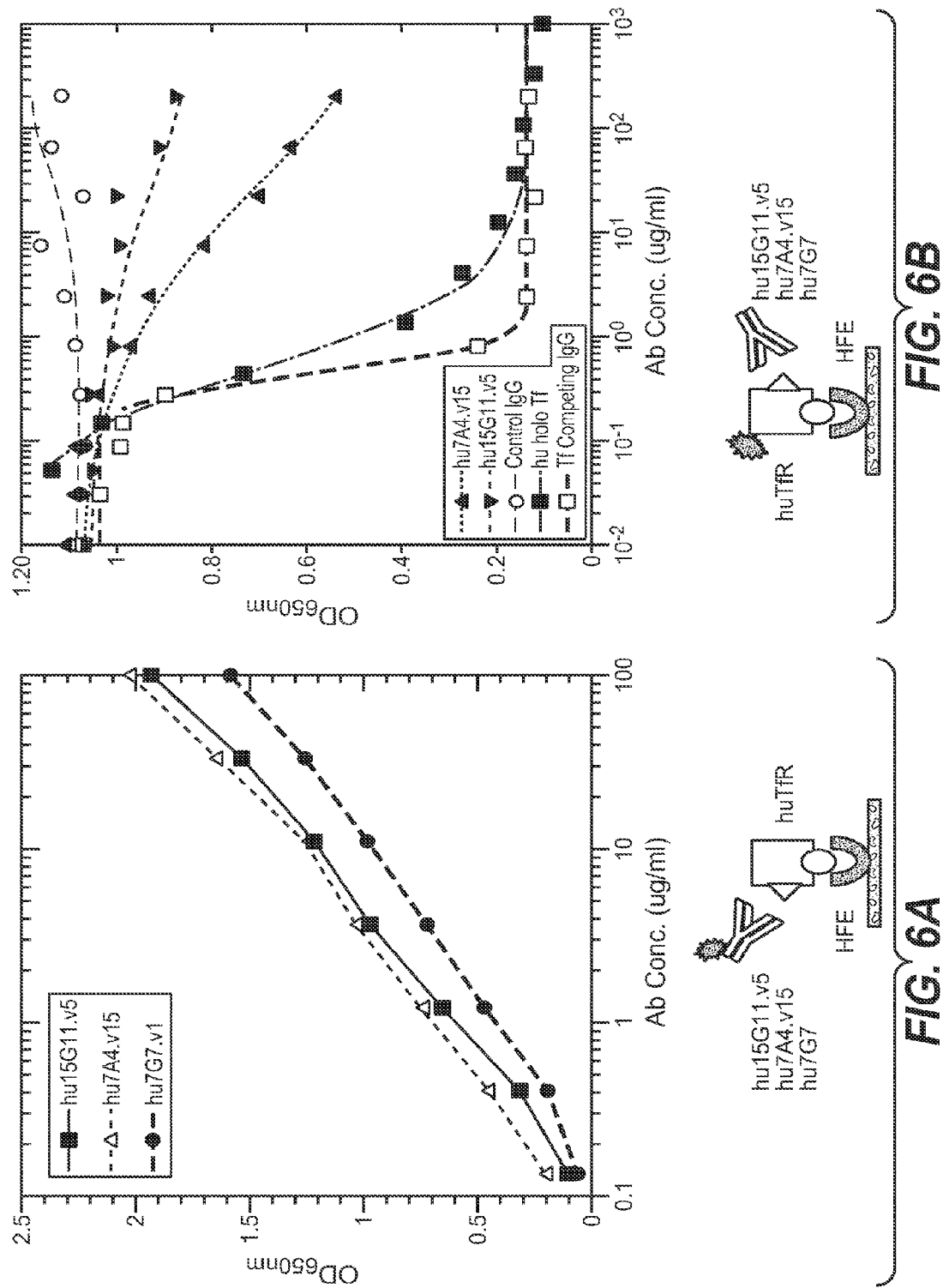

| 15G11 Variant IgG | | ELIZA (EC50) Using IgG | | Biacore (SCK) 1:1 fit (IgG) | | Biacore Steady State (IgG) | | Biacore (Fab) | |
|---|---|---|---|---|---|---|---|---|---|
| | | huTfR (ng/ml) | CynoTfR (ng/ml) | huTfR (nM) | CynoTfR (nM) | huTfR (nM) | CynoTfR (nM) | huTfR (nM) | CynoTfR (nM) |
| 15G11.v5 | | 16±1 | 20±2 | 3.3 | 12 | | | 4.7 | 16 |
| CDR-H3 | T96A | 274 | 3378 | 173 | | 433 | | | |
| | V99A | 16.1 | 21.8 | | | | | | |
| | H101A | 14.2 | 21.6 | | | | | | |
| | V102A | 15.7 | 22.3 | | | | | | |
| | Q89A | 30 | 506 | 125 | 268 | 212 | 591 | | |
| | H90A | 13 | 24 | | | | | | |
| | F91A | 45.8 | 953.3 | 167 ± 69 | | 228 ± 152 | | 383 | |
| | W92A | 11.8 | 44.1 | 31 | 32 | 123 | 327 | 280 | 370 |
| | G93A | 14.5 | 50.8 | 40 | 61 | 150 | 412 | 245 | 1300 |
| CDR-L3 | T94A | 16.8 | 29.3 | | | | | | |
| | P95A | 10.6 | 40.6 | 29 | 57 | 94 | 258 | 170 | 886 |
| | L96A | 9.9 | 18 | | | | | | |
| | T97A | 13.4 | 15.7 | | | | | | |

CDR L3
89 90 91 92 93 94 95 96 97     SEQ ID NO: 128
Q  H  F  W  G  T  P  L  T

CDR H3
95 96 97 98 99 101 102     SEQ ID NO: 129
G  T  R  A  Y  H   Y

FIG. 7A

| 7A4 Variant IgG | | ELIZA (EC50) Using IgG | | Biacore (SCK) 1:1 fit (IgG) | | Biacore Steady State (IgG) | | Biacore (Fab) | |
|---|---|---|---|---|---|---|---|---|---|
| | | huTfR (ng/ml) | CynoTfR (ng/ml) | huTfR (nM) | CynoTfR (nM) | huTfR (nM) | CynoTfR (nM) | huTfR (nM) | CynoTfR (nM) |
| | 7A4.v15 | 14.8 | 14.2 | 0.58 | 7.8 | | | 0.4 | 4.3 |
| CDR-H3 | G95A | 13.5 | 41.8 | | | | | | |
| | L96A | 15.5 | 28.7 | | | | | | |
| | S97A | | | | | | | | |
| | G98A | 19.4 | 24.7 | | | | | | |
| | N99A | 17 | 82.2 | 11 | 22 | 19 | 77 | | |
| | Y100A | 15.9 | 24 | | | | | | |
| | V100aA | | | | | | | | |
| | M100bA | 16.1 | 16.9 | | | | | | |
|

FIG. 16A

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | Kabat - CDR H1 | | | | | | | | | | |
| | | | | | | | | | | | | | | | | | | | | | | | | | Chothia - CDR H1 | | | | | | | | | | | | | | |
| | | | | | | | | | | | | | | | | | | | | | | | | | | | | | | Contact - CDR H1 | | | | | | | | | |
| YW412.8    | E | V | Q | L | V | E | S | G | G | G | L | V | Q | P | G | G | S | L | R | L | S | C | A | A | S | G | F | T | F | S | S | G | Y | A | I | H | W | V | R | Q |
| YW412.8.31 | E | V | Q | L | V | E | S | G | G | G | L | V | Q | P | G | G | S | L | R | L | S | C | A | A | S | G | F | T | F | L | G | Y | G | I | H | W | V | R | Q |
| YW412.8.30 | E | V | Q | L | V | E | S | G | G | G | L | V | Q | P | G | G | S | L | R | L | S | C | A | A | S | G | F | T | F | S | G | Y | A | I | H | W | V | R | Q |
| YW412.8.2  | E | V | Q | L | V | E | S | G | G | G | L | V | Q | P | G | G | S | L | R | L | S | C | A | A | S | G | F | T | F | S | G | Y | A | I | H | W | V | R | Q |
| YW412.8.29 | E | V | Q | L | V | E | S | G | G | G | L | V | Q | P | G | G | S | L | R | L | S | C | A | A | S | G | F | T | F | S | G | Y | A | I | H | W | V | R | Q |
| YW412.8.51 | E | V | Q | L | V | E | S | G | G | G | L | V | Q | P | G | G | S | L | R | L | S | C | A | A | S | G | F | T | F | S | G | Y | A | I | H | W | V | R | Q |

| Kabat# | 41 | 42 | 43 | 44 | 45 | 46 | 47 | 48 | 49 | 50 | 51 | 52 | A | B | C | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | Kabat - CDR H2 | | | | | | | | | | | | | | | | | | | | | | | | | | | | | | | |
| | | | | | | | | | Chothia - CDR H2 | | | | | | | | | | | | | | | | | | | | | | | | | | | | | | | | |
| | | | | | | | | | | Contact - CDR H2 | | | | | | | | | | | | | | | | | | | | | | | | | | | | | | |
| YW412.8    | P | G | K | G | L | E | W | V | G | W | I | S | P | Y | G | G | S | T | D | Y | A | D | S | V | K | G | R | F | T | I | S | A | D | T | S | K | N | T | A |
| YW412.8.31 | P | G | K | G | L | E | W | V | G | W | I | S | A | Y | G | G | S | T | D | Y | A | D | S | V | K | G | R | F | T | I | S | A | D | T | S | K | N | T | A |
| YW412.8.30 | P | G | K | G | L | E | W | V | G | W | I | S | A | Y | G | G | S | T | D | Y | A | D | S | V | K | G | R | F | T | I | S | A | D | T | S | K | N | T | A |
| YW412.8.2  | P | G | K | G | L | E | W | V | G | W | I | S | P | Y | G | G | S | T | D | Y | A | D | S | V | K | G | R | F | T | I | S | A | D | T | S | K | N | T | A |
| YW412.8.29 | P | G | K | G | L | E | W | V | G | W | I | S | A | Y | G | G | S | T | D | Y | A | D | S | V | K | G | R | F | T | I | S | A | D | T | S | K | N | T | A |
| YW412.8.51 | P | G | K | G | L | E | W | V | G | W | I | S | P | Y | G | G | S | T | D | Y | A | D | S | V | K | G | R | F | T | I | S | A | D | T | S | K | N | T | A |

| Kabat# | 79 | 80 | 81 | 82 | A | B | C | 83 | 84 | 85 | 86 | 87 | 88 | 89 | 90 | 91 | 92 | 93 | 94 | 95 | 96 | 97 | 98 | 99 | 100 | A | B | C | D | E | F | G | H | K | 101 | 102 | 103 | 104 | 105 | 106 | 107 | 108 | 109 | 110 | 111 | 112 | 113 | SEQ ID NO: |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | Kabat - CDR H3 | | | | | | | | | | | | | | | | | | | |
| | | | | | | | | | | | | | | | | | | | | | | | | | Chothia - CDR H3 | | | | | | | | | | | | | | | | | | | | |
| | | | | | | | | | | | | | | | | | | | | | | | | | | | Contact - CDR H3 | | | | | | | | | | | | | | | | | |
| YW412.8    | Y | L | Q | M | N | S | L | R | A | E | D | T | A | V | Y | Y | C | A | R | G | P | P | S | P | W | V | | | | | | | | | M | D | Y | W | G | Q | G | T | L | V | T | V | S | S | 138 |
| YW412.8.31 | Y | L | Q | M | N | S | L | R | A | E | D | T | A | V | Y | Y | C | A | R | G | P | P | S | P | W | V | | | | | | | | | M | D | Y | W | G | Q | G | T | L | V | T | V | S | S | 139 |
| YW412.8.30 | Y | L | Q | M | N | S | L | R | A | E | D | T | A | V | Y | Y | C | A | R | G | P | P | S | P | W | V | | | | | | | | | M | D | Y | W | G | Q | G | T | L | V | T | V | S | S | 138 |
| YW412.8.2  | Y | L | Q | M | N | S | L | R | A | E | D | T | A | V | Y | Y | C | A | R | G | P | P | S | P | W | V | | | | | | | | | M | D | Y | W | G | Q | G | T | L | V | T | V | S | S | 138 |
| YW412.8.29 | Y | L | Q | M | N | S | L | R | A | E | D | T | A | V | Y | Y | C | A | R | G | P | P | S | P | W | V | | | | | | | | | M | D | Y | W | G | Q | G | T | L | V | T | V | S | S | 138 |
| YW412.8.51 | Y | L | Q | M | N | S | L | R | A | E | D | T | A | V | Y | Y | C | A | R | G | P | P | S | P | W | V | | | | | | | | | M | D | Y | W | G | Q | G | T | L | V | T | V | S | S | 138 |

| | SEQ ID NO: 140 |
| | SEQ ID NO: 141 |
| | SEQ ID NO: 142 |
| | SEQ ID NO: 143 |

FIG. 17B

```
  1  EVQLVESGGG  LVQPGGSLRL  SCAASGFTFS  SYGMSWVRQA  PGKGLELVAS
 51  INSNGGSTYY  PDSVKGRFTI  SRDNAKNSLY  LQMNSLRAED  TAVYYCASGD
101  YWGQGTTVTV  SSASTKGPSV  FPLAPCSRST  SESTAALGCL  VKDYFPEPVT
151  VSWNSGALTS  GVHTFPAVLQ  SSGLYSLSSV  VTVPSSSLGT  KTYTCNVDHK
201  PSNTKVDKRV  ESKYGPPCPP  CPAPEFLGGP  SVFLFPPKPK  DTLMISRTPE
251  VTCVVVDVSQ  EDPEVQFNWY  VDGVEVHNAK  TKPREEQFNS  TYRVVSVLTV
301  LHQDWLNGKE  YKCKVSNKGL  PSSIEKTISK  AKGQPREPQV  YTLPPSQEEM
351  TKNQVSLTCL  VKGFYPSDIA  VEWESNGQPE  NNYKTTPPVL  DSDGSFFLYS
401  RLTVDKSRWQ  EGNVFSCSVM  HEALHNHYTQ  KSLSLSLG  (SEQ ID NO: 145)
```

FIG. 18A

```
  1  DIVMTQSPLS  LPVTPGEPAS  ISCRSSQSLV  YSNGDTYLHW  YLQKPGQSPQ
 51  LLIYKVSNRF  SGVPDRFSGS  GSGTDFTLKI  SRVEAEDVGV  YYCSQSTHVP
101  WTFGQGTKVE  IKRTVAAPSV  FIFPPSDEQL  KSGTASVVCL  LNNFYPREAK
151  VQWKVDNALQ  SGNSQESVTE  QDSKDSTYSL  SSTLTLSKAD  YEKHKVYACE
201  VTHQGLSSPV  TKSFNRGEC  (SEQ ID NO: 146)
```

FIG. 18B

Light Chain Variable Region

| Kabat Number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| hu15G11.v5 (TfR1) | D | I | Q | M | T | Q | S | P | S | S | L | S | A | S | V | G | D | R | V | T | I | T | C | R | A | S | D | N | L | Y | S | N | L | A | W | Y | Q | Q | K | P | G | K |
| hu15G11.52A | D | I | Q | M | T | Q | S | P | S | S | L | S | A | S | V | G | D | R | V | T | I | T | C | R | A | S | D | N | L | Y | S | N | L | A | W | Y | Q | Q | K | P | G | K |
| hu15G11.53A | D | I | Q | M | T | Q | S | P | S | S | L | S | A | S | V | G | D | R | V | T | I | T | C | R | A | S | D | N | L | Y | S | N | L | A | W | Y | Q | Q | K | P | G | K |
| hu15G11.92A (TfR2) | D | I | Q | M | T | Q | S | P | S | S | L | S | A | S | V | G | D | R | V | T | I | T | C | R | A | S | D | N | L | Y | S | N | L | A | W | Y | Q | Q | K | P | G | K |

CDR L1 - Contact: 30-36
CDR L1 - Chothia: 24-34
CDR L1 - Kabat: 24-34

| Kabat Number | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| hu15G11.v5 (TfR1) | S | P | K | L | L | V | Y | D | A | T | N | L | A | D | G | V | P | S | R | F | S | G | S | G | S | G | T | D | Y | T | L | T | I | S | S | L | Q | P | E | D | F | A |
| hu15G11.52A | S | P | K | L | L | V | Y | D | A | T | N | L | A | D | G | V | P | S | R | F | S | G | S | G | S | G | T | D | Y | T | L | T | I | S | S | L | Q | P | E | D | F | A |
| hu15G11.53A | S | P | K | L | L | V | Y | D | A | T | N | L | A | D | G | V | P | S | R | F | S | G | S | G | S | G | T | D | Y | T | L | T | I | S | S | L | Q | P | E | D | F | A |
| hu15G11.92A (TfR2) | S | P | K | L | L | V | Y | D | A | T | N | L | A | D | G | V | P | S | R | F | S | G | S | G | S | G | T | D | Y | T | L | T | I | S | S | L | Q | P | E | D | F | A |

CDR L2 - Contact: 46-55
CDR L2 - Chothia: 50-56
CDR L2 - Kabat: 50-56

| Kabat Number | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|
| hu15G11.v5 (TfR1) | T | Y | Y | C | Q | Q | H | F | W | G | T | P | L | T | F | G | Q | G | T | K | V | E | I | K |
| hu15G11.52A | T | Y | Y | C | Q | Q | H | F | W | G | T | P | L | T | F | G | Q | G | T | K | V | E | I | K |
| hu15G11.53A | T | Y | Y | C | Q | Q | H | F | W | G | T | P | L | T | F | G | Q | G | T | K | V | E | I | K |
| hu15G11.92A (TfR2) | T | Y | Y | C | Q | Q | H | F | W | G | A | P | L | T | F | G | Q | G | T | K | V | E | I | K |

CDR L3 - Contact: 89-96
CDR L3 - Chothia: 89-97
CDR L3 - Kabat: 89-97

*FIG. 24A*

Heavy Chain Variable Region

| Kabat Number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| hu15G11.v5 (TfR1) | E | V | Q | L | V | Q | S | G | A | E | V | K | K | P | G | A | S | V | K | V | S | C | K | A | S | G | Y | T | F | T | S | Y | W | M | H | W | V | R | Q | A | P | G |
| hu15G11.52A | E | V | Q | L | V | Q | S | G | A | E | V | K | K | P | G | A | S | V | K | V | S | C | K | A | S | G | Y | T | F | T | S | Y | W | M | H | W | V | R | Q | A | P | G |
| hu15G11.53A | E | V | Q | L | V | Q | S | G | A | E | V | K | K | P | G | A | S | V | K | V | S | C | K | A | S | G | Y | T | F | T | S | Y | W | M | H | W | V | R | Q | A | P | G |
| hu15G11.92A (TfR2) | E | V | Q | L | V | Q | S | G | A | E | V | K | K | P | G | A | S | V | K | V | S | C | K | A | S | G | Y | T | F | T | S | Y | W | M | H | W | V | R | Q | A | P | G |

CDR H1 - Contact: 30–35
CDR H1 - Chothia: 26–32
CDR H1 - Kabat: 31–35

| Kabat Number | 43 | 44 | 45 | 46 | 47 | 48 | 49 | 50 | 51 | 52 | 52a | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 82a |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| hu15G11.v5 (TfR1) | Q | R | L | E | W | I | G | E | I | N | P | T | N | G | R | T | N | Y | I | E | K | F | K | S | R | A | T | L | T | V | D | K | S | A | S | T | A | Y | M | E | L | S |
| hu15G11.52A | Q | R | L | E | W | I | G | E | I | A | P | T | N | G | R | T | N | Y | I | E | K | F | K | S | R | A | T | L | T | V | D | K | S | A | S | T | A | Y | M | E | L | S |
| hu15G11.53A | Q | R | L | E | W | I | G | E | I | N | A | T | N | G | R | T | N | Y | I | E | K | F | K | S | R | A | T | L | T | V | D | K | S | A | S | T | A | Y | M | E | L | S |
| hu15G11.92A (TfR2) | Q | R | L | E | W | I | G | E | I | N | P | T | N | G | R | T | N | Y | I | E | K | F | K | S | R | A | T | L | T | V | D | K | S | A | S | T | A | Y | M | E | L | S |

CDR H2 - Contact: 47–58
CDR H2 - Chothia: 50–52
CDR H2 - Kabat: 50–65

| Kabat Number | 82b | 82c | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|---|---|---|---|---|
| hu15G11.v5 (TfR1) | S | L | R | S | E | D | T | A | V | Y | Y | C | A | R | G | T | R | A | Y | H | Y | W | G | Q | G | T | T | V | T | V | S | S |   |
| hu15G11.52A | S | L | R | S | E | D | T | A | V | Y | Y | C | A | R | G | T | R | A | Y | H | Y | W | G | Q | G | T | T | V | T | V | S | S |   |
| hu15G11.53A | S | L | R | S | E | D | T | A | V | Y | Y | C | A | R | G | T | R | A | Y | H | Y | W | G | Q | G | T | T | V | T | V | S | S |   |
| hu15G11.92A (TfR2) | S | L | R | S | E | D | T | A | V | Y | Y | C | A | R | G | T | R | A | Y | H | Y | W | G | Q | G | T | T | V | T | V | S | S |   |

CDR H3 - Contact: 93–101
CDR H3 - Chothia: 95–102
CDR H3 - Kabat: 95–102

FIG. 24B

SEQUENCE LISTING

<160> NUMBER OF SEQ ID NOS: 163

<210> SEQ ID NO 1
<211> LENGTH: 760
<212> TYPE: PRT
<213> ORGANISM: Homo sapiens

<400> SEQUENCE: 1

```
Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Glu Asn Ala
        35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Ser Thr Ile
    130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255
```

-continued

```
Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
            275                 280                 285

Pro Ile Val Asn Ala Glu Leu Ser Phe Phe Gly His Ala His Leu Gly
            290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
            325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
            355                 360                 365

Glu Ser Lys Asn Val Lys Leu Thr Val Ser Asn Val Leu Lys Glu Ile
            370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
            405                 410                 415

Ala Lys Ser Gly Val Gly Thr Ala Leu Leu Lys Leu Ala Gln Met
            420                 425                 430

Phe Ser Asp Met Val Leu Lys Asp Gly Phe Gln Pro Ser Arg Ser Ile
            435                 440                 445

Ile Phe Ala Ser Trp Ser Ala Gly Asp Phe Gly Ser Val Gly Ala Thr
            450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
            485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
            515                 520                 525

Ala Ser Lys Val Glu Lys Leu Thr Leu Asp Asn Ala Ala Phe Pro Phe
            530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
            565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
            595                 600                 605

Leu Asp Tyr Glu Arg Tyr Asn Ser Gln Leu Leu Ser Phe Val Arg Asp
            610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
            645                 650                 655

Thr Thr Asp Phe Gly Asn Ala Glu Lys Thr Asp Arg Phe Val Met Lys
            660                 665                 670
```

```
Lys Leu Asn Asp Arg Val Met Arg Val Glu Tyr His Phe Leu Ser Pro
            675                 680                 685

Tyr Val Ser Pro Lys Glu Ser Pro Phe Arg His Val Phe Trp Gly Ser
    690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
            725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
    755                 760

<210> SEQ ID NO 2
<211> LENGTH: 760
<212> TYPE: PRT
<213> ORGANISM: Macaca mulatta

<400> SEQUENCE: 2

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Gly Val Asp Glu Glu Asn Thr
            35                  40                  45

Asp Asn Asn Thr Lys Pro Asn Gly Thr Lys Pro Lys Arg Cys Gly Gly
50                  55                  60

Asn Ile Cys Tyr Gly Thr Ile Ala Val Ile Ile Phe Phe Leu Ile Gly
65                  70                  75                  80

Phe Met Ile Gly Tyr Leu Gly Tyr Cys Lys Gly Val Glu Pro Lys Thr
            85                  90                  95

Glu Cys Glu Arg Leu Ala Gly Thr Glu Ser Pro Ala Arg Glu Glu Pro
            100                 105                 110

Glu Glu Asp Phe Pro Ala Ala Pro Arg Leu Tyr Trp Asp Asp Leu Lys
            115                 120                 125

Arg Lys Leu Ser Glu Lys Leu Asp Thr Thr Asp Phe Thr Ser Thr Ile
130                 135                 140

Lys Leu Leu Asn Glu Asn Leu Tyr Val Pro Arg Glu Ala Gly Ser Gln
145                 150                 155                 160

Lys Asp Glu Asn Leu Ala Leu Tyr Ile Glu Asn Gln Phe Arg Glu Phe
            165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Gly
            195                 200                 205

Leu Val Tyr Leu Val Glu Asn Pro Gly Gly Tyr Val Ala Tyr Ser Lys
            210                 215                 220

Ala Ala Thr Val Thr Gly Lys Leu Val His Ala Asn Phe Gly Thr Lys
225                 230                 235                 240

Lys Asp Phe Glu Asp Leu Asp Ser Pro Val Asn Gly Ser Ile Val Ile
            245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
            275                 280                 285
```

```
Pro Ile Val Lys Ala Asp Leu Ser Phe Phe Gly His Ala His Leu Gly
    290                 295                 300
Thr Gly Asp Pro Tyr Thr Pro Gly Phe Pro Ser Phe Asn His Thr Gln
305                 310                 315                 320
Phe Pro Pro Ser Gln Ser Ser Gly Leu Pro Asn Ile Pro Val Gln Thr
                325                 330                 335
Ile Ser Arg Ala Ala Ala Glu Lys Leu Phe Gly Asn Met Glu Gly Asp
                340                 345                 350
Cys Pro Ser Asp Trp Lys Thr Asp Ser Thr Cys Lys Met Val Thr Ser
        355                 360                 365
Glu Asn Lys Ser Val Lys Leu Thr Val Ser Asn Val Leu Lys Glu Thr
    370                 375                 380
Lys Ile Leu Asn Ile Phe Gly Val Ile Lys Gly Phe Val Glu Pro Asp
385                 390                 395                 400
His Tyr Val Val Val Gly Ala Gln Arg Asp Ala Trp Gly Pro Gly Ala
                405                 410                 415
Ala Lys Ser Ser Val Gly Thr Ala Leu Leu Lys Leu Ala Gln Met
                420                 425                 430
Phe Ser Asp Met Val Leu Lys Asp Gly Phe Gln Pro Ser Arg Ser Ile
        435                 440                 445
Ile Phe Ala Ser Trp Ser Ala Gly Asp Phe Gly Ser Val Gly Ala Thr
    450                 455                 460
Glu Trp Leu Glu Gly Tyr Leu Ser Ser Leu His Leu Lys Ala Phe Thr
465                 470                 475                 480
Tyr Ile Asn Leu Asp Lys Ala Val Leu Gly Thr Ser Asn Phe Lys Val
                485                 490                 495
Ser Ala Ser Pro Leu Leu Tyr Thr Leu Ile Glu Lys Thr Met Gln Asp
        500                 505                 510
Val Lys His Pro Val Thr Gly Arg Ser Leu Tyr Gln Asp Ser Asn Trp
    515                 520                 525
Ala Ser Lys Val Glu Lys Leu Thr Leu Asp Asn Ala Ala Phe Pro Phe
530                 535                 540
Leu Ala Tyr Ser Gly Ile Pro Ala Val Ser Phe Cys Phe Cys Glu Asp
545                 550                 555                 560
Thr Asp Tyr Pro Tyr Leu Gly Thr Thr Met Asp Thr Tyr Lys Glu Leu
                565                 570                 575
Val Glu Arg Ile Pro Glu Leu Asn Lys Val Ala Arg Ala Ala Ala Glu
        580                 585                 590
Val Ala Gly Gln Phe Val Ile Lys Leu Thr His Asp Thr Glu Leu Asn
    595                 600                 605
Leu Asp Tyr Glu Arg Tyr Asn Ser Gln Leu Leu Leu Phe Leu Arg Asp
610                 615                 620
Leu Asn Gln Tyr Arg Ala Asp Val Lys Glu Met Gly Leu Ser Leu Gln
625                 630                 635                 640
Trp Leu Tyr Ser Ala Arg Gly Asp Phe Phe Arg Ala Thr Ser Arg Leu
                645                 650                 655
Thr Thr Asp Phe Arg Asn Ala Glu Lys Arg Asp Lys Phe Val Met Lys
        660                 665                 670
Lys Leu Asn Asp Arg Val Met Arg Val Glu Tyr Tyr Phe Leu Ser Pro
    675                 680                 685
Tyr Val Ser Pro Lys Glu Ser Pro Phe Arg His Val Phe Trp Gly Ser
    690                 695                 700
```

```
Gly Ser His Thr Leu Ser Ala Leu Leu Glu Ser Leu Lys Leu Arg Arg
705                 710                 715                 720

Gln Asn Asn Ser Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
            755                 760

<210> SEQ ID NO 3
<211> LENGTH: 763
<212> TYPE: PRT
<213> ORGANISM: Mus musculus

<400> SEQUENCE: 3

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
                20                  25                  30

Asn Ser His Val Glu Met Lys Leu Ala Ala Asp Glu Glu Asn Ala
            35                  40                  45

Asp Asn Asn Met Lys Ala Ser Val Arg Lys Pro Lys Arg Phe Asn Gly
    50                  55                  60

Arg Leu Cys Phe Ala Ala Ile Ala Leu Val Ile Phe Phe Leu Ile Gly
65                  70                  75                  80

Phe Met Ser Gly Tyr Leu Gly Tyr Cys Lys Arg Val Glu Gln Lys Glu
                85                  90                  95

Glu Cys Val Lys Leu Ala Glu Thr Glu Glu Thr Asp Lys Ser Glu Thr
            100                 105                 110

Met Glu Thr Glu Asp Val Pro Thr Ser Ser Arg Leu Tyr Trp Ala Asp
            115                 120                 125

Leu Lys Thr Leu Leu Ser Glu Lys Leu Asn Ser Ile Glu Phe Ala Asp
130                 135                 140

Thr Ile Lys Gln Leu Ser Gln Asn Thr Tyr Thr Pro Arg Glu Ala Gly
145                 150                 155                 160

Ser Gln Lys Asp Glu Ser Leu Ala Tyr Tyr Ile Glu Asn Gln Phe His
                165                 170                 175

Glu Phe Lys Phe Ser Lys Val Trp Arg Asp Glu His Tyr Val Lys Ile
            180                 185                 190

Gln Val Lys Ser Ser Ile Gly Gln Asn Met Val Thr Ile Val Gln Ser
        195                 200                 205

Asn Gly Asn Leu Asp Pro Val Glu Ser Pro Glu Gly Tyr Val Ala Phe
    210                 215                 220

Ser Lys Pro Thr Glu Val Ser Gly Lys Leu Val His Ala Asn Phe Gly
225                 230                 235                 240

Thr Lys Lys Asp Phe Glu Glu Leu Ser Tyr Ser Val Asn Gly Ser Leu
                245                 250                 255

Val Ile Val Arg Ala Gly Glu Ile Thr Phe Ala Glu Lys Val Ala Asn
            260                 265                 270

Ala Gln Ser Phe Asn Ala Ile Gly Val Leu Ile Tyr Met Asp Lys Asn
        275                 280                 285

Lys Phe Pro Val Val Glu Ala Asp Leu Ala Leu Phe Gly His Ala His
    290                 295                 300

Leu Gly Thr Gly Asp Pro Tyr Thr Pro Gly Phe Pro Ser Phe Asn His
305                 310                 315                 320
```

-continued

```
Thr Gln Phe Pro Pro Ser Gln Ser Ser Gly Leu Pro Asn Ile Pro Val
                325                 330                 335
Gln Thr Ile Ser Arg Ala Ala Ala Glu Lys Leu Phe Gly Lys Met Glu
            340                 345                 350
Gly Ser Cys Pro Ala Arg Trp Asn Ile Asp Ser Ser Cys Lys Leu Glu
            355                 360                 365
Leu Ser Gln Asn Gln Asn Val Lys Leu Ile Val Lys Asn Val Leu Lys
        370                 375                 380
Glu Arg Arg Ile Leu Asn Ile Phe Gly Val Ile Lys Gly Tyr Glu Glu
385                 390                 395                 400
Pro Asp Arg Tyr Val Val Val Gly Ala Gln Arg Asp Ala Leu Gly Ala
                405                 410                 415
Gly Val Ala Ala Lys Ser Ser Val Gly Thr Gly Leu Leu Leu Lys Leu
            420                 425                 430
Ala Gln Val Phe Ser Asp Met Ile Ser Lys Asp Gly Phe Arg Pro Ser
            435                 440                 445
Arg Ser Ile Ile Phe Ala Ser Trp Thr Ala Gly Asp Phe Gly Ala Val
        450                 455                 460
Gly Ala Thr Glu Trp Leu Glu Gly Tyr Leu Ser Ser Leu His Leu Lys
465                 470                 475                 480
Ala Phe Thr Tyr Ile Asn Leu Asp Lys Val Val Leu Gly Thr Ser Asn
                485                 490                 495
Phe Lys Val Ser Ala Ser Pro Leu Leu Tyr Thr Leu Met Gly Lys Ile
            500                 505                 510
Met Gln Asp Val Lys His Pro Val Asp Gly Lys Ser Leu Tyr Arg Asp
            515                 520                 525
Ser Asn Trp Ile Ser Lys Val Glu Lys Leu Ser Phe Asp Asn Ala Ala
        530                 535                 540
Tyr Pro Phe Leu Ala Tyr Ser Gly Ile Pro Ala Val Ser Phe Cys Phe
545                 550                 555                 560
Cys Glu Asp Ala Asp Tyr Pro Tyr Leu Gly Thr Arg Leu Asp Thr Tyr
                565                 570                 575
Glu Ala Leu Thr Gln Lys Val Pro Gln Leu Asn Gln Met Val Arg Thr
            580                 585                 590
Ala Ala Glu Val Ala Gly Gln Leu Ile Ile Lys Leu Thr His Asp Val
            595                 600                 605
Glu Leu Asn Leu Asp Tyr Glu Met Tyr Asn Ser Lys Leu Leu Ser Phe
        610                 615                 620
Met Lys Asp Leu Asn Gln Phe Lys Thr Asp Ile Arg Asp Met Gly Leu
625                 630                 635                 640
Ser Leu Gln Trp Leu Tyr Ser Ala Arg Gly Asp Tyr Phe Arg Ala Thr
                645                 650                 655
Ser Arg Leu Thr Thr Asp Phe His Asn Ala Glu Lys Thr Asn Arg Phe
            660                 665                 670
Val Met Arg Glu Ile Asn Asp Arg Ile Met Lys Val Glu Tyr His Phe
            675                 680                 685
Leu Ser Pro Tyr Val Ser Pro Arg Glu Ser Pro Phe Arg His Ile Phe
        690                 695                 700
Trp Gly Ser Gly Ser His Thr Leu Ser Ala Leu Val Glu Asn Leu Lys
705                 710                 715                 720
Leu Arg Gln Lys Asn Ile Thr Ala Phe Asn Glu Thr Leu Phe Arg Asn
                725                 730                 735
```

Gln Leu Ala Leu Ala Thr Trp Thr Ile Gln Gly Val Ala Asn Ala Leu
                740                 745                 750

Ser Gly Asp Ile Trp Asn Ile Asp Asn Glu Phe
        755                 760

<210> SEQ ID NO 4
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 4

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asp Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Ala Pro Pro Thr Phe Gly Gly Gly Thr Lys Leu Glu Ile Arg
            100                 105                 110

<210> SEQ ID NO 5
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 5

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Gly Pro Pro Thr Phe Gly Gly Gly Thr Lys Leu Glu Ile Lys
            100                 105                 110

<210> SEQ ID NO 6
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 6

Asp Ile Val Leu Thr Gln Ser Pro Ala Ser Leu Ala Val Ser Leu Gly

```
                1               5                  10                  15
            Gln Arg Ala Thr Ile Ser Cys Arg Ala Ser Glu Ser Val Asp Ser Tyr
                               20                  25                  30

Gly Pro Ser Phe Met His Trp Tyr Gln Gln Lys Pro Gly Gln Pro Pro
                        35                  40                  45

Lys Leu Leu Ile Tyr Arg Ala Ser Asn Leu Glu Ser Gly Ile Pro Ala
                    50                  55                  60

Arg Phe Ser Gly Ser Gly Ser Arg Thr Asp Phe Thr Leu Thr Ile Asn
            65                  70                  75                  80

Pro Val Glu Ala Asp Asp Val Ala Thr Tyr Tyr Cys Gln His Ser Asn
                                85                  90                  95

Glu Asp Pro Pro Thr Phe Gly Gly Gly Thr Arg Leu Glu Ile Lys
                            100                 105                 110

<210> SEQ ID NO 7
            <211> LENGTH: 119
            <212> TYPE: PRT
            <213> ORGANISM: Artificial Sequence
            <220> FEATURE:
            <223> OTHER INFORMATION: Synthetic polypeptide

<400> SEQUENCE: 7

Gln Val Gln Leu Gln Gln Ser Gly Pro Glu Leu Val Arg Pro Gly Val
            1               5                  10                  15

Ser Val Lys Ile Ser Cys Lys Gly Ser Gly Tyr Thr Phe Thr Asp Tyr
                               20                  25                  30

Ala Met His Trp Val Lys Gln Ser His Ala Lys Ser Leu Glu Trp Ile
                        35                  40                  45

Gly Gly Ile Ser Thr Tyr Phe Gly Arg Thr Asn Tyr Asn Gln Lys Phe
                    50                  55                  60

Lys Gly Arg Ala Thr Met Thr Val Asp Lys Ser Ser Ser Thr Ala Tyr
            65                  70                  75                  80

Met Glu Leu Ala Arg Leu Thr Ser Glu Asp Ser Ala Leu Tyr Tyr Cys
                                85                  90                  95

Ala Arg Gly Leu Ser Gly Asn Tyr Val Met Asp Tyr Trp Gly Gln Gly
                            100                 105                 110

Thr Ser Val Thr Val Ser Ser
                    115

<210> SEQ ID NO 8
            <211> LENGTH: 119
            <212> TYPE: PRT
            <213> ORGANISM: Artificial Sequence
            <220> FEATURE:
            <223> OTHER INFORMATION: Synthetic polypeptide

<400> SEQUENCE: 8

Gln Val Gln Leu Gln Gln Ser Gly Pro Glu Leu Val Arg Pro Gly Val
            1               5                  10                  15

Ser Val Lys Ile Ser Cys Lys Gly Ser Gly Tyr Thr Phe Thr Asp Tyr
                               20                  25                  30

Gly Met His Trp Val Lys Gln Ser His Ala Lys Ser Leu Glu Trp Ile
                        35                  40                  45

Gly Val Ile Ser Pro Tyr Ser Gly Arg Thr Asn Tyr Asn Gln Asn Phe
                    50                  55                  60

Lys Gly Lys Ala Thr Met Thr Val Asp Lys Ser Ser Ser Thr Ala Tyr
            65                  70                  75                  80
```

Leu Glu Leu Ala Arg Leu Thr Ser Glu Asp Ser Ala Ile Tyr Tyr Cys
            85                  90                  95

Ala Arg Gly Leu Ser Gly Asn Tyr Val Asp Tyr Trp Gly Gln Gly
        100                 105                 110

Thr Ser Val Thr Val Ser Ser
        115

<210> SEQ ID NO 9
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 9

Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Thr Val Thr Asp Tyr
            20                  25                  30

Ala Met His Trp Val Lys Gln Ser His Ala Lys Ser Leu Glu Trp Ile
        35                  40                  45

Gly Val Ile Ser Phe Tyr Ser Gly Lys Thr Asn Tyr Asn Gln Lys Phe
    50                  55                  60

Met Gly Lys Ala Thr Met Thr Val Asp Lys Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Gly Leu Ser Gly Asn Tyr Val Met Asp Tyr Trp Gly Gln Gly
            100                 105                 110

Thr Ser Val Thr Val Ser Ser
        115

<210> SEQ ID NO 10
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 10

Gln Val Gln Leu Gln Gln Ser Gly Pro Glu Leu Val Arg Pro Gly Val
1               5                   10                  15

Ala Val Lys Ile Ser Cys Lys Gly Ser Gly Tyr Lys Phe Ile Asp Tyr
            20                  25                  30

Gly Met His Trp Val Lys Gln Ser His Thr Lys Ser Leu Gln Trp Ile
        35                  40                  45

Gly Val Ile Ser Pro Tyr Ser Gly Lys Thr Asn Tyr Ser Gln Lys Phe
    50                  55                  60

Lys Gly Lys Ala Thr Met Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Gly Leu Ser Gly Asn Phe Val Met Asp Phe Trp Gly Gln Gly
            100                 105                 110

Thr Ser Val Thr Val Ser Ser
        115

<210> SEQ ID NO 11

<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 11

```
Asp Ile Gln Met Thr Gln Ser Pro Ala Ser Leu Ser Val Ser Val Gly
1               5                   10                  15

Glu Thr Val Thr Ile Thr Cys Arg Ala Ser Asp Asn Leu Tyr Ser Asn
            20                  25                  30

Leu Ala Trp Tyr Gln Gln Lys Gln Gly Lys Ser Pro Gln Leu Leu Val
        35                  40                  45

Tyr Asp Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Phe Trp Gly Thr Pro Leu
                85                  90                  95

Thr Phe Gly Ala Gly Thr Lys Leu Glu Leu Lys
            100                 105
```

<210> SEQ ID NO 12
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 12

```
Asp Ile Gln Leu Thr Gln Thr Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asp Leu Ala Asp Gly Val Pro Ser Arg Phe Arg Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Leu
                85                  90                  95

Thr Phe Gly Ala Gly Thr Lys Leu Glu Leu Ile
            100                 105
```

<210> SEQ ID NO 13
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 13

```
Asp Ile Gln Met Thr Gln Ser Pro Ala Ser Leu Ser Val Ser Val Gly
1               5                   10                  15

Glu Thr Val Thr Ile Thr Cys Arg Ala Ser Asp Asn Ile Tyr Ser Asn
            20                  25                  30

Leu Ala Trp Tyr Gln Gln Lys Gln Gly Lys Ser Pro Gln Leu Leu Val
        35                  40                  45
```

```
Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Leu
                85                  90                  95

Met Phe Gly Ser Gly Thr Lys Leu Glu Leu Lys
                100                 105

<210> SEQ ID NO 14
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 14

Asp Ile Gln Met Thr Gln Ser Pro Ala Ser Leu Ser Val Ser Val Gly
1               5                   10                  15

Glu Thr Val Thr Ile Thr Cys Arg Ala Ser Asp Asn Ile Tyr Ser Asn
                20                  25                  30

Leu Ala Trp Tyr Gln Gln Lys Gln Gly Lys Ser Pro Gln Leu Leu Val
            35                  40                  45

Tyr Ala Val Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Leu
                85                  90                  95

Thr Phe Gly Ala Gly Thr Lys Leu Glu Leu Lys
                100                 105

<210> SEQ ID NO 15
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 15

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Glu Ile Asn Pro Thr Asn Gly Arg Thr Asn Tyr Ile Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Thr Arg Ala Tyr His Tyr Trp Gly Gln Gly Thr Ser Val
                100                 105                 110

Thr Val Ser Ser
        115

<210> SEQ ID NO 16
```

```
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 16

Gln Val Gln Leu Gln Gln Pro Gly Ala Glu Leu Val Arg Pro Gly Ala
1               5                  10                  15

Ala Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Thr Asn Gly Arg Thr Asn Tyr Asn Glu Asn Phe
    50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Gly Thr Arg Ala Tyr His Phe Trp Gly Gln Gly Thr Ser Val
            100                 105                 110

Thr Val Ser Ser
        115

<210> SEQ ID NO 17
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 17

Gln Val Gln Leu Gln Gln Pro Gly Ala Glu Leu Val Lys Pro Gly Ala
1               5                  10                  15

Ser Val Lys Leu Ser Cys Lys Ala Ser Gly Tyr Thr Phe Ala Ser Tyr
            20                  25                  30

Trp Met His Trp Val Lys Gln Arg Pro Gly Gln Gly Leu Glu Trp Ile
        35                  40                  45

Gly Glu Ile Asn Pro Ile Asn Gly Arg Thr Asn Tyr Ser Glu Lys Phe
    50                  55                  60

Lys Lys Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Gly Thr Arg Ala Tyr His Tyr Trp Gly Gln Gly Thr Ser Val
            100                 105                 110

Thr Val Ser Ser
        115

<210> SEQ ID NO 18
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 18

Gln Val Gln Leu Gln Gln Pro Gly Ala Glu Leu Val Lys Pro Gly Ala
1               5                  10                  15
```

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Thr Phe
 50                  55                  60

Lys Ser Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                85                  90                  95

Ala Arg Gly Thr Arg Ala Tyr His Tyr Trp Gly Gln Gly Thr Ser Val
            100                 105                 110

Thr Val Ser Ser
        115

<210> SEQ ID NO 19
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 19

Asp Val Gln Ile Thr Gln Ser Pro Ser Tyr Leu Thr Ala Ser Pro Gly
 1               5                  10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
 50                  55                  60

Ser Gly Ser Gly Thr Asp Phe Thr Leu Thr Ile Ser Asn Leu Glu Pro
 65                  70                  75                  80

Glu Asp Phe Ala Met Tyr Tyr Cys Gln Gln His Asn Glu Tyr Pro Trp
                85                  90                  95

Thr Phe Gly Gly Gly Thr Lys Leu Glu Ile Lys
            100                 105

<210> SEQ ID NO 20
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 20

Asp Val Gln Leu Gln Glu Ser Gly Pro Gly Leu Val Lys Pro Ser Gln
 1               5                  10                  15

Ser Leu Ser Leu Thr Cys Thr Val Thr Gly Asn Ser Ile Thr Ser Glu
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Thr Thr Ser Tyr Asn Pro Ser Leu
 50                  55                  60

Lys Ser Arg Ile Ser Ile Thr Arg Asp Thr Ser Lys Asn Gln Leu Phe
 65                  70                  75                  80

Leu Gln Leu Asn Ser Val Thr Thr Glu Asp Thr Ala Thr Tyr Phe Cys
                85                  90                  95

```
Ala Arg Tyr Gly Tyr Gly Asn Pro Ala Thr Arg Tyr Phe Asp Val Trp
            100                 105                 110

Gly Ala Gly Thr Thr Val Thr Val Ser Ser
            115                 120

<210> SEQ ID NO 21
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 21

Asp Ile Val Leu Thr Gln Ser Pro Ala Ser Leu Ala Val Ser Leu Gly
1               5                   10                  15

Gln Arg Ala Thr Ile Ser Cys Arg Ala Arg Gln Ser Val Ser Thr Ser
            20                  25                  30

Ser Tyr Ser Phe Met His Trp Tyr Arg Gln Lys Ala Gly Gln Pro Pro
        35                  40                  45

Lys Leu Leu Ile Lys Tyr Ala Ser Ile Gln Glu Ser Gly Val Pro Ala
    50                  55                  60

Arg Phe Ser Gly Ser Gly Ser Gly Thr Asp Phe Thr Leu Asn Ile Leu
65                  70                  75                  80

Pro Val Glu Glu Glu Asp Thr Ala Thr Tyr Tyr Cys Gln His Thr Trp
                85                  90                  95

Glu Ile Pro Phe Thr Phe Gly Ser Gly Thr Lys Leu Glu Ile Lys
            100                 105                 110

<210> SEQ ID NO 22
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 22

Asp Ile Val Leu Thr Gln Ser Pro Ala Ser Leu Ala Val Ser Leu Gly
1               5                   10                  15

Gln Arg Ala Thr Ile Ser Cys Arg Ala Arg Gln Ser Val Ser Thr Ser
            20                  25                  30

Ser Tyr Ser Phe Met His Trp Tyr Gln Gln Lys Pro Gly Gln Pro Pro
        35                  40                  45

Lys Leu Leu Ile Lys Tyr Ala Ser Ile Gln Glu Ser Gly Val Pro Ala
    50                  55                  60

Arg Phe Ser Gly Ser Gly Ser Gly Thr Asp Phe Thr Leu Asn Ile Leu
65                  70                  75                  80

Pro Val Glu Glu Glu Asp Thr Ala Thr Tyr Tyr Cys Gln His Thr Trp
                85                  90                  95

Glu Ile Pro Phe Thr Phe Gly Ser Gly Thr Asn Leu Glu Ile Lys
            100                 105                 110

<210> SEQ ID NO 23
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 23
```

Gln Ile Val Leu Thr Gln Ser Pro Ala Ile Met Ser Ala Ser Leu Gly
1               5                   10                  15

Gly Arg Val Thr Met Thr Cys Thr Ser Ser Val Pro Ser Ser
            20                  25                  30

Tyr Phe His Trp Tyr Gln Gln Lys Pro Gly Ser Ser Pro Lys Leu Trp
            35                  40                  45

Ile Tyr Ser Thr Ser Asn Leu Ala Ser Gly Val Pro Ala Arg Phe Ser
50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
            85                  90                  95

Phe Thr Phe Gly Ser Gly Thr Lys Leu Glu Ile Lys
            100                 105

<210> SEQ ID NO 24
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 24

Asp Ile Gln Met Thr Gln Thr Thr Ser Ser Leu Ser Ala Ser Leu Gly
1               5                   10                  15

Asp Arg Val Thr Ile Asn Cys Arg Ala Gly Gln Asp Ile Thr Asn Tyr
            20                  25                  30

Leu Asn Trp Phe Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Thr Asn Leu Glu Gln
65                  70                  75                  80

Glu Asp Ile Ala Thr Tyr Phe Cys Gln Gln Ala Asn Thr Leu Pro Tyr
            85                  90                  95

Thr Phe Gly Gly Gly Thr Lys Leu Glu Ile Lys
            100                 105

<210> SEQ ID NO 25
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 25

Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg His Gly Gln Gly Leu Glu Trp Ile
            35                  40                  45

Gly Asn Ile Tyr Pro Gly Ser Gly Ser Thr Lys Tyr Asp Glu Arg Phe
50                  55                  60

Lys Ser Lys Gly Thr Leu Thr Val Asp Thr Ser Ser Ser Thr Ala Tyr
65                  70                  75                  80

Met His Leu Ser Ser Leu Thr Ser Glu Asp Ser Ala Val Tyr Tyr Cys
            85                  90                  95

```
Thr Arg Gly Gly Tyr Asp Ser Arg Ala Trp Phe Ala Tyr Trp Gly Gln
            100                 105                 110

Gly Thr Leu Val Thr Val Ser Ala
        115                 120

<210> SEQ ID NO 26
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 26

Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg His Gly Gln Gly Leu Glu Trp Ile
        35                  40                  45

Gly Asn Ile Tyr Pro Gly Ser Gly Ser Thr Lys Tyr Asp Glu Lys Phe
    50                  55                  60

Lys Ser Lys Gly Thr Leu Thr Val Asp Thr Ser Ser Ser Thr Ala Tyr
65                  70                  75                  80

Met His Leu Ser Ser Leu Thr Ser Glu Asp Ser Ala Val Tyr Tyr Cys
                85                  90                  95

Thr Arg Gly Gly Tyr Asp Ser Arg Ala Trp Phe Ala His Trp Gly Gln
            100                 105                 110

Gly Thr Leu Val Thr Val Ser Ala
        115                 120

<210> SEQ ID NO 27
<211> LENGTH: 124
<212> TYPE: PRT
<213> ORGANISM: Artificial Sequence
<220> FEATURE:
<223> OTHER INFORMATION: Synthetic polypeptide

<400> SEQUENCE: 27

Glu Val Lys Leu Val Glu Ser Gly Gly Gly Leu Val Gln Pro Gly Gly
1               5                   10                  15

Phe Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Ser Ile Ser Asn Gly Gly Asp Asn Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Gln Gly Ala Leu Tyr Asp Gly Tyr Tyr Arg Gly Ala Met Asp
            100                 105                 110

Tyr Trp Gly Gln Gly Thr Ser Val Thr Val Ser Ser
        115                 120

<210> SEQ ID NO 28
<211> LENGTH: 121
<212> TYPE: PRT
```

```
<213> ORGANISM: Artificial Sequence
<220> FEATURE:
<223> OTHER INFORMATION: Synthetic polypeptide

<400> SEQUENCE: 28

Gln Val Gln Leu Gln Gln Ser Gly Ala Glu Leu Met Lys Pro Gly Ala
1               5                   10                  15

Ser Val Lys Ile Ser Cys Lys Ala Ala Gly Tyr Thr Phe Ser Asn Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Lys Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Arg Gly Gly Tyr Gly Tyr Asp Gly Glu Phe Ala Tyr Trp Gly
            100                 105                 110

Gln Gly Thr Leu Val Thr Val Ser Ala
        115                 120

<210> SEQ ID NO 29
<211> LENGTH: 15
<212> TYPE: PRT
<213> ORGANISM: Artificial Sequence
<220> FEATURE:
<223> OTHER INFORMATION: Synthetic peptide

<400> SEQUENCE: 29

Arg Ala Ser Glu Ser Val Asp Ser Tyr Gly Asn Ser Phe Met His
1               5                   10                  15

<210> SEQ ID NO 30
<211> LENGTH: 7
<212> TYPE: PRT
<213> ORGANISM: Artificial Sequence
<220> FEATURE:
<223> OTHER INFORMATION: Synthetic peptide

<400> SEQUENCE: 30

Arg Ala Ser Asn Leu Glu Ser
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic peptide

<400> SEQUENCE: 31

Gln Gln Ser Asn Glu Ala Pro Pro Thr
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic peptide

<400> SEQUENCE: 32
```

```
Asp Tyr Ala Met His
1               5

<210> SEQ ID NO 33
<211> LENGTH: 17
<212> TYPE: PRT
<213> ORGANISM: Artificial Sequence
<220> FEATURE:
<223> OTHER INFORMATION: Synthetic peptide

<400> SEQUENCE: 33

Gly Ile Ser Thr Tyr Phe Gly Arg Thr Asn Tyr Asn Gln Lys Phe Lys
1               5                   10                  15

Gly

<210> SEQ ID NO 34
<211> LENGTH: 10
<212> TYPE: PRT
<213> ORGANISM: Artificial Sequence
<220> FEATURE:
<223> OTHER INFORMATION: Synthetic peptide

<400> SEQUENCE: 34

Gly Leu Ser Gly Asn Tyr Val Met Asp Tyr
1               5                   10

<210> SEQ ID NO 35
<211> LENGTH: 15
<212> TYPE: PRT
<213> ORGANISM: Artificial Sequence
<220> FEATURE:
<223> OTHER INFORMATION: Synthetic peptide

<400> SEQUENCE: 35

Arg Ala Ser Glu Ser Val Asp Ser Tyr Gly Asn Ser Phe Met His
1               5                   10                  15

<210> SEQ ID NO 36
<211> LENGTH: 9
<212> TYPE: PRT
<213> ORGANISM: Artificial Sequence
<220> FEATURE:
<223> OTHER INFORMATION: Synthetic peptide

<400> SEQUENCE: 36

Gln Gln Ser Asn Glu Gly Pro Pro Thr
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic peptide

<400> SEQUENCE: 37

Asp Tyr Gly Met His
1               5

<210> SEQ ID NO 38
<211> LENGTH: 17
<212> TYPE: PRT
<213> ORGANISM: Artificial Sequence
<220> FEATURE:
<223> OTHER INFORMATION: Synthetic peptide

<400> SEQUENCE: 38
```

```
Val Ile Ser Pro Tyr Ser Gly Arg Thr Asn Tyr Asn Gln Asn Phe Lys
1               5                   10                  15

Gly

<210> SEQ ID NO 39
<211> LENGTH: 10
<212> TYPE: PRT
<213> ORGANISM: Artificial Sequence
<220> FEATURE:
<223> OTHER INFORMATION: Synthetic peptide

<400> SEQUENCE: 39

Gly Leu Ser Gly Asn Tyr Val Val Asp Tyr
1               5                   10

<210> SEQ ID NO 40
<211> LENGTH: 17
<212> TYPE: PRT
<213> ORGANISM: Artificial Sequence
<220> FEATURE:
<223> OTHER INFORMATION: Synthetic peptide

<400> SEQUENCE: 40

Val Ile Ser Phe Tyr Ser Gly Lys Thr Asn Tyr Asn Gln Lys Phe Met
1               5                   10                  15

Gly

<210> SEQ ID NO 41
<211> LENGTH: 15
<212> TYPE: PRT
<213> ORGANISM: Artificial Sequence
<220> FEATURE:
<223> OTHER INFORMATION: Synthetic peptide

<400> SEQUENCE: 41

Arg Ala Ser Glu Ser Val Asp Ser Tyr Gly Asn Ser Phe Met His
1               5                   10                  15

<210> SEQ ID NO 42
<211> LENGTH: 9
<212> TYPE: PRT
<213> ORGANISM: Artificial Sequence
<220> FEATURE:
<223> OTHER INFORMATION: Synthetic peptide

<400> SEQUENCE: 42

Gln His Ser Asn Glu Asp Pro Pro Thr
1               5

<210> SEQ ID NO 43
<211> LENGTH: 17
<212> TYPE: PRT
<213> ORGANISM: Artificial Sequence
<220> FEATURE:
<223> OTHER INFORMATION: Synthetic peptide

<400> SEQUENCE: 43

Val Ile Ser Pro Tyr Ser Gly Lys Thr Asn Tyr Ser Gln Lys Phe Lys
1               5                   10                  15

Gly

<210> SEQ ID NO 44
<211> LENGTH: 10
<212> TYPE: PRT
```

```
<213> ORGANISM: Artificial Sequence
<220> FEATURE:
<223> OTHER INFORMATION: Synthetic peptide

<400> SEQUENCE: 44

Gly Leu Ser Gly Asn Phe Val Met Asp Phe
1               5                   10

<210> SEQ ID NO 45
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (8)..(8)
<223> OTHER INFORMATION: Xaa is Ser or Asp
<220> FEATURE:
<221> NAME/KEY: VARIANT
<222> LOCATION: (11)..(11)
<223> OTHER INFORMATION: Xaa is Pro or Asn

<400> SEQUENCE: 45

Arg Ala Ser Glu Ser Val Asp Xaa Tyr Gly Xaa Ser Phe Met His
1               5                   10                  15

<210> SEQ ID NO 46
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (2)..(2)
<223> OTHER INFORMATION: Xaa is His or Gln
<220> FEATURE:
<221> NAME/KEY: VARIANT
<222> LOCATION: (6)..(6)
<223> OTHER INFORMATION: Xaa is Gly or Ala or Asp

<400> SEQUENCE: 46

Gln Xaa Ser Asn Glu Xaa Pro Pro Thr
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is Ala or Gly

<400> SEQUENCE: 47

Asp Tyr Xaa Met His
1               5

<210> SEQ ID NO 48
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(1)
<223> OTHER INFORMATION: Xaa is Val or Gly
```

```
<220> FEATURE:
<221> NAME/KEY: VARIANT
<222> LOCATION: (4)..(4)
<223> OTHER INFORMATION: Xaa is Phe or Thr or Pro
<220> FEATURE:
<221> NAME/KEY: VARIANT
<222> LOCATION: (6)..(6)
<223> OTHER INFORMATION: Xaa is Ser or Phe
<220> FEATURE:
<221> NAME/KEY: VARIANT
<222> LOCATION: (8)..(8)
<223> OTHER INFORMATION: Xaa is Lys or Arg
<220> FEATURE:
<221> NAME/KEY: VARIANT
<222> LOCATION: (12)..(12)
<223> OTHER INFORMATION: Xaa is Ser or Asn
<220> FEATURE:
<221> NAME/KEY: VARIANT
<222> LOCATION: (14)..(14)
<223> OTHER INFORMATION: Xaa is Asn or Lys
<220> FEATURE:
<221> NAME/KEY: VARIANT
<222> LOCATION: (16)..(16)
<223> OTHER INFORMATION: Xaa is Met or Lys

<400> SEQUENCE: 48

Xaa Ile Ser Xaa Tyr Xaa Gly Xaa Thr Asn Tyr Xaa Gln Xaa Phe Xaa
1               5                   10                  15

Gly

<210> SEQ ID NO 49
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (6)..(6)
<223> OTHER INFORMATION: Xaa is Phe or Tyr
<220> FEATURE:
<221> NAME/KEY: VARIANT
<222> LOCATION: (8)..(8)
<223> OTHER INFORMATION: Xaa is Val or Met
<220> FEATURE:
<221> NAME/KEY: VARIANT
<222> LOCATION: (10)..(10)
<223> OTHER INFORMATION: Xaa is Phe or Tyr

<400> SEQUENCE: 49

Gly Leu Ser Gly Asn Xaa Val Xaa Asp Xaa
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthetic peptide

<400> SEQUENCE: 50

Arg Ala Ser Asp Asn Leu Tyr Ser Asn Leu Ala
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Synthetic peptide

<400> SEQUENCE: 51
```

Asp Ala Thr Asn Leu Ala Asp
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic peptide

<400> SEQUENCE: 52

Gln His Phe Trp Gly Thr Pro Leu Thr
1               5

<210> SEQ ID NO 53
<211> LENGTH: 5
<212> TYPE: PRT
<213> ORGANISM: Artificial Sequence
<220> FEATURE:
<223> OTHER INFORMATION: Synthetic peptide

<400> SEQUENCE: 53

Ser Tyr Trp Met His
1               5

<210> SEQ ID NO 54
<211> LENGTH: 17
<212> TYPE: PRT
<213> ORGANISM: Artificial Sequence
<220> FEATURE:
<223> OTHER INFORMATION: Synthetic peptide

<400> SEQUENCE: 54

Glu Ile Asn Pro Thr Asn Gly Arg Thr Asn Tyr Ile Glu Lys Phe Lys
1               5                   10                  15

Ser

<210> SEQ ID NO 55
<211> LENGTH: 7
<212> TYPE: PRT
<213> ORGANISM: Artificial Sequence
<220> FEATURE:
<223> OTHER INFORMATION: Synthetic peptide

<400> SEQUENCE: 55

Gly Thr Arg Ala Tyr His Tyr
1               5

<210> SEQ ID NO 56
<211> LENGTH: 11
<212> TYPE: PRT
<213> ORGANISM: Artificial Sequence
<220> FEATURE:
<223> OTHER INFORMATION: Synthetic peptide

<400> SEQUENCE: 56

Arg Ala Ser Glu Asn Ile Tyr Ser Asn Leu Ala
1               5                   10

<210> SEQ ID NO 57
<211> LENGTH: 7
<212> TYPE: PRT
<213> ORGANISM: Artificial Sequence
<220> FEATURE:
<223> OTHER INFORMATION: Synthetic peptide

<400> SEQUENCE: 57

Ala Ala Thr Asp Leu Ala Asp
1               5

<210> SEQ ID NO 58
<211> LENGTH: 17
<212> TYPE: PRT
<213> ORGANISM: Artificial Sequence
<220> FEATURE:
<223> OTHER INFORMATION: Synthetic peptide

<400> SEQUENCE: 58

Glu Ile Asn Pro Thr Asn Gly Arg Thr Asn Tyr Asn Glu Asn Phe Lys
1               5                   10                  15

Ser

<210> SEQ ID NO 59
<211> LENGTH: 7
<212> TYPE: PRT
<213> ORGANISM: Artificial Sequence
<220> FEATURE:
<223> OTHER INFORMATION: Synthetic peptide

<400> SEQUENCE: 59

Gly Thr Arg Ala Tyr His Phe
1               5

<210> SEQ ID NO 60
<211> LENGTH: 11
<212> TYPE: PRT
<213> ORGANISM: Artificial Sequence
<220> FEATURE:
<223> OTHER INFORMATION: Synthetic peptide

<400> SEQUENCE: 60

Arg Ala Ser Asp Asn Ile Tyr Ser Asn Leu Ala
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Synthetic peptide

<400> SEQUENCE: 61

Ala Ala Thr Asn Leu Ala Asp
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic peptide

<400> SEQUENCE: 62

Gln His Phe Trp Gly Thr Pro Leu Met
1               5

<210> SEQ ID NO 63
<211> LENGTH: 17
<212> TYPE: PRT
<213> ORGANISM: Artificial Sequence
<220> FEATURE:
<223> OTHER INFORMATION: Synthetic peptide -continued

```
<400> SEQUENCE: 63

Glu Ile Asn Pro Ile Asn Gly Arg Thr Asn Tyr Ser Glu Lys Phe Lys
1               5                   10                  15

Lys

<210> SEQ ID NO 64
<211> LENGTH: 7
<212> TYPE: PRT
<213> ORGANISM: Artificial Sequence
<220> FEATURE:
<223> OTHER INFORMATION: Synthetic peptide

<400> SEQUENCE: 64

Ala Val Thr Asn Leu Ala Asp
1               5

<210> SEQ ID NO 65
<211> LENGTH: 17
<212> TYPE: PRT
<213> ORGANISM: Artificial Sequence
<220> FEATURE:
<223> OTHER INFORMATION: Synthetic peptide

<400> SEQUENCE: 65

Glu Ile Asn Pro Ser Asn Gly Arg Thr Asn Tyr Asn Glu Thr Phe Lys
1               5                   10                  15

Ser

<210> SEQ ID NO 66
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (4)..(4)
<223> OTHER INFORMATION: Xaa is Asp or Glu
<220> FEATURE:
<221> NAME/KEY: VARIANT
<222> LOCATION: (6)..(6)
<223> OTHER INFORMATION: Xaa is Ile or Leu

<400> SEQUENCE: 66

Arg Ala Ser Xaa Asn Xaa Tyr Ser Asn Leu Ala
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa is Ala or Asp
<220> FEATURE:
<221> NAME/KEY: VARIANT
<222> LOCATION: (2)..(2)
<223> OTHER INFORMATION: Xaa is Val or Ala
<220> FEATURE:
<221> NAME/KEY: VARIANT
<222> LOCATION: (4)..(4)
<223> OTHER INFORMATION: Xaa is Asp or Asn

<400> SEQUENCE: 67
```

Xaa Xaa Thr Xaa Leu Ala Asp
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (9)..(9)
<223> OTHER INFORMATION: Xaa is Met or Thr

<400> SEQUENCE: 68

Gln His Phe Trp Gly Thr Pro Leu Xaa
1               5

<210> SEQ ID NO 69
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (5)..(5)
<223> OTHER INFORMATION: Xaa is Ile or Thr or Ser
<220> FEATURE:
<221> NAME/KEY: VARIANT
<222> LOCATION: (12)..(12)
<223> OTHER INFORMATION: Xaa is Asn or Ile or Ser
<220> FEATURE:
<221> NAME/KEY: VARIANT
<222> LOCATION: (14)..(14)
<223> OTHER INFORMATION: Xaa is Asn or Lys or Thr
<220> FEATURE:
<221> NAME/KEY: VARIANT
<222> LOCATION: (17)..(17)
<223> OTHER INFORMATION: Xaa is Lys or Ser

<400> SEQUENCE: 69

Glu Ile Asn Pro Xaa Asn Gly Arg Thr Asn Tyr Xaa Glu Xaa Phe Lys
1               5                   10                  15

Xaa

<210> SEQ ID NO 70
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (7)..(7)
<223> OTHER INFORMATION: Xaa is Phe or Tyr

<400> SEQUENCE: 70

Gly Thr Arg Ala Tyr His Xaa
1               5

<210> SEQ ID NO 71
<211> LENGTH: 11
<212> TYPE: PRT
<213> ORGANISM: Artificial Sequence
<220> FEATURE:
<223> OTHER INFORMATION: Synthetic peptide

<400> SEQUENCE: 71

Arg Ala Ser Lys Ser Ile Ser Lys Tyr Leu Ala

```
<210> SEQ ID NO 72
<211> LENGTH: 7
<212> TYPE: PRT
<213> ORGANISM: Artificial Sequence
<220> FEATURE:
<223> OTHER INFORMATION: Synthetic peptide

<400> SEQUENCE: 72

Ser Gly Ser Thr Leu Gln Ser
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic peptide

<400> SEQUENCE: 73

Gln Gln His Asn Glu Tyr Pro Trp Thr
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic peptide

<400> SEQUENCE: 74

Ser Glu Tyr Ala Trp Asn
1               5

<210> SEQ ID NO 75
<211> LENGTH: 16
<212> TYPE: PRT
<213> ORGANISM: Artificial Sequence
<220> FEATURE:
<223> OTHER INFORMATION: Synthetic peptide

<400> SEQUENCE: 75

Tyr Ile Ser Tyr Ser Gly Thr Thr Ser Tyr Asn Pro Ser Leu Lys Ser
1               5                   10                  15

<210> SEQ ID NO 76
<211> LENGTH: 13
<212> TYPE: PRT
<213> ORGANISM: Artificial Sequence
<220> FEATURE:
<223> OTHER INFORMATION: Synthetic peptide

<400> SEQUENCE: 76

Tyr Gly Tyr Gly Asn Pro Ala Thr Arg Tyr Phe Asp Val
1               5                   10

<210> SEQ ID NO 77
<211> LENGTH: 15
<212> TYPE: PRT
<213> ORGANISM: Artificial Sequence
<220> FEATURE:
<223> OTHER INFORMATION: Synthetic peptide

<400> SEQUENCE: 77

Arg Ala Arg Gln Ser Val Ser Thr Ser Ser Tyr Ser Phe Met His
1               5                   10                  15
```

<210> SEQ ID NO 78
<211> LENGTH: 7
<212> TYPE: PRT
<213> ORGANISM: Artificial Sequence
<220> FEATURE:
<223> OTHER INFORMATION: Synthetic peptide

<400> SEQUENCE: 78

Tyr Ala Ser Ile Gln Glu Ser
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic peptide

<400> SEQUENCE: 79

Gln His Thr Trp Glu Ile Pro Phe Thr
1               5

<210> SEQ ID NO 80
<211> LENGTH: 5
<212> TYPE: PRT
<213> ORGANISM: Artificial Sequence
<220> FEATURE:
<223> OTHER INFORMATION: Synthetic peptide

<400> SEQUENCE: 80

Ser Tyr Trp Met His
1               5

<210> SEQ ID NO 81
<211> LENGTH: 17
<212> TYPE: PRT
<213> ORGANISM: Artificial Sequence
<220> FEATURE:
<223> OTHER INFORMATION: Synthetic peptide

<400> SEQUENCE: 81

Asn Ile Tyr Pro Gly Ser Gly Ser Thr Lys Tyr Asp Glu Arg Phe Lys
1               5                   10                  15

Ser

<210> SEQ ID NO 82
<211> LENGTH: 11
<212> TYPE: PRT
<213> ORGANISM: Artificial Sequence
<220> FEATURE:
<223> OTHER INFORMATION: Synthetic peptide

<400> SEQUENCE: 82

Gly Gly Tyr Asp Ser Arg Ala Trp Phe Ala Tyr
1               5                   10

<210> SEQ ID NO 83
<211> LENGTH: 17
<212> TYPE: PRT
<213> ORGANISM: Artificial Sequence
<220> FEATURE:
<223> OTHER INFORMATION: Synthetic peptide

<400> SEQUENCE: 83

Asn Ile Tyr Pro Gly Ser Gly Ser Thr Lys Tyr Asp Glu Lys Phe Lys

```
1               5                   10                  15
Ser
```

<210> SEQ ID NO 84
<211> LENGTH: 11
<212> TYPE: PRT
<213> ORGANISM: Artificial Sequence
<220> FEATURE:
<223> OTHER INFORMATION: Synthetic peptide

<400> SEQUENCE: 84

```
Gly Gly Tyr Asp Ser Arg Ala Trp Phe Ala His
1               5                   10
```

<210> SEQ ID NO 85
<211> LENGTH: 12
<212> TYPE: PRT
<213> ORGANISM: Artificial Sequence
<220> FEATURE:
<223> OTHER INFORMATION: Synthetic peptide

<400> SEQUENCE: 85

```
Thr Thr Ser Ser Ser Val Pro Ser Ser Tyr Phe His
1               5                   10
```

<210> SEQ ID NO 86
<211> LENGTH: 7
<212> TYPE: PRT
<213> ORGANISM: Artificial Sequence
<220> FEATURE:
<223> OTHER INFORMATION: Synthetic peptide

<400> SEQUENCE: 86

```
Ser Thr Ser Asn Leu Ala Ser
1               5
```

<210> SEQ ID NO 87
<211> LENGTH: 9
<212> TYPE: PRT
<213> ORGANISM: Artificial Sequence
<220> FEATURE:
<223> OTHER INFORMATION: Synthetic peptide

<400> SEQUENCE: 87

```
His Gln Tyr His Arg Ser Pro Phe Thr
1               5
```

<210> SEQ ID NO 88
<211> LENGTH: 5
<212> TYPE: PRT
<213> ORGANISM: Artificial Sequence
<220> FEATURE:
<223> OTHER INFORMATION: Synthetic peptide

<400> SEQUENCE: 88

```
Asp Tyr Tyr Met Tyr
1               5
```

<210> SEQ ID NO 89
<211> LENGTH: 17
<212> TYPE: PRT
<213> ORGANISM: Artificial Sequence
<220> FEATURE:
<223> OTHER INFORMATION: Synthetic peptide

<400> SEQUENCE: 89

```
Ser Ile Ser Asn Gly Gly Asp Asn Thr Tyr Tyr Pro Asp Thr Val Lys
1               5                   10                  15
Gly

<210> SEQ ID NO 90
<211> LENGTH: 15
<212> TYPE: PRT
<213> ORGANISM: Artificial Sequence
<220> FEATURE:
<223> OTHER INFORMATION: Synthetic peptide

<400> SEQUENCE: 90

Gln Gly Ala Leu Tyr Asp Gly Tyr Tyr Arg Gly Ala Met Asp Tyr
1               5                   10                  15

<210> SEQ ID NO 91
<211> LENGTH: 11
<212> TYPE: PRT
<213> ORGANISM: Artificial Sequence
<220> FEATURE:
<223> OTHER INFORMATION: Synthetic peptide

<400> SEQUENCE: 91

Arg Ala Gly Gln Asp Ile Thr Asn Tyr Leu Asn
1               5                   10

<210> SEQ ID NO 92
<211> LENGTH: 7
<212> TYPE: PRT
<213> ORGANISM: Artificial Sequence
<220> FEATURE:
<223> OTHER INFORMATION: Synthetic peptide

<400> SEQUENCE: 92

Tyr Thr Ser Arg Leu His Ser
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic peptide

<400> SEQUENCE: 93

Gln Gln Ala Asn Thr Leu Pro Tyr Thr
1               5

<210> SEQ ID NO 94
<211> LENGTH: 5
<212> TYPE: PRT
<213> ORGANISM: Artificial Sequence
<220> FEATURE:
<223> OTHER INFORMATION: Synthetic peptide

<400> SEQUENCE: 94

Asn Tyr Trp Ile Glu
1               5

<210> SEQ ID NO 95
<211> LENGTH: 17
<212> TYPE: PRT
<213> ORGANISM: Artificial Sequence
<220> FEATURE:
<223> OTHER INFORMATION: Synthetic peptide

<400> SEQUENCE: 95
```

```
Glu Ile Leu Pro Gly Ser Gly Ser Thr Lys Tyr Asn Glu Lys Phe Lys
1               5                   10                  15

Gly

<210> SEQ ID NO 96
<211> LENGTH: 12
<212> TYPE: PRT
<213> ORGANISM: Artificial Sequence
<220> FEATURE:
<223> OTHER INFORMATION: Synthetic peptide

<400> SEQUENCE: 96

Arg Gly Gly Tyr Gly Tyr Asp Gly Glu Phe Ala Tyr
1               5                   10

<210> SEQ ID NO 97
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(1)
<223> OTHER INFORMATION: Xaa is Arg or Thr
<220> FEATURE:
<221> NAME/KEY: VARIANT
<222> LOCATION: (2)..(2)
<223> OTHER INFORMATION: Xaa is Thr or Ala
<220> FEATURE:
<221> NAME/KEY: VARIANT
<222> LOCATION: (3)..(3)
<223> OTHER INFORMATION: Xaa is Arg or Ser or Gly
<220> FEATURE:
<221> NAME/KEY: VARIANT
<222> LOCATION: (4)..(4)
<223> OTHER INFORMATION: Xaa is Ser or Gln
<220> FEATURE:
<221> NAME/KEY: VARIANT
<222> LOCATION: (5)..(5)
<223> OTHER INFORMATION: Xaa, if present, is Ser
<220> FEATURE:
<221> NAME/KEY: VARIANT
<222> LOCATION: (6)..(6)
<223> OTHER INFORMATION: Xaa if present, is Val
<220> FEATURE:
<221> NAME/KEY: VARIANT
<222> LOCATION: (7)..(7)
<223> OTHER INFORMATION: Xaa if present, is Ser
<220> FEATURE:
<221> NAME/KEY: VARIANT
<222> LOCATION: (8)..(8)
<223> OTHER INFORMATION: Xaa if present, is Thr
<220> FEATURE:
<221> NAME/KEY: VARIANT
<222> LOCATION: (9)..(9)
<223> OTHER INFORMATION: Xaa is Ser or Val or Asp
<220> FEATURE:
<221> NAME/KEY: VARIANT
<222> LOCATION: (10)..(10)
<223> OTHER INFORMATION: Xaa is Ser or Pro or Ile
<220> FEATURE:
<221> NAME/KEY: VARIANT
<222> LOCATION: (11)..(11)
<223> OTHER INFORMATION: Xaa is Tyr or Ser or Thr
<220> FEATURE:
<221> NAME/KEY: VARIANT
<222> LOCATION: (12)..(12)
<223> OTHER INFORMATION: Xaa is Ser or Asn
<220> FEATURE:
<221> NAME/KEY: VARIANT
<222> LOCATION: (13)..(13)
<223> OTHER INFORMATION: Xaa is Phe or Tyr
<220> FEATURE:
```

```
<221> NAME/KEY: VARIANT
<222> LOCATION: (14)..(14)
<223> OTHER INFORMATION: Xaa is Met or Phe or Leu
<220> FEATURE:
<221> NAME/KEY: VARIANT
<222> LOCATION: (15)..(15)
<223> OTHER INFORMATION: Xaa is His or Asn

<400> SEQUENCE: 97

Xaa Xaa Xaa Xaa Xaa Xaa Xaa Xaa Xaa Xaa Xaa Xaa Xaa Xaa Xaa
1               5                   10                  15

<210> SEQ ID NO 98
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(1)
<223> OTHER INFORMATION: Xaa is Tyr or Ser
<220> FEATURE:
<221> NAME/KEY: VARIANT
<222> LOCATION: (2)..(2)
<223> OTHER INFORMATION: Xaa is Ala or Thr
<220> FEATURE:
<221> NAME/KEY: VARIANT
<222> LOCATION: (4)..(4)
<223> OTHER INFORMATION: Xaa is Ile or Asn or Arg
<220> FEATURE:
<221> NAME/KEY: VARIANT
<222> LOCATION: (5)..(5)
<223> OTHER INFORMATION: Xaa is Gln or Leu
<220> FEATURE:
<221> NAME/KEY: VARIANT
<222> LOCATION: (6)..(6)
<223> OTHER INFORMATION: Xaa is Glu or Ala or His

<400> SEQUENCE: 98

Xaa Xaa Ser Xaa Xaa Xaa Ser
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(1)
<223> OTHER INFORMATION: Xaa is Gln or His
<220> FEATURE:
<221> NAME/KEY: VARIANT
<222> LOCATION: (2)..(2)
<223> OTHER INFORMATION: Xaa is His or Gln
<220> FEATURE:
<221> NAME/KEY: VARIANT
<222> LOCATION: (3)..(3)
<223> OTHER INFORMATION: Xaa is Thr or Tyr or Ala
<220> FEATURE:
<221> NAME/KEY: VARIANT
<222> LOCATION: (4)..(4)
<223> OTHER INFORMATION: Xaa is Trp or His or Asn
<220> FEATURE:
<221> NAME/KEY: VARIANT
<222> LOCATION: (5)..(5)
<223> OTHER INFORMATION: Xaa is Glu or Arg or Thr
<220> FEATURE:
<221> NAME/KEY: VARIANT
<222> LOCATION: (6)..(6)
<223> OTHER INFORMATION: Xaa is Ile or Ser or Leu
<220> FEATURE:
<221> NAME/KEY: VARIANT
```

```
<222> LOCATION: (8)..(8)
<223> OTHER INFORMATION: Xaa is Phe or Tyr

<400> SEQUENCE: 99

Xaa Xaa Xaa Xaa Xaa Xaa Pro Xaa Thr
1               5

<210> SEQ ID NO 100
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(1)
<223> OTHER INFORMATION: Xaa is Ser or Asp or Asn
<220> FEATURE:
<221> NAME/KEY: VARIANT
<222> LOCATION: (3)..(3)
<223> OTHER INFORMATION: Xaa is Trp or Tyr
<220> FEATURE:
<221> NAME/KEY: VARIANT
<222> LOCATION: (4)..(4)
<223> OTHER INFORMATION: Xaa is Met or Ile
<220> FEATURE:
<221> NAME/KEY: VARIANT
<222> LOCATION: (5)..(5)
<223> OTHER INFORMATION: Xaa is His or Tyr or Glu

<400> SEQUENCE: 100

Xaa Tyr Xaa Xaa Xaa
1               5

<210> SEQ ID NO 101
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(1)
<223> OTHER INFORMATION: Xaa is Asn or Ser or Glu
<220> FEATURE:
<221> NAME/KEY: VARIANT
<222> LOCATION: (3)..(3)
<223> OTHER INFORMATION: Xaa is Tyr or Ser or Leu
<220> FEATURE:
<221> NAME/KEY: VARIANT
<222> LOCATION: (4)..(4)
<223> OTHER INFORMATION: Xaa is Pro or Asn
<220> FEATURE:
<221> NAME/KEY: VARIANT
<222> LOCATION: (6)..(6)
<223> OTHER INFORMATION: Xaa is Ser or Gly
<220> FEATURE:
<221> NAME/KEY: VARIANT
<222> LOCATION: (7)..(7)
<223> OTHER INFORMATION: Xaa is Gly or Asp
<220> FEATURE:
<221> NAME/KEY: VARIANT
<222> LOCATION: (8)..(8)
<223> OTHER INFORMATION: Xaa is Ser or Asn
<220> FEATURE:
<221> NAME/KEY: VARIANT
<222> LOCATION: (10)..(10)
<223> OTHER INFORMATION: Xaa is Lys or Tyr
<220> FEATURE:
<221> NAME/KEY: VARIANT
<222> LOCATION: (12)..(12)
<223> OTHER INFORMATION: Xaa is Asp or Pro or Asn
<220> FEATURE:
<221> NAME/KEY: VARIANT
<222> LOCATION: (13)..(13)
```

```
<223> OTHER INFORMATION: Xaa is Glu or Asp
<220> FEATURE:
<221> NAME/KEY: VARIANT
<222> LOCATION: (14)..(14)
<223> OTHER INFORMATION: Xaa is Arg or Lys or Thr
<220> FEATURE:
<221> NAME/KEY: VARIANT
<222> LOCATION: (15)..(15)
<223> OTHER INFORMATION: Xaa is Phe or Val
<220> FEATURE:
<221> NAME/KEY: VARIANT
<222> LOCATION: (17)..(17)
<223> OTHER INFORMATION: Xaa is Ser or Gly

<400> SEQUENCE: 101

Xaa Ile Xaa Xaa Gly Xaa Xaa Xaa Thr Xaa Tyr Xaa Xaa Xaa Xaa Lys
1               5                   10                  15

Xaa

<210> SEQ ID NO 102
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(1)
<223> OTHER INFORMATION: Xaa is Gly or Gln or Arg
<220> FEATURE:
<221> NAME/KEY: VARIANT
<222> LOCATION: (3)..(3)
<223> OTHER INFORMATION: Xaa is Tyr or Ala or Gly
<220> FEATURE:
<221> NAME/KEY: VARIANT
<222> LOCATION: (4)..(4)
<223> OTHER INFORMATION: Xaa is Asp or Leu or Tyr
<220> FEATURE:
<221> NAME/KEY: VARIANT
<222> LOCATION: (5)..(5)
<223> OTHER INFORMATION: Xaa is Ser or Tyr or Gly
<220> FEATURE:
<221> NAME/KEY: VARIANT
<222> LOCATION: (6)..(6)
<223> OTHER INFORMATION: Xaa is Arg or Asp or Tyr
<220> FEATURE:
<221> NAME/KEY: VARIANT
<222> LOCATION: (7)..(7)
<223> OTHER INFORMATION: Xaa is Ala or Gly or Asp
<220> FEATURE:
<221> NAME/KEY: VARIANT
<222> LOCATION: (8)..(8)
<223> OTHER INFORMATION: Xaa is Trp or Tyr or Gly
<220> FEATURE:
<221> NAME/KEY: VARIANT
<222> LOCATION: (9)..(9)
<223> OTHER INFORMATION: Xaa is Phe or Tyr or Glu
<220> FEATURE:
<221> NAME/KEY: VARIANT
<222> LOCATION: (10)..(10)
<223> OTHER INFORMATION: Xaa, if present, is Arg or Phe
<220> FEATURE:
<221> NAME/KEY: VARIANT
<222> LOCATION: (11)..(11)
<223> OTHER INFORMATION: Xaa, if present, is Gly
<220> FEATURE:
<221> NAME/KEY: VARIANT
<222> LOCATION: (12)..(12)
<223> OTHER INFORMATION: Xaa, if present, is Ala
<220> FEATURE:
<221> NAME/KEY: VARIANT
<222> LOCATION: (13)..(13)
<223> OTHER INFORMATION: Xaa, if present, is Met
<220> FEATURE:
<221> NAME/KEY: VARIANT
<222> LOCATION: (14)..(14)
```

<223> OTHER INFORMATION: Xaa is Ala or Asp
<220> FEATURE:
<221> NAME/KEY: VARIANT
<222> LOCATION: (15)..(15)
<223> OTHER INFORMATION: Xaa is Tyr or His

<400> SEQUENCE: 102

Xaa Gly Xaa Xaa Xaa Xaa Xaa Xaa Xaa Xaa Xaa Xaa Xaa Xaa Xaa
1               5                   10                  15

<210> SEQ ID NO 103
<211> LENGTH: 107
<212> TYPE: PRT
<213> ORGANISM: Homo sapiens

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Ser
            20                  25                  30

Leu Ala Trp Tyr Gln Gln Lys Pro Gly Lys Ala Pro Lys Leu Leu Leu
        35                  40                  45

Tyr Ala Ala Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Pro Tyr
                85                  90                  95

Thr Phe Gly Gln Gly Thr Lys Leu Glu Ile Lys
            100                 105

<210> SEQ ID NO 104
<211> LENGTH: 107
<212> TYPE: PRT
<213> ORGANISM: Mus musculus

<400> SEQUENCE: 104

Asp Ile Gln Met Thr Gln Ser Pro Ala Ser Leu Ser Val Ser Val Gly
1               5                   10                  15

Glu Thr Val Thr Ile Thr Cys Arg Ala Ser Asp Asn Leu Tyr Ser Asn
            20                  25                  30

Leu Ala Trp Tyr Gln Gln Lys Gln Gly Lys Ser Pro Gln Leu Leu Val
        35                  40                  45

Tyr Asp Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Phe Trp Gly Thr Pro Leu
                85                  90                  95

Thr Phe Gly Ala Gly Thr Lys Leu Glu Leu Lys
            100                 105

<210> SEQ ID NO 105
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 105

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Asp Asn Leu Tyr Ser Asn
            20                  25                  30

Leu Ala Trp Tyr Gln Gln Lys Pro Gly Lys Ser Pro Lys Leu Leu Val
        35                  40                  45

Tyr Asp Ala Thr Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Gly Thr Pro Leu
                85                  90                  95

Thr Phe Gly Gln Gly Thr Lys Val Glu Ile Lys
                100                 105

<210> SEQ ID NO 106
<211> LENGTH: 112
<212> TYPE: PRT
<213> ORGANISM: Homo sapiens

<400> SEQUENCE: 106

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Asp Val Trp Gly Gln Gly Thr Met Val Thr Val Ser Ser
                100                 105                 110

<210> SEQ ID NO 107
<211> LENGTH: 116
<212> TYPE: PRT
<213> ORGANISM: Mus musculus

<400> SEQUENCE: 107

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Thr Asn Gly Arg Thr Asn Tyr Ile Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Thr Arg Ala Tyr His Tyr Trp Gly Gln Gly Thr Ser Val
                100                 105                 110
```

Thr Val Ser Ser
        115

<210> SEQ ID NO 108
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 108

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Arg Leu Glu Trp Ile
        35                  40                  45

Gly Glu Ile Asn Pro Thr Asn Gly Arg Thr Asn Tyr Ile Glu Lys Phe
    50                  55                  60

Lys Ser Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Thr Arg Ala Tyr His Tyr Trp Gly Gln Gly Thr Met Val
            100                 105                 110

Thr Val Ser Ser
        115

<210> SEQ ID NO 109
<211> LENGTH: 113
<212> TYPE: PRT
<213> ORGANISM: Homo sapiens

<400> SEQUENCE: 109

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Leu Glu Ile
            100                 105                 110

Lys

<210> SEQ ID NO 110
<211> LENGTH: 111
<212> TYPE: PRT
<213> ORGANISM: Mus musculus

<400> SEQUENCE: 110

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Gly Pro Pro Thr Phe Gly Gly Gly Thr Lys Leu Glu Ile Lys
            100                 105                 110

<210> SEQ ID NO 111
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 111

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Ala Pro Pro Thr Phe Gly Gln Gly Thr Lys Leu Glu Ile Lys
            100                 105                 110

<210> SEQ ID NO 112
<211> LENGTH: 112
<212> TYPE: PRT
<213> ORGANISM: Homo sapiens

<400> SEQUENCE: 112

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Met Asp Tyr Trp Gly Gln Gly Thr Thr Val Thr Val Ser Ser
            100                 105                 110

<210> SEQ ID NO 113
<211> LENGTH: 119
<212> TYPE: PRT
<213> ORGANISM: Mus musculus

<400> SEQUENCE: 113

Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Gly Ile Ser Thr Tyr Phe Gly Arg Thr Asn Tyr Asn Gln Lys Phe
    50                  55                  60

Lys Gly Arg Ala Thr Met Thr Val Asp Lys Ser Ser Thr Ala Tyr
65                  70                  75                  80

Met Glu Leu Ala Arg Leu Thr Ser Glu Asp Ser Ala Leu Tyr Tyr Cys
                85                  90                  95

Ala Arg Gly Leu Ser Gly Asn Tyr Val Met Asp Tyr Trp Gly Gln Gly
            100                 105                 110

Thr Ser Val Thr Val Ser Ser
        115

<210> SEQ ID NO 114
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 114

Glu Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Met His Trp Val Arg Gln Ala Pro Gly Gln Gly Leu Glu Trp Met
        35                  40                  45

Gly Gly Ile Ser Thr Tyr Phe Gly Arg Thr Asn Tyr Asn Gln Lys Phe
    50                  55                  60

Lys Gly Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Leu Ser Gly Asn Tyr Val Met Asp Tyr Trp Gly Gln Gly
            100                 105                 110

Thr Thr Val Thr Val Ser Ser
        115

<210> SEQ ID NO 115
<211> LENGTH: 113
<212> TYPE: PRT
<213> ORGANISM: Homo sapiens

<400> SEQUENCE: 115

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

```
Ser Asn Asn Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
 50                      55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro Phe Thr Phe Gly Gln Gly Thr Lys Val Glu Ile
                100                 105                 110

Lys

<210> SEQ ID NO 116
<211> LENGTH: 111
<212> TYPE: PRT
<213> ORGANISM: Mus musculus

<400> SEQUENCE: 116

Asp Ile Val Leu Thr Gln Ser Pro Ala Ser Leu Ala Val Ser Leu Gly
 1               5                  10                  15

Gln Arg Ala Thr Ile Ser Cys Arg Ala Arg Gln Ser Val Ser Thr Ser
             20                  25                  30

Ser Tyr Ser Phe Met His Trp Tyr Arg Gln Lys Ala Gly Gln Pro Pro
         35                  40                  45

Lys Leu Leu Ile Lys Tyr Ala Ser Ile Gln Glu Ser Gly Val Pro Ala
 50                      55                  60

Arg Phe Ser Gly Ser Gly Ser Gly Thr Asp Phe Thr Leu Asn Ile Leu
 65                  70                  75                  80

Pro Val Glu Glu Glu Asp Thr Ala Thr Tyr Tyr Cys Gln His Thr Trp
                 85                  90                  95

Glu Ile Pro Phe Thr Phe Gly Ser Gly Thr Lys Leu Glu Ile Lys
                100                 105                 110

<210> SEQ ID NO 117
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 117

Asp Ile Val Met Thr Gln Ser Pro Asp Ser Leu Ala Val Ser Leu Gly
 1               5                  10                  15

Glu Arg Ala Thr Ile Asn Cys Arg Ala Arg Gln Ser Val Ser Thr Ser
             20                  25                  30

Ser Tyr Ser Phe Met His Trp Tyr Gln Gln Pro Ala Gly Gln Pro Pro
         35                  40                  45

Lys Leu Leu Ile Lys Tyr Ala Ser Ile Gln Glu Ser Gly Val Pro Asp
 50                      55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln His Thr Trp
                 85                  90                  95

Glu Ile Pro Phe Thr Phe Gly Gln Gly Thr Lys Val Glu Ile Lys
                100                 105                 110

<210> SEQ ID NO 118
```

```
<211> LENGTH: 112
<212> TYPE: PRT
<213> ORGANISM: Homo sapiens

<400> SEQUENCE: 118

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Asn Pro Gly Ser Gly Asn Thr Asn Tyr Ala Gln Lys Phe
    50                  55                  60

Gln Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Phe Asp Tyr Trp Gly Gln Gly Thr Leu Val Thr Val Ser Ser
            100                 105                 110

<210> SEQ ID NO 119
<211> LENGTH: 120
<212> TYPE: PRT
<213> ORGANISM: Mus musculus

<400> SEQUENCE: 119

Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg His Gly Gln Gly Leu Glu Trp Ile
        35                  40                  45

Gly Asn Ile Tyr Pro Gly Ser Gly Ser Thr Lys Tyr Asp Glu Arg Phe
    50                  55                  60

Lys Ser Lys Gly Thr Leu Thr Val Asp Thr Ser Ser Ser Thr Ala Tyr
65                  70                  75                  80

Met His Leu Ser Ser Leu Thr Ser Glu Asp Ser Ala Val Tyr Tyr Cys
                85                  90                  95

Thr Arg Gly Gly Tyr Asp Ser Arg Ala Trp Phe Ala Tyr Trp Gly Gln
            100                 105                 110

Gly Thr Leu Val Thr Val Ser Ala
        115                 120

<210> SEQ ID NO 120
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 120

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Asn Ile Tyr Pro Gly Ser Gly Ser Thr Lys Tyr Asp Glu Arg Phe
```

```
                50                  55                  60
Lys Ser Arg Val Thr Ile Thr Val Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Thr Arg Gly Gly Tyr Asp Ser Arg Ala Trp Phe Ala Tyr Trp Gly Gln
            100                 105                 110

Gly Thr Leu Val Thr Val Ser Ser
        115                 120

<210> SEQ ID NO 121
<211> LENGTH: 107
<212> TYPE: PRT
<213> ORGANISM: Homo sapiens

<400> SEQUENCE: 121

Asp Ile Gln Leu Thr Gln Ser Pro Ser Phe Leu Ser Ala Ser Val Gly
 1               5                  10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
         35                  40                  45

Tyr Ala Ala Ser Thr Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Trp
                 85                  90                  95

Thr Phe Gly Gln Gly Thr Lys Val Glu Ile Lys
            100                 105

<210> SEQ ID NO 122
<211> LENGTH: 107
<212> TYPE: PRT
<213> ORGANISM: Mus musculus

<400> SEQUENCE: 122

Asp Val Gln Ile Thr Gln Ser Pro Ser Tyr Leu Thr Ala Ser Pro Gly
 1               5                  10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
         35                  40                  45

Tyr Ser Gly Ser Thr Leu Gln Ser Gly Ile Pro Ser Arg Phe Ser Gly
     50                  55                  60

Ser Gly Ser Gly Thr Asp Phe Thr Leu Thr Ile Ser Asn Leu Glu Pro
 65                  70                  75                  80

Glu Asp Phe Ala Met Tyr Tyr Cys Gln Gln His Asn Glu Tyr Pro Trp
                 85                  90                  95

Thr Phe Gly Gly Gly Thr Lys Leu Glu Ile Lys
            100                 105

<210> SEQ ID NO 123
<211> LENGTH: 107
<212> TYPE: PRT
<213> ORGANISM: Artificial Sequence
<220> FEATURE:
<223> OTHER INFORMATION: Synthetic polypeptide
```

<400> SEQUENCE: 123

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Thr Asn Lys Leu Leu Leu
        35                  40                  45

Tyr Ser Gly Ser Thr Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln His Asn Glu Tyr Pro Trp
                85                  90                  95

Thr Phe Gly Gln Gly Thr Lys Val Glu Ile Lys
            100                 105

<210> SEQ ID NO 124
<211> LENGTH: 111
<212> TYPE: PRT
<213> ORGANISM: Homo sapiens

<400> SEQUENCE: 124

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Met Asp Val Trp Gly Lys Gly Thr Thr Val Thr Val Ser Ser
            100                 105                 110

<210> SEQ ID NO 125
<211> LENGTH: 122
<212> TYPE: PRT
<213> ORGANISM: Mus musculus

<400> SEQUENCE: 125

Asp Val Gln Leu Gln Glu Ser Gly Pro Gly Leu Val Lys Pro Ser Gln
1               5                   10                  15

Ser Leu Ser Leu Thr Cys Thr Val Thr Gly Asn Ser Ile Thr Ser Glu
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Thr Thr Ser Tyr Asn Pro Ser Leu
    50                  55                  60

Lys Ser Arg Ile Ser Ile Thr Arg Asp Thr Ser Lys Asn Gln Leu Phe
65                  70                  75                  80

Leu Gln Leu Asn Ser Val Thr Thr Glu Asp Thr Ala Thr Tyr Phe Cys
                85                  90                  95

-continued

Ala Arg Tyr Gly Tyr Gly Asn Pro Ala Thr Arg Tyr Phe Asp Val Trp
            100                 105                 110

Gly Ala Gly Thr Thr Val Thr Val Ser Ser
        115                 120

<210> SEQ ID NO 126
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 126

Glu Val Gln Leu Val Glu Ser Gly Pro Gly Leu Val Lys Pro Ser Glu
1               5                   10                  15

Thr Leu Ser Leu Thr Cys Thr Val Ser Gly Asn Ser Ile Thr Ser Glu
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Thr Thr Ser Tyr Asn Pro Ser Leu
    50                  55                  60

Lys Ser Arg Val Thr Ile Ser Arg Asp Thr Ser Lys Asn Gln Leu Ser
65                  70                  75                  80

Leu Lys Leu Ser Ser Val Thr Ala Ala Asp Thr Ala Val Tyr Tyr Cys
                85                  90                  95

Ala Arg Tyr Gly Tyr Gly Asn Pro Ala Thr Arg Tyr Phe Asp Val Trp
            100                 105                 110

Gly Gln Gly Thr Leu Val Thr Val Ser Ser
        115                 120

<210> SEQ ID NO 127
<211> LENGTH: 9
<212> TYPE: PRT
<213> ORGANISM: Artificial Sequence
<220> FEATURE:
<223> OTHER INFORMATION: Synthetic peptide

<400> SEQUENCE: 127

Gln Gln Ser Asn Glu Ala Pro Pro Thr
1               5

<210> SEQ ID NO 128
<211> LENGTH: 9
<212> TYPE: PRT
<213> ORGANISM: Artificial Sequence
<220> FEATURE:
<223> OTHER INFORMATION: Synthetic peptide

<400> SEQUENCE: 128

Gln His Phe Trp Gly Thr Pro Leu Thr
1               5

<210> SEQ ID NO 129
<211> LENGTH: 7
<212> TYPE: PRT
<213> ORGANISM: Artificial Sequence
<220> FEATURE:
<223> OTHER INFORMATION: Synthetic peptide

<400> SEQUENCE: 129

Gly Thr Arg Ala Tyr His Tyr
1               5

<210> SEQ ID NO 130
<211> LENGTH: 9
<212> TYPE: PRT
<213> ORGANISM: Artificial Sequence
<220> FEATURE:
<223> OTHER INFORMATION: Synthetic peptide

<400> SEQUENCE: 130

Gln Gln Ser Asn Glu Ala Pro Pro Thr
1               5

<210> SEQ ID NO 131
<211> LENGTH: 10
<212> TYPE: PRT
<213> ORGANISM: Artificial Sequence
<220> FEATURE:
<223> OTHER INFORMATION: Synthetic peptide

<400> SEQUENCE: 131

Gly Leu Ser Gly Asn Tyr Val Met Asp Tyr
1               5                   10

<210> SEQ ID NO 132
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 132

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg
            100                 105

<210> SEQ ID NO 133
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Pro Thr Tyr Leu Pro
                85                  90                  95

Thr Phe Gly Gln Gly Thr Lys Val Glu Ile Lys Arg
            100                 105

<210> SEQ ID NO 134
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Asn Asp Pro Pro
                85                  90                  95

Thr Phe Gly Gln Gly Thr Lys Val Glu Ile Lys Arg
            100                 105

<210> SEQ ID NO 135
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Thr Asp Pro Thr
                85                  90                  95

Thr Phe Gly Gln Gly Thr Lys Val Glu Ile Lys Arg
            100                 105

<210> SEQ ID NO 136
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Val Ala Asn Ser
            20                  25                  30

Leu Ala Trp Tyr Gln Gln Lys Pro Gly Lys Ala Pro Lys Leu Leu Ile
        35                  40                  45

Tyr Leu Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Ala Thr Ser Pro Pro
                85                  90                  95

Thr Phe Gly Gln Gly Thr Lys Val Glu Ile Lys Arg
            100                 105

<210> SEQ ID NO 137
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 137

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ala Thr Asp Pro Pro
                85                  90                  95

Thr Phe Gly Gln Gly Thr Lys Val Glu Ile Lys Arg
            100                 105

<210> SEQ ID NO 138
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 138

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Ile His Trp Val Arg Gln Ala Pro Gly Lys Gly Leu Glu Trp Val
        35                  40                  45

Gly Trp Ile Ser Pro Ala Gly Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

```
Leu Gln Met Asn Ser Leu Arg Ala Glu Asp Thr Ala Val Tyr Tyr Cys
                85                  90                  95

Ala Arg Gly Pro Phe Ser Pro Trp Val Met Asp Tyr Trp Gly Gln Gly
            100                 105                 110

Thr Leu Val Thr Val Ser Ser
        115
```

<210> SEQ ID NO 139
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 139

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Leu Gly Tyr
            20                  25                  30

Gly Ile His Trp Val Arg Gln Ala Pro Gly Lys Gly Leu Glu Trp Val
        35                  40                  45

Gly Trp Ile Ser Pro Ala Gly Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Pro Phe Ser Pro Trp Val Met Asp Tyr Trp Gly Gln Gly
            100                 105                 110

Thr Leu Val Thr Val Ser Ser
        115
```

<210> SEQ ID NO 140
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 140

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Tyr Ser Pro Phe
                85                  90                  95

Thr Phe Gly Gln Gly Thr Lys Val Glu Ile Lys Arg
            100                 105
```

<210> SEQ ID NO 141
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 141

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Ser Trp Ala Ser Trp Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Tyr Ser Pro Phe
                85                  90                  95

Thr Phe Gly Gln Gly Thr Lys Val Glu Ile Lys Arg
            100                 105

<210> SEQ ID NO 142
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 142

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Trp Tyr Ala Ser Trp Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Tyr Ser Pro Phe
                85                  90                  95

Thr Phe Gly Gln Gly Thr Lys Val Glu Ile Lys Arg
            100                 105

<210> SEQ ID NO 143
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 143

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Trp Trp Ala Ser Ser Leu Tyr Ser Gly Val Pro Ser Arg Phe Ser Gly
50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Tyr Ser Pro Phe
                 85                  90                  95

Thr Phe Gly Gln Gly Thr Lys Val Glu Ile Lys Arg
                100                 105
```

<210> SEQ ID NO 144
<211> LENGTH: 126
<212> TYPE: PRT
<213> ORGANISM: Artificial Sequence
<220> FEATURE:
<223> OTHER INFORMATION: Synthetic polypeptide

<400> SEQUENCE: 144

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Phe Tyr Tyr Ser
                 20                  25                  30

Ser Ile His Trp Val Arg Gln Ala Pro Gly Lys Gly Leu Glu Trp Val
             35                  40                  45

Ala Ser Ile Ser Pro Tyr Ser Gly Tyr Thr Ser Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gln Pro Thr His Tyr Tyr Tyr Ala Lys Gly Tyr Lys Ala
                100                 105                 110

Met Asp Tyr Trp Gly Gln Gly Thr Leu Val Thr Val Ser Ser
            115                 120                 125
```

<210> SEQ ID NO 145
<211> LENGTH: 438
<212> TYPE: PRT
<213> ORGANISM: Artificial Sequence
<220> FEATURE:
<223> OTHER INFORMATION: Synthetic polypeptide

<400> SEQUENCE: 145

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Gly Met Ser Trp Val Arg Gln Ala Pro Gly Lys Gly Leu Glu Leu Val
             35                  40                  45

Ala Ser Ile Asn Ser Asn Gly Gly Ser Thr Tyr Tyr Pro Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Ser Gly Asp Tyr Trp Gly Gln Gly Thr Thr Val Thr Val Ser Ser
                100                 105                 110

Ala Ser Thr Lys Gly Pro Ser Val Phe Pro Leu Ala Pro Cys Ser Arg
            115                 120                 125

Ser Thr Ser Glu Ser Thr Ala Ala Leu Gly Cys Leu Val Lys Asp Tyr
            130                 135                 140
```

```
Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Ser Lys Tyr Gly Pro Pro Cys Pro Pro Cys Pro Ala Pro
    210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
        275                 280                 285

Asn Ser Thr Tyr Arg Val Val Ser Val Leu Thr Val Leu His Gln Asp
    290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Met Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415

Cys Ser Val Met His Glu Ala Leu His Asn His Tyr Thr Gln Lys Ser
            420                 425                 430

Leu Ser Leu Ser Leu Gly
        435

<210> SEQ ID NO 146
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 146

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
            20                  25                  30

Asn Gly Asp Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 147
<211> LENGTH: 10
<212> TYPE: PRT
<213> ORGANISM: Artificial Sequence
<220> FEATURE:
<223> OTHER INFORMATION: Synthetic peptide

<400> SEQUENCE: 147

Gly Tyr Thr Phe Thr Ser Tyr Trp Met His
1               5                   10

<210> SEQ ID NO 148
<211> LENGTH: 10
<212> TYPE: PRT
<213> ORGANISM: Artificial Sequence
<220> FEATURE:
<223> OTHER INFORMATION: Synthetic peptide

<400> SEQUENCE: 148

Gly Tyr Thr Phe Thr Asp Tyr Ala Met His
1               5                   10

<210> SEQ ID NO 149
<211> LENGTH: 9
<212> TYPE: PRT
<213> ORGANISM: Artificial Sequence
<220> FEATURE:
<223> OTHER INFORMATION: Synthetic peptide

<400> SEQUENCE: 149

Gly Tyr Thr Phe Ser Tyr Trp Met His
1               5

<210> SEQ ID NO 150
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 150

Asp Ile Gln Met Thr Gln Ser Pro Ser Ser Leu Ser Ala Ser Val Gly
1               5                   10                  15

Asp Arg Val Thr Ile Thr Cys Arg Ala Ser Asp Asn Leu Tyr Ser Asn
            20                  25                  30

Leu Ala Trp Tyr Gln Gln Lys Pro Gly Lys Ser Pro Lys Leu Leu Val
        35                  40                  45

Tyr Asp Ala Thr Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Gly Thr Pro Leu
                85                  90                  95

Thr Phe Gly Gln Gly Thr Lys Val Glu Ile Lys
                100                 105

<210> SEQ ID NO 151
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 151

Asp Ile Gln Met Thr Gln Ser Pro Ser Ser Leu Ser Ala Ser Val Gly
1               5                   10                  15

Asp Arg Val Thr Ile Thr Cys Arg Ala Ser Asp Asn Leu Tyr Ser Asn
            20                  25                  30

Leu Ala Trp Tyr Gln Gln Lys Pro Gly Lys Ser Pro Lys Leu Leu Val
        35                  40                  45

Tyr Asp Ala Thr Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Ala Gly Thr Pro Leu
                85                  90                  95

Thr Phe Gly Gln Gly Thr Lys Val Glu Ile Lys
                100                 105

<210> SEQ ID NO 152
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 152

Asp Ile Gln Met Thr Gln Ser Pro Ser Ser Leu Ser Ala Ser Val Gly
1               5                   10                  15

Asp Arg Val Thr Ile Thr Cys Arg Ala Ser Asp Asn Leu Tyr Ser Asn
            20                  25                  30

Leu Ala Trp Tyr Gln Gln Lys Pro Gly Lys Ser Pro Lys Leu Leu Val
        35                  40                  45

Tyr Asp Ala Thr Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Gly Thr Pro Leu 85                  90                  95

Thr Phe Gly Gln Gly Thr Lys Val Glu Ile Lys
                100                 105

<210> SEQ ID NO 153
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 153

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Arg Leu Glu Trp Ile
            35                  40                  45

Gly Glu Ile Ala Pro Thr Asn Gly Arg Thr Asn Tyr Ile Glu Lys Phe
        50                  55                  60

Lys Ser Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Thr Arg Ala Tyr His Tyr Trp Gly Gln Gly Thr Met Val
                100                 105                 110

Thr Val Ser Ser
        115

<210> SEQ ID NO 154
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 154

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Arg Leu Glu Trp Ile
            35                  40                  45

Gly Glu Ile Asn Pro Ala Asn Gly Arg Thr Asn Tyr Ile Glu Lys Phe
        50                  55                  60

Lys Ser Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Thr Arg Ala Tyr His Tyr Trp Gly Gln Gly Thr Met Val
                100                 105                 110

Thr Val Ser Ser
        115

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158
<211> LENGTH: 116
<212> TYPE: PRT
<213> ORGANISM: Artificial Sequence
<220> FEATURE:
<223> OTHER INFORMATION: Synthetic

<400> SEQUENCE: 158

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Arg Leu Glu Trp Ile
        35                  40                  45

Gly Glu Ile Ala Pro Thr Asn Gly Arg Thr Asn Tyr Ile Glu Lys Phe
    50                  55                  60

Lys Ser Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Thr Arg Ala Tyr His Tyr Trp Gly Gln Gly Thr Leu Val
            100                 105                 110

Thr Val Ser Ser
            115
```

<210> SEQ ID NO 159
<211> LENGTH: 116
<212> TYPE: PRT
<213> ORGANISM: Artificial Sequence
<220> FEATURE:
<223> OTHER INFORMATION: Synthetic

<400> SEQUENCE: 159

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Arg Leu Glu Trp Ile
        35                  40                  45

Gly Glu Ile Asn Pro Thr Asn Gly Arg Thr Asn Tyr Ile Glu Lys Phe
    50                  55                  60

Lys Ser Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Thr Arg Ala Tyr His Tyr Trp Gly Gln Gly Thr Leu Val
            100                 105                 110
```

Thr Val Ser Ser
        115

<210> SEQ ID NO 160
<211> LENGTH: 446
<212> TYPE: PRT
<213> ORGANISM: Artificial Sequence
<220> FEATURE:
<223> OTHER INFORMATION: Synthetic

<400> SEQUENCE: 160

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Arg Leu Glu Trp Ile
        35                  40                  45

Gly Glu Ile Asn Pro Thr Asn Gly Arg Thr Asn Tyr Ile Glu Lys Phe
    50                  55                  60

Lys Ser Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Thr Arg Ala Tyr His Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Tyr Ile Thr Arg Glu Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

```
Ser Arg Glu Glu Met Thr Lys Asn Gln Val Ser Leu Ser Cys Ala Val
            355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 161
<211> LENGTH: 214
<212> TYPE: PRT
<213> ORGANISM: Artificial Sequence
<220> FEATURE:
<223> OTHER INFORMATION: Synthetic

<400> SEQUENCE: 161

Asp Ile Gln Met Thr Gln Ser Pro Ser Ser Leu Ser Ala Ser Val Gly
1               5                   10                  15

Asp Arg Val Thr Ile Thr Cys Arg Ala Ser Asn Leu Tyr Ser Asn
            20                  25                  30

Leu Ala Trp Tyr Gln Gln Lys Pro Gly Lys Ser Pro Lys Leu Leu Val
            35                  40                  45

Tyr Asp Ala Thr Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Ala Gly Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 162
<211> LENGTH: 107
<212> TYPE: PRT
<213> ORGANISM: Artificial Sequence
<220> FEATURE:
<223> OTHER INFORMATION: Synthetic
```

```
<400> SEQUENCE: 162

Asp Ile Gln Met Thr Gln Ser Pro Ser Ser Leu Ser Ala Ser Val Gly
1               5                   10                  15

Asp Arg Val Thr Ile Thr Cys Arg Ala Ser Asp Asn Leu Tyr Ser Asn
            20                  25                  30

Leu Ala Trp Tyr Gln Gln Lys Pro Gly Lys Ser Pro Lys Leu Leu Val
        35                  40                  45

Tyr Asp Ala Thr Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Gly Thr Pro Leu
                85                  90                  95

Thr Phe Gly Gln Gly Thr Lys Val Glu Ile Lys
                100                 105

<210> SEQ ID NO 163
<211> LENGTH: 107
<212> TYPE: PRT
<213> ORGANISM: Artificial Sequence
<220> FEATURE:
<223> OTHER INFORMATION: Synthetic

<400> SEQUENCE: 163

Asp Ile Gln Met Thr Gln Ser Pro Ser Ser Leu Ser Ala Ser Val Gly
1               5                   10                  15

Asp Arg Val Thr Ile Thr Cys Arg Ala Ser Asp Asn Leu Tyr Ser Asn
            20                  25                  30

Leu Ala Trp Tyr Gln Gln Lys Pro Gly Lys Ser Pro Lys Leu Leu Val
        35                  40                  45

Tyr Asp Ala Thr Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Ala Gly Thr Pro Leu
                85                  90                  95

Thr Phe Gly Gln Gly Thr Lys Val Glu Ile Lys
                100                 105
```

ANTI-TRANSFERRIN RECEPTOR ANTIBODIES AND METHODS OF USE

CROSS-REFERENCE TO RELATED APPLICATIONS

This application is a national phase entry pursuant to 35 U.S.C. § 371 of International Application No. PCT/US2015/061405, filed Nov. 18, 2015, which claims the benefit of priority of U.S. Provisional Application No. 62/081,827, filed Nov. 19, 2014, which is incorporated by reference herein in its entirety for any purpose.

SEQUENCE LISTING

The present application is filed with a Sequence Listing in electronic format. The Sequence Listing is provided as a file entitled "2015-11-18_01146-0042-00PCT_ST25.txt" created on Nov. 18, 2015, which is 130,420 bytes in size. The information in the electronic format of the sequence listing is incorporated herein by reference in its entirety.

FIELD OF THE INVENTION

The present invention relates to anti-transferrin receptor antibodies and methods of using the same.

BACKGROUND

Brain penetration of large molecule drugs is severely limited by the largely impermeable blood-brain barrier (BBB). Among the many strategies to overcome this obstacle is to utilize transcytosis trafficking pathways of endogenous receptors expressed at the brain capillary endothelium. Recombinant proteins such as monoclonal antibodies have been designed against these receptors to enable receptor-mediated delivery of large molecules to the brain. Strategies to maximize brain uptake while minimizing reverse transcytosis back to the blood, and to also maximize the extent of accumulation after therapeutic dosing have been addressed with the finding that antibodies with low affinity to BBB receptors offer the potential to substantially increase BBB transport and CNS retention of associated therapeutic moieties/molecules relative to typical high-affinity antibodies to such receptors (Atwal et al., Sci. Transl. Med. 3, 84ra43 (2011); Yu et al., Sci. Transl. Med. 25 May 2011: Vol. 3, Issue 84, p. 84ra44). However, those antibodies did not specifically bind to human and primate TfR.

SUMMARY

Monoclonal antibodies have vast therapeutic potential for treatment of neurological or central nervous system (CNS) diseases, but their passage into the brain is restricted by the blood-brain barrier (BBB). Past studies have shown that a very small percentage (approximately 0.1%) of an IgG circulating in the bloodstream crosses through the BBB into the CNS (Felgenhauer, Klin. Wschr. 52: 1158-1164 (1974)), where the CNS concentration of the antibody may be insufficient to permit a robust effect. It was previously found that the percentage of the antibody that distributes into the CNS could be improved by exploiting BBB receptors (ie, transferrin receptor, insulin receptor and the like) (see, e.g., WO9502421). For example, the anti-BBB receptor antibody can be made multispecific to target one or more desired antigens in the CNS, or one or more heterologous molecules can be coupled to the anti-BBB receptor antibody; in either case, the anti-BBB receptor antibody can assist in delivering a therapeutic molecule into the CNS across the BBB.

However, targeting a BBB receptor with a traditional specific high-affinity antibody generally resulted in limited increase in BBB transport. It was later found by Applicants that the magnitude of antibody uptake into and distribution in the CNS is inversely related to its binding affinity for the BBB receptor amongst the anti-BBB antibodies studied. For example, a low-affinity antibody to transferrin receptor (TfR) dosed at therapeutic dose levels greatly improves BBB transport and CNS retention of the anti-TfR antibody relative to a higher-affinity anti-TfR antibody, and makes it possible to more readily attain therapeutic concentrations in the CNS (Atwal et al., Sci. Transl. Med. 3, 84ra43 (2011)). Proof of such BBB transport was achieved using a bispecific antibody that binds both TfR and the amyloid precursor protein (APP) cleavage enzyme, β-secretase (BACE1). A single systemic dose of the bispecific anti-TfR/BACE1 antibody engineered using the methodology of the invention not only resulted in significant antibody uptake in brain, but also dramatically reduced levels of brain $A\beta_{1-40}$ compared to monospecific anti-BACE1 alone, suggesting that BBB penetrance affects the potency of anti-BACE1. (Atwal et al., Sci. Transl. Med. 3, 84ra43 (2011); Yu et al., Sci. Transl. Med. 3, 84ra44 (2011)).

Those data and experiments highlighted several causative mechanisms behind increasing uptake of an antibody into the CNS using a lower-affinity antibody approach. First, high affinity anti-BBB receptor (BBB-R) antibodies (e.g., anti-TfR[A] from Atwal et al. and Yu et al., supra) limit brain uptake by quickly saturating the BBB-R in the brain vasculature, thus reducing the total amount of antibody taken up into the brain and also restricting its distribution to the vasculature. Strikingly, lowering affinity for the BBB-R improves brain uptake and distribution, with a robust shift observed in localization from the vasculature to neurons and associated neuropil distributed within the CNS. Second, the lower affinity of the antibody for the BBB-R is proposed to impair the ability of the antibody to return to the vascular side of the BBB via the BBB-R from the CNS side of the membrane because the overall affinity of the antibody for the BBB-R is low and the local concentration of the antibody on the CNS side of the BBB is non-saturating due to the rapid dispersal of the antibody into the CNS compartment. Third, in vivo, and as observed for the TfR system, antibodies with less affinity for the BBB-R are not cleared from the system as efficiently as those with greater affinity for the BBB-R, and thus remain at higher circulating concentrations than their higher-affinity counterparts. This is advantageous because the circulating antibody levels of the lower-affinity antibody are sustained at therapeutic levels for a longer period of time than the higher-affinity antibody, which consequently improves uptake of antibody in brain for a longer period of time. Furthermore, this improvement in both plasma and brain exposure may reduce the frequency of dosing in the clinic, which would have potential benefit not only for patient compliance and convenience but also in lessening any potential side effects or off-target effects of the antibody and/or of a therapeutic compound coupled thereto.

The low-affinity BBB-R antibodies described in the above-referenced work were selected/engineered to avoid interference with the natural binding between transferrin and the TfR, and thus to avoid potential iron transport-related side effects. Nonetheless, upon administration of certain of these antibodies in mice, some marked side effects were observed. The mice displayed a primary response of robust depletion of reticulocyte populations accompanied by rapid onset acute clinical symptoms. Though the mice recovered from both the acute clinical symptoms and the decreased reticulocyte levels in due course, avoiding or otherwise mitigating this impact on reticulocytes is clearly desirable for an anti-TfR antibody to be able to be used safely as a therapeutic molecule. It was found that the primary response to anti-TfR administration (robust reticulocyte depletion and acute clinical signs) is driven in large part by the antibody-dependent cell-mediated cytotoxicity (ADCC) activity of the antibody, while the residual reticulocyte depletion effect is mediated by the complement pathway.

These prior studies utilized mouse antibodies which bound specifically to mouse TfR, but which did not specifically recognize primate or human TfR. Accordingly, the invention provides antibodies and functional parts thereof which do specifically recognize both primate and human TfR, in order to facilitate safety and efficacy studies in primates with the antibodies prior to therapeutic or diagnostic use in humans. In vitro studies using a human erythroblast cell line and primary bone marrow cells treated with the anti-human TfR antibodies of the invention demonstrated that a robust depletion of TfR-positive erythroid cells is also observable in human/primate cellular systems as it is in mice (see, e.g., Example 4). Accordingly, also provided herein are modifications to the antibodies of the invention to greatly reduce or eliminate the unwanted reduction in the TfR-expressing reticulocyte population upon anti-TfR administration while still enabling the enhanced BBB transport, increased CNS distribution and CNS retention provided by the anti-human/primate TfR antibodies administered at therapeutic concentrations. Several general approaches to mitigate the observed effect of the anti-TfR antibodies of the invention on both the primary and residual reticulocyte depletion are provided herein, and may be used singly or in combination.

In one approach, the effector function of the anti-human/cyno TfR antibody is reduced or eliminated in order to reduce or eliminate ADCC activity. In another approach, the affinity of the anti-human/cyno TfR antibody for human or primate TfR is further lessened such that interactions of the antibody with the reticulocyte population are less detrimental to that population. A third approach is directed to reducing the amount of anti-human/cyno TfR antibody that is present in the plasma to reduce exposure of the reticulocyte population to potentially detrimental concentrations of the antibody. A fourth approach seeks to protect, stabilize and/or replenish reticulocyte populations such that any potential depletion of the reticulocyte population in circulation or in bone marrow by administration of the anti-human/cyno TfR antibody is avoided, lessened, or mitigated.

Effector function reduction or elimination, as described herein, may be accomplished by: (i) reduction or elimination of wild-type mammalian glycosylation of the antibody, (for example, by producing the antibody in an environment where such glycosylation cannot occur, by mutating one or more carbohydrate attachment points such that the antibody cannot be glycosylated, or by chemically or enzymatically removing one or more carbohydrates from the antibody after it has been glycosylated); (ii) by reduction or elimination of the Fc receptor-binding capability of the anti-human/cyno TfR antibody (for example, by mutation of the Fc region, by deletion within the Fc region or elimination of the Fc region); or (iii) by utilization of an antibody isotype known to have minimal or no effector function (ie., including but not limited to IgG4).

Decreasing antibody complement activation, as described herein, may be accomplished by reduction or elimination of the C1q binding capability of the anti-human/cyno TfR antibody (for example, by mutation of, deletion within or elimination of the Fc region, or by modifying the non-Fc portion of the anti-human/cyno TfR antibody), or by otherwise suppressing activation or activity of the complement system (for example, by co-administering one or more complement pathway activation or complement pathway activity inhibitors).

When binding of anti-human/cyno TfR antibody to human or cyno TfR on reticulocytes or other cell types expressing high levels of TfR triggers their depletion, as with the anti-human/cyno TfR antibodies exemplified herein, reduction of binding of the antibodies to the human or cyno TfR on the reticulocytes or other cell types should in turn decrease the amount of reticulocyte or other cell type depletion in circulation or in bone marrow observed upon antibody administration. The affinity of the anti-human/cyno TfR antibody for primate or human TfR may be modified using any of the methods described herein and as shown in the Examples.

Reducing the amount of anti-human/cyno TfR antibody present in the plasma in order to reduce exposure of the reticulocyte population to potentially detrimental concentrations of the antibody may be accomplished in several ways. One method is to simply decrease the amount of the antibody that is dosed, potentially while also increasing the frequency of the dosing, such that the maximal concentration in the plasma is lowered but a sufficient serum level is maintained for efficacy, while still below the threshold of the cell-depleting side effect. Another method, which may be combined with dosing modifications, is to select or engineer an anti-TfR antibody that has pH-sensitive binding to TfR such that it binds to cell surface TfR in the plasma at pH 7.4 with desirably low affinity as described herein, but upon internalization into an endosomal compartment, such binding to TfR is rapidly and significantly reduced at the relatively lower pH of that compartment (pH 5.5-6.0). Such dissociation may protect the antibody from antigen-mediated clearance, or increase the amount of antibody that is either delivered to the CNS or recycled back across the BBB—in either case, the effective concentration of the antibody is increased relative to an anti-TfR antibody that does not comprise such pH sensitivity, without increasing the administered dose of the antibody, and in turn potentially permitting a lower dose of the antibody with concomitantly lesser risk of side effects.

Protecting, stabilizing and/or replenishing reticulocyte populations may be accomplished using pharmaceutical or physical methods. In addition to the anti-human/cyno TfR antibody, at least one further therapeutic agent may be coadministered (simultaneously or sequentially) that mitigates negative side effects of the antibody on reticulocyte populations. Examples of such therapeutic agents include, but are not limited to, erythropoietin (EPO), iron supplements, vitamin C, folic acid, and vitamin B12. Physical replacement of red blood cells (ie, reticulocytes) is also possible by, for example, transfusion with similar cells, which may be from another individual of similar blood type or may have been previously extracted from the subject to whom the anti-human/cyno TfR antibody is administered.

One of ordinary skill in the art will appreciate that any combination of the foregoing methods may be employed to engineer an antibody (and/or dosage regimen for same) with the optimum balance between (i) the desirably low affinity for primate or human TfR that will maximize transport of the antibody and any conjugated compounds into the CNS; (ii) the affinity of the conjugated compound (including as a nonlimiting example, a second or further antigen-binding specificity in the anti-human/cyno TfR antibody) for its CNS antigen, since this is relevant to the amount of the compound that needs to be present in the CNS to have a therapeutic effect; (iii) the clearance rate of the anti-human/cynoTfR antibody; (iv) the liability of the anti-TfR/conjugated compound at low pH to facilitate release of the conjugated compound on the CNS/brain side of the BBB, and (v) the impact on reticulocyte populations.

It will also be appreciated that the reticulocyte-depleting effect recognized herein of anti-TfR antibody administration may be useful in the treatment of any disease or disorder where overproliferation of reticulocytes is problematic. For example, in congenital polycythemia or neoplastic polycythemia vera, raised red blood cell counts due to hyperproliferation of, e.g., reticulocytes, results in thickening of blood and concomitant physiological symptoms. Administration of an anti-human/cyno TfR antibody of the invention wherein at least partial effector function of the antibody was preserved would permit selective removal of immature reticulocyte populations without impacting normal transferrin transport into the CNS. Dosing of such an antibody could be modulated such that acute clinical symptoms could be minimized (ie, by dosing at a very low dose or at widely-spaced intervals), as well-understood in the art.

Anti-TfR/BACE1 and anti-TfR/Abeta are each promising and novel therapeutic candidates for the treatment of Alzheimer's disease. Furthermore, receptor mediated transport (RMT)-based bispecific targeting technology opens the door for a wide range of potential therapeutics for CNS diseases. The invention provides methods of engineering BBB-penetrant therapeutics that greatly improve transport across the BBB and CNS distribution of the therapeutic without depletion of reticulocytes.

Accordingly, in a first embodiment, the invention provides an isolated antibody that binds to human transferrin receptor (TfR) and primate TfR, wherein the antibody does not inhibit the binding of transferrin to TfR. In some aspects, the binding is specific binding. In another aspect, the antibody further does not inhibit the binding of human hemachromatosis protein ("HFE") to TfR. In some aspects, the binding is specific binding. In some aspects, the antibody is a monoclonal antibody. In another aspect, the antibody is a human antibody. In another aspect, the antibody is a humanized antibody. In another aspect, the antibody is a chimeric antibody. In another aspect, the antibody is an antibody fragment that binds human TfR and primate TfR. In another aspect, the primate TfR is from cynomolgous monkey.

In any of the embodiments described herein, the antibody comprises a heavy chain variable region (VH) sequence of SEQ ID NO: 158 or 159. In any of the embodiments described herein, the antibody further comprises a light chain variable region (VL) sequence of SEQ ID NO: 162 or 163. In some embodiments, the antibody comprises a heavy chain variable region amino acid sequence of SEQ ID NO: 158 and a light chain variable region amino acid sequence of SEQ ID NO: 162, or a heavy chain variable region amino acid sequence of SEQ ID NO: 159 and a light chain variable region amino acid sequence of SEQ ID NO: 163.

In some aspects of the above embodiment, the antibody is coupled to a therapeutic compound. In another aspect of the above embodiment, the antibody is coupled to an imaging agent or a label. In one such aspect, the antibody is a multispecific antibody and the therapeutic compound optionally forms one portion of the multispecific antibody.

In one such aspect, the multispecific antibody comprises a first antigen binding site which binds TfR and a second antigen binding site which binds a brain antigen. In one such aspect, the brain antigen is selected from the group consisting of: beta-secretase 1 (BACE1), Abeta, epidermal growth factor receptor (EGFR), human epidermal growth factor receptor 2 (HER2), tau, apolipoprotein E (ApoE), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), and caspase 6. In another such aspect, the multispecific antibody binds both TfR and BACE1. In another such aspect, the multispecific antibody binds both TfR and Abeta. In another such aspect, the therapeutic compound is a neurological disorder drug.

In some embodiments, the multispecific antibody comprises a first heavy chain comprising the sequence of SEQ ID NO: 160 and a first light chain comprising the sequence of SEQ ID NO: 161.

In some aspects of the above embodiment, the invention provides an isolated nucleic acid encoding any of the foregoing antibodies. In another aspect, the invention provides a host cell comprising such nucleic acid. In another aspect, the invention provides a method of producing any of the foregoing antibodies comprising culturing such host cell so that the antibody is produced and optionally further comprising recovering the antibody from the host cell.

In some aspects of the above embodiment, the invention provides a pharmaceutical formulation comprising any of the foregoing antibodies and a pharmaceutically acceptable carrier.

In some aspects of the above embodiment, the invention provides any of the foregoing antibodies for use as a medicament. In another aspect of the above embodiment, the invention provides the use of any of the foregoing antibodies in the manufacture of a medicament for treating a neurological disorder. In one such aspect, the neurological disorder is selected from the group consisting of a neuropathy disorder, a neurodegenerative disease, cancer, an ocular disease disorder, a seizure disorder, a lysosomal storage disease, amyloidosis, a viral or microbial disease, ischemia, a behavioral disorder, and CNS inflammation.

In another aspect of the above embodiment, the invention provides any of the foregoing antibodies for use in treating a neurological disorder. In one such aspect, the neurological disorder is selected from the group consisting of a neuropathy disorder, a neurodegenerative disease, cancer, an ocular disease disorder, a seizure disorder, a lysosomal storage disease, amyloidosis, a viral or microbial disease, ischemia, a behavioral disorder, and CNS inflammation.

In another aspect of the above embodiment, the invention provides any of the foregoing antibodies for use in transporting one or more compounds across the BBB. In another aspect of the above embodiment, use of any of the foregoing antibodies in the manufacture of a medicament for transporting one or more compounds across the BBB is provided.

In some aspects of the above embodiment, a method of transporting a compound across the BBB in a subject is provided, comprising exposing any of the foregoing antibodies to the BBB such that the antibody transports the compound coupled thereto across the BBB. In another such aspect, the BBB is in a human subject. In another such aspect, the dose amount and/or frequency of administration is modulated to reduce the concentration of antibody to which red blood cells are exposed. In another such aspect, the method further comprises the step of monitoring the subject for depletion of red blood cells. In another such aspect, the antibody coupled to the compound is administered at a therapeutic dose. In one such aspect, the therapeutic dose is TfR-saturating. In another such aspect, administration of the antibody is at a dose and/or dose frequency calibrated to minimize acute clinical symptoms of the antibody administration.

In another aspect of the above embodiment, a method of increasing exposure of the CNS of a subject to a compound is provided, comprising exposing any of the foregoing antibodies to the BBB such that the antibody transports the compound coupled thereto across the BBB. In another such aspect, the BBB is in a human subject. In another such aspect, the dose amount and/or frequency of administration is modulated to reduce the concentration of antibody to which red blood cells are exposed. In another such aspect, the method further comprises the step of monitoring the subject for depletion of red blood cells. In another such aspect, the antibody coupled to the compound is administered at a therapeutic dose. In one such aspect, the therapeutic dose is TfR-saturating. In another such aspect, administration of the antibody is at a dose and/or dose frequency calibrated to minimize acute clinical symptoms of the antibody administration.

In some aspects of the above embodiment, a method of increasing rentention in the CNS of a compound administered to a subject is provided, comprising exposing any of the foregoing antibodies to the BBB such that the retention in the CNS of the compound is increased. In another such aspect, the BBB is in a human subject. In another such aspect, the dose amount and/or frequency of administration is modulated to reduce the concentration of antibody to which red blood cells are exposed. In another such aspect, the method further comprises the step of monitoring the subject for depletion of red blood cells. In another such aspect, the antibody coupled to the compound is administered at a therapeutic dose. In one such aspect, the therapeutic dose is TfR-saturating. In another such aspect, administration of the antibody is at a dose and/or dose frequency calibrated to minimize acute clinical symptoms of the antibody administration.

In some aspects of the above embodiment, a method of treating a neurological disorder in a mammal is provided, comprising treating the mammal with any of the foregoing antibodies. In one such aspect, the neurological disorder is selected from the group consisting of a neuropathy disorder, a neurodegenerative disease, cancer, an ocular disease disorder, a seizure disorder, a lysosomal storage disease, amyloidosis, a viral or microbial disease, ischemia, a behavioral disorder, and CNS inflammation. In another such aspect, the neurological disorder is in a human subject. In another such aspect, the dose amount and/or frequency of administration is modulated to reduce the concentration of antibody to which the re blood cells are exposed. In another such aspect, the method further comprises the step of monitoring the subject for depletion of red blood cells. In another such aspect, the antibody coupled to the compound is administered at a therapeutic dose. In one such aspect, the therapeutic dose is TfR-saturating. In another such aspect, administration of the antibody is at a dose and/or dose frequency calibrated to minimize acute clinical symptoms of the antibody administration.

In another embodiment, the invention provides an isolated antibody that binds to human TfR and primate TfR, wherein the antibody does not inhibit the binding of transferrin to TfR, and wherein one or more properties of the antibody have been modified to reduce or eliminate the impact of the antibody on reticulocytes and/or reduce the severity or presence of acute clinical symptoms in a subject or mammal treated with the antibody. In some aspects, the binding is specific binding. In another aspect, the antibody further does not inhibit the binding of HFE to TfR. In some aspects, the antibody is a monoclonal antibody. In another aspect, the antibody is a human antibody. In another aspect, the antibody is a humanized antibody. In another aspect, the antibody is a chimeric antibody. In another aspect, the antibody is an antibody fragment that binds human TfR and primate TfR. In another aspect, the primate TfR is from cynomolgous monkey.

In some aspects of the above embodiment, the one or more properties of the antibody are selected from the effector function of the antibody Fc region, the complement activation function of the antibody and the affinity of the antibody for TfR. In one such aspect, the property is the effector function of the antibody Fc region. In another such aspect, the property is the complement activation function of the antibody. In another such aspect, the property is the affinity of the antibody for TfR. In one such aspect, the effector function or complement activation function has been reduced or eliminated relative to a wild-type antibody of the same isotype. In some aspects, the effector function is reduced or eliminated by a method selected from reduction of glycosylation of the antibody, modification of the antibody isotype to an isotype that naturally has reduced or eliminated effector function, and modification of the Fc region.

In one such aspect, the effector function is reduced or eliminated by reduction of glycosylation of the antibody. In one such aspect, the glycosylation of the antibody is reduced by a method selected from: production of the antibody in an environment that does not permit wild-type glycosylation; removal of carbohydrate groups already present on the antibody; and modification of the antibody such that wild-type glycosylation does not occur. In one such aspect, the glycosylation of the antibody is reduced by a production of the antibody in an environment that does not permit wild-type glycosylation, such as production in a non-mammalian cell production system or where the antibody is produced synthetically. In one such aspect, the antibody is produced in a non-mammalian cell production system. In another such aspect, the antibody is produced synthetically. In another such aspect, the glycosylation of the antibody is reduced by modification of the antibody such that wild-type glycosylation does not occur, such as wherein the Fc region of the antibody comprises a mutation at position 297 such that the wild-type asparagine residue at that position is replaced with another amino acid that interferes with glycosylation at that position.

In another such aspect, the effector function is reduced or eliminated by at least one modification of the Fc region. In one such aspect, the effector function or complement activation function is reduced or eliminated by deletion of all or a portion of the Fc region, or by engineering the antibody such that it does not include an Fc region or non-Fc region competent for effector function or complement activation function. In another such aspect, the at least one modification of the Fc region is selected from: a point mutation of the Fc region to impair binding to one or more Fc receptors selected from the following positions: 238, 239, 248, 249, 252, 254, 265, 268, 269, 270, 272, 278, 289, 292, 293, 294, 295, 296, 297, 298, 301, 303, 322, 324, 327, 329, 333, 335, 338, 340, 373, 376, 382, 388, 389, 414, 416, 419, 434, 435, 437, 438, and 439; a point mutation of the Fc region to impair binding to C1q selected from the following positions:

270, 322, 329, and 321; eliminating some or all of the Fc region, and a point mutation at position 132 of the CH1 domain. In one such aspect, the modification is a point mutation of the Fc region to impair binding to C1q selected from the following positions: 270, 322, 329, and 321. In another such aspect, the modification is elimination of some or all of the Fc region. In another such aspect, complement-triggering triggering function is reduced or eliminated by deletion of all or a portion of the Fc region, or by engineering the antibody such that it does not include an Fc region that engages the complement pathway. In one such aspect, the antibody is selected from a Fab or a single chain antibody. In another such aspect, the non-Fc region of the antibody is modified to reduce or eliminate activation of the complement pathway by the antibody. In one such aspect, the modification is a point mutation of the CH1 region to impair binding to C3. In one such aspect, the point mutation is at position 132 (see, e.g., Vidarte et al., (2001) J. Biol. Chem. 276(41): 38217-38223).

In some aspects, the antibody the half-life of the antibody is increased by a modification in the FcRn binding region. In some aspects, the modification is a substitution in an amino acid selected from the following positions: 251 256, 285, 290, 308, 314, 385, 389, 428, 434, 436, 238, 265, 272, 286, 303, 305, 307, 311, 312, 317, 340, 356, 360, 362, 376, 378, 380, 382, 413, 424 or 434. In some aspects the modification is a substitution selected from the following: M252Y, S254T, T256E, N434A and Y436I.

In some aspects, the antibody is combined with a further compound that mitigates or contributes to the reduction of impact on reticulocyte levels or acute clinical symptoms. In one such aspect, the further compound protects reticulocytes from antibody-related depletion or supports the growth, development, or reestablishment of reticulocytes. In another such aspect, the further compound is selected from erythropoietin (EPO), an iron supplement, vitamin C, folic acid, and vitamin B12, or is red blood cells or reticulocytes.

In some aspects of the above embodiment, the affinity of the antibody for TfR is decreased, as measured relative to a wild-type antibody of the same isotype not having lowered affinity for TfR. In one such aspect, the antibody has a KD or IC50 for TfR of about 1 pM to about 100 µM, or about 10 nM to 100 nM, or about 20 nM to 100 nM. In another aspect, the dose amount and/or frequency of administration of the antibody is modulated to reduce the concentration of the antibody to which the red blood cells are exposed.

In another embodiment, a method of decreasing clearance of a compound administered to a subject is provided, wherein the compound is coupled to an antibody which binds with low affinity to TfR, such that the clearance of the compound is decreased, and wherein reduction of red blood cell levels in the subject upon compound-coupled antibody administration to the subject is decreased or eliminated.

In another embodiment, a method of optimizing the pharmcokinetics and/or pharmacodynamics of a compound to be efficacious in the CNS in a subject is provided, wherein the compound is coupled to an antibody which binds with low affinity to TfR, and the antibody is selected such that its affinity for TfR after coupling to the compound results in an amount of transport of the antibody conjugated to the compound across the BBB that optimizes the pharmacokinetics and/or pharmacodynamics of the compound in the CNS, wherein reduction of red blood cell levels in the subject upon compound-coupled antibody administration to the subject is decreased or eliminated.

It will be understood that any of the foregoing methods and compositions of the invention may be combined with one another and/or with the further aspects of the invention described in the specification herein.

BRIEF DESCRIPTION OF THE FIGURES

FIG. 2C depicts the results of human/cynomolgous cross-reactive antibody competition assays as described in Example 1. Nine of the fourteen clones were found to block binding of the apical binding antibody displayed on phage.

FIGS. 3A-1, 3A-2, 3B-1, 3B-2, 3C-1, 3C-2, 3D-1and 3D-2 depict the heavy and light chain variable region sequences of hybridoma clones that bind to apical and non-apical regions of TfR. The sequences can be further subdivided by epitope and sequence similarity into class I-III (apical binders) and class IV (non-apical binders). The HVRs according to Kabat are indicated by underlining.

Figure 4D-1:
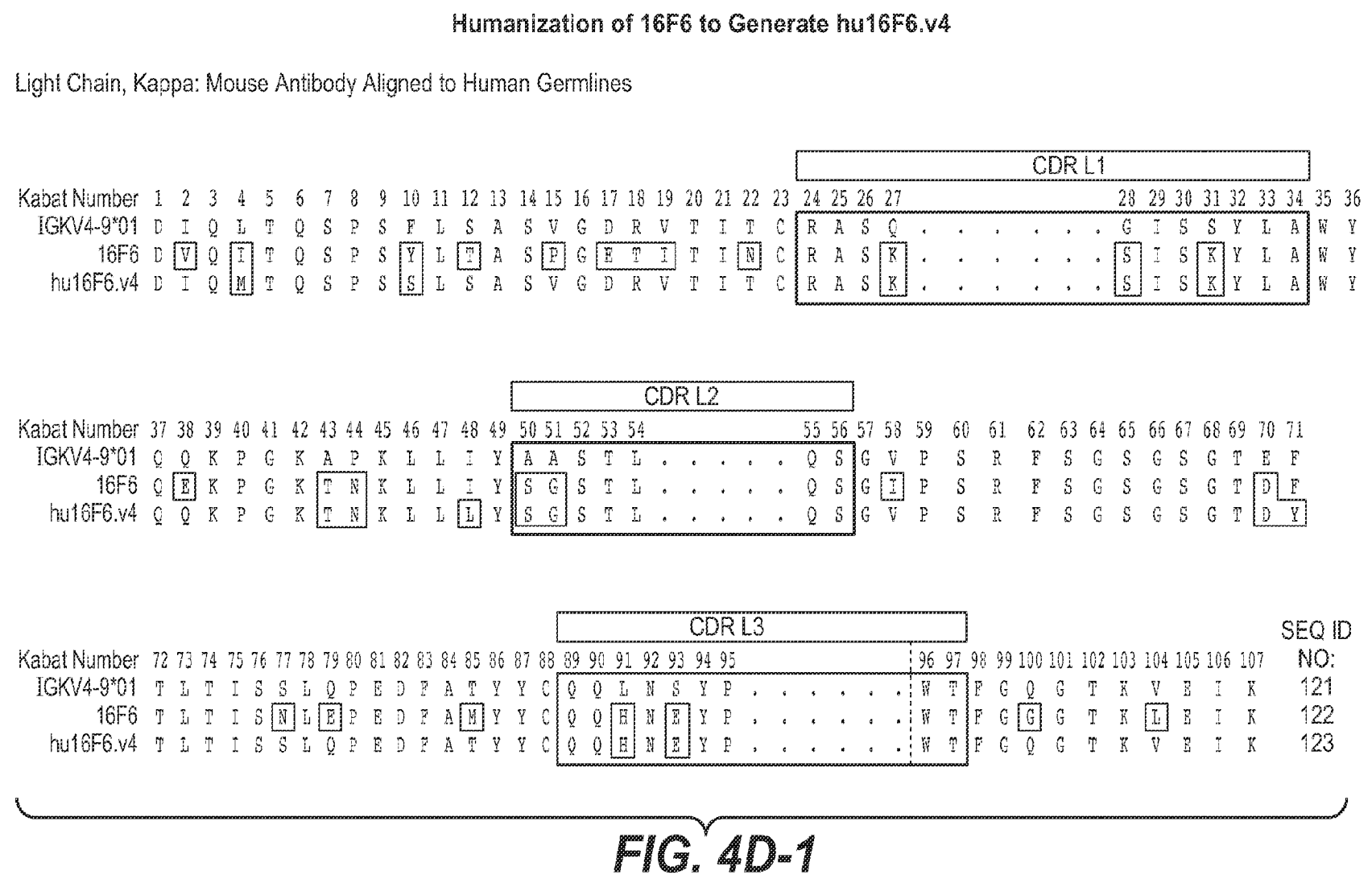

FIGS. 4A-1, 4A-2, 4B-1, 4B-2, 4C-1, 4C-2, 4D-1 and 4D-2 depict alignments of humanized sequences for (A) 15G11, (B) 7A4/8A2, (C) 7G7 and (D) 16F6. Each mouse light or heavy variable domain sequence (second line) is aligned to the closest human germline or consensus variable domain (first line). The humanized version for each antibody is shown at the bottom (third line). Differences from the human germline or consensus sequences are shaded. HVR sequences that were grafted into the human framework are boxed. CDR definitions according to Kabat are indicated.

FIGS. 4E-1 and 4E-2 show that for the class I-III groups of antibodies, variant forms of the antibodies with modifications at one or more residues of an FR retained affinity and binding specifity.

FIGS. 6A-B depict the results of the HFE—HuTfR binding and the HFE blocking assays described in Example 1. FIG. 6A shows the binding of antibody to increasing concentrations of huTfR captured via immobilized HFE. FIG. 6B shows the binding of huTfR to immobilized HFE in the presence of increasing concentrations of antibody.

FIG. 7A-B depict binding analyses of 15G11.v5 and 7A4.v5 IgG and Fab Ala variants on cyno and human TfR, demonstrating the effects on affinity of Ala mutations in CDR-L3 and CDR-H3 of each antibody assessed as IgG by ELISA binding and IgG or Fab by SPR analysis to immobilized human or cyno TfR, as described in Example 2.

FIG. 15A shows individual and group mean anti-TfR$^1$/BACE1, anti-TfR$^2$/BACE1, anti-gD, and anti-BACE1 ration of sAPPβ/sAPPα in CSF versus time following a single IV bolus administration at 30 mg/kg in cynomolgus monkeys. FIG. 15B show individual anti-TfR$^1$/BACE1, anti-TfR$^2$/BACE1, anti-gD, and anti-BACE1 concentrations of antibody in various brain regions at 24 hours post-dose.

FIGS. 16A-B depict the light and heavy chain amino acid sequences of anti-BACE1 clone YW412.8 obtained from a naïve sort of the natural diversity phage display library and affinity-matured forms of YW412.8. FIG. 16A depicts the variable light (VL) sequence alignments (SEQ ID NOs. 132-137). FIG. 16B depicts the variable heavy (VH) sequence alignments (SEQ ID Nos. 138-139). In both figures, the HVR sequences for each clone are indicated by the boxed regions, with the first box indicating HVR-L1 (FIG. 16A) or HVR-H1 (FIG. 16B), the second box indicating HVR-L2 (FIG. 16A) or HVR-H2 (FIG. 16B), and the third box indicating HVR-L3 (FIG. 16A) or HVR-H3 (FIG. 16B).

Figure 17A:
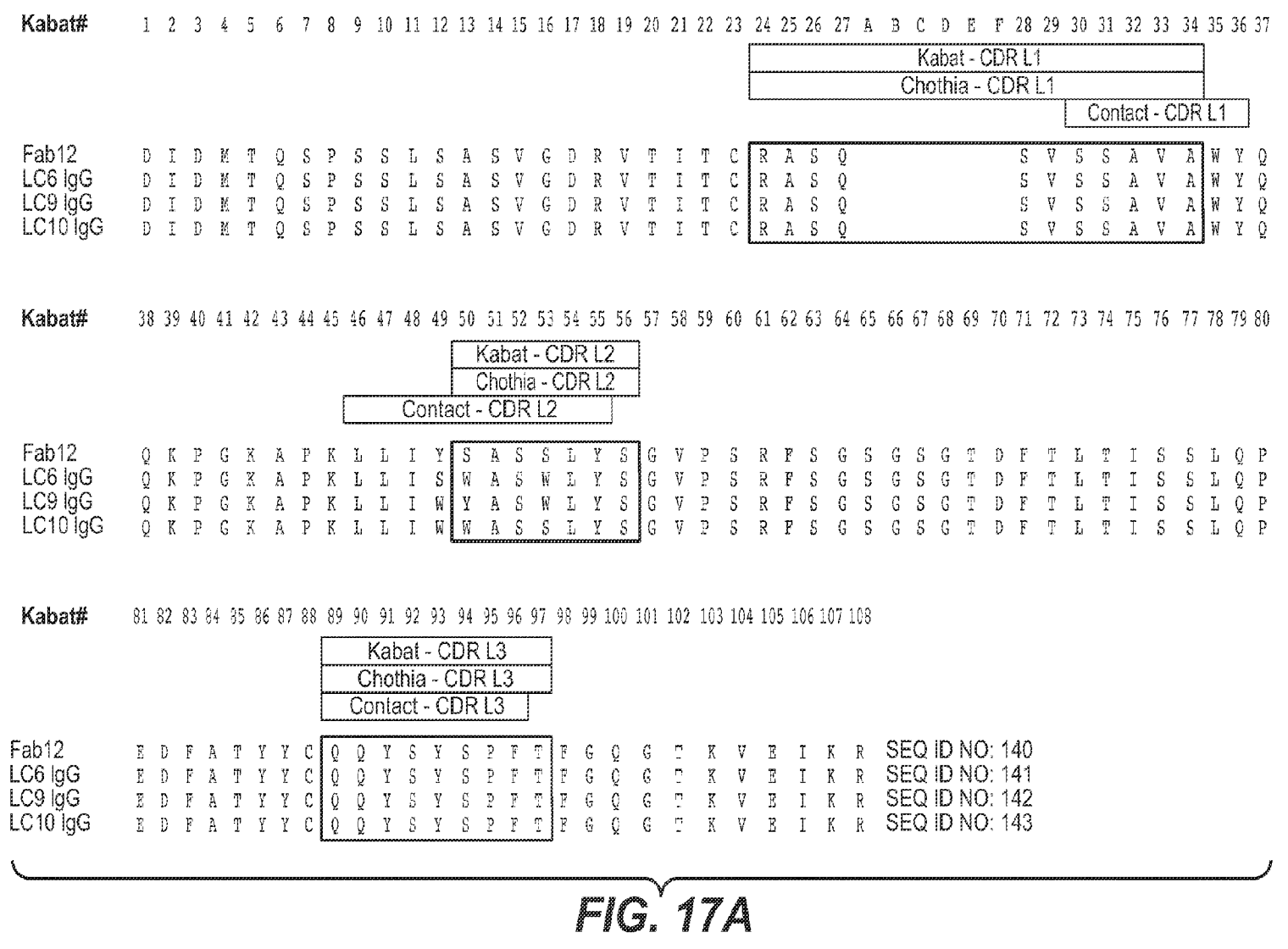
Figure 17B:
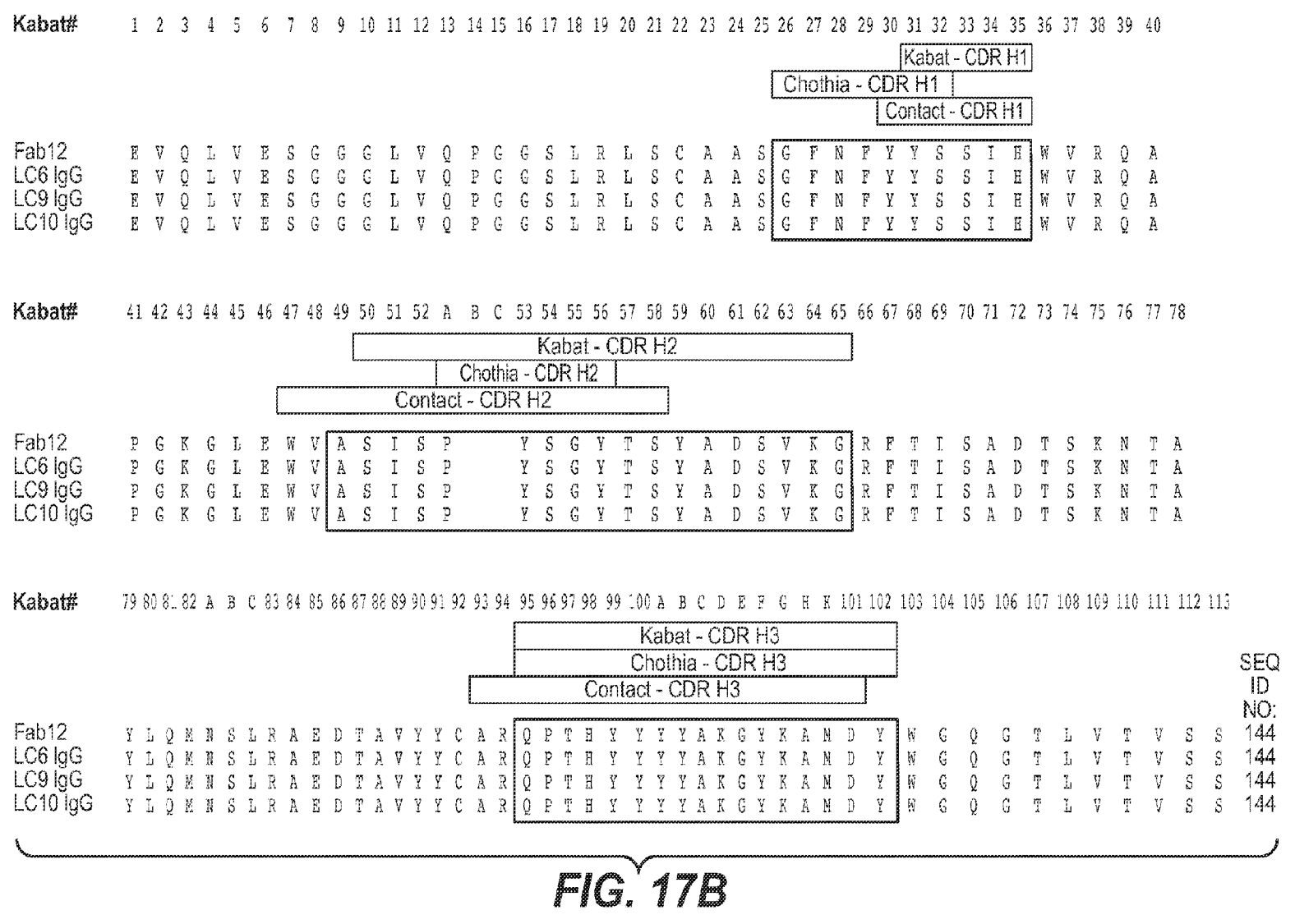

FIGS. 17A-B depict the light and heavy chain amino acid sequences of anti-BACE1 antibody clone Fab 12 obtained from a naïve sort of a synthetic diversity phage display library and affinity-matured forms of Fab 12. FIG. 17A depicts the light chain sequence alignments (SEQ ID NOs. 140-143). FIG. 17B depicts the heavy chain sequence alignments (SEQ ID NO. 144). In both figures, the HVR sequences for each clone are indicated by the boxed regions, with the first box indicating HVR-L1 (FIG. 17A) or HVR-H1 (FIG. 17B), the second box indicating HVR-L2 (FIG. 17A) or HVR-H2 (FIG. 17B), and the third box indicating HVR-L3 (FIG. 17A) or HVR-H3 (FIG. 17B).

FIGS. 18A-B depict the heavy chain (FIG. 18A; SEQ ID NO. 145) and light chain (FIG. 18B; SEQ ID NO. 146) of an exemplary anti-Abeta antibody.

FIG. 24 depicts the heavy and light chain variable region sequences of 1511Gv.5 (light chain—SEQ ID NO: 152 and heavy chain—SEQ ID NO: 108) and affinity variants 15G11.52A (light chain—SEQ ID NO:152 and heavy chain—SEQ ID NO: 153), 15G11.53A (light chain—SEQ ID NO: 152 and heavy chain—SEQ ID NO: 154) and 15G11.92A (light chain—SEQ ID NO: 151 and heavy chain—SEQ ID NO: 108). The HVRs according to Kabat are indicated by underlining.

DETAILED DESCRIPTION OF EMBODIMENTS OF THE INVENTION

1. Definitions

Figure 1:
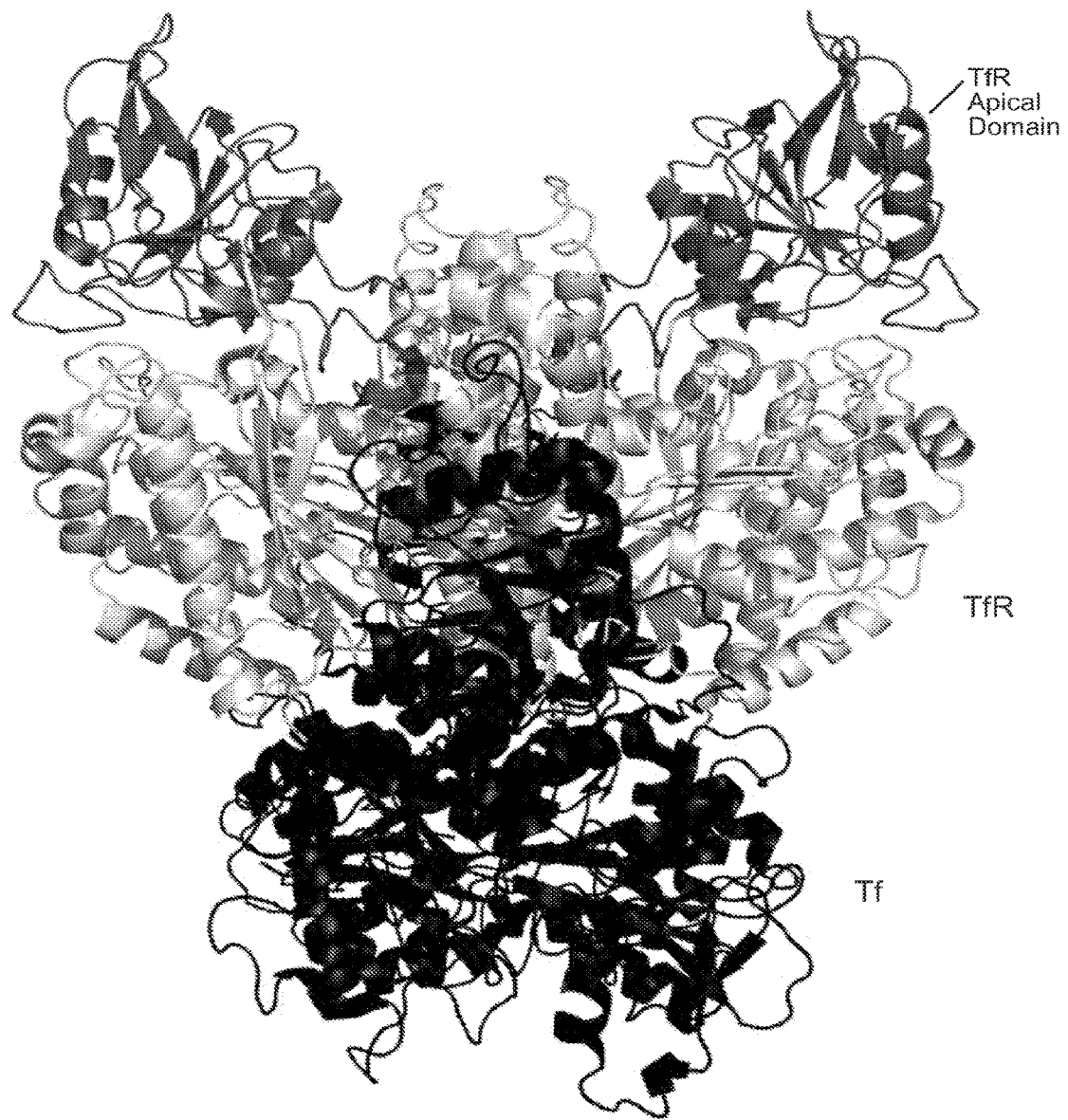
FIG. 1 depicts a three-dimensional crystal structure of a TfR dimer in complex with Tf, based on the pdb file 3SM9. The non-Tf-binding apical region of TfR is labeled.

"Affinity" refers to the strength of the sum total of noncovalent interactions between a single binding site of a molecule (e.g., and antibody) and its binding partner (e.g., an antigen). Unless indicted otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (KD, which is a ratio of the off-rate of X from Y (kd or Koff) to the on-rate of X to Y (ka or kon)). A surrogate measurement for the affinity of one or more antibodies for its target is its half maximal inhibitory concentration (IC50), a measure of how much of the antibody is needed to inhibit the binding of a known ligand to the antibody target by 50%. Affinity can be measured by common methods known in the art, including those described herein. Specific illustrative and exemplary embodiments for measuring binding affinity are described herein. The "blood-brain barrier" or "BBB" refers to the physiological barrier between the peripheral circulation and the brain and spinal cord (i.e., the CNS) which is formed by tight junctions within the brain capillary endothelial plasma membranes, creating a tight barrier that restricts the transport of molecules into the brain, even very small molecules such as urea (60 Daltons). The blood-brain barrier within the brain, the blood-spinal cord barrier within the spinal cord, and the blood-retinal barrier within the retina are contiguous capillary barriers within the CNS, and are herein collectively referred to a the blood-brain barrier or BBB. The BBB also encompasses the blood-CSF barrier (choroid plexus) where the barrier is comprised of ependymal cells rather than capillary endothelial cells.

The terms "amyloid beta," "beta-amyloid," "Abeta," "amyloidβ," and "Aβ", used interchangeably herein, refer to the fragment of amyloid precursor protein ("APP") that is produced upon β-secretase 1 ("BACE1") cleavage of APP, as well as modifications, fragments and any functional equivalents thereof, including, but not limited to, $A\beta_{1-40}$, and $A\beta_{1-42}$. Aβ is known to exist in monomeric form, as well as to associate to form oligomers and fibril structures, which may be found as constituent members of amyloid plaque. The structure and sequences of such Aβ peptides are well known to one of ordinary skill in the art and methods of producing said peptides or of extracting them from brain and other tissues are described, for example, in Glenner and Wong, Biochem Biophys Res. Comm. 129: 885-890 (1984). Moreover, Aβ peptides are also commercially available in various forms.

"Anti-Abeta immunoglobulin," "anti-Abeta antibody," and "antibody that binds Abeta" are used interchangeably herein, and refer to an antibody that specifically binds to human Abeta. A nonlimiting example of an anti-Abeta antibody is crenezumab. Other non-limiting examples of anti-Abeta antibodies are solanezumab, bapineuzumab, gantenerumab, aducanumab, ponezumab and any anti-Abeta antibodies disclosed in the following publications: WO2000162801, WO2002046237, WO2002003911, WO2003016466, WO2003016467, WO2003077858, WO2004029629, WO2004032868, WO2004032868, WO2004108895, WO2005028511, WO2006039470, WO2006036291, WO2006066089, WO2006066171, WO2006066049, WO2006095041, WO2009027105.

The terms "crenezumab" and "MABT5102A" are used interchangeably herein, and refer to a specific anti-Abeta antibody that binds to monomeric, oligomeric, and fibril forms of Abeta, and which is associated with CAS registry number 1095207. In some embodiments, such antibody comprises sequences set forth in FIGS. 18A and 18B.

"Apolipoprotein E4 carrier" or "ApoE4 carrier," used interchangeably herein with "apolipoprotein E4 positive" or "ApoE4 positive," refers to an individual having at least one apolipoprotein E4 (or "ApoE4") allele. An individual with zero ApoE4 alleles is referred to herein as being "ApoE4 negative" or an "ApoE4 non-carrier." See also Prekumar, et al., 1996, Am. J Pathol. 148:2083-95.

The term "cerebral vasogenic edema" refers to an excess accumulation of intravascular fluid or protein in the intracellular or extracellular spaces of the brain. Cerebral vasogenic edema is detectable by, e.g., brain MRI, including, but not limited to FLAIR MRI, and can be asymptomatic ("asymptomatic vasogenic edema") or associated with neurological symptoms, such as confusion, dizziness, vomiting, and lethargy ("symptomatic vasogenic edema") (see *Sperling et al. Alzheimer's & Dementia,* 7:367, 2011).

The term "cerebral macrohemorrhage" refers to an intracranial hemorrhage, or bleeding in the brain, of an area that is more than about 1 cm in diameter. Cerebral macrohemorrhage is detectable by, e.g., brain MRI, including but not limited to T2*-weighted GRE MRI, and can be asymptomatic ("asymptomatic macrohemorrhage") or associated with symptoms such as transient or permanent focal motor or sensory impairment, ataxia, aphasia, and dysarthria ("symptomatic macrohemorrhage") (see, e.g., Chalela J A, Gomes J. Expert Rev. Neurother. 2004 4:267, 2004 and Sperling et al. *Alzheimer's & Dementia,* 7:367, 2011).

The term "cerebral microhemorrhage" refers to an intracranial hemorrhage, or bleeding in the brain, of an area that is less than about 1 cm in diameter. Cerebral microhemorrhage is detectable by, e.g., brain MRI, including, but not limited to T2*-weighted GRE MRI, and can be asymptomatic ("asymptomatic microhemorrhage") or can potentially be associated with symptoms such as transient or permanent focal motor or sensory impairment, ataxia, aphasia, and dysarthria ("symptomatic microhemorrhage"). See, e.g., Greenberg, et al., 2009, *Lancet Neurol.* 8:165-74.

The term "sulcal effusion" refers to an effusion of fluid in the furrows, or sulci, of the brain. Sulcal effusions are detectable by, e.g., brain MRI, including but not limited to FLAIR MRI. See Sperling et al. *Alzheimer's & Dementia,* 7:367, 2011.

The term "superficial siderosis of the central nervous system" refers to bleeding or hemorrhage into the subarachnoid space of the brain and is detectable by, e.g., brain MRI, including but not limited to T2*-weighted GRE MRI. Symptoms indicative of superficial siderosis of the central nervous system include sensorineural deafness, cerebellar ataxia, and pyramidal signs. See Kumara-N, *Am J Neuroradiol.* 31:5, 2010.

The term "amyloidosis," as used herein, refers to a group of diseases and disorders caused by or associated with amyloid or amyloid-like proteins and includes, but is not limited to, diseases and disorders caused by the presence or activity of amyloid-like proteins in monomeric, fibril, or polymeric state, or any combination of the three, including by amyloid plaques. Such diseases include, but are not limited to, secondary amyloidosis and age-related amyloidosis, such as diseases including, but not limited to, neurological disorders such as Alzheimer's Disease ("AD"), diseases or conditions characterized by a loss of cognitive memory capacity such as, for example, mild cognitive impairment (MCI), Lewy body dementia, Down's syndrome, hereditary cerebral hemorrhage with amyloidosis (Dutch type), the Guam Parkinson-Demential complex and other diseases which are based on or associated with amyloid-like proteins such as progressive supranuclear palsy, multiple sclerosis, Creutzfeld Jacob disease, Parkinson's disease, HIV-related dementia, ALS (amyotropic lateral sclerosis), inclusion-body myositis (IBM), adult onset diabetes, endocrine tumor and senile cardiac amyloidosis, and various eye diseases including macular degeneration, drusen-related optic neuropathy, glaucoma, and cataract due to beta-amyloid deposition.

Glaucoma is a group of diseases of the optic nerve involving loss of retinal ganglion cells (RGCs) in a characteristic pattern of optic neuropathy. RGCs are the nerve cells that transmit visual signals from the eye to the brain. Caspase-3 and Caspase-8, two major enzymes in the apoptotic process, are activated in the process leading to apoptosis of RGCs. Caspase-3 cleaves amyloid precursor protein (APP) to produce neurotoxic fragments, including Abeta. Without the protective effect of APP, Abeta accumulation in the retinal ganglion cell layer results in the death of RGCs and irreversible loss of vision.

Glaucoma is often, but not always, accompanied by an increased eye pressure, which may be a result of blockage of the circulation of aqueous, or its drainage. Although raised intraocular pressure is a significant risk factor for developing glaucoma, no threshold of intraocular pressure can be defined which would be determinative for causing glaucoma. The damage may also be caused by poor blood supply to the vital optic nerve fibers, a weakness in the structure of the nerve, and/or a problem in the health of the nerve fibers themselves. Untreated glaucoma leads to permanent damage of the optic nerve and resultant visual field loss, which can progress to blindness.

The term "mild Alzheimer's Disease" or "mild AD" as used herein (e.g., a "patient diagnosed with mild AD") refers to a stage of AD characterized by an MMSE score of 20 to 26. The term "mild to moderate Alzheimer's Disease" or "mild to moderate AD" as used herein encompasses both mild and moderate AD, and is characterized by an MMSE score of 18 to 26.

The term "moderate Alzheimer's Disease" or "moderate AD" as used herein (e.g., a "patient diagnosed with moderate AD") refers to a stage of AD characterized by an MMSE score of 18 to 19.

The "central nervous system" or "CNS" refers to the complex of nerve tissues that control bodily function, and includes the brain and spinal cord.

A "blood-brain barrier receptor" (abbreviated "BBB-R" herein) is a transmembrane receptor protein expressed on brain endothelial cells which is capable of transporting molecules across the blood-brain barrier. Examples of BBB-R include, but are not limited to: transferrin receptor (TfR), insulin receptor, insulin-like growth factor receptor (IGF-R), low density lipoprotein receptors including without limitation low density lipoprotein receptor-related protein 1 (LRP1) and low density lipoprotein receptor-related protein 8 (LRP8), glucose transporter 1 (Glut1) and heparin-binding epidermal growth factor-like growth factor (HB-EGF). An exemplary BBB-R herein is transferrin receptor (TfR).

The term "transferrin receptor" or "TfR", as used herein, refers to any native TfR from any vertebrate source, including mammals such as primates (e.g., humans) and rodents (e.g., mice and rats), unless otherwise indicated. The term encompasses "full-length," unprocessed TfR as well as any form of TfR that results from processing in the cell. The term also encompasses naturally occurring variants of TfR, e.g., splice variants or allelic variants. TfR is a transmembrane glycoprotein (with a molecular weight of about 180,000) composed of two disulphide-bonded sub-units (each of apparent molecular weight of about 90,000) involved in iron uptake in vertebrates. In some embodiments, the TfR herein is human TfR ("hTfR") comprising the amino acid sequence as set forth in Schneider et al. Nature 311: 675-678 (1984), for example (SEQ ID NO: 1). In another embodiment, the TfR herein is primate TfR ("pTfR") comprising the amino acid sequence as set forth in Genbank reference AFD18260.1 (SEQ ID NO: 2). For comparison, the mouse TfR sequence may be found in Genbank reference AAH54522.1 (SEQ ID NO: 3).

A "neurological disorder" as used herein refers to a disease or disorder which affects the CNS and/or which has an etiology in the CNS. Exemplary CNS diseases or disorders include, but are not limited to, neuropathy, amyloidosis, cancer, an ocular disease or disorder, viral or microbial infection, inflammation, ischemia, neurodegenerative disease, seizure, behavioral disorders, and a lysosomal storage disease. For the purposes of this application, the CNS will be understood to include the eye, which is normally sequestered from the rest of the body by the blood-retina barrier. Specific examples of neurological disorders include, but are not limited to, neurodegenerative diseases (including, but not limited to, Lewy body disease, postpoliomyelitis syndrome, Shy-Draeger syndrome, olivopontocerebellar atrophy, Parkinson's disease, multiple system atrophy, striatonigral degeneration, tauopathies (including, but not limited to, Alzheimer disease and supranuclear palsy), prion diseases (including, but not limited to, bovine spongiform encephalopathy, scrapie, Creutzfeldt-Jakob syndrome, kuru, Gerstmann-Straussler-Scheinker disease, chronic wasting disease, and fatal familial insomnia), bulbar palsy, motor neuron disease, and nervous system heterodegenerative disorders (including, but not limited to, Canavan disease, Huntington's disease, neuronal ceroid-lipofuscinosis, Alexander's disease, Tourette's syndrome, Menkes kinky hair syndrome, Cockayne syndrome, Halervorden-Spatz syndrome, lafora disease, Rett syndrome, hepatolenticular degeneration, Lesch-Nyhan syndrome, and Unverricht-Lundborg syndrome), dementia (including, but not limited to, Pick's disease, and spinocerebellar ataxia), cancer (e.g. of the CNS, including brain metastases resulting from cancer elsewhere in the body).

A "neurological disorder drug" is a drug or therapeutic agent that treats one or more neurological disorder(s). Neurological disorder drugs of the invention include, but are not limited to, antibodies, peptides, proteins, natural ligands of one or more CNS target(s), modified versions of natural ligands of one or more CNS target(s), aptamers, inhibitory nucleic acids (i.e., small inhibitory RNAs (siRNA) and short hairpin RNAs (shRNA)), ribozymes, and small molecules, or active fragments of any of the foregoing. Exemplary neurological disorder drugs of the invention are described herein and include, but are not limited to: antibodies, aptamers, proteins, peptides, inhibitory nucleic acids and small molecules and active fragments of any of the foregoing that either are themselves or specifically recognize and/or act upon (i.e., inhibit, activate, or detect) a CNS antigen or target molecule such as, but not limited to, amyloid precursor protein or portions thereof, amyloid beta, beta-secretase, gamma-secretase, tau, alpha-synuclein, parkin, huntingtin, DR6, presenilin, ApoE, glioma or other CNS cancer markers, and neurotrophins. Non-limiting examples of neurological disorder drugs and the disorders they may be used to treat are provided in the following Table 1:

TABLE 1

Non-limiting examples of neurological disorder drugs and the corresponding disorders they may be used to treat

| Drug | Neurological disorder |
|---|---|
| Anti-BACE1 Antibody | Alzheimer's, acute and chronic brain injury, stroke |
| Anti-Abeta Antibody | Alzheimer's disease |
| Anti-Tau Antibody | Alzheimer's disease, tauopathies |
| Neurotrophin | Stroke, acute brain injury, spinal cord injury |
| Brain-derived neurotrophic factor (BDNF), Fibroblast growth factor 2 (FGF-2) | Chronic brain injury (Neurogenesis) |
| Anti-Epidermal Growth Factor Receptor (EGFR)-antibody | Brain cancer |

TABLE 1-continued

Non-limiting examples of neurological disorder drugs and
the corresponding disorders they may be used to treat

| Drug | Neurological disorder |
|---|---|
| Glial cell-line derived neural factor (GDNF) | Parkinson's disease |
| Brain-derived neurotrophic factor (BDNF) | Amyotrophic lateral sclerosis, depression |
| Lysosomal enzyme | Lysosomal storage disorders of the brain |
| Ciliary neurotrophic factor (CNTF) | Amyotrophic lateral sclerosis |
| Neuregulin-1 | Schizophrenia |
| Anti-HER2 antibody (e.g. trastuzumab, pertuzumab, etc.) | Brain metastasis from HER2-positive cancer |
| Anti-VEGF antibody (e.g., bevacizumab) | Recurrent or newly diagnosed glioblastoma, recurrent malignant glioma, brain metastasis |

An "imaging agent" is a compound that has one or more properties that permit its presence and/or location to be detected directly or indirectly. Examples of such imaging agents include proteins and small molecule compounds incorporating a labeled moiety that permits detection.

A "CNS antigen" or "brain antigen" is an antigen expressed in the CNS, including the brain, which can be targeted with an antibody or small molecule. Examples of such antigens include, without limitation: beta-secretase 1 (BACE1), amyloid beta (Abeta), epidermal growth factor receptor (EGFR), human epidermal growth factor receptor 2 (HER2), tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), interleukin 6 receptor (IL6R), TNF receptor 1 (TNFR1), interleukin 1 beta (IL1β), and caspase 6. In some embodiments, the antigen is BACE1.

The term "BACE1," as used herein, refers to any native beta-secretase 1 (also called β-site amyloid precursor protein cleaving enzyme 1, membrane-associated aspartic protease 2, memapsin 2, aspartyl protease 2 or Asp2) from any vertebrate source, including mammals such as primates (e.g. humans) and rodents (e.g., mice and rats), unless otherwise indicated. The term encompasses "full-length," unprocessed BACE1 as well as any form of BACE1 which results from processing in the cell. The term also encompasses naturally occurring variants of BACE1, e.g., splice variants or allelic variants. The amino acid sequence of an exemplary BACE1 polypeptide is the sequence for human BACE1, isoform A as reported in Vassar et al., Science 286:735-741 (1999), which is incorporated herein by reference in its entirety. Several other isoforms of human BACE1 exist including isoforms B, C and D. See UniProtKB/Swiss-Prot Entry P56817, which is incorporated herein by reference in its entirety.

The terms "anti-beta-secretase antibody", "anti-BACE1 antibody", "an antibody that binds to beta-secretase" and "an antibody that binds to BACE1" refer to an antibody that is capable of binding BACE1 with sufficient affinity such that the antibody is useful as a diagnostic and/or therapeutic agent in targeting BACE1. In some embodiments, the extent of binding of an anti-BACE1 antibody to an unrelated, non-BACE1 protein is less than about 10% of the binding of the antibody to BACE1 as measured, e.g., by a radioimmunoassay (RIA). In certain embodiments, an antibody that binds to BACE1 has a dissociation constant (Kd) of ≤1 µM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M). In certain embodiments, an anti-BACE1 antibody binds to an epitope of BACE1 that is conserved among BACE1 from different species and isoforms. In some embodiments, an antibody is provided that binds to the epitope on BACE1 bound by anti-BACE1 antibody YW412.8.31. In other embodiments, an antibody is provided that binds to an exosite within BACE1 located in the catalytic domain of BACE1. In some embodiments an antibody is provided that competes with the peptides identified in Kornacker et al., Biochem. 44:11567-11573 (2005), which is incorporated herein by reference in its entirety, (i.e., Peptides 1, 2, 3, 1-11, 1-10, 1-9, 1-8, 1-7, 1-6, 2-12, 3-12, 4-12, 5-12, 6-12, 7-12, 8-12, 9-12, 10-12, 4, 5, 6, 5-10, 5-9, scrambled, YSA, P6A, Y7A, F8A, I9A, P10A and L11A) for binding to BACE1. Exemplary BACE1 antibody sequences are depicted in FIG. 15A-B and FIG. 16A-B. One exemplary antibody herein comprises the variable domains of the antibody YW412.8.31 (e.g. as in FIGS. 15A-B).

A "native sequence" protein herein refers to a protein comprising the amino acid sequence of a protein found in nature, including naturally occurring variants of the protein. The term as used herein includes the protein as isolated from a natural source thereof or as recombinantly produced.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments are well known in the art (see, e.g., Nelson, MAbs (2010) 2(1): 77-83) and include but are not limited to Fab, Fab', Fab'-SH, F(ab')$_2$, and Fv; diabodies; linear antibodies; single-chain antibody molecules including but not limited to single-chain variable fragments (scFv), fusions of light and/or heavy-chain antigen-binding domains with or without a linker (and optionally in tandem); and monospecific or multispecific antigen-binding molecules formed from antibody fragments (including, but not limited to multispecific antibodies constructed from multiple variable domains which lack Fc regions).

The term "monoclonal antibody" as used herein refers to an antibody obtained from a population of substantially homogeneous antibodies, i.e., the individual antibodies comprising the population are identical and/or bind the same epitope, except for possible variants, e.g., containing naturally occurring mutations or that may arise during production of the monoclonal antibody, such variants generally being present in minor amounts. In contrast to polyclonal antibody preparations, which typically include different antibodies directed against different determinants (epitopes), each monoclonal antibody of a monoclonal antibody preparation is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method (see, e.g., Kohler et al., *Nature,* 256:495 (1975)), recombinant DNA methods (see, e.g., U.S. Pat. No. 4,816,567), phage-display methods (e.g., using the techniques described in Clackson et al., *Nature,* 352:624-628 (1991) and Marks et al., *J. Mol. Biol.,* 222:581-597 (1991)), and methods utilizing transgenic animals containing all or part of the human immunoglobulin loci, such methods and other exemplary methods for making monoclonal antibodies being described herein. Specific examples of monoclonal antibodies herein include chimeric antibodies, humanized antibodies, and human antibodies, including antigen-binding fragments thereof.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA,* 81:6851-6855 (1984)).

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest,* Fifth Edition, NIH Publication 91-3242, Bethesda Md. (1991), vols. 1-3. In some embodiments, for the VL, the subgroup is subgroup kappa I as in Kabat et al., supra. In some embodiments, for the VH, the subgroup is subgroup III as in Kabat et al., supra.

"Humanized" forms of non-human (e.g., murine) antibodies are chimeric antibodies that contain minimal sequence derived from non-human antibodies. For the most part, humanized antibodies are human antibodies (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. For example, in certain embodiments, a humanized antibody will comprise substantially all of at least one, and typically two, variable domains, in which all or substantially all of the HVRs (e.g., CDRs) correspond to those of a non-human antibody, and all or substantially all of the framework regions (FRs) correspond to those of a human antibody. In some instances, FR residues of the human immunoglobulin are replaced by corresponding non-human residues. Furthermore, humanized antibodies may comprise residues that are not found in the recipient antibody or in the donor antibody. These modifications are made to further refine antibody performance. In certain embodiments, a humanized antibody will comprise substantially all of at least one, and typically two, variable domains, in which all or substantially all of the hypervariable regions correspond to those of a non-human antibody and all or substantially all of the FRs are those of a human antibody, except for FR substitution(s) as noted above. The humanized antibody optionally also will comprise at least a portion of an antibody constant region, typically that of a human antibody. A "humanized form" of an antibody, e.g., a non-human antibody, refers to an antibody that has undergone humanization. For further details, see Jones et al., *Nature* 321:522-525 (1986); Riechmann et al., Nature 332:323-329 (1988); and Presta, *Curr. Op. Struct. Biol.* 2:593-596 (1992).

A "human antibody" herein is an antibody comprising an amino acid sequence structure that corresponds with the amino acid sequence structure of an antibody produced by a human or a human cell or derived from a non-human source that utilizes human antibody repertoires or other human antibody-encoding sequences. This definition of a human antibody specifically excludes a humanized antibody comprising non-human antigen-binding residues. Such antibodies can be identified or made by a variety of techniques, including, but not limited to: production by transgenic animals (e.g., mice) that are capable, upon immunization, of producing human antibodies in the absence of endogenous immunoglobulin production (see, e.g., Jakobovits et al., *Proc. Natl. Acad. Sci. USA,* 90:2551 (1993); Jakobovits et al., *Nature,* 362:255-258 (1993); Bruggermann et al., *Year in Immuno.,* 7:33 (1993); and U.S. Pat. Nos. 5,591,669, 5,589, 369 and 5,545,807)); selection from phage display libraries expressing human antibodies or human antibody fragments (see, for example, McCafferty et al., *Nature* 348:552-553 (1990); Johnson et al., *Current Opinion in Structural Biology* 3:564-571 (1993); Clackson et al., *Nature,* 352:624-628 (1991); Marks et al., *J. Mol. Biol.* 222:581-597 (1991); Griffith et al., *EMBO J.* 12:725-734 (1993); U.S. Pat. Nos. 5,565,332 and 5,573,905); generation via in vitro activated B cells (see U.S. Pat. Nos. 5,567,610 and 5,229,275); and isolation from human antibody-producing hybridomas.

A "multispecific antibody" herein is an antibody having binding specificities for at least two different epitopes. Exemplary multispecific antibodies may bind both a TfR and a brain antigen. Multispecific antibodies can be prepared as full-length antibodies or antibody fragments (e.g. F(ab')$_2$ bispecific antibodies). Engineered antibodies with two, three or more (e.g. four) functional antigen binding sites are also contemplated (see, e.g., US Appln No. US 2002/0004587 A1, Miller et al.). Multispecific antibodies can be prepared as full length antibodies or as antibody fragments.

Antibodies herein include "amino acid sequence variants" with altered antigen-binding or biological activity. Examples of such amino acid alterations include antibodies with enhanced affinity for antigen (e.g. "affinity matured" antibodies), and antibodies with altered Fc region, if present, e.g. with altered (increased or diminished) antibody dependent cellular cytotoxicity (ADCC) and/or complement dependent cytotoxicity (CDC) (see, for example, WO 00/42072, Presta, L. and WO 99/51642, Iduosogie et al.); and/or increased or diminished serum half-life (see, for example, WO00/42072, Presta, L.).

An "affinity modified variant" has one or more substituted hypervariable region or framework residues of a parent antibody (e.g. of a parent chimeric, humanized, or human antibody) that alter (increase or reduce) affinity. A convenient way for generating such substitutional variants uses phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity). In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and its target. Such contact residues and neighboring residues are candidates for substitution according to the techniques elaborated herein. Once such variants are generated, the panel of variants is subjected to screening and antibodies with altered affinity may be selected for further development.

A "pH-sensitive antibody variant" is an antibody variant which has a different binding binding affinity for a target antigen at a first pH than it does for that target antigen at a different pH. As a nonlimiting example, an anti-TfR antibody of the invention may be selected for or engineered to have pH-sensitive binding to TfR such that it binds with desirably low affinity (as described herein) to cell surface TfR in the plasma at pH 7.4, but upon internalization into an endosomal compartment, rapidly dissociates from TfR at the relatively lower pH (pH 5.5-6.0); such dissociation may protect the antibody from antigen-mediated clearance, and increase the amount of antibody that is either delivered to the CNS or recycled back across the BBB—in either case, the effective concentration of the antibody is increased relative to an anti-TfR antibody that does not comprise such pH sensitivity (see, e.g., Chaparro-Riggers et al. J. Biol. Chem. 287(14): 11090-11097; Igawa et al., Nature Biotechnol. 28(11): 1203-1208). The desired combination of affinities at the serum pH and the endosomal compartment pH can be readily determined for a TfR and conjugated compound by one of ordinary skill in the art.

The antibody herein may be conjugated with a "heterologous molecule" for example to increase half-life or stability or otherwise improve the antibody. For example, the antibody may be linked to one of a variety of non-proteinaceous polymers, e.g., polyethylene glycol (PEG), polypropylene glycol, polyoxyalkylenes, or copolymers of polyethylene glycol and polypropylene glycol. Antibody fragments, such as Fab', linked to one or more PEG molecules are an exemplary embodiment of the invention. In another example, the heterologous molecule is a therapeutic compound or a visualization agent (ie., a detectable label), and the antibody is being used to transport such heterologous molecule across the BBB. Examples of heterologous molecules include, but are not limited to, a chemical compound, a peptide, a polymer, a lipid, a nucleic acid, and a protein.

The antibody herein may be a "glycosylation variant" such that any carbohydrate attached to the Fc region, if present, is altered, either modified in presence/absence, or modified in type. For example, antibodies with a mature carbohydrate structure that lacks fucose attached to an Fc region of the antibody are described in US Pat Appl No US 2003/0157108 (Presta, L.). See also US 2004/0093621 (Kyowa Hakko Kogyo Co., Ltd). Antibodies with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju, S.) and WO 1999/22764 (Raju, S.) concerning antibodies with altered carbohydrate attached to the Fc region thereof. See also US 2005/0123546 (Umana et al.) describing antibodies with modified glycosylation. Mutation of the consensus glycosylation sequence in the Fc region (Asn-X-Ser/Thr at positions 297-299, where X cannot be proline), for example by mutating the Asn of this sequence to any other amino acid, by placing a Pro at position 298, or by modifying position 299 to any amino acid other than Ser or Thr should abrogate glycosylation at that position (see, e.g., Fares Al-Ejeh et al., Clin. Cancer Res. (2007) 13:5519s-5527s; Imperiali and Shannon, Biochemistry (1991) 30(18): 4374-4380; Katsuri, Biochem J. (1997) 323(Pt 2): 415-419; Shakin-Eshleman et al., J. Biol. Chem. (1996) 271: 6363-6366).

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contact"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

In some embodiments, HVR residues comprise those identified in FIGS. 3A-D or 4A-D, Table 4 or Table 5 or elsewhere in the specification.

Unless otherwise indicated, HVR residues and other residues in the variable domain (e.g., FR residues) are numbered herein according to Kabat et al., supra.

"Framework" or "FR" residues are those variable domain residues other than the hypervariable region residues as herein defined. The FR of a variable domain generally consists of four FR domains: FR1, FR2, FR3 and FR4.

Accordingly, the HVR and FR sequences generally appear in the following sequence in VH (or VL): FR1-H1(L1)-FR2-H2(L2)-FR3-H3(L3)-FR4. In certain embodiments, one or more FR residue may be modified to modulate the stability of the antibody or to modulate the three-dimensional positioning of one or more HVR of the antibody to, e.g., enhance binding.

A "full length antibody" is one which comprises an antigen-binding variable region as well as a light chain constant domain (CL) and heavy chain constant domains, CH1, CH2 and CH3. The constant domains may be native sequence constant domains (e.g. human native sequence constant domains) or amino acid sequence variants thereof.

The terms "full length antibody," "intact antibody," and "whole antibody" are used herein interchangeably to refer to an antibody having a structure substantially similar to a native antibody structure or having heavy chains that contain an Fc region as defined herein.

A "naked antibody" refers to an antibody that is not conjugated to a heterologous moiety (e.g., a cytotoxic moiety or radiolabel). The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2 and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

Antibody "effector functions" refer to those biological activities of an antibody that result in activation of the immune system other than activation of the complement pathway. Such activities are largely found in the Fc region (a native sequence Fc region or amino acid sequence variant Fc region) of an antibody. Examples of antibody effector functions include, for example, Fc receptor binding and antibody-dependent cell-mediated cytotoxicity (ADCC). In some embodiments, the antibody herein essentially lacks effector function. In another embodiment, the antibody herein retains minimal effector function. Methods of modifying or eliminating effector function are well-known in the art and include, but are not limited to, eliminating all or a portion of the Fc region responsible for the effector function (ie, using an antibody or antibody fragment in a format lacking all or a portion of the Fc region such as, but not limited to, a Fab fragment, a single-chain antibody, and the like as described herein and as known in the art; modifying the Fc region at one or more amino acid positions to eliminate effector function (Fc binding-impacting: positions 238, 239, 248, 249, 252, 254, 256, 265, 268, 269, 270, 272, 278, 289, 292, 293, 294, 295, 296, 297, 298, 301, 303, 311, 322, 324, 327, 329, 333, 335, 338, 340, 373, 376, 382, 388, 389, 414, 416, 419, 434, 435, 436, 437, 438, and 439; and modifying the glycosylation of the antibody (including, but not limited to, producing the antibody in an environment that does not permit wild-type mammalian glycosylation, removing one or more carbohydrate groups from an already-glycosylated antibody, and modifying the antibody at one or more amino acid positions to eliminate the ability of the antibody to be glycosylated at those positions (including, but not limited to N297G and N297A and D265A).

Antibody "complement activation" functions, or properties of an antibody that enable or trigger "activation of the complement pathway" are used interchangeably, and refer to those biological activities of an antibody that engage or stimulate the complement pathway of the immune system in a subject. Such activities include, e.g., C1q binding and complement dependent cytotoxicity (CDC), and may be mediated by both the Fc portion and the non-Fc portion of the antibody. Methods of modifying or eliminating complement activation function are well-known in the art and include, but are not limited to, eliminating all or a portion of the Fc region responsible for complement activation (ie., using an antibody or antibody fragment in a format lacking all or a portion of the Fc region such as, but not limited to, a Fab fragment, a single-chain antibody, and the like as described herein and as known in the art, or modifying the Fc region at one or more amino acid positions to eliminate or lessen interactions with complement components or the ability to activate complement components, such as positions 270, 322, 329 and 321, known to be involved in C1q binding), and modifying or eliminating a portion of the non-Fc region responsible for complement activation (ie, modifying the CH1 region at position 132 (see, e.g., Vidarte et al., (2001) J. Biol. Chem. 276(41): 38217-38223)).

Depending on the amino acid sequence of the constant domain of their heavy chains, full length antibodies can be assigned to different "classes". There are five major classes of full length antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called alpha, delta, epsilon, gamma, and mu, respectively. The subunit structures and three-dimensional configurations of different classes of immunoglobulins are well known in the art.

The term "recombinant antibody", as used herein, refers to an antibody (e.g. a chimeric, humanized, or human antibody or antigen-binding fragment thereof) that is expressed by a recombinant host cell comprising nucleic acid encoding the antibody.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cells and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. Examples of "host cells" for producing recombinant antibodies include: (1) mammalian cells, for example, Chinese Hamster Ovary (CHO), COS, myeloma cells (including Y0 and NS0 cells), baby hamster kidney (BHK), Hela and Vero cells; (2) insect cells, for example, sf9, sf21 and Tn5; (3) plant cells, for example plants belonging to the genus Nicotiana (e.g. Nicotiana tabacum); (4) yeast cells, for example, those belonging to the genus Saccharomyces (e.g. Saccharomyces cerevisiae) or the genus Aspergillus (e.g. Aspergillus niger); (5) bacterial cells, for example Escherichia coli cells or Bacillus subtilis cells, etc.

As used herein, "specifically binding" or "binds specifically to" refers to an antibody selectively or preferentially binding to an antigen. The binding affinity is generally determined using a standard assay, such as Scatchard analysis, or surface plasmon resonance technique (e.g. using BIACORE®).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. In some embodiments, an anti-BACE1 antibody forming one of the bispecific or multispecific antibodies of the invention binds to the BACE1 epitope bound by YW412.8.31. An exemplary competition assay is provided herein.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed herein.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In some embodiments, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

The term "FcRn receptor" or "FcRn" as used herein refers to an Fc receptor ("n" indicates neonatal) which is known to be involved in transfer of maternal IgGs to a fetus through the human or primate placenta, or yolk sac (rabbits) and to a neonate from the colostrum through the small intestine. It is also known that FcRn is involved in the maintenance of constant serum IgG levels by binding the IgG molecules and recycling them into the serum. "FcRn binding region" or "FcRn receptor binding region" refers to that portion an antibody which interacts with the FcRn receptor. Certain modifications in the FcRn binding region of an antibody increase the affinity of the antibody or fragment thereof, for the FcRn, and also increase the in vivo half-life of the molecule. Amino acid substitutions in one or more of the following amino acid positions 251 256, 285, 290, 308, 314, 385, 389, 428, 434 and 436 increases the interaction of the antibody with the FcRn receptor. Substitutions at the following positions also increases the interaction of an antibody with the FcRn receptor 238, 265, 272, 286, 303, 305, 307, 311, 312, 317, 340, 356, 360, 362, 376, 378, 380, 382, 413, 424 or 434, e.g., substitution of (U.S. Pat. No. 7,371, 826).

An "immunoconjugate" is an antibody conjugated to one or more heterologous molecule(s), including but not limited to a label or cytotoxic agent. Optionally such conjugation is via a linker.

A "linker" as used herein is a structure that covalently or non-covalently connects the anti-TfR antibody to heterologous molecule. In certain embodiments, a linker is a peptide. In other embodiments, a linker is a chemical linker.

A "label" is a marker coupled with the antibody herein and used for detection or imaging. Examples of such labels include: radiolabel, a fluorophore, a chromophore, or an affinity tag. In some embodiments, the label is a radiolabel used for medical imaging, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese, iron, etc.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) methods. For review of methods for assessment of antibody purity, see, e.g., Flatman et al., *J. Chromatogr. B* 848:79-87 (2007).

An "isolated nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-TfR antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject., A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W. H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., Nature 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

2. Compositions and Methods

A. Production of Anti-TfR Antibodies and Conjugates Thereof

In some aspects, the invention is based, in part, on anti-TfR antibodies that can be used to transport desired molecules across the BBB. In certain embodiments, antibodies that bind to human TfR are provided. In certain embodiments, antibodies that bind to both human TfR and primate TfR are provided. Antibodies of the invention are useful, e.g., for the diagnosis or treatment of diseases affecting the brain and/or CNS.

A. Exemplary Anti-TfR Antibodies

In some aspects, the invention provides isolated antibodies that bind to TfR. In certain embodiments, an anti-TfR antibody of the invention binds specifically to both human TfR and primate TfR. In certain such embodiments, an anti-TfR antibody of the invention does not inhibit binding of transferrin to the TfR. In certain such embodiments, an anti-TfR antibody of the invention binds to an apical domain of TfR. In other certain such embodiments, an anti-TfR antibody of the invention binds to a non-apical domain of TfR. In certain aspects, the anti-TfR antibodies may be used to transport one or more conjugated imaging or therapeutic compounds across the BBB.

Figure 3A-2:
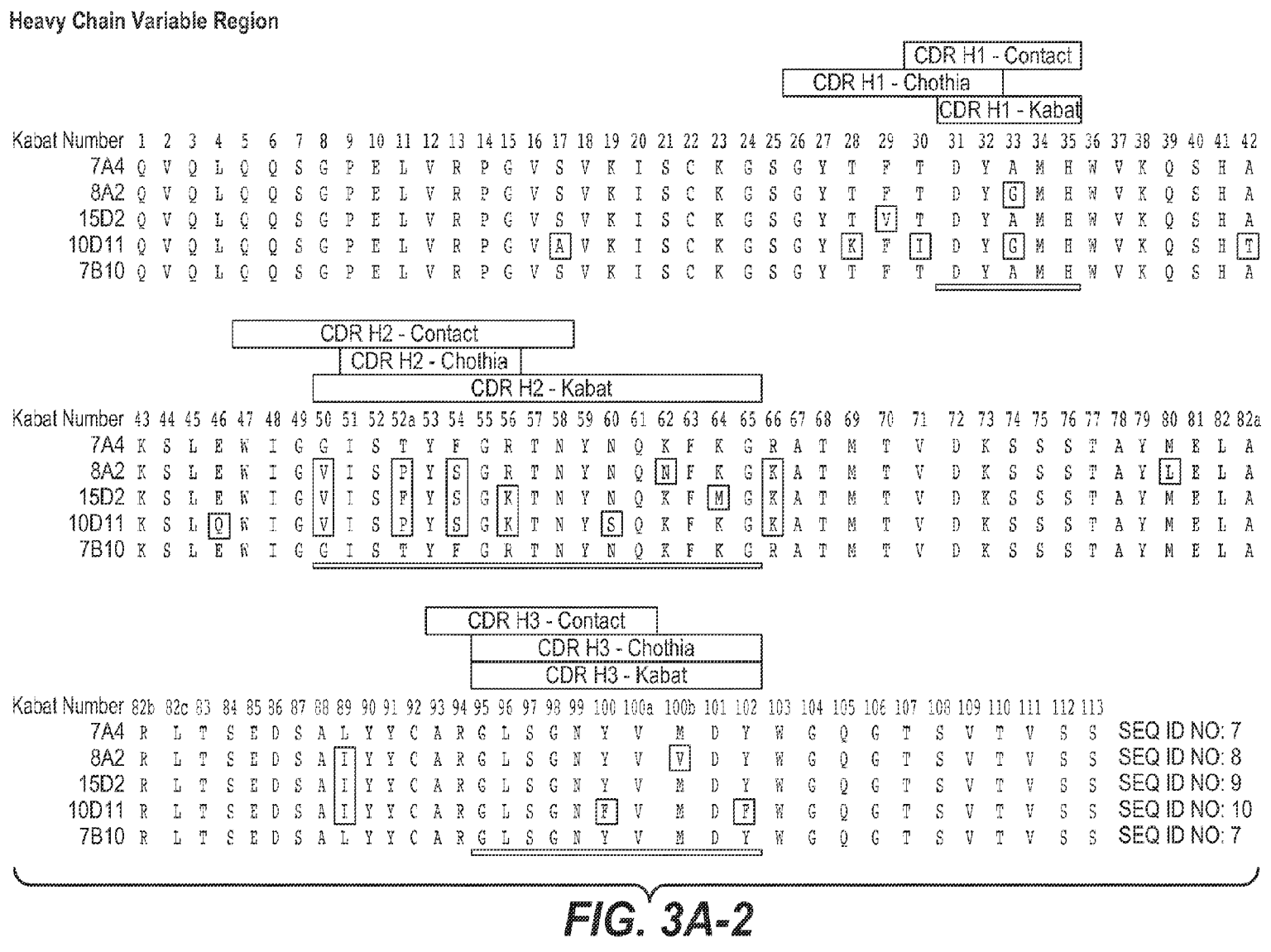

In some aspects, an anti-TfR antibody is provided comprising at least one, two, three, four, five, or six HVRs selected from (a) HVR-H1 comprising the amino acid sequence of SEQ ID NO:32; (b) HVR-H2 comprising the amino acid sequence of SEQ ID NO:33; (c) HVR-H3 comprising the amino acid sequence of SEQ ID NO:34; (d) HVR-L1 comprising the amino acid sequence of SEQ ID NO:29; (e) HVR-L2 comprising the amino acid sequence of SEQ ID NO:30; and (f) HVR-L3 comprising the amino acid sequence of SEQ ID NO:31. In some aspects, the antibody comprises all six of the above-recited HVR sequences. In another aspect, the antibody is clone 7A4, as shown in FIG. 3A and Table 3.

In some aspects, an anti-TfR antibody is provided comprising at least one, two, three, four, five, or six HVRs selected from (a) HVR-H1 comprising the amino acid sequence of SEQ ID NO:37; (b) HVR-H2 comprising the amino acid sequence of SEQ ID NO:38; (c) HVR-H3 comprising the amino acid sequence of SEQ ID NO:39; (d) HVR-L1 comprising the amino acid sequence of SEQ ID NO:35; (e) HVR-L2 comprising the amino acid sequence of SEQ ID NO:30; and (f) HVR-L3 comprising the amino acid sequence of SEQ ID NO:36. In some aspects, the antibody comprises all six of the above-recited HVR sequences. In another aspect, the antibody is clone 8A2, as shown in FIG. 3A and Table 3.

In some aspects, an anti-TfR antibody is provided comprising at least one, two, three, four, five, or six HVRs selected from (a) HVR-H1 comprising the amino acid sequence of SEQ ID NO: 32; (b) HVR-H2 comprising the amino acid sequence of SEQ ID NO:40; (c) HVR-H3 comprising the amino acid sequence of SEQ ID NO: 34; (d) HVR-L1 comprising the amino acid sequence of SEQ ID NO: 35; (e) HVR-L2 comprising the amino acid sequence of SEQ ID NO: 30; and (f) HVR-L3 comprising the amino acid sequence of SEQ ID NO: 36. In some aspects, the antibody comprises all six of the above-recited HVR sequences. In another aspect, the antibody is clone 15D2, as shown in FIG. 3A and Table 3.

In some aspects, an anti-TfR antibody is provided comprising at least one, two, three, four, five, or six HVRs selected from (a) HVR-H1 comprising the amino acid sequence of SEQ ID NO: 37; (b) HVR-H2 comprising the amino acid sequence of SEQ ID NO: 43; (c) HVR-H3 comprising the amino acid sequence of SEQ ID NO: 44; (d) HVR-L1 comprising the amino acid sequence of SEQ ID NO: 41; (e) HVR-L2 comprising the amino acid sequence of SEQ ID NO: 30; and (f) HVR-L3 comprising the amino acid sequence of SEQ ID NO: 42. In some aspects, the antibody comprises all six of the above-recited HVR sequences. In another aspect, the antibody is clone 10D11, as shown in FIG. 3A and Table 3.

In some aspects, an anti-TfR antibody is provided comprising at least one, two, three, four, five, or six HVRs selected from (a) HVR-H1 comprising the amino acid sequence of SEQ ID NO: 32; (b) HVR-H2 comprising the amino acid sequence of SEQ ID NO: 33; (c) HVR-H3 comprising the amino acid sequence of SEQ ID NO: 34; (d) HVR-L1 comprising the amino acid sequence of SEQ ID NO: 29; (e) HVR-L2 comprising the amino acid sequence of SEQ ID NO: 30; and (f) HVR-L3 comprising the amino acid sequence of SEQ ID NO:31. In some aspects, the antibody comprises all six of the above-recited HVR sequences. In another aspect, the antibody is clone 7B10, as shown in FIG. 3A and Table 3.

In some aspects, an anti-TfR antibody is provided comprising at least one, two, three, four, five, or six HVRs selected from (a) HVR-H1 comprising the amino acid sequence of SEQ ID NO:53; (b) HVR-H2 comprising the amino acid sequence of SEQ ID NO:54; (c) HVR-H3 comprising the amino acid sequence of SEQ ID NO:55; (d) HVR-L1 comprising the amino acid sequence of SEQ ID NO:50; (e) HVR-L2 comprising the amino acid sequence of SEQ ID NO:51; and (f) HVR-L3 comprising the amino acid sequence of SEQ ID NO:52. In some aspects, the antibody comprises all six of the above-recited HVR sequences. In another aspect, the antibody is clone 15G11, as shown in FIG. 3B and Table 3.

In some aspects, an anti-TfR antibody is provided comprising at least one, two, three, four, five, or six HVRs selected from (a) HVR-H1 comprising the amino acid sequence of SEQ ID NO:53; (b) HVR-H2 comprising the amino acid sequence of SEQ ID NO:58; (c) HVR-H3 comprising the amino acid sequence of SEQ ID NO:59; (d) HVR-L1 comprising the amino acid sequence of SEQ ID NO:56; (e) HVR-L2 comprising the amino acid sequence of SEQ ID NO:57; and (f) HVR-L3 comprising the amino acid sequence of SEQ ID NO:52. In some aspects, the antibody comprises all six of the above-recited HVR sequences. In another aspect, the antibody is clone 16G5, as shown in FIG. 3B and Table 3.

In some aspects, an anti-TfR antibody is provided comprising at least one, two, three, four, five, or six HVRs selected from (a) HVR-H1 comprising the amino acid sequence of SEQ ID NO:53; (b) HVR-H2 comprising the amino acid sequence of SEQ ID NO:63; (c) HVR-H3 comprising the amino acid sequence of SEQ ID NO:55; (d) HVR-L1 comprising the amino acid sequence of SEQ ID NO:60; (e) HVR-L2 comprising the amino acid sequence of SEQ ID NO:61; and (f) HVR-L3 comprising the amino acid sequence of SEQ ID NO:62. In some aspects, the antibody comprises all six of the above-recited HVR sequences. In another aspect, the antibody is clone 13C3, as shown in FIG. 3B and Table 3.

In some aspects, an anti-TfR antibody is provided comprising at least one, two, three, four, five, or six HVRs selected from (a) HVR-H1 comprising the amino acid sequence of SEQ ID NO:53; (b) HVR-H2 comprising the amino acid sequence of SEQ ID NO:65; (c) HVR-H3 comprising the amino acid sequence of SEQ ID NO:55; (d) HVR-L1 comprising the amino acid sequence of SEQ ID NO:60; (e) HVR-L2 comprising the amino acid sequence of SEQ ID NO:64; and (f) HVR-L3 comprising the amino acid sequence of SEQ ID NO:52. In some aspects, the antibody comprises all six of the above-recited HVR sequences. In another aspect, the antibody is clone 16G4, as shown in FIG. 3B and Table 3.

In some aspects, an anti-TfR antibody is provided comprising at least one, two, three, four, five, or six HVRs selected from (a) HVR-H1 comprising the amino acid sequence of SEQ ID NO:74; (b) HVR-H2 comprising the amino acid sequence of SEQ ID NO:75; (c) HVR-H3 comprising the amino acid sequence of SEQ ID NO:76; (d) HVR-L1 comprising the amino acid sequence of SEQ ID NO:71; (e) HVR-L2 comprising the amino acid sequence of SEQ ID NO:72; and (f) HVR-L3 comprising the amino acid sequence of SEQ ID NO:73. In some aspects, the antibody comprises all six of the above-recited HVR sequences. In another aspect, the antibody is clone 16F6, as shown in FIG. 3C and Table 3.

Figure 3D-2:
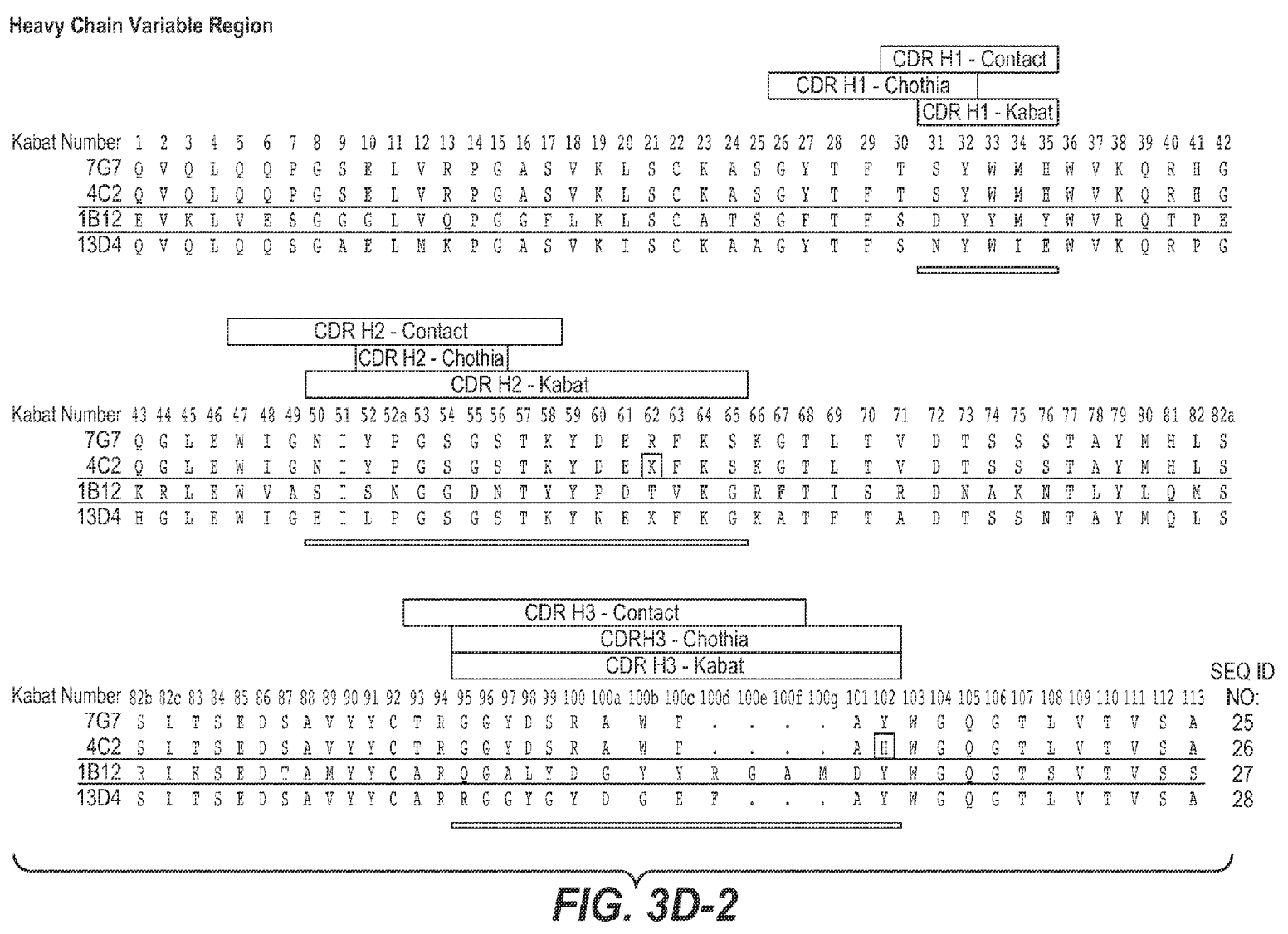

In some aspects, an anti-TfR antibody is provided comprising at least one, two, three, four, five, or six HVRs selected from (a) HVR-H1 comprising the amino acid sequence of SEQ ID NO:80; (b) HVR-H2 comprising the amino acid sequence of SEQ ID NO:81; (c) HVR-H3 comprising the amino acid sequence of SEQ ID NO:82; (d) HVR-L1 comprising the amino acid sequence of SEQ ID NO:77; (e) HVR-L2 comprising the amino acid sequence of SEQ ID NO:78; and (f) HVR-L3 comprising the amino acid sequence of SEQ ID NO:79. In some aspects, the antibody comprises all six of the above-recited HVR sequences. In another aspect, the antibody is clone 7G7, as shown in FIG. 3D and Table 3.

In some aspects, an anti-TfR antibody is provided comprising at least one, two, three, four, five, or six HVRs selected from (a) HVR-H1 comprising the amino acid sequence of SEQ ID NO: 80; (b) HVR-H2 comprising the amino acid sequence of SEQ ID NO:83; (c) HVR-H3 comprising the amino acid sequence of SEQ ID NO:84; (d) HVR-L1 comprising the amino acid sequence of SEQ ID NO:77; (e) HVR-L2 comprising the amino acid sequence of SEQ ID NO:78; and (f) HVR-L3 comprising the amino acid sequence of SEQ ID NO:79. In some aspects, the antibody comprises all six of the above-recited HVR sequences. In another aspect, the antibody is clone 4C2, as shown in FIG. 3D and Table 3.

In some aspects, an anti-TfR antibody is provided comprising at least one, two, three, four, five, or six HVRs selected from (a) HVR-H1 comprising the amino acid sequence of SEQ ID NO:88; (b) HVR-H2 comprising the amino acid sequence of SEQ ID NO:89; (c) HVR-H3 comprising the amino acid sequence of SEQ ID NO:90; (d) HVR-L1 comprising the amino acid sequence of SEQ ID NO:85; (e) HVR-L2 comprising the amino acid sequence of SEQ ID NO:86; and (f) HVR-L3 comprising the amino acid sequence of SEQ ID NO:87. In some aspects, the antibody comprises all six of the above-recited HVR sequences. In another aspect, the antibody is clone 1B12, as shown in FIG. 3D and Table 3.

In some aspects, an anti-TfR antibody is provided comprising at least one, two, three, four, five, or six HVRs selected from (a) HVR-H1 comprising the amino acid sequence of SEQ ID NO:94; (b) HVR-H2 comprising the amino acid sequence of SEQ ID NO:95; (c) HVR-H3 comprising the amino acid sequence of SEQ ID NO:96; (d) HVR-L1 comprising the amino acid sequence of SEQ ID NO:91; (e) HVR-L2 comprising the amino acid sequence of SEQ ID NO:92; and (f) HVR-L3 comprising the amino acid sequence of SEQ ID NO:93. In some aspects, the antibody comprises all six of the above-recited HVR sequences. In another aspect, the antibody is clone 13D4, as shown in FIG. 3D and Table 3.

In some aspects, an anti-TfR antibody is provided comprising at least one, two, three, four, five, or six HVRs selected from (a) HVR-H1 comprising the amino acid sequence of SEQ ID NO:32; (b) HVR-H2 comprising the amino acid sequence of SEQ ID NO:33; (c) HVR-H3 comprising the amino acid sequence of SEQ ID NO:34; (d) HVR-L1 comprising the amino acid sequence of SEQ ID NO:29; (e) HVR-L2 comprising the amino acid sequence of SEQ ID NO:30; and (f) HVR-L3 comprising the amino acid sequence of SEQ ID NO:127. In some aspects, the antibody comprises all six of the above-recited HVR sequences. In another aspect, the antibody is clone 7A4.v15, as shown in FIG. 4B and Table 4.

The clones above fall into four complementation groups, with sequence similarity within the HVRs. As shown in Table 3, consensus sequences are readily derivable from the provided antibody sequences for each HVR. As one non-limiting example, the class I antibody consensus HVRs are as follows:

```
HVR-L1:
                                        (SEQ ID NO: 45)
Arg-Ala-Ser-Glu-Ser-Val-Asp-[Ser or Asp]-Tyr-Gly-
[Asn or Pro]-Ser-Phe-Met-His;

HVR-L2:
                                        (SEQ ID NO: 30)
Arg-Ala-Ser-Asn-Leu-Glu-Ser;

HVR-L3:
                                        (SEQ ID NO: 46)
Gln-[Gln or His]-Ser-Asn-Glu-[Ala, Gly or Asp]-
Pro-Pro-Thr;

HVR-H1:
                                        (SEQ ID NO: 47)
Asp-Tyr-[Ala or Gly]-Met-His;

HVR-H2:
                                        (SEQ ID NO: 48)
[Gly or Val]-Ile-Ser-[Thr, Phe or Pro]-Tyr-

[Phe or Ser]-Gly-[Arg or Lys]-Thr-Asn-Tyr-

[Asn or Ser]-Gln-[Lys or Asn]-Phe-[Lys or Met]-

Gly;

HVR-H3:
                                        (SEQ ID NO: 49)
Gly-Leu-Ser-Gly-Asn-[Tyr or Phe]-Val-[Met or
Val]-Asp-[Thr or Phe].
```

(see Table 4). The consensus sequences for class II and IV are also provided in Table 4.

In some aspects, an anti-TfR antibody is provided comprising at least one, two, three, four, five, or six HVRs selected from (a) HVR-H1 comprising the amino acid sequence of SEQ ID NO:47; (b) HVR-H2 comprising the amino acid sequence of SEQ ID NO:48; (c) HVR-H3 comprising the amino acid sequence of SEQ ID NO:49; (d) HVR-L1 comprising the amino acid sequence of SEQ ID NO:45; (e) HVR-L2 comprising the amino acid sequence of SEQ ID NO:30; and (f) HVR-L3 comprising the amino acid sequence of SEQ ID NO:46. In some aspects, the antibody comprises all six of the above-recited HVR sequences.

In some aspects, an anti-TfR antibody is provided comprising at least one, two, three, four, five, or six HVRs selected from (a) HVR-H1 comprising the amino acid sequence of SEQ ID NO:53; (b) HVR-H2 comprising the amino acid sequence of SEQ ID NO:69; (c) HVR-H3 comprising the amino acid sequence of SEQ ID NO:70; (d) HVR-L1 comprising the amino acid sequence of SEQ ID NO:66; (e) HVR-L2 comprising the amino acid sequence of SEQ ID NO:67; and (f) HVR-L3 comprising the amino acid sequence of SEQ ID NO:68. In some aspects, the antibody comprises all six of the above-recited HVR sequences.

In some aspects, an anti-TfR antibody is provided comprising at least one, two, three, four, five, or six HVRs selected from (a) HVR-H1 comprising the amino acid sequence of SEQ ID NO:100; (b) HVR-H2 comprising the amino acid sequence of SEQ ID NO:101; (c) HVR-H3 comprising the amino acid sequence of SEQ ID NO:102; (d) HVR-L1 comprising the amino acid sequence of SEQ ID NO:97; (e) HVR-L2 comprising the amino acid sequence of SEQ ID NO:98; and (f) HVR-L3 comprising the amino acid sequence of SEQ ID NO:99. In some aspects, the antibody comprises all six of the above-recited HVR sequences.

In some aspects, an antibody is provided comprising at least one, at least two, or all three VH HVR sequences of any of the antibodies described above. In some embodiments, the antibody comprises the HVR-H3 sequence of any one of the antibodies described above. In another embodiment, the antibody comprises the HVR-H3 and HVR-L3 sequences of any one of the antibodies described above. In a further embodiment, the antibody comprises the HVR-H3, HVR-L3 and HVR-H2 sequences of any one of the antibodies described above. In another embodiment, the antibody comprises the HVR-H1, HVR-H2 and HVR-H3 sequences of any one of the antibodies described above. In another aspect, an antibody is provided comprising at least one, at least two or all three VL HVR sequences of any of the antibodies described above. In some embodiments, the antibody comprises the HVR-L1, HVR-L2, and HVR-L3 sequences of any one of the antibodies described above.

In another aspect, an antibody of the invention comprises (a) a VH domain comprising at least one, at least two, or all three VH HVR sequences selected from the HVR-H1, HVR-H2, and HVR-H3 sequences of any one of the antibodies described above, wherein the VH domain comprises an M108L mutation; and (b) a VL domain comprising at least one, at least two, or all three VL HVR sequences selected from the HVR-L1, HVR-L2 and HVR-L3 sequences of any one of the antibodies described above.

In any of the above embodiments, an anti-TfR antibody is humanized. In some embodiments, an anti-TfR antibody comprises HVRs as in any of the above embodiments, and further comprises an acceptor human framework, e.g. a human immunoglobulin framework or a human consensus framework. In another embodiment, an anti-TfR antibody comprises HVRs as in any of the above embodiments, and further comprises a VH or VL comprising one or more amino acid substitutions in one or more FR regions. Per Example 2 herein, Applicants performed alanine scanning on certain antibodies selected from those above, and determined that similar or improved binding was obtained despite amino acid modifications at selected FR positions. As shown in FIGS. 6-1 and 6-2 and Example 2 herein, for the class I-III groups of antibodies, variant forms of the antibodies with modifications at one or more residues of an FR retained affinity and binding specifity. For example, for antibody 15G11, positions 43 and 48 in the light chain FR2, position 48 in the heavy chain FR2 and positions 67, 69, 71 and 73 in the heavy chain FR3 could be modified as shown in FIGS. 6-1 and 6-2 and the resulting antibody still retained specificity and strong binding affinity for human/primate TfR. In another example, for antibody 7A4, positions 58 and 68 of the light chain FR3, position 24 in the heavy chain FR1 and position 71 in the heavy chain FR3 could be modified as shown in FIGS. 6-1 and 6-2 and the resulting antibody still retained specificity and strong binding affinity for human/primate TfR. In a third example, for antibody 16F6, positions 43 and 44 of the light chain FR2 and positions 71 and 78 of the heavy chain FR3 could be modified as shown in FIGS. 6-1 and 6-2 and the resulting antibody still retained specificity and strong binding affinity for human/primate TfR. In some embodiments, an antibody comprises an VH domain with an M108L mutation.

In another aspect, an anti-TfR antibody comprises a heavy chain variable domain (VH) sequence having at least 90%, 91%, 92%, 93%, 94%, 95%, 96%, 97%, 98%, 99%, or 100% sequence identity to the amino acid sequence of any one of SEQ ID NOs: 7-10, 15-18, 20, 25-28, 108, 114, 120, 126, 153, and 154. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-TfR antibody comprising that sequence retains the ability to bind to TfR. In certain embodiments, a total of 1 to 10 amino acids have been substituted, inserted and/or deleted in any one of SEQ ID NOs:7-10, 15-18, 20, 25-28, 108, 114, 120, 126, 153, and 154. In certain embodiments, substitutions, insertions, or deletions occur in regions outside the HVRs (i.e., in the FRs). Optionally, the anti-TfR antibody comprises the VH sequence of any one of SEQ ID NOs: 7-10, 15-18, 20 25-28, 108, 114, 120, 126, 153, and 154, including post-translational modifications of that sequence. In a particular embodiment, the VH for a particular antibody comprises one, two or three HVRs selected from: the HVRs set forth above and in Table 3 or 4 for that particular antibody. VH sequences for certain antibodies are shown in FIGS. 3 and 4 herein. In some embodiments, the invention provides an anti-TfR antibody comprising a VH sequence of SEQ ID NO: 158 or 159.

In another aspect, an anti-TfR antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of any one of SEQ ID NOs:4-6, 11-14, 19, 21-24, 105, 111, 117, 123, 151, and 152. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-TfR antibody comprising that sequence retains the ability to bind to TfR. In certain embodiments, a total of 1 to 10 amino acids have been substituted, inserted and/or deleted in any one of SEQ ID NOs:4-6, 11-14, 19, 21-24, 105, 111, 117, 123, 151, and 152. In certain embodiments, the substitutions, insertions, or deletions occur in regions outside the HVRs (i.e., in the FRs). Optionally, the anti-TfR antibody comprises the VL sequence in any of SEQ ID NOs:4-6, 11-14, 19, 21-24, 105, 111, 117, 123, 151, and 152, including post-translational modifications of that sequence. In a particular embodiment, the VL comprises one, two or three HVRs selected from the HVRs set forth above and in Table 4 or 5 for that particular antibody. VL sequences for certain antibodies are shown in FIGS. 3 and 4 herein. In some embodiments, the invention provides an anti-TfR antibody comprising a VL sequence of SEQ ID NO: 162 or 163.

In another aspect, an anti-TfR antibody is provided, wherein the antibody comprises a VH as in any of the embodiments provided above, and a VL as in any of the embodiments provided above. In some embodiments, the antibody comprises the VL and VH sequences, respectively, in SEQ ID NOs: 4 and 7; 5 and 8; 5 and 9; 6 and 10; 4 and 7; 11 and 15; 12 and 16; 13 and 17; 14 and 18; 19 and 20; 21 and 25; 22 and 26; 23 and 27; 24 and 28; 105 and 108; 152 and 108; 151 and 108; 152 and 153; 152 and 154; 105 and 153; 105 and 154; 111 and 114; 117 and 120; and 123 and 126, including post-translational modifications of those sequences. In some embodiments, the invention provides an anti-TfR antibody comprising a VH sequence of SEQ ID NO: 158 or 159 and a VL sequence of SEQ ID NO: 162 or 163. In some embodiments, the invention provides an anti-TfR antibody comprising a VH sequence of SEQ ID NO: 158 and a VL sequence of SEQ ID NO: 162, or a VH sequence of SEQ ID NO: 159 and a VL sequence of SEQ ID NO: 163.

In a further aspect, an antibody is provided that binds to the same epitope as an anti-TfR antibody provided herein. For example, in certain embodiments, an antibody is provided that binds to the same epitope as an anti-TfR antibody comprising VL and VH sequences, respectively, of SEQ ID NOs: 4 and 7; 5 and 8; 5 and 9; 6 and 10; 4 and 7; 11 and 15; 12 and 16; 13 and 17; 14 and 18; 19 and 20; 21 and 25; 22 and 26; 23 and 27; 24 and 28; 105 and 108; 152 and 108; 151 and 108; 152 and 153; 152 and 154; 105 and 153; 105 and 154; 111 and 114; 117 and 120; or 123 and 126. In some aspects, the antibody competes with any of the antibodies in Class I (ie., clones 7A4, 8A2, 15D2, 10D11, or 7B10, or affinity-matured versions of any of those antibodies) for binding to TfR. In another aspect, the antibody competes with any of the antibodies in Class II (ie, clones 15G11, 16G5, 13C3 or 16G, or affinity-matured versions of any of those antibodies) for binding to TfR. In another aspect, the antibody competes with clone 16F6 or affinity-matured versions thereof for binding to TfR. In another aspect, the antibody competes with any of the antibodies in Class IV (ie, clones 7G7, 4C2, 1B12 or 13D4, or affinity matured versions thereof) for binding to TfR.

In a further aspect of the invention, an anti-TfR antibody according to any of the above embodiments is a monoclonal antibody, including a chimeric, humanized or human antibody. In some embodiments, an anti-TfR antibody is an antibody fragment, e.g., a Fv, Fab, Fab', scFv, diabody, or F(ab')2 fragment. In another embodiment, the antibody is a full length antibody, e.g., an intact IgG1, IgG2, IgG3, or IgG4 antibody or other antibody class or isotype as defined herein.

In some embodiments, the invention provides an anti-TfR antibody comprising a heavy chain having the sequence of SEQ ID NO: 160 and a light chain having the sequence of SEQ ID NO: 61. In some such embodiments, the antibody is a multispecific antibody.

In a further aspect, an anti-TfR antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

In certain aspects of the present invention, a "low affinity" anti-TfR antibody of the invention is selected, based, e.g., on the results in Example 5 and in Atwal et al., Sci. Transl. Med. 3, 84ra43 (2011) and Yu et al., Sci. Transl. Med. 25 May 2011: Vol. 3, Issue 84, p. 84ra44, showing that such lower-affinity antibodies to TfR display improved CNS (for example, brain) uptake and/or persistence in the brain/CNS. In order to identify such low affinity antibodies, various assays for measuring antibody affinity are available including, without limitation: Scatchard assay and surface plasmon resonance technique (e.g. using BIACORE®). According to some embodiments of the invention, the antibody has an affinity for human or primate TfR from about 5 nM, or from about 20 nM, or from about 100 nM, to about 50 µM, or to about 30 µM, or to about 10 µM, or to about 1 µM, or to about 500 nM. Thus, the affinity may be in the range from about 5 nM to about 50 µM, or in the range from about 20 nM to about 30 µM, or in the range from about 30 nM to about 30 µM, or in the range from about 50 nM to about 1 µM, or in the range from about 100 nM to about 500 nM, e.g. as measured by Scatchard analysis or BIACORE®. In another embodiment of the invention, the antibody has a dissociation half-life from TfR of less than 1 minute, less than 2 minutes, less than 3 minutes, less than four minutes, less than 5 minutes, or less than 10 minutes to about 20 minutes, or to about 30 minutes, as measured by competition binding analysis or BIACORE®.

Thus, the invention provides a method of making an antibody useful for transporting a neurological disorder drug across the blood-brain barrier comprising selecting an antibody from a panel of antibodies against TfR because it has an affinity for TfR which is in the range from about 5 nM, or from about 20 nM, or from about 100 nM, to about 50 µM, or to about 30 µM, or to about 10 µM, or to about 1 µM, or to about 500 mM. Thus, the affinity may be in the range from about 5 nM to about 50 µM, or in the range from about 20 nM to about 30 µM, or in the range from about 30 nM to about 30 µM, or in the range from about 50 nM to about 1 µM, or in the range from about 100 nM to about 500 nM, e.g. as measured by Scatchard analysis or BIACORE®. As will be understood by one of ordinary skill in the art, conjugating a heterologous molecule/compound to an antibody will often decrease the affinity of the antibody for its target due, e.g., to steric hindrance or even to elimination of one binding arm if the antibody is made multispecific with one or more arms binding to a different antigen than the antibody's original target. In some embodiments, a low affinity antibody of the invention specific for TfR conjugated to anti-BACE1 had a Kd for TfR as measured by BIACORE of about 30 nM. In another embodiment, a low affinity antibody of the invention specific for TfR conjugated to BACE1 had a Kd for TfR as measured by BIACORE of about 600 nM. In another embodiment, a low affinity antibody of the invention specific for TfR conjugated to BACE1 had a Kd for TfR as measured by BIACORE of about 20 µM. In another embodiment, a low affinity antibody of the invention specific for TfR conjugated to BACE1 had a Kd for TfR as measured by BIACORE of about 30 µM.

In some embodiments, Kd is measured by a radiolabeled antigen binding assay (RIA). In some embodiments, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

In some aspects, the RIA is a Scatchard analysis. For example, the anti-TfR antibody of interest can be iodinated using the lactoperoxidase method (Bennett and Horuk, Methods in Enzymology 288 pg. 134-148 (1997)). A radiolabeled anti-TfR antibody is purified from free $^{125}$I-Na by gel filtration using a NAP-5 column and its specific activity measured. Competition reaction mixtures of 50 µL containing a fixed concentration of iodinated antibody and decreasing concentrations of serially diluted unlabeled antibody are placed into 96-well plates. Cells transiently expressing TfR are cultured in growth media, consisting of Dulbecco's modified eagle's medium (DMEM) (Genentech) supplemented with 10% FBS, 2 mM L-glutamine and 1×penicillin-streptomycin at 37° C. in 5% $CO_2$. Cells are detached from the dishes using Sigma Cell Dissociation Solution and washed with binding buffer (DMEM with 1% bovine serum albumin, 50 mM HEPES, pH 7.2, and 0.2% sodium azide). The washed cells are added at an approximate density of 200,000 cells in 0.2 mL of binding buffer to the 96-well plates containing the 50-µL competition reaction mixtures. The final concentration of the unlabeled antibody in the competition reaction with cells is varied, starting at 1000 nM and then decreasing by 1:2 fold dilution for 10 concentrations and including a zero-added, buffer-only sample. Competition reactions with cells for each concentration of unlabeled antibody are assayed in triplicate. Competition reactions with cells are incubated for 2 hours at room temperature. After the 2-hour incubation, the competition reactions are transferred to a filter plate and washed four times with binding buffer to separate free from bound iodinated antibody. The filters are counted by gamma counter and the binding data are evaluated using the fitting algorithm of Munson and Rodbard (1980) to determine the binding affinity of the antibody.

An exemplary BIACOREO analysis using the compositions of the invention may be performed as follows. Kd was measured using surface plasmon resonance assays using a BIACORE®-2000 (BlAcore, Inc., Piscataway, N.J.) at 25° C. using anti-human Fc kit (BiAcore Inc., Piscataway, N.J.). Briefly, carboxymethylated dextran biosensor chips (CM5, BIACORE, Inc.) were activated with N-ethyl-N'-(3-dimethylaminopropyl)-carbodiimide hydrochloride (EDC) and N-hydroxysuccinimide (NHS) according to the supplier's instructions. Anti-human Fc antibody was diluted with 10 mM sodium acetate, pH 4.0, to 50 µg/ml before injection at a flow rate of 5 µl/minute to achieve approximately 10000 response units (RU) of coupled protein. Following the injection of antibody, 1 M ethanolamine was injected to block unreacted groups. For kinetics measurements, monospecific or multispecific anti-TfR antibody variants were injected in HBS-P to reach about 220 RU, then two-fold serial dilutions of MuTfR-His (0.61 nM to 157 nM) were injected in HBS-P at 25° C. at a flow rate of approximately 30 µl/min. Association rates (kon) and dissociation rates (koff) were calculated using a simple one-to-one Langmuir binding model (BIACORE® Evaluation Software version 3.2) by simultaneously fitting the association and dissociation sensorgrams. The equilibrium dissociation constant (Kd) was calculated as the ratio koff/kon. See, e.g., Chen et al., *J. Mol. Biol.* 293:865-881 (1999)

According to another embodiment, Kd is measured using surface plasmon resonance assays with a BIACORE®-2000 device (BlAcore, Inc., Piscataway, N.J.) at 25° C. using anti-human Fc kit (BiAcore Inc., Piscataway, N.J.). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Anti-human Fc antibody is diluted with 10 mM sodium acetate, pH 4.0, to 50 µg/ml before injection at a flow rate of 5 µl/minute to achieve approximately 10000 response units (RU) of coupled protein. Following the injection of antibody, 1 M ethanolamine is injected to block unreacted groups. For kinetics measurements, anti-TfR antibody variants are injected in HBS-P to reach about 220 RU, then two-fold serial dilutions of TfR-His (0.61 nM to 157 nM) are injected in HBS-P at 25° C. at a flow rate of approximately 30 µl/min. Association rates (kon) and dissociation rates (koff) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio koff/kon. See, e.g., Chen et al., *J. Mol. Biol.* 293:865-881 (1999).

Several methods of determining the IC50 for a given compound are art-known; a common approach is to perform a competition binding assay, such as that described herein. In general, a high IC50 indicates that more of the antibody is required to inhibit binding of the known ligand, and thus that the antibody's affinity for that ligand is relatively low. Conversely, a low IC50 indicates that less of the antibody is required to inhibit binding of the known ligand, and thus that the antibody's affinity for that ligand is relatively high.

An exemplary competitive ELISA assay to measure IC50 is one in which increasing concentrations of anti-TfR or anti-TfR/brain antigen (i.e., anti-TfR/BACE1, anti-TfR/ Abeta and the like) variant antibodies are used to compete against a biotinylated known anti-TfR antibody for binding to TfR. The anti-TfR competition ELISA was performed in Maxisorp plates (Neptune, N.J.) coated with 2.5 µg/ml of purified murine TfR extracellular domain in PBS at 4° C. overnight. Plates were washed with PBS/0.05% Tween 20 and blocked using Superblock blocking buffer in PBS (Thermo Scientific, Hudson, N.H.). A titration of each individual anti-TfR or anti-TfR/brain antigen (i.e., anti-TfR/ BACE1 or anti-TfR/Abeta) (1:3 serial dilution) was combined with biotinylated known anti-TfR (0.5 nM final concentration) and added to the plate for 1 hour at room temperature. Plates were washed with PBS/0.05% Tween 20, and HRP-streptavidin (Southern Biotech, Birmingham) was added to the plate and incubated for 1 hour at room temperature. Plates were washed with PBS/0.05% Tween 20, and biotinylated anti-TfR antibody bound to the plate was detected using TMB substrate (BioFX Laboratories, Owings Mills).

2. Antibody Fragments

In certain embodiments, an antibody provided herein is an antibody fragment. Antibody fragments include, but are not limited to, Fab, Fab', Fab'-SH, F(ab')2, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies,* vol. 113, Rosenburg and Moore eds., (Springer-Verlag, N.Y., pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences (U.S. Pat. No. 5,693,780). In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., Methods 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, Front. *Biosci.* 13:1619-1633 (2008)); and framework regions derived from screening FR libraries (see, e.g., Baca et al., *J. Biol. Chem.* 272:10678-10684 (1997) and Rosok et al., *J Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and *Winter, J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for TfR and the other is for any other antigen. In certain embodiments, bispecific antibodies may bind to two different epitopes of TfR. Bispecific antibodies may also be used to localize cytotoxic agents to cells which express TfR. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tuft et al. *J. Immunol.* 147: 60 (1991).

The antibody or fragment herein also includes a "Dual Acting FAb" or "DAF" comprising an antigen binding site that binds to TfR as well as another, different antigen (see, US 2008/0069820, for example).

According to some embodiments of the invention, the "coupling" is achieved by generating a multispecific antibody (e.g. a bispecific antibody). Multispecific antibodies are monoclonal antibodies that have binding specificities for at least two different antigens or epitopes. In some embodiments, the multispecific antibody comprises a first antigen binding site which binds the TfR and a second antigen binding site which binds a brain antigen, such as beta-secretase 1 (BACE1) or Abeta, and the other brain antigens disclosed herein.

Figure 16A:
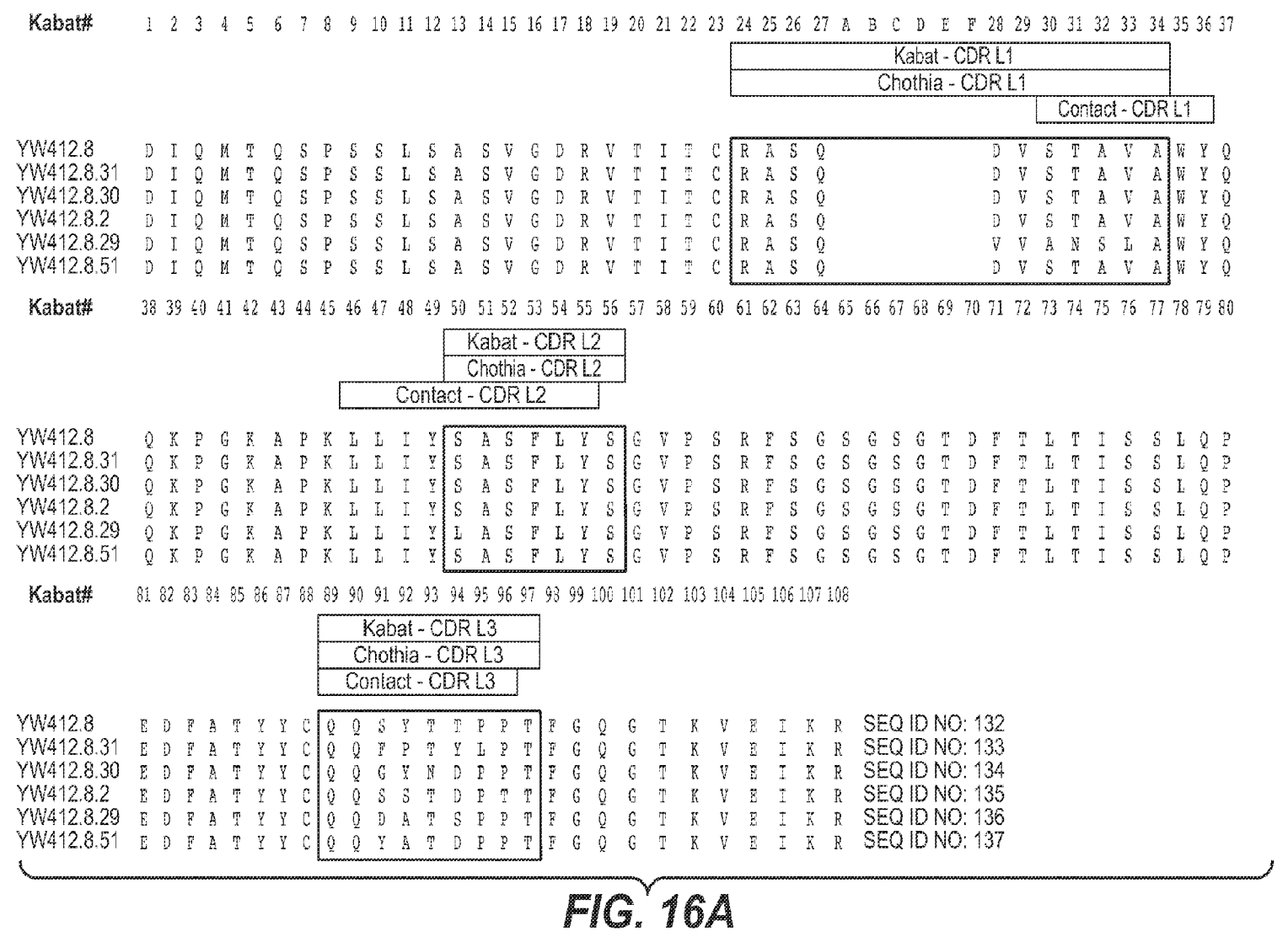

An exemplary brain antigen bound by such multispecific/bispecific antibody is BACE1, and an exemplary antibody binding thereto is the YW412.8.31 antibody in FIGS. 16A-B herein.

Figure 11A:
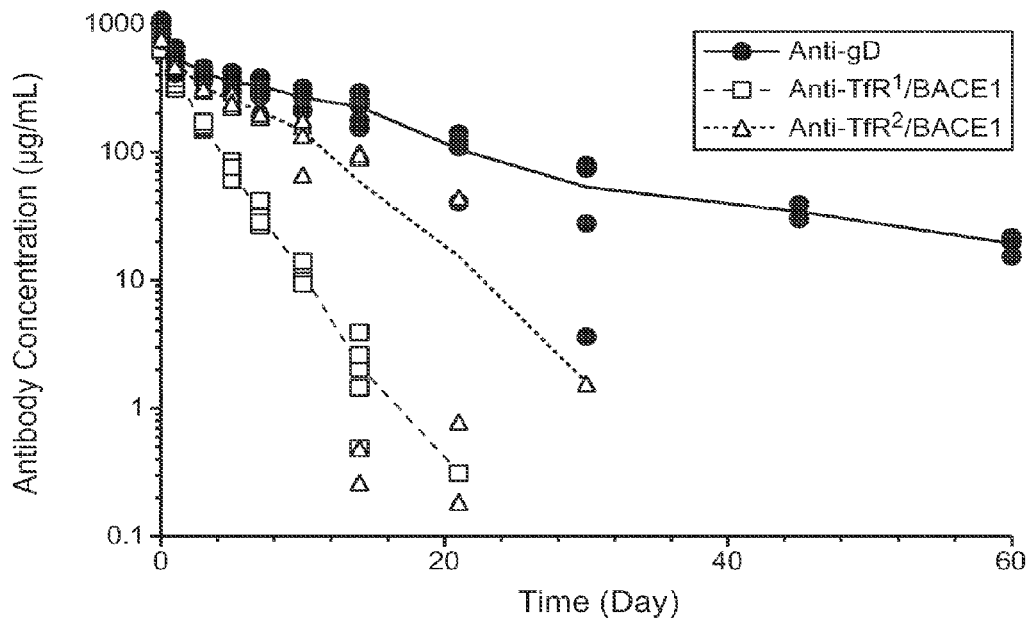
FIGS. 11A-11B depict the pharmacokinetic results of the experiments described in Example 5, specifically individual and group mean anti-TfR$^1$/BACE1, anti-TfR$^2$/BACE1 and anti-gD serum concentrations versus time following a single IV bolus administration at 30 mg/kg in cynomolgus monkeys in serum (FIG. 11A) and CSF (FIG. 11B).
Figure 11B:
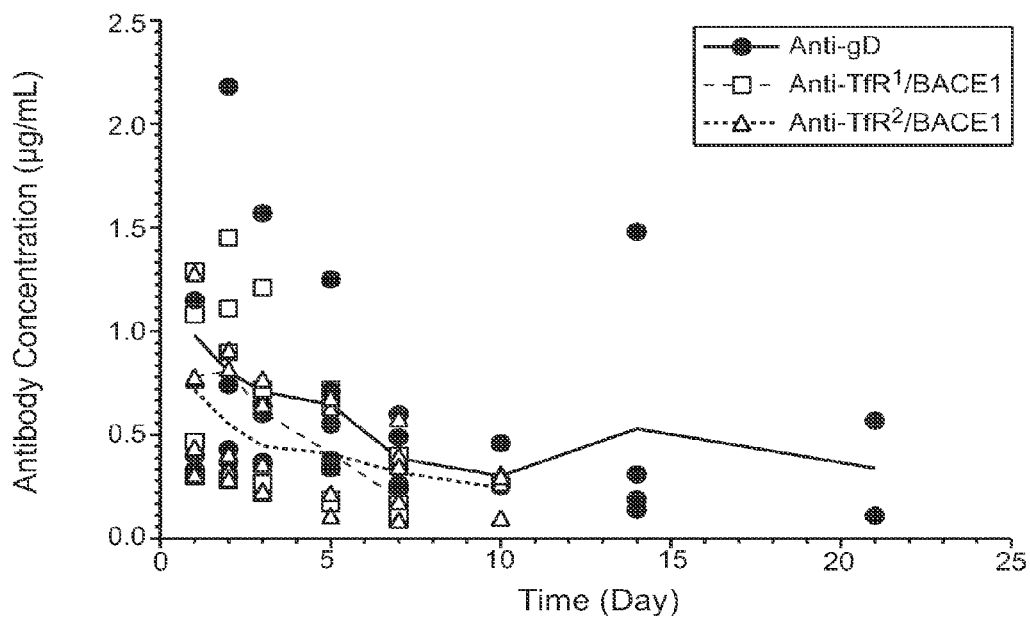
Figure 12A:
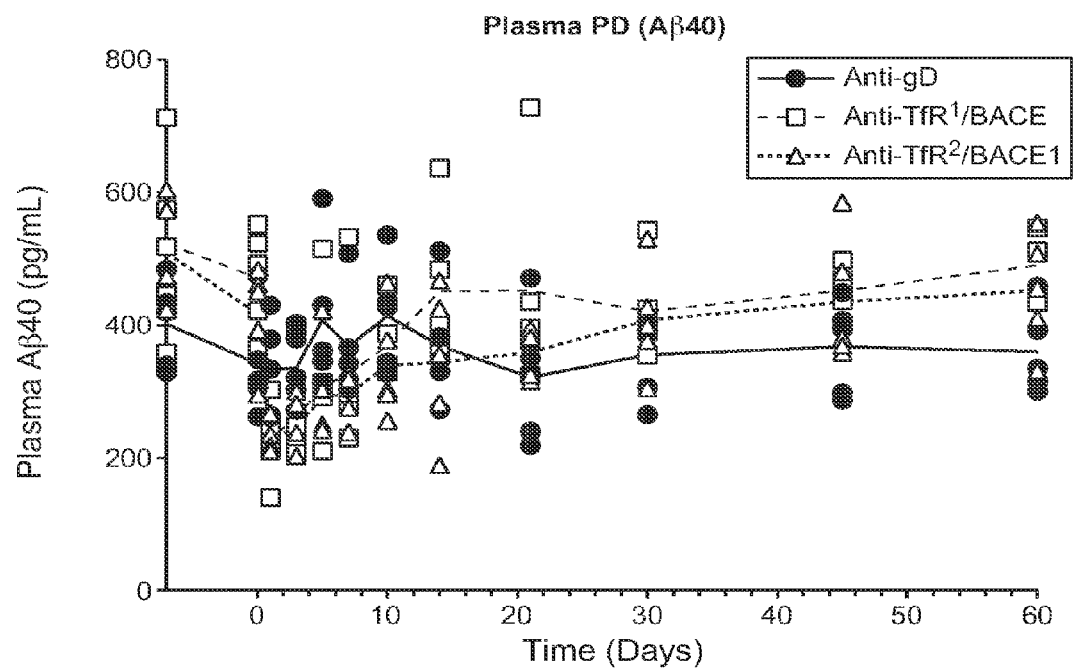
FIGS. 12A-12E depict the pharmacodynamic results of the experiments described in Example 5, specifically individual and group mean anti-TfR$^1$/BACE1, anti-TfR$^2$/BACE1 and anti-gD plasma (A) or CSF (B-E) concentrations versus time following a single IV bolus administration at 30 mg/kg in cynomolgus monkeys. The upper panels show Abetal-40 levels in plasma (FIG. 12A) and CSF (FIG. 12B), while the lower panels show soluble APPα levels (FIG. 12C), soluble APPβ levels (FIG. 12D), and sAPPβ/sAPPα ratio (FIG. 12E) over time.
Figure 12B:
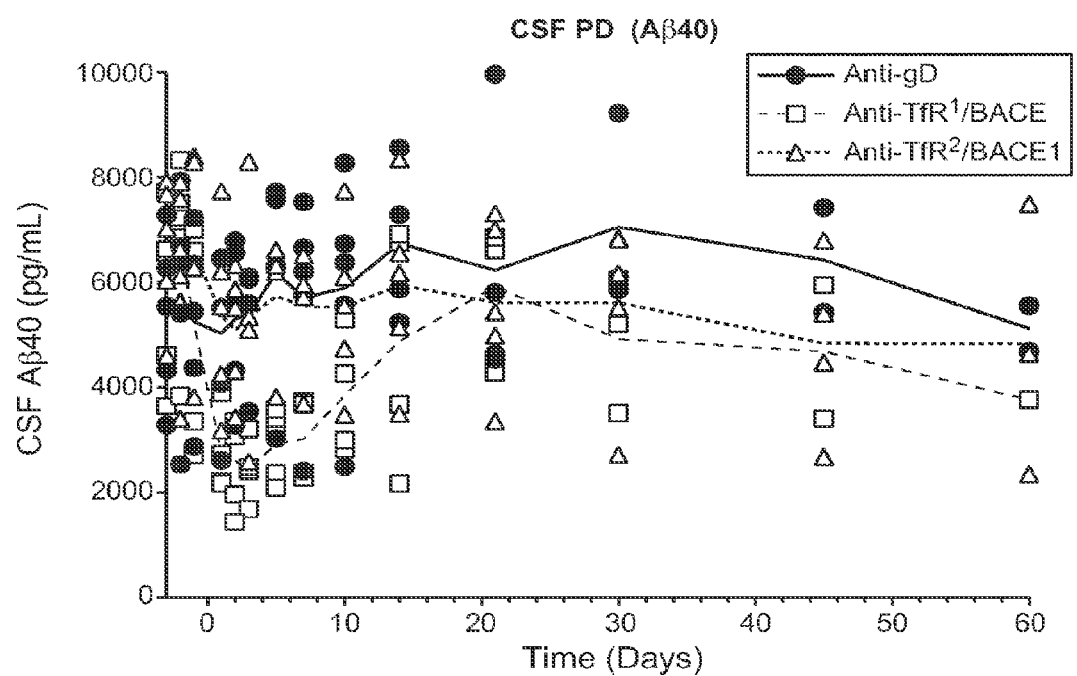
Figure 12C:
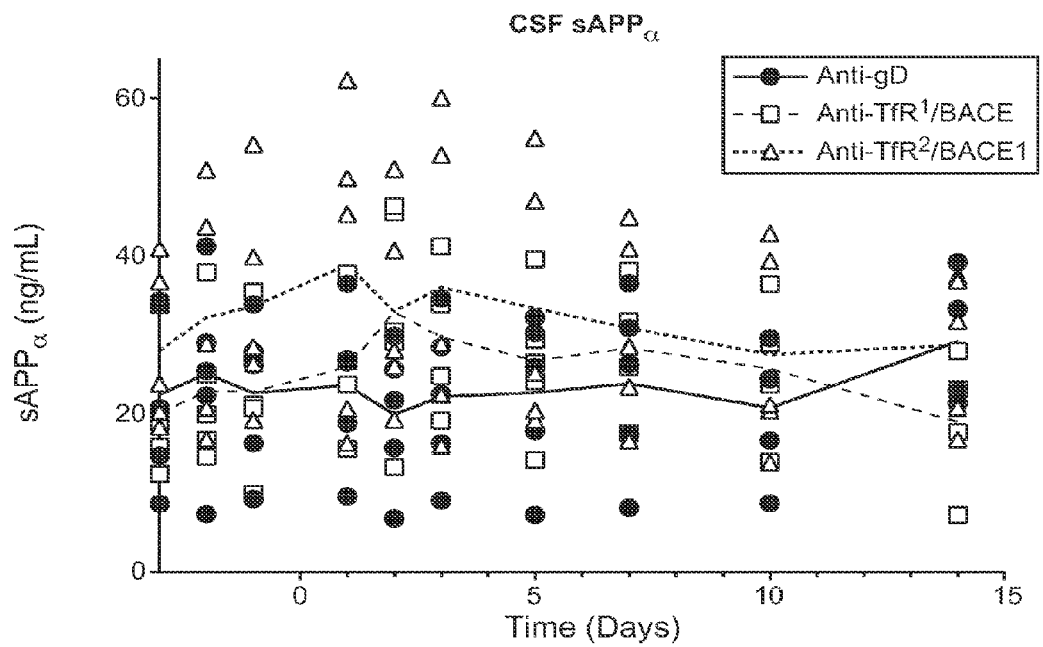
Figure 12D:
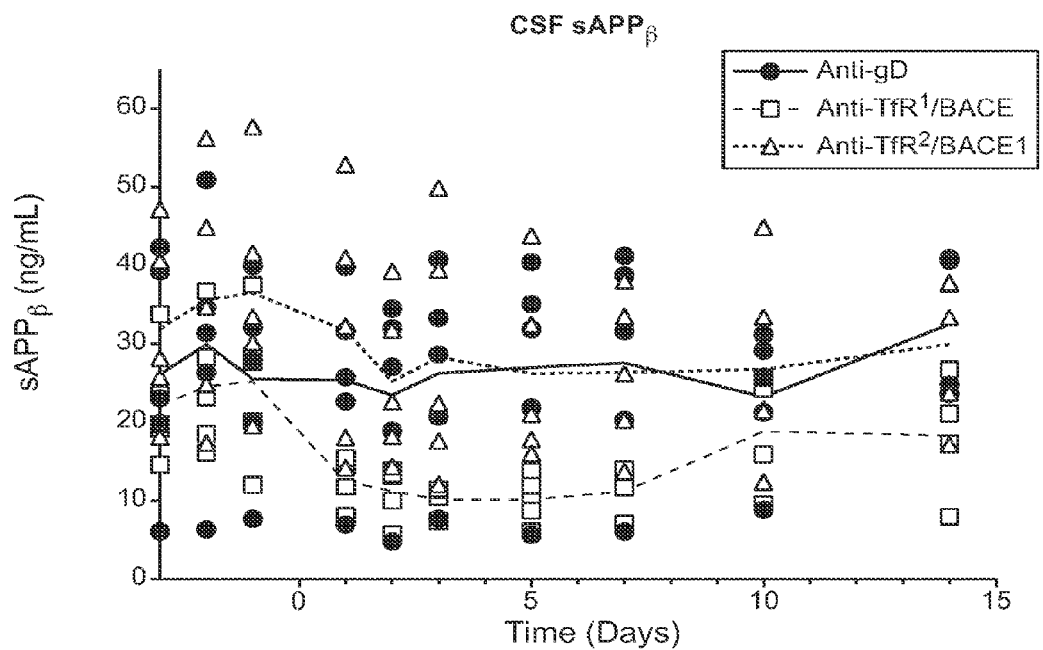
Figure 12E:
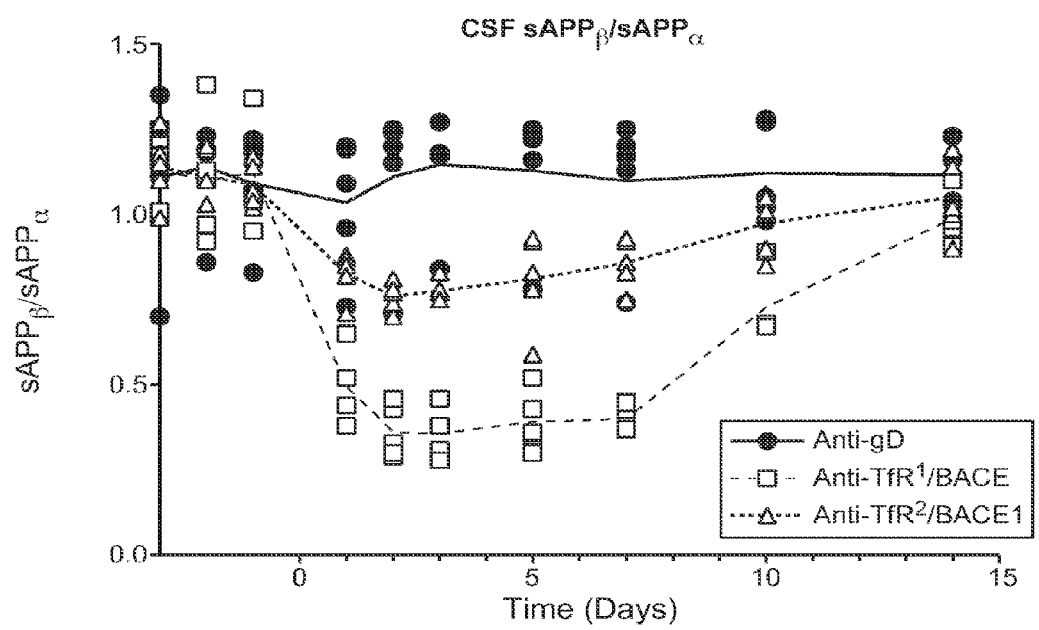
Figure 13A:
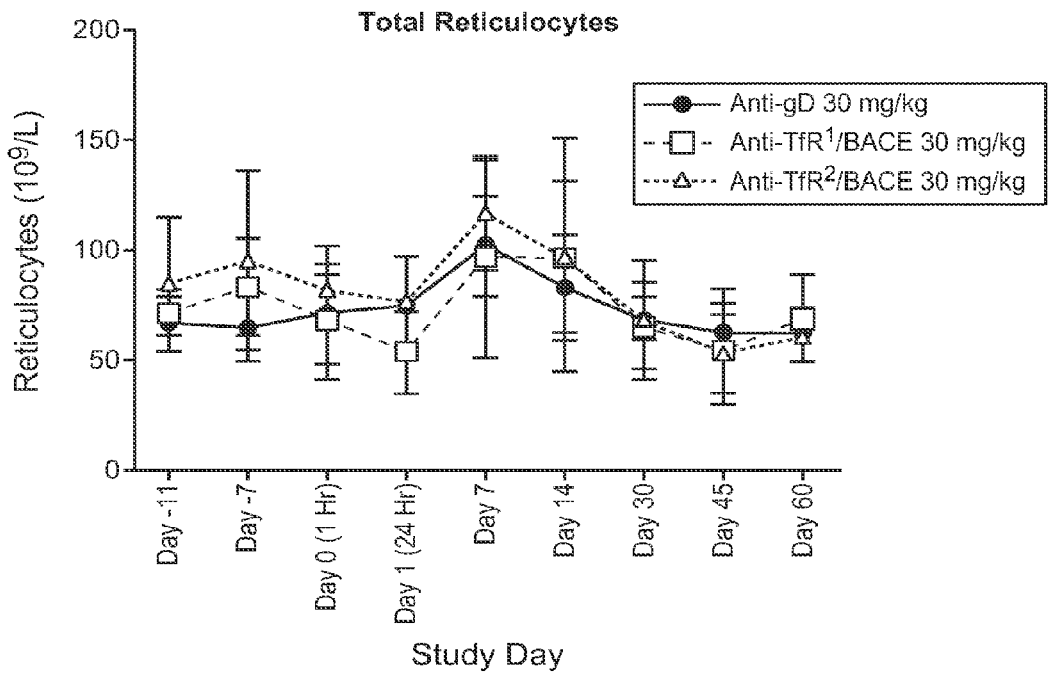
FIGS. 13A-13D depict the results of hematological sampling performed during the studies described in Example 5. At each of the indicated time points, total reticulocytes (FIG. 13A), red blood cells (FIG. 13B), hemoglobin (FIG. 13D) and the percentage of immature reticulocytes in the total reticulocyte pool (FIG. 13C) were measured using standard techniques.
Figure 13B:
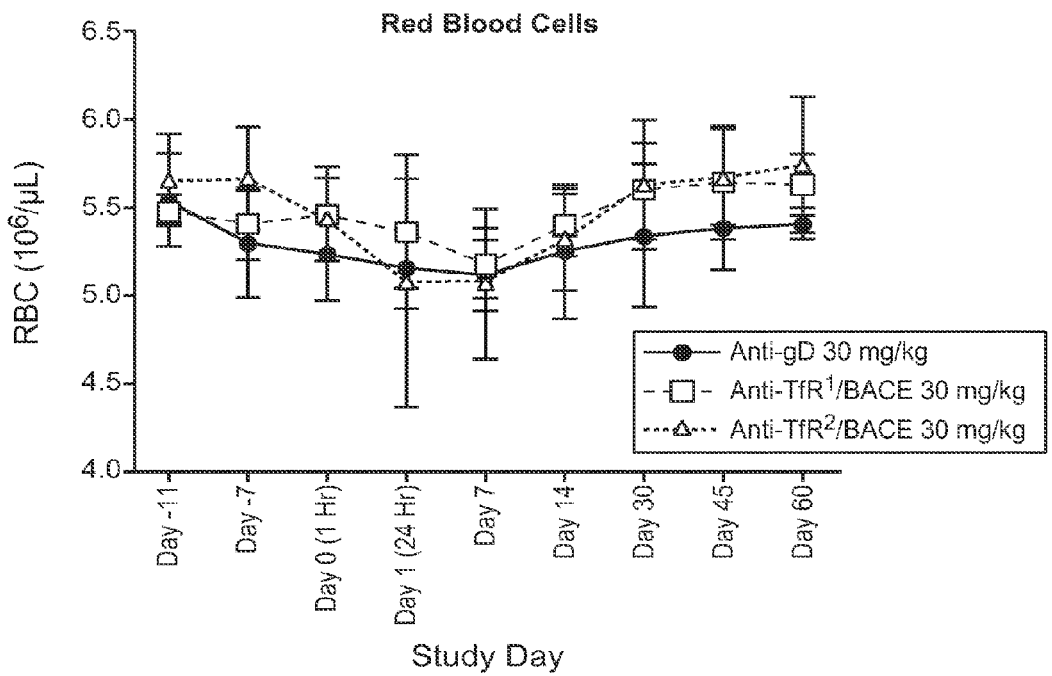
Figure 13C:
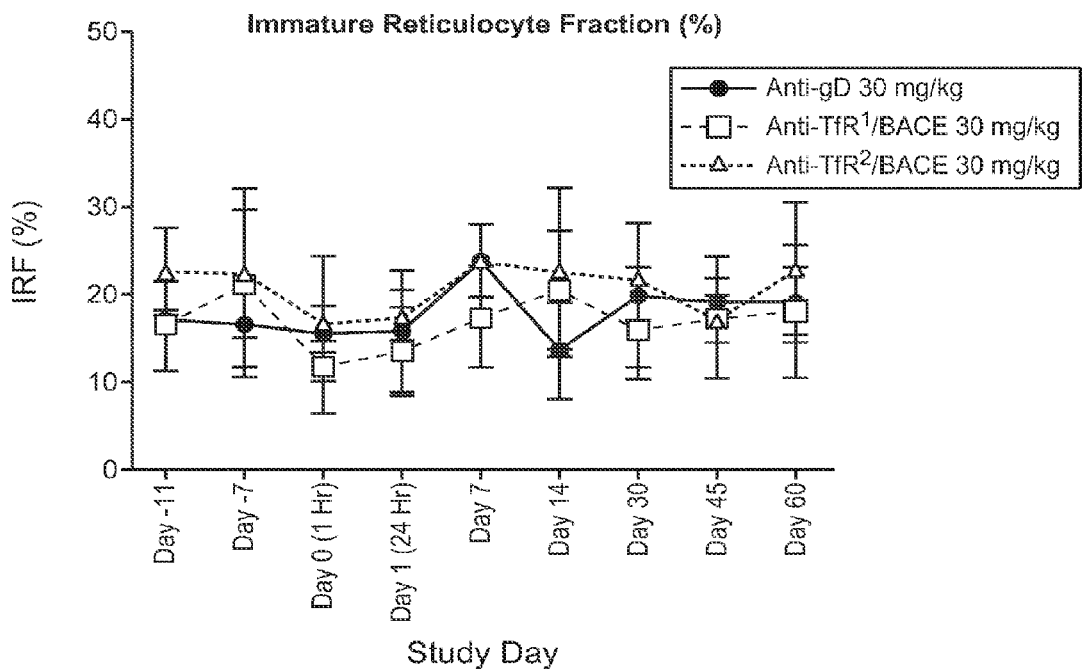
Figure 13D:
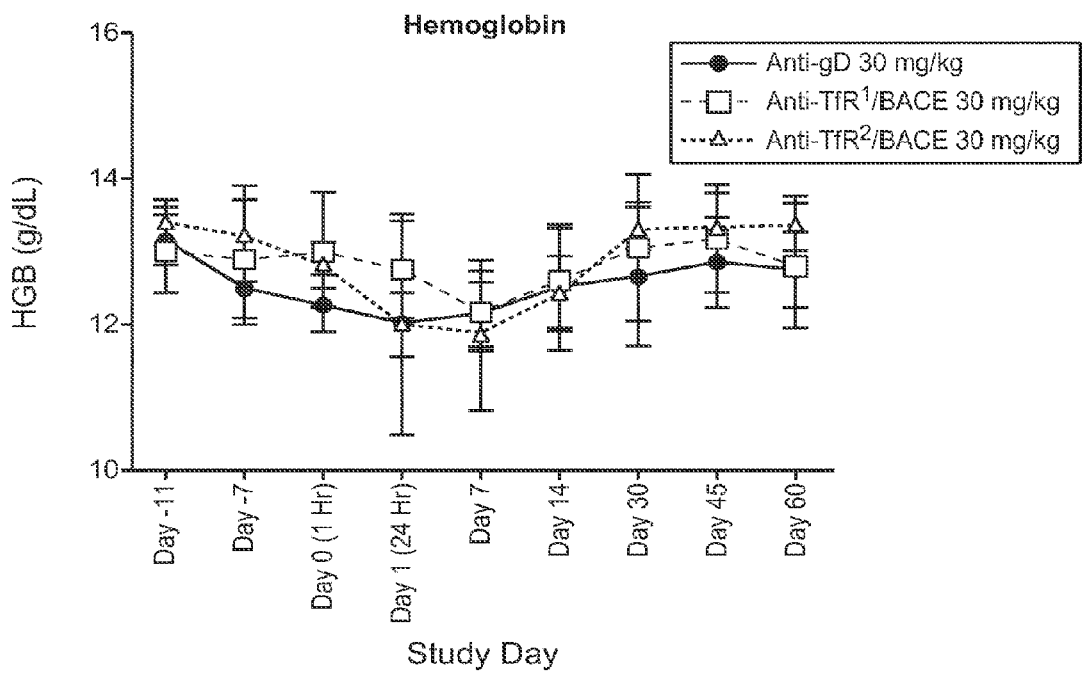

In another embodiment, the brain antigen is Abeta, exemplary such antibodies being described in WO2007068412, WO2008011348, WO20080156622, and WO2008156621, expressly incorporated herein by reference, with an exemplary Abeta antibody comprising the IgG4 MABT5102A antibody comprising the heavy and light chain amino acid sequences in FIGS. 11A and 11B, respectively.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tuft et al. *J. Immunol.* 147: 60 (1991).

Engineered antibodies with three or more functional antigen binding sites, including "Octopus antibodies" or "dual-variable domain immunoglobulins" (DVDs) are also included herein (see, e.g. US 2006/0025576A1, and Wu et al. Nature Biotechnology (2007)).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 2 under the heading of "preferred substitutions." More substantial changes are provided in Table 2 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 2

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., Blood 101:1045-1052 (2003); and Cragg, M. S. and M. J. Glennie, *Blood* 103: 2738-2743 (2004)). FcRn binding and in vivo clearance/half life determinations can also be performed using methods known in the art (see, e.g., Petkova, S. B. et al., *Intl. Immunol.* 18(12):1759-1769 (2006)).

Non-limiting examples of antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such, non-limiting, Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In some embodiments, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In some embodiments, isolated nucleic acid encoding an anti-TfR antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In some embodiments, the host cell is eukaryotic, e.g. a Chinese Hamster Ovary (CHO) cell or lymphoid cell (e.g., Y0, NS0, Sp20 cell). In some embodiments, a method of making an anti-TfR antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-TfR antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B.K.C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251

(1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B.K.C. Lo, ed., Humana Press, Totowa, N.J.), pp. 255-268 (2003).

C. Assays

Anti-TfR antibodies provided herein may be identified, screened for, or characterized for their physical/chemical properties and/or biological activities by various assays known in the art.

1. Binding Assays and Other Assays

Various techniques are available for determining binding of the antibody to the TfR. One such assay is an enzyme linked immunosorbent assay (ELISA) for confirming an ability to bind to human TfR (and brain antigen). According to this assay, plates coated with antigen (e.g. recombinant TfR) are incubated with a sample comprising the anti-TfR antibody and binding of the antibody to the antigen of interest is determined.

In some aspects, an antibody of the invention is tested for its antigen binding activity, e.g., by known methods such as ELISA, Western blot, etc.

In another aspect, competition assays may be used to identify an antibody that competes with any of the antibodies of the invention for binding to TfR. In certain embodiments, such a competing antibody binds to the same epitope (e.g., a linear or a conformational epitope) that is bound by any of the antibodies of the invention, more specifically, any of the epitopes specifically bound by antibodies in class I, class II, class III or class IV as described herein (see, e.g., Example 1 and Table 4. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized TfR is incubated in a solution comprising a first labeled antibody that binds to TfR (e.g., one or more of the antibodies disclosed herein) and a second unlabeled antibody that is being tested for its ability to compete with the first antibody for binding to TfR. The second antibody may be present in a hybridoma supernatant. As a control, immobilized TfR is incubated in a solution comprising the first labeled antibody but not the second unlabeled antibody. After incubation under conditions permissive for binding of the first antibody to TfR, excess unbound antibody is removed, and the amount of label associated with immobilized TfR is measured. If the amount of label associated with immobilized TfR is substantially reduced in the test sample relative to the control sample, then that indicates that the second antibody is competing with the first antibody for binding to TfR. See Harlow and Lane (1988) *Antibodies: A Laboratory Manual* ch. 14 (Cold Spring Harbor Laboratory, Cold Spring Harbor, N.Y.).

2. Activity Assays

In some aspects, assays are provided for identifying anti-TfR antibodies thereof having biological activity. Biological activity may include, e.g., transporting a compound associated with/conjugated to the antibody across the BBB into the brain and/or CNS. Antibodies having such biological activity in vivo and/or in vitro are also provided.

In certain embodiments, an antibody of the invention is tested for such biological activity.

D. Immunoconjugates

The invention also provides immunoconjugates comprising an anti-TfR antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In some embodiments, the anti-TfR antibody herein is coupled with a neurological disorder drug, a chemotherapeutic agent and/or an imaging agent in order to more efficiently transport the drug, chemotherapeutic agent and/or the imaging agent across the BBB.

Covalent conjugation can either be direct or via a linker. In certain embodiments, direct conjugation is by construction of a protein fusion (i.e., by genetic fusion of the two genes encoding the anti-TfR antibody and e.g., the neurological disorder drug and expression as a single protein). In certain embodiments, direct conjugation is by formation of a covalent bond between a reactive group on one of the two portions of the anti-TfR antibody and a corresponding group or acceptor on the, e.g., neurological drug. In certain embodiments, direct conjugation is by modification (i.e., genetic modification) of one of the two molecules to be conjugated to include a reactive group (as nonlimiting examples, a sulfhydryl group or a carboxyl group) that forms a covalent attachment to the other molecule to be conjugated under appropriate conditions. As one nonlimiting example, a molecule (i.e., an amino acid) with a desired reactive group (i.e., a cysteine residue) may be introduced into the anti-TfR antibody and a disulfide bond formed with the e.g., neurological drug. Methods for covalent conjugation of nucleic acids to proteins are also known in the art (i.e., photocrosslinking, see, e.g., Zatsepin et al. *Russ. Chem. Rev.* 74: 77-95 (2005))

Non-covalent conjugation can be by any nonconvalent attachment means, including hydrophobic bonds, ionic bonds, electrostatic interactions, and the like, as will be readily understood by one of ordinary skill in the art.

Conjugation may also be performed using a variety of linkers. For example, an anti-TfR antibody and a neurological drug may be conjugated using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. Peptide linkers, comprised of from one to twenty amino acids joined by peptide bonds, may also be used. In certain such embodiments, the amino acids are selected from the twenty naturally-occurring amino acids. In certain other such embodiments, one or more of the amino acids are selected from glycine, alanine, proline, asparagine, glutamine and lysine. The linker may be a "cleavable linker" facilitating release of the neurological drug upon delivery to the brain. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The invention herein expressly contemplates, but is not limited to, conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

In some embodiments, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

E. Methods and Compositions for Diagnostics and Detection

In certain embodiments, any of the anti-TfR antibodies provided herein is useful for detecting the presence of TfR in a biological sample. The term "detecting" as used herein encompasses quantitative or qualitative detection. In certain embodiments, a biological sample comprises a cell or tissue, such as blood (i.e., immature red blood cells), CSF, and BBB-containing tissue.

In some embodiments, an anti-TfR antibody for use in a method of diagnosis or detection is provided. In a further aspect, a method of detecting the presence of TfR in a biological sample is provided. In certain embodiments, the method comprises contacting the biological sample with an anti-TfR antibody as described herein under conditions permissive for binding of the anti-TfR antibody to TfR, and detecting whether a complex is formed between the anti-TfR antibody and TfR. Such method may be an in vitro or in vivo method. In some embodiments, an anti-TfR antibody is used to select subjects eligible for therapy with an anti-TfR antibody, e.g. where TfR is a biomarker for selection of patients.

Exemplary disorders that may be diagnosed using an antibody of the invention include disorders involving immature red blood cells, due to the fact that TfR is expressed in reticulocytes and is therefore detectable by any of the antibodies of the invention. Such disorders include anemia and other disorders arising from reduced levels of reticulocytes, or congenital polycythemia or neoplastic polycythemia vera, where raised red blood cell counts due to hyperproliferation of, e.g., reticulocytes, results in thickening of blood and concomitant physiological symptoms.

In certain embodiments, labeled anti-TfR antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

In some embodiments, the intact antibody lacks effector function. In another embodiment, the intact antibody has reduced effector function. In another embodiment, the intact antibody is engineered to have reduced effector function. In some aspects, the antibody is a Fab. In another aspect, the antibody has one or more Fc mutations reducing or eliminating effector function. In another aspect, the antibody has modified glycosylation due, e.g., to producing the antibody in a system lacking normal human glycosylation enzymes. In another aspect, the Ig backbone is modified to one which naturally possesses limited or no effector function.

Various techniques are available for determining binding of the antibody to the TfR. One such assay is an enzyme linked immunosorbent assay (ELISA) for confirming an ability to bind to human TfR (and brain antigen). According to this assay, plates coated with antigen (e.g. recombinant TfR) are incubated with a sample comprising the anti-TfR antibody and binding of the antibody to the antigen of interest is determined.

Assays for evaluating uptake of systemically administered antibody and other biological activity of the antibody can be performed as disclosed in the examples or as known for the anti-CNS antigen antibody of interest.

In some aspects, assays are provided for identifying anti-TfR antibodies conjugated (either covalently or non-covalently) to anti-BACE1 antibodies having biological activity. Biological activity may include, e.g., inhibition of BACE1 aspartyl protease activity. Antibodies having such biological activity in vivo and/or in vitro are also provided, e.g. as evaluated by homogeneous time-resolved fluorescence HTRF assay or a microfluidic capillary electrophoretic (MCE) assay using synthetic substrate peptides, or in vivo in cell lines which express BACE1 substrates such as APP.

F. Pharmaceutical Formulations

Pharmaceutical formulations of an anti-TfR as described herein are prepared by mixing such antibody having the desired degree of purity with one or more optional pharmaceutically acceptable carriers, excipients or stabilizers (*Remington's Pharmaceutical Sciences* 16th edition, Osol, A. Ed. (1980)), in the form of lyophilized formulations or aqueous solutions. Pharmaceutically acceptable carriers, excipients, or stabilizers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In some aspects, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredient as necessary for the particular indication being treated, preferably those with complementary activities that do not adversely affect each other. For example, it may be desirable to further provide one or more active ingredients for treating a neuropathy disorder, a neurodegenerative disease, cancer, an ocular disease disorder, a seizure disorder, a lysosomal storage disease, an amyloidosis, a viral or microbial disease, ischemia, a behavioral disorder or CNS inflammation. Exemplary such medicaments are discussed hereinbelow. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in, for example, *Remington's Pharmaceutical Sciences* 16th edition, Osol, A. Ed. (1980). One or more active ingredients may be encapsulated in liposomes that are coupled to anti-TfR antibodies described herein (see e.g., U.S. Patent Application Publication No. 20020025313).

Sustained-release preparations may be prepared. Suitable examples of sustained-release preparations include semipermeable matrices of solid hydrophobic polymers containing the antibody, which matrices are in the form of shaped articles, e.g. films, or microcapsules. Nonlimiting examples of sustained-release matrices include polyesters, hydrogels (for example, poly(2-hydroxyethyl-methacrylate), or poly (vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration are generally sterile. Sterility may be readily accomplished, e.g., by filtration through sterile filtration membranes.

G. Therapeutic Methods and Compositions

Any of the anti-TfR antibodies provided herein may be used in therapeutic methods. In some aspects, an anti-TfR antibody for use as a medicament is provided. For example, the invention provides a method of transporting a therapeutic compound across the blood-brain barrier with reduced or eliminated impact on red blood cell populations comprising exposing the anti-TfR antibody coupled to a therapeutic compound (e.g. a multispecific antibody which binds both the TfR and a brain antigen) to the BBB such that the antibody transports the therapeutic compound coupled thereto across the BBB. In another example, the invention provides a method of transporting a neurological disorder drug across the blood-brain barrier comprising exposing an anti-TfR antibody of the invention coupled to a brain disorder drug (e.g. a multispecific antibody which binds both the TfR and a brain antigen) to the BBB such that the antibody transports the neurological disorder drug coupled thereto across the BBB with reduced or eliminated impact on red blood cell populations. In some embodiments, the BBB is in a mammal (e.g. a human), e.g. one which has a neurological disorder, including, without limitation: Alzheimer's disease (AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer, traumatic brain injury, etc.

In some embodiments, the neurological disorder is selected from: a neuropathy, an amyloidosis, cancer (e.g. involving the CNS or brain), an ocular disease or disorder, a viral or microbial infection, inflammation (e.g. of the CNS or brain), ischemia, neurodegenerative disease, seizure, behavioral disorder, lysosomal storage disease, etc. The antibodies of the invention are particularly suited to treatment of such neurological disorders due to their ability to transport one or more associated active ingredients/coupled therapeutic compounds across the BBB and into the CNS/brain where such disorders find their molecular, cellular, or viral/microbial basis.

Neuropathy disorders are diseases or abnormalities of the nervous system characterized by inappropriate or uncontrolled nerve signaling or lack thereof, and include, but are not limited to, chronic pain (including nociceptive pain), pain caused by an injury to body tissues, including cancer-related pain, neuropathic pain (pain caused by abnormalities in the nerves, spinal cord, or brain), and psychogenic pain (entirely or mostly related to a psychological disorder), headache, migraine, neuropathy, and symptoms and syndromes often accompanying such neuropathy disorders such as vertigo or nausea.

For a neuropathy disorder, a neurological drug may be selected that is an analgesic including, but not limited to, a narcotic/opioid analgesic (i.e., morphine, fentanyl, hydrocodone, meperidine, methadone, oxymorphone, pentazocine, propoxyphene, tramadol, codeine and oxycodone), a non-steroidal anti-inflammatory drug (NSAID) (i.e., ibuprofen, naproxen, diclofenac, diflunisal, etodolac, fenoprofen, flurbiprofen, indomethacin, ketorolac, mefenamic acid, meloxicam, nabumetone, oxaprozin, piroxicam, sulindac, and tolmetin), a corticosteroid (i.e., cortisone, prednisone, prednisolone, dexamethasone, methylprednisolone and triamcinolone), an anti-migraine agent (i.e., sumatriptin, almotriptan, frovatriptan, sumatriptan, rizatriptan, eletriptan, zolmitriptan, dihydroergotamine, eletriptan and ergotamine), acetaminophen, a salicylate (i.e., aspirin, choline salicylate, magnesium salicylate, diflunisal, and salsalate), a anti-convulsant (i.e., carbamazepine, clonazepam, gabapentin, lamotrigine, pregabalin, tiagabine, and topiramate), an anaesthetic (i.e., isoflurane, trichloroethylene, halothane, sevoflurane, benzocaine, chloroprocaine, cocaine, cyclomethycaine, dimethocaine, propoxycaine, procaine, novocaine, proparacaine, tetracaine, articaine, bupivacaine, carticaine, cinchocaine, etidocaine, levobupivacaine, lidocaine, mepivacaine, piperocaine, prilocaine, ropivacaine, trimecaine, saxitoxin and tetrodotoxin), and a cox-2-inhibitor (i.e., celecoxib, rofecoxib, and valdecoxib). For a neuropathy disorder with vertigo involvement, a neurological drug may be selected that is an anti-vertigo agent including, but not limited to, meclizine, diphenhydramine, promethazine and diazepam. For a neuropathy disorder with nausea involvement, a neurological drug may be selected that is an anti-nausea agent including, but not limited to, promethazine, chlorpromazine, prochlorperazine, trimethobenzamide, and metoclopramide.

Amyloidoses are a group of diseases and disorders associated with extracellular proteinaceous deposits in the CNS, including, but not limited to, secondary amyloidosis, age-related amyloidosis, Alzheimer's Disease (AD), mild cognitive impairment (MCI), Lewy body dementia, Down's syndrome, hereditary cerebral hemorrhage with amyloidosis (Dutch type); the Guam Parkinson-Dementia complex, cerebral amyloid angiopathy, Huntington's disease, progressive supranuclear palsy, multiple sclerosis; Creutzfeld Jacob disease, Parkinson's disease, transmissible spongiform encephalopathy, HIV-related dementia, amyotropic lateral sclerosis (ALS), inclusion-body myositis (IBM), and ocular diseases relating to beta-amyloid deposition (i.e., macular degeneration, drusen-related optic neuropathy, and cataract).

For amyloidosis, a neurological drug may be selected that includes, but is not limited to, an antibody or other binding molecule (including, but not limited to a small molecule, a peptide, an aptamer, or other protein binder) that specifically binds to a target selected from: beta secretase, tau, presenilin, amyloid precursor protein or portions thereof, amyloid beta peptide or oligomers or fibrils thereof, death receptor 6 (DR6), receptor for advanced glycation endproducts (RAGE), parkin, and huntingtin; a cholinesterase inhibitor (i.e., galantamine, donepezil, rivastigmine and tacrine); an NMDA receptor antagonist (i.e., memantine), a monoamine depletor (i.e., tetrabenazine); an ergoloid mesylate; an anti-cholinergic antiparkinsonism agent (i.e., procyclidine, diphenhydramine, trihexylphenidyl, benztropine, biperiden and trihexyphenidyl); a dopaminergic antiparkinsonism agent (i.e., entacapone, selegiline, pramipexole, bromocriptine, rotigotine, selegiline, ropinirole, rasagiline, apomorphine, carbidopa, levodopa, pergolide, tolcapone and amantadine); a tetrabenazine; an anti-inflammatory (including, but not limited to, a nonsteroidal anti-inflammatory drug (i.e., indomethicin and other compounds listed above); a hormone (i.e., estrogen, progesterone and leuprolide); a vitamin (i.e., folate and nicotinamide); a dimebolin; a homo-taurine (i.e., 3-aminopropanesulfonic acid; 3APS); a serotonin receptor activity modulator (i.e., xaliproden); an, an interferon, and a glucocorticoid.

Cancers of the CNS are characterized by aberrant proliferation of one or more CNS cell (i.e., a neural cell) and include, but are not limited to, glioma, glioblastoma multiforme, meningioma, astrocytoma, acoustic neuroma, chondroma, oligodendroglioma, medulloblastomas, ganglioglioma, Schwannoma, neurofibroma, neuroblastoma, and extradural, intramedullary or intradural tumors.

For cancer, a neurological drug may be selected that is a chemotherapeutic agent. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphor-amide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gamma1I and calicheamicin omega1I (see, e.g., Agnew, Chem Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovorin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition of chemotherapeutic agents are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® R zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

Another group of compounds that may be selected as neurological drugs for cancer treatment or prevention are anti-cancer immunoglobulins (including, but not limited to, trastuzumab, pertuzumab, bevacizumab, alemtuxumab, cetuximab, gemtuzumab ozogamicin, ibritumomab tiuxetan, panitumumab and rituximab). In some instances, antibodies in conjunction with a toxic label or conjugate may be used to target and kill desired cells (i.e., cancer cells), including, but not limited to, tositumomab with a $^{131}$I radiolabel, or trastuzumab emtansine.

Ocular diseases or disorders are diseases or disorders of the eye, which for the purposes herein is considered a CNS organ segregated by the BBB. Ocular diseases or disorders include, but are not limited to, disorders of sclera, cornea, iris and ciliary body (i.e., scleritis, keratitis, corneal ulcer, corneal abrasion, snow blindness, arc eye, Thygeson's superficial punctate keratopathy, corneal neovascularisation, Fuchs' dystrophy, keratoconus, keratoconjunctivitis sicca, iritis and uveitis), disorders of the lens (i.e., cataract), disorders of choroid and retina (i.e., retinal detachment, retinoschisis, hypertensive retinopathy, diabetic retinopathy, retinopathy, retinopathy of prematurity, age-related macular degeneration, macular degeneration (wet or dry), epiretinal membrane, retinitis pigmentosa and macular edema), glaucoma, floaters, disorders of optic nerve and visual pathways (i.e., Leber's hereditary optic neuropathy and optic disc drusen), disorders of ocular muscles/binocular movement accommodation/refraction (i.e., strabismus, ophthalmoparesis, progressive external opthalmoplegia, esotropia, exotropia, hypermetropia, myopia, astigmatism, anisometropia, presbyopia and ophthalmoplegia), visual disturbances and blindness (i.e., amblyopia, Lever's congenital amaurosis, scotoma, color blindness, achromatopsia, nyctalopia, blindness, river blindness and micro-opthalmia/coloboma), red eye, Argyll Robertson pupil, keratomycosis, xerophthalmia and andaniridia.

For an ocular disease or disorder, a neurological drug may be selected that is an anti-angiogenic ophthalmic agent (i.e., bevacizumab, ranibizumab and pegaptanib), an ophthalmic glaucoma agent (i.e., carbachol, epinephrine, demecarium bromide, apraclonidine, brimonidine, brinzolamide, levobunolol, timolol, betaxolol, dorzolamide, bimatoprost, carteolol, metipranolol, dipivefrin, travoprost and latanoprost), a carbonic anhydrase inhibitor (i.e., methazolamide and acetazolamide), an ophthalmic antihistamine (i.e., naphazoline, phenylephrine and tetrahydrozoline), an ocular lubricant, an ophthalmic steroid (i.e., fluorometholone, prednisolone, loteprednol, dexamethasone, difluprednate, rimexolone, fluocinolone, medrysone and triamcinolone), an ophthalmic anesthetic (i.e., lidocaine, proparacaine and tetracaine), an ophthalmic anti-infective (i.e., levofloxacin, gatifloxacin, ciprofloxacin, moxifloxacin, chloramphenicol, bacitracin/polymyxin b, sulfacetamide, tobramycin, azithromycin, besifloxacin, norfloxacin, sulfisoxazole, gentamicin, idoxuridine, erythromycin, natamycin, gramicidin, neomycin, ofloxacin, trifluridine, ganciclovir, vidarabine), an ophthalmic anti-inflammatory agent (i.e., nepafenac, ketorolac, flurbiprofen, suprofen, cyclosporine, triamcinolone, diclofenac and bromfenac), and an ophthalmic antihistamine or decongestant (i.e., ketotifen, olopatadine, epinastine, naphazoline, cromolyn, tetrahydrozoline, pemirolast, bepotastine, naphazoline, phenylephrine, nedocromil, lodoxamide, phenylephrine, emedastine and azelastine).

Viral or microbial infections of the CNS include, but are not limited to, infections by viruses (i.e., influenza, HIV, poliovirus, rubella), bacteria (i.e., *Neisseria* sp., *Streptococcus* sp., *Pseudomonas* sp., *Proteus* sp., *E. coli, S. aureus, Pneumococcus* sp., *Meningococcus* sp., *Haemophilus* sp., and *Mycobacterium tuberculosis*) and other microorganisms such as fungi (i.e., yeast, *Cryptococcus neoformans*), parasites (i.e., *Toxoplasma gondii*) or amoebas resulting in CNS pathophysiologies including, but not limited to, meningitis, encephalitis, myelitis, vasculitis and abscess, which can be acute or chronic.

For a viral or microbial disease, a neurological drug may be selected that includes, but is not limited to, an antiviral compound (including, but not limited to, an adamantane antiviral (i.e., rimantadine and amantadine), an antiviral interferon (i.e., peginterferon alfa-2b), a chemokine receptor antagonist (i.e., maraviroc), an integrase strand transfer inhibitor (i.e., raltegravir), a neuraminidase inhibitor (i.e., oseltamivir and zanamivir), a non-nucleoside reverse transcriptase inhibitor (i.e., efavirenz, etravirine, delavirdine and nevirapine), a nucleoside reverse transcriptase inhibitors (tenofovir, abacavir, lamivudine, zidovudine, stavudine, entecavir, emtricitabine, adefovir, zalcitabine, telbivudine and didanosine), a protease inhibitor (i.e., darunavir, atazanavir, fosamprenavir, tipranavir, ritonavir, nelfinavir, amprenavir, indinavir and saquinavir), a purine nucleoside (i.e., valacyclovir, famciclovir, acyclovir, ribavirin, ganciclovir, valganciclovir and cidofovir), and a miscellaneous antiviral (i.e., enfuvirtide, foscarnet, palivizumab and fomivirsen)), an antibiotic (including, but not limited to, an aminopenicillin (i.e., amoxicillin, ampicillin, oxacillin, nafcillin, cloxacillin, dicloxacillin, flucoxacillin, temocillin, azlocillin, carbenicillin, ticarcillin, mezlocillin, piperacillin and bacampicillin), a cephalosporin (i.e., cefazolin, cephalexin, cephalothin, cefamandole, ceftriaxone, cefotaxime, cefpodoxime, ceftazidime, cefadroxil, cephradine, loracarbef, cefotetan, cefuroxime, cefprozil, cefaclor, and cefoxitin), a carbapenemipenem (i.e., imipenem, meropenem, ertapenem, faropenem and doripenem), a monobactam (i.e., aztreonam, tigemonam, norcardicin A and tabtoxinine-beta-lactam, a beta-lactamase inhibitor (i.e., clavulanic acid, tazobactam and sulbactam) in conjunction with another beta-lactam antibiotic, an aminoglycoside (i.e., amikacin, gentamicin, kanamycin, neomycin, netilmicin, streptomycin, tobramycin, and paromomycin), an ansamycin (i.e., geldanamycin and herbimycin), a carbacephem (i.e., loracarbef), a glycopeptides (i.e., teicoplanin and vancomycin), a macrolide (i.e., azithromycin, clarithromycin, dirithromycin, erythromycin, roxithromycin, troleandomycin, telithromycin and spectinomycin), a monobactam (i.e., aztreonam), a quinolone (i.e., ciprofloxacin, enoxacin, gatifloxacin, levofloxacin, lomefloxacin, moxifloxacin, norfloxacin, ofloxacin, trovafloxacin, grepafloxacin, sparfloxacin and temafloxacin), a sulfonamide (i.e., mafenide, sulfonamidochrysoidine, sulfacetamide, sulfadiazine, sulfamethizole, sulfanilamide, sulfasalazine, sulfisoxazole, trimethoprim, trimethoprim and sulfamethoxazole), a tetracycline (i.e., tetracycline, demeclocycline, doxycycline, minocycline and oxytetracycline), an antineoplastic or cytotoxic antibiotic (i.e., doxorubicin, mitoxantrone, bleomycin, daunorubicin, dactinomycin, epirubicin, idarubicin, plicamycin, mitomycin, pentostatin and valrubicin) and a miscellaneous antibacterial compound (i.e., bacitracin, colistin and polymyxin B)), an antifungal (i.e., metronidazole, nitazoxanide, tinidazole, chloroquine, iodoquinol and paromomycin), and an antiparasitic (including, but not limited to, quinine, chloroquine, amodiaquine, pyrimethamine, sulphadoxine, proguanil, mefloquine, atovaquone, primaquine, artemesinin, halofantrine, doxycycline, clindamycin, mebendazole, pyrantel pamoate, thiabendazole, diethylcarbamazine, ivermectin, rifampin, amphotericin B, melarsoprol, eflornithine and albendazole).

Inflammation of the CNS includes, but is not limited to, inflammation that is caused by an injury to the CNS, which can be a physical injury (i.e., due to accident, surgery, brain trauma, spinal cord injury, concussion) and an injury due to or related to one or more other diseases or disorders of the CNS (i.e., abscess, cancer, viral or microbial infection).

For CNS inflammation, a neurological drug may be selected that addresses the inflammation itself (i.e., a non-steroidal anti-inflammatory agent such as ibuprofen or naproxen), or one which treats the underlying cause of the inflammation (i.e., an anti-viral or anti-cancer agent).

Ischemia of the CNS, as used herein, refers to a group of disorders relating to aberrant blood flow or vascular behavior in the brain or the causes therefor, and includes, but is not limited to: focal brain ischemia, global brain ischemia, stroke (i.e., subarachnoid hemorrhage and intracerebral hemorrhage), and aneurysm.

For ischemia, a neurological drug may be selected that includes, but is not limited to, a thrombolytic (i.e., urokinase, alteplase, reteplase and tenecteplase), a platelet aggregation inhibitor (i.e., aspirin, cilostazol, clopidogrel, prasugrel and dipyridamole), a statin (i.e., lovastatin, pravastatin, fluvastatin, rosuvastatin, atorvastatin, simvastatin, cerivastatin and pitavastatin), and a compound to improve blood flow or vascular flexibility, including, e.g., blood pressure medications.

Neurodegenerative diseases are a group of diseases and disorders associated with neural cell loss of function or death in the CNS, and include, but are not limited to: adrenoleukodystrophy, Alexander's disease, Alper's disease, amyotrophic lateral sclerosis, ataxia telangiectasia, Batten disease, cockayne syndrome, corticobasal degeneration, degeneration caused by or associated with an amyloidosis, Friedreich's ataxia, frontotemporal lobar degeneration, Kennedy's disease, multiple system atrophy, multiple sclerosis, primary lateral sclerosis, progressive supranuclear palsy, spinal muscular atrophy, transverse myelitis, Refsum's disease, and spinocerebellar ataxia.

For a neurodegenerative disease, a neurological drug may be selected that is a growth hormone or neurotrophic factor; examples include but are not limited to brain-derived neurotrophic factor (BDNF), nerve growth factor (NGF), neurotrophin-4/5, fibroblast growth factor (FGF)-2 and other FGFs, neurotrophin (NT)-3, erythropoietin (EPO), hepatocyte growth factor (HGF), epidermal growth factor (EGF), transforming growth factor (TGF)-alpha, TGF-beta, vascular endothelial growth factor (VEGF), interleukin-1 receptor antagonist (IL-1ra), ciliary neurotrophic factor (CNTF), glial-derived neurotrophic factor (GDNF), neurturin, platelet-derived growth factor (PDGF), heregulin, neuregulin, artemin, persephin, interleukins, glial cell line derived neurotrophic factor (GFR), granulocyte-colony stimulating factor (CSF), granulocyte-macrophage-CSF, netrins, cardiotrophin-1, hedgehogs, leukemia inhibitory factor (LIF), midkine, pleiotrophin, bone morphogenetic proteins (BMPs), netrins, saposins, semaphorins, and stem cell factor (SCF).

Seizure diseases and disorders of the CNS involve inappropriate and/or abnormal electrical conduction in the CNS, and include, but are not limited to epilepsy (i.e., absence seizures, atonic seizures, benign Rolandic epilepsy, childhood absence, clonic seizures, complex partial seizures, frontal lobe epilepsy, febrile seizures, infantile spasms, juvenile myoclonic epilepsy, juvenile absence epilepsy, Lennox-Gastaut syndrome, Landau-Kleffner Syndrome, Dravet's syndrome, Otahara syndrome, West syndrome, myoclonic seizures, mitochondrial disorders, progressive myoclonic epilepsies, psychogenic seizures, reflex epilepsy, Rasmussen's Syndrome, simple partial seizures, secondarily generalized seizures, temporal lobe epilepsy, toniclonic seizures, tonic seizures, psychomotor seizures, limbic epilepsy, partial-onset seizures, generalized-onset seizures, status epilepticus, abdominal epilepsy, akinetic seizures, autonomic seizures, massive bilateral myoclonus, catamenial epilepsy, drop seizures, emotional seizures, focal seizures, gelastic seizures, Jacksonian March, Lafora Disease, motor seizures, multifocal seizures, nocturnal seizures, photosensitive seizure, pseudo seizures, sensory seizures, subtle seizures, sylvan seizures, withdrawal seizures, and visual reflex seizures).

For a seizure disorder, a neurological drug may be selected that is an anticonvulsant or antiepileptic including, but not limited to, barbiturate anticonvulsants (i.e., primidone, metharbital, mephobarbital, allobarbital, amobarbital, aprobarbital, alphenal, barbital, brallobarbital and phenobarbital), benzodiazepine anticonvulsants (i.e., diazepam, clonazepam, and lorazepam), carbamate anticonvulsants (i.e. felbamate), carbonic anhydrase inhibitor anticonvulsants (i.e., acetazolamide, topiramate and zonisamide), dibenzazepine anticonvulsants (i.e., rufinamide, carbamazepine, and oxcarbazepine), fatty acid derivative anticonvulsants (i.e., divalproex and valproic acid), gamma-aminobutyric acid analogs (i.e., pregabalin, gabapentin and vigabatrin), gamma-aminobutyric acid reuptake inhibitors (i.e., tiagabine), gamma-aminobutyric acid transaminase inhibitors (i.e., vigabatrin), hydantoin anticonvulsants (i.e. phenytoin, ethotoin, fosphenytoin and mephenytoin), miscellaneous anticonvulsants (i.e., lacosamide and magnesium sulfate), progestins (i.e., progesterone), oxazolidinedione anticonvulsants (i.e., paramethadione and trimethadione), pyrrolidine anticonvulsants (i.e., levetiracetam), succinimide anticonvulsants (i.e., ethosuximide and methsuximide), triazine anticonvulsants (i.e., lamotrigine), and urea anticonvulsants (i.e., phenacemide and pheneturide).

Behavioral disorders are disorders of the CNS characterized by aberrant behavior on the part of the afflicted subject and include, but are not limited to: sleep disorders (i.e., insomnia, parasomnias, night terrors, circadian rhythm sleep disorders, and narcolepsy), mood disorders (i.e., depression, suicidal depression, anxiety, chronic affective disorders, phobias, panic attacks, obsessive-compulsive disorder, attention deficit hyperactivity disorder (ADHD), attention deficit disorder (ADD), chronic fatigue syndrome, agoraphobia, post-traumatic stress disorder, bipolar disorder), eating disorders (i.e., anorexia or bulimia), psychoses, developmental behavioral disorders (i.e., autism, Rett's syndrome, Aspberger's syndrome), personality disorders and psychotic disorders (i.e., schizophrenia, delusional disorder, and the like).

For a behavioral disorder, a neurological drug may be selected from a behavior-modifying compound including, but not limited to, an atypical antipsychotic (i.e., risperidone, olanzapine, apripiprazole, quetiapine, paliperidone, asenapine, clozapine, iloperidone and ziprasidone), a phenothiazine antipsychotic (i.e., prochlorperazine, chlorpromazine, fluphenazine, perphenazine, trifluoperazine, thioridazine and mesoridazine), a thioxanthene (i.e., thiothixene), a miscellaneous antipsychotic (i.e., pimozide, lithium, molindone, haloperidol and loxapine), a selective serotonin reuptake inhibitor (i.e., citalopram, escitalopram, paroxetine, fluoxetine and sertraline), a serotonin-norepinephrine reuptake inhibitor (i.e., duloxetine, venlafaxine, desvenlafaxine, a tricyclic antidepressant (i.e., doxepin, clomipramine, amoxapine, nortriptyline, amitriptyline, trimipramine, imipramine, protriptyline and desipramine), a tetracyclic antidepressant (i.e., mirtazapine and maprotiline), a phenylpiperazine antidepressant (i.e., trazodone and nefazodone), a monoamine oxidase inhibitor (i.e., isocarboxazid, phenelzine, selegiline and tranylcypromine), a benzodiazepine (i.e., alprazolam, estazolam, flurazeptam, clonazepam, lorazepam and diazepam), a norepinephrine-dopamine reuptake inhibitor (i.e., bupropion), a CNS stimulant (i.e., phentermine, diethylpropion, methamphetamine, dextroamphetamine, amphetamine, methylphenidate, dexmethylphenidate, lisdexamfetamine, modafinil, pemoline, phendimetrazine, benzphetamine, phendimetrazine, armodafinil, diethylpropion, caffeine, atomoxetine, doxapram, and mazindol), an anxiolytic/sedative/hypnotic (including, but not limited to, a barbiturate (i.e., secobarbital, phenobarbital and mephobarbital), a benzodiazepine (as described above), and a miscellaneous anxiolytic/sedative/hypnotic (i.e. diphenhydramine, sodium oxybate, zaleplon, hydroxyzine, chloral hydrate, aolpidem, buspirone, doxepin, eszopiclone, ramelteon, meprobamate and ethclorvynol)), a secretin (see, e.g., Ratliff-Schaub et al. *Autism* 9: 256-265 (2005)), an opioid peptide (see, e.g., Cowen et al., *J. Neurochem.* 89:273-285 (2004)), and a neuropeptide (see, e.g., Hethwa et al. *Am. J. Physiol.* 289: E301-305 (2005)).

Lysosomal storage disorders are metabolic disorders which are in some cases associated with the CNS or have CNS-specific symptoms; such disorders include, but are not limited to: Tay-Sachs disease, Gaucher's disease, Fabry disease, mucopolysaccharidosis (types I, II, III, IV, V, VI and VII), glycogen storage disease, GM1-gangliosidosis, metachromatic leukodystrophy, Farber's disease, Canavan's leukodystrophy, and neuronal ceroid lipofuscinoses types 1 and 2, Niemann-Pick disease, Pompe disease, and Krabbe's disease.

For a lysosomal storage disease, a neurological drug may be selected that is itself or otherwise mimics the activity of the enzyme that is impaired in the disease. Exemplary recombinant enzymes for the treatment of lysosomal storage disorders include, but are not limited to those set forth in e.g., U.S. Patent Application publication no. 2005/0142141 (i.e., alpha-L-iduronidase, iduronate-2-sulphatase, N-sulfatase, alpha-N-acetylglucosaminidase, N-acetyl-galactosamine-6-sulfatase, beta-galactosidase, arylsulphatase B, beta-glucuronidase, acid alpha-glucosidase, glucocerebrosidase, alpha-galactosidase A, hexosaminidase A, acid sphingomyelinase, beta-galactocerebrosidase, beta-galactosidase, arylsulfatase A, acid ceramidase, aspartoacylase, palmitoyl-protein thioesterase 1 and tripeptidyl amino peptidase 1).

In another embodiment, diseases related to or caused by inappropriate overproduction of red blood cells, or wherein the overproduction of red blood cells is an effect of the disease, can be prevented or treated by the reticulocyte-depleting effect recognized herein of anti-TfR antibodies retaining at least partial effector function. For example, in congenital or neoplastic polycythemia vera, elevated red blood cell counts due to hyperproliferation of, e.g., reticulocytes, results in thickening of blood and concomitant physiological symptoms (d'Onofrio et al., Clin. Lab. Haematol. (1996) Suppl. 1: 29-34). Administration of an anti-TfR antibody of the invention wherein at least partial effector function of the antibody was preserved would permit selective removal of immature reticulocyte populations without impacting normal transferrin transport into the CNS. Dosing of such an antibody could be modulated such that acute clinical symptoms could be minimized (ie, by dosing at a very low dose or at widely-spaced intervals), as well-understood in the art.

In some aspects, an antibody of the invention is used to detect a neurological disorder before the onset of symptoms and/or to assess the severity or duration of the disease or disorder. In some aspects, the antibody permits detection and/or imaging of the neurological disorder, including imaging by radiography, tomography, or magnetic resonance imaging (MRI).

In some aspects, a low affinity anti-TfR antibody of the invention for use as a medicament is provided. In further aspects, a low affinity anti-TfR antibody for use in treating a neurological disease or disorder (e.g., Alzheimer's disease) without depleting red blood cells (ie, reticulocytes) is provided. In certain embodiments, a modified low affinity anti-TfR antibody for use in a method of treatment as described herein is provided. In certain embodiments, the invention provides a low affinity anti-TfR antibody modified to improve its safety for use in a method of treating an individual having a neurological disease or disorder comprising administering to the individual an effective amount of the anti-TfR antibody (optionally coupled to a neurological disorder drug). In one such embodiment, the method further comprises administering to the individual an effective amount of at least one additional therapeutic agent. In further embodiments, the invention provides an anti-TfR antibody modified to improve its safety for use in reducing or inhibiting amlyoid plaque formation in a patient at risk or suffering from a neurological disease or disorder (e.g., Alzheimer's disease). An "individual" according to any of the above embodiments is optionally a human. In certain aspects, the anti-TfR antibody of the invention for use in the methods of the invention improves uptake of the neurological disorder drug with which it is coupled.

In a further aspect, the invention provides for the use of a low affinity anti-TfR antibody of the invention in the manufacture or preparation of a medicament. In some embodiments, the medicament is for treatment of neurological disease or disorder. In a further embodiment, the medicament is for use in a method of treating neurological disease or disorder comprising administering to an individual having neurological disease or disorder an effective amount of the medicament. In one such embodiment, the method further comprises administering to the individual an effective amount of at least one additional therapeutic agent.

In a further aspect, the invention provides a method for treating Alzheimer's disease. In some embodiments, the method comprises administering to an individual having Alzheimer's disease an effective amount of a multispecific antibody of the invention which binds both BACE1 and TfR or both Abeta and TfR. In one such embodiment, the method further comprises administering to the individual an effective amount of at least one additional therapeutic agent. An "individual" according to any of the above embodiments may be a human.

The anti-TfR antibodies of the invention can be used either alone or in combination with other agents in a therapy. For instance, the anti-TfR antibody of the invention may be co-administered with at least one additional therapeutic agent. In certain embodiments, an additional therapeutic agent is a therapeutic agent effective to treat the same or a different neurological disorder as the anti-TfR antibody is being employed to treat. Exemplary additional therapeutic agents include, but are not limited to: the various neurological drugs described above, cholinesterase inhibitors (such as donepezil, galantamine, rovastigmine, and tacrine), NMDA receptor antagonists (such as memantine), amyloid beta peptide aggregation inhibitors, antioxidants, γ-secretase modulators, nerve growth factor (NGF) mimics or NGF gene therapy, PPARγ agonists, HMS-CoA reductase inhibitors (statins), ampakines, calcium channel blockers, GABA receptor antagonists, glycogen synthase kinase inhibitors, intravenous immunoglobulin, muscarinic receptor agonists, nicrotinic receptor modulators, active or passive amyloid beta peptide immunization, phosphodiesterase inhibitors, serotonin receptor antagonists and anti-amyloid beta peptide antibodies. In certain embodiments, the at least one additional therapeutic agent is selected for its ability to mitigate one or more side effects of the neurological drug.

As exemplified herein, certain anti-TfR antibodies may have side effects that negatively impact reticulocyte populations in a subject treated with the anti-TfR antibody. Thus, in certain embodiments, at least one further therapeutic agent selected for its ability to mitigate such negative side effect on reticulocyte populations is coadministered with an anti-TfR antibody of the invention. Examples of such therapeutic agents include, but are not limited to, agents to increase red blood cell (ie, reticulocyte) populations, agents to support growth and development of red blood cells (ie, reticulocytes), and agents to protect red blood cell populations from the effects of the anti-TfR antibody; such agents include, but are not limited to, erythropoietin (EPO), iron supplements, vitamin C, folic acid, and vitamin B12, as well as physical replacement of red blood cells (ie, reticulocytes) by, for example, transfusion with similar cells, which may be from another individual of similar blood type or may have been previously extracted from the subject to whom the anti-TfR antibody is administered. It will be understood by one of ordinary skill in the art that in some instances, agents intended to protect existing red blood cells (ie, reticulocytes) are preferably administered to the subject preceding or concurrent with the anti-TfR antibody therapy, while agents intended to support or initiate the regrowth/development of red blood cells or blood cell populations (ie, reticulocytes or reticulocyte populations) are preferably administered concurrent with or after the anti-TfR antibody therapy such that such blood cells can be replenished after the anti-TfR antibody treatment.

In certain other such embodiments, the at least one further therapeutic agent is selected for its ability to inhibit or prevent the activation of the complement pathway upon administration of the anti-TfR antibody. Examples of such therapeutic agents include, but are not limited to, agents that interfere with the ability of the anti-TfR antibody to bind to or activate the complement pathway and agents that inhibit one or more molecular interactions within the complement pathway, and are described generally in Mollnes and Kirschfink (2006) Molec. Immunol 43:107-121, the contents of which are expressly incorporated herein by reference.

Such combination therapies noted above and herein encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. In some embodiments, administration of the anti-TfR antibody and administration of an additional therapeutic agent occur within about one month, or within about one, two or three weeks, or within about one, two, three, four, five or six days, of each other. Antibodies of the invention can also be used in combination with other interventional therapies such as, but not limited to, radiation therapy, behavioral therapy, or other therapies known in the art and appropriate for the neurological disorder to be treated or prevented.

An anti-TfR antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question or to prevent, mitigate or ameliorate one or more side effects of antibody administration. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 40 mg/kg. Thus, one or more doses of about 0.5 mg/kg, 2.0 mg/kg, 4.0 mg/kg, 5.0 mg/kg, 7.5 mg/kg, 10 mg/kg, 15 mg/kg, 20 mg/kg, 25 mg/kg, 30 mg/kg, 35 mg/kg or 40 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. It will be appreciated that one method to reduce impact on reticulocyte populations by administration of anti-TfR antibodies is to modify the amount or timing of the doses such that overall lower quantities of circulating antibody are present in the bloodstream to interact with reticulocytes. In one nonlimiting example, a lower dose of the anti-TfR antibodies may be administered with greater frequency than a higher dose would be. The dosage used may be balanced between the amount of antibody necessary to be delivered to the CNS (itself related to the affinity of the CNS antigen-specific portion of the antibody), the affinity of that antibody for TfR, and whether or not red blood cell (ie, reticulocyte)-protecting, growth and development-stimulating, or complement pathway-inhibiting compound(s) are being co- or serially administered with the antibody. The progress of this therapy is easily monitored by conventional techniques and assays as described herein and as known in the art.

It is understood that any of the above formulations or therapeutic methods may be carried out using an immunoconjugate of the invention in place of or in addition to an anti-TfR antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-TfR antibody.

EXAMPLES

Example 1: Generation, Characterization and Humanization of Human/Cyno Cross-Reactive Anti-TfR Antibodies Initially, a naïve antibody phage panning process was performed in an attempt to identify antibodies cross-reactive with both human TfR and TfR from cynomolgous ("cyno") monkeys that further did not compete with Tf for binding to TfR (Lee et al. *JMB* (2004) 1073-1093). No such cross-reactive, non-Tf-competing clone was identified from this phage panning process. However, two antibodies were identified that were useful in characterizing subsequently generated hybridoma clones.

A species cross-reactive antibody was identified that competes with Tf for binding to human or cyno TfR (Tf-competing antibody). The epitope of another clone, specific for human TfR, was mapped to the apical domain of huTfR using mouse/human chimeric TfR receptors (FIG. 1). This apical domain-binding clone lost binding to huTfR when the mouse TfR sequence in the apical domain was substituted into huTfR.

Next, an immunization-based approach to generate cross-reactive anti-human/cyno TfR antibodies was performed. Human TfR extracellular domain ("ecd") containing an N-terminal His tag and human hemachromatosis protein ("HFE") were expressed and purified as described (*Bennet et al, Nature* (2000) 403, 46-53). An analogous cyno TfR ecd construct was also made. Cyno TfR was expressed and purified in a similar manner. Human and cyno cross-reactive TfR antibodies were generated by immunizing 5 Balb/C mice in the footpad with 6 doses (twice per week) containing 2 μg each of cynoTfR and huTfR ecd. All mice sera were FACS positive and all mice were fused. Of 1632 hybridomas screened, 111 were ELISA positive for binding to both human and cyno TfR.

The resulting ELISA-positive hybridomas were screened by FACS in the presence of 1 μM human holo-Tf for binding to 293 cells transiently expressing human or cyno TfR. Briefly, FACS analysis was performed using 293 cells transfected with full length human or cyno TfR using lipofectamin 2000 plus (Invitrogen) 48-72 h before FACS analysis. Non-transfected (control) and transfected 293 cells were washed twice with FACS buffer (PBS containing 1% BSA), 50 μM of hybridoma supernatant (normalized to 10 μg/ml) was added to 293 cells in the presence of 1 μM human holo-Tf and incubated on ice for 30 min. Cells were washed twice with FACS buffer, 50 μl of PE-Goat-anti-murine Fcγ (Jackson ImmunoResearch) was added to cells and they were incubated on ice for 30 min. Cells were washed with FACS buffer and resuspended in 100 μl FACS buffer for analysis.

Figure 2A:
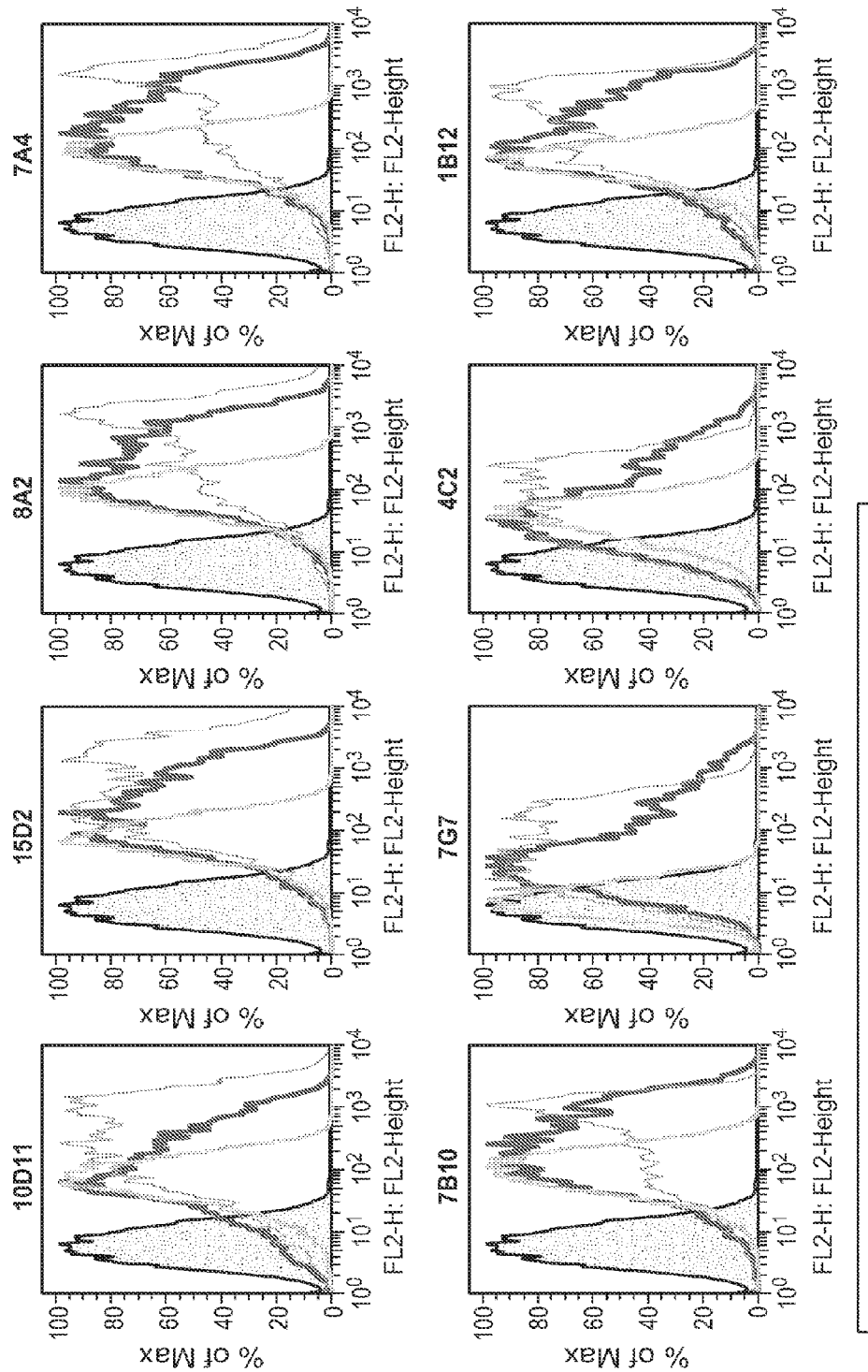
FIGS. 2A-2B depict FACS analysis of mouse hybridoma parental clone supernatants binding to human and cynomolgus TfR transiently expressed in 293 cells in the presence of 1 µM human holo-Tf. Unless otherwise indicated, the filled grey trace in each graph is background from the detection antibody, the medium grey trace is binding to 293 cells that endogenously express basal levels of human TfR, the bold black trace represents binding to transiently expressed human TfR and the thin grey trace represents binding to transiently expressed cyno TfR.
Figure 2B:
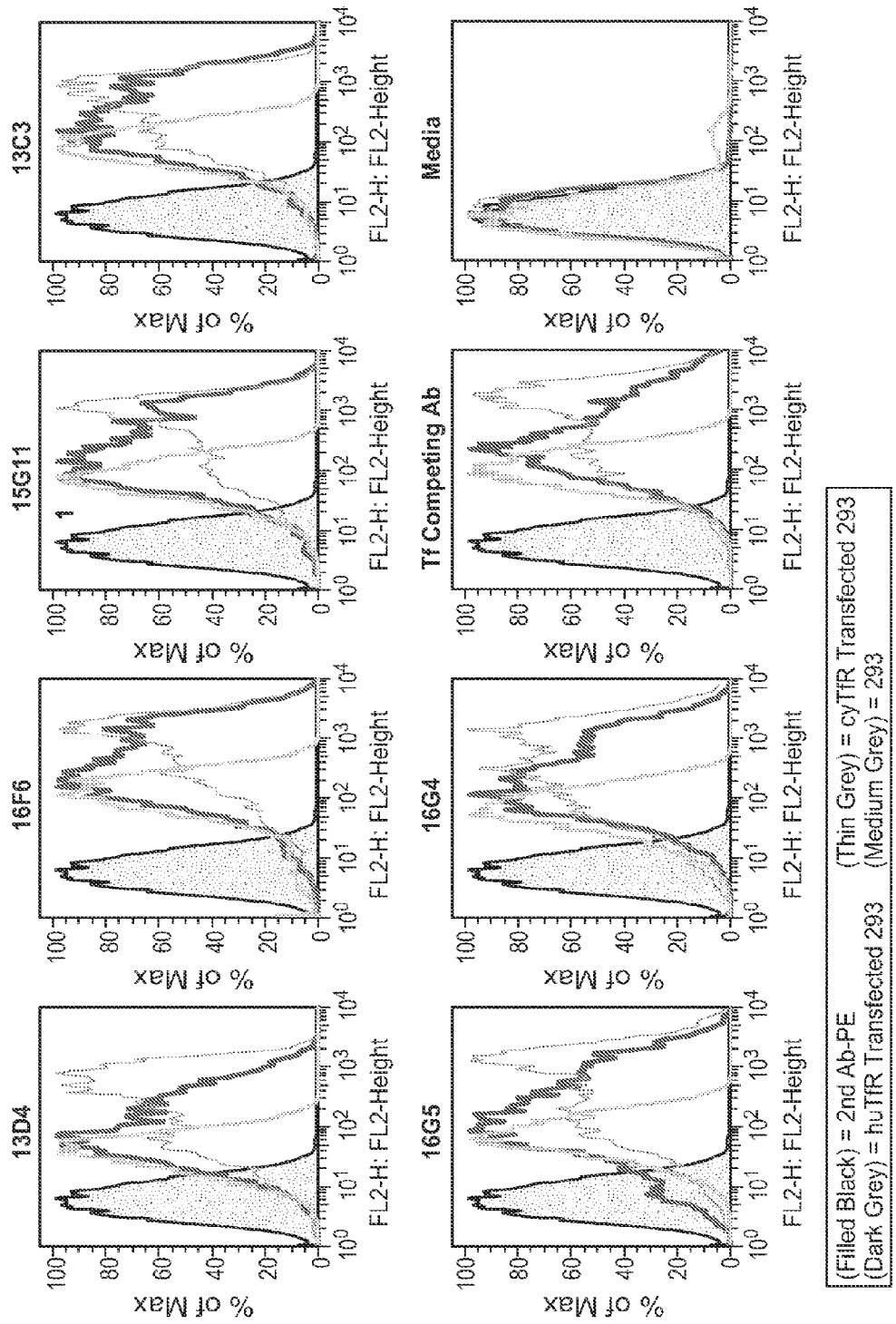

14 clones were positive for binding to both human and cyno TfR (FIGS. 2A and 2B). These clones were further subcloned and evaluated for binding to both human and cyno TfR by ELISA, and epitope mapped on huTfR using the apical binding phage clone identified above. Briefly, the apical domain phage competition ELISA was performed in maxisorp plates coated with 2 μg/ml of purified human or cyno TfR in PBS at 4° C. overnight. Plates were washed with PBS/0.05% Tween 20 and blocked using Superblock with casein (Thermo Scientific, Hudson, N.H.). A 30 μl aliquot of hybridoma supernatant (normalized to 10 μg/ml) was added to each well for 45 min. This was followed by the addition of 30 μl apical domain-binding phage at OD 0.05 for 15 min. Plates were washed with PBS/0.05% Tween 20 and 1:1000 diluted HRP-Mouse-anti M13 (GE healthcare) was added the plate and incubated for 1 h at room temperature. Plates were washed with PBS/0.05% Tween 20 and bound phage were detected using TMB substrate (BioFX Laboratories, Owings Mills). Nine of the fourteen clones were found to block binding of the apical binding antibody displayed on phage (see FIG. 2C).

Antibody affinities were measured using surface plasmon resonance ("SPR") (Biacore™, GE Healthcare). Anti-His antibody (Qiagen) was coupled onto four different flow cells of a BIACORE™ CM5 sensor chip (Biacore, Inc., Piscataway, N.J.) at between 6000 and 8000 RU Immobilization was achieved by random coupling through amino groups using a protocol provided by the manufacturer. 10×HBS-P (Biacore, Inc., Piscataway, N.J.) was diluted in water and served as the dilution and running buffer. Purified human or cyno TfR was captured, followed by a 3-fold dilution series of IgG or Fab that was injected at a flow rate of 30 ml/min using the single cycle kinetics method. Affinity constants were determined using a simple 1:1 Langmuir binding model or using a steady state model when $k_{on}$ or $k_{off}$ was beyond the detection limit. The equilibrium dissociation constant ($K_D$) was calculated as the ratio of association rate constant ($k_{on}$) and dissociation rate constant ($k_{off}$). The results are shown in FIG. 2C.

Each hybridoma was cloned. Total RNA was isolated from hybridoma using an RNeasy mini kit (Qiagen). cDNA was generated using a SMART 5' RACE cDNA Amplification kit (Clontech) based on the manufacturer's instructions. The variable region of each antibody was amplified using UPM (5' oligo) provided in the kit and a 3' oligo that anneals to the constant region. The entire PCR product was then cloned into pCR4Blunt-TOPO vector (Invitrogen) for sequencing. After sequence analysis, the hybridomas could be further subdivided into 4 groups (FIGS. 3A-3D). Clones that competed with the apical binding antibody fell into 3 related sequence classes (FIG. 3 A-C). The 4 non-apical clones (FIG. 3D) consisted of 2 related clones and 2 other unique sequences. The light and heavy chain CDRs of each clone are provided in Table 3.

TABLE 3

Light and Heavy Chain CDRs of Cross-Reactive Anti-Cyno/Human TfR Antibodies

| Clone name | Heavy/ Light | HVR1 | SEQ ID # | HVR2 | SEQ ID # | HVR3 | SEQ ID # |
|---|---|---|---|---|---|---|---|
| 7A4 | Light | RASESVDSYGNSFMH | 29 | RASNLES | 30 | QQSNEAPPT | 31 |
|  | Heavy | DYAMH | 32 | GISTYFGRTNYNQKFKG | 33 | GLSGNYVMDY | 34 |
| 8A2 | Light | RASESVDSYGNSFMH | 35 | RASNLES | 30 | QQSNEGPPT | 36 |
|  | Heavy | DYGMH | 37 | VISPYSGRTNYNQNFKG | 38 | GLSGNYVVDY | 39 |
| 15D2 | Light | RASESVDSYGNSFMH | 35 | RASNLES | 30 | QQSNEGPPT | 36 |
|  | Heavy | DYAMH | 32 | VISFYSGKTNYNQKFMG | 40 | GLSGNYVMDY | 34 |
| 10D11 | Light | RASESVDSYGNSFMH | 41 | RASNLES | 30 | QHSNEDPPT | 42 |
|  | Heavy | DYGMH | 37 | VISPYSGKTNYSQKFKG | 43 | GLSGNFVMDF | 44 |
| 7B10 | Light | RASESVDSYGNSFMH | 29 | RASNLES | 30 | QQSNEAPPT | 31 |
|  | Heavy | DYAMH | 32 | GISTYFGRTNYNQKFKG | 33 | GLSGNYVMDY | 34 |
| Consensus Class I Light CDRs |  | RASESVD(S/D)YG(N/P)SFMH | 45 | RASNLES | 30 | Q(Q/H)SNE(A/G/D)PPT | 46 |
| Consensus Class I heavy CDRs |  | DY(A/G)MH | 47 | (G/V)IS(T/F/P)Y(F/S)G(R/K)TNY(N/S)Q(K/N)F(K/M)G | 48 | GLSGN(Y/F)V(M/V)D(Y/F) | 49 |
| 15G11 | Light | RASDNLYSNLA | 50 | DATNLAD | 51 | QHFWGTPLT | 52 |
|  | Heavy | SYWMH | 53 | EINPTNGRTNYIEKFKS | 54 | GTRAYHY | 55 |
| 16G5 | Light | RASENIYSNLA | 56 | AATDLAD | 57 | QHFWGTPLT | 52 |
|  | Heavy | SYWMH | 53 | EINPTNGRTNYNENFKS | 58 | GTRAYHF | 59 |
| 13C3 | Light | RASDNIYSNLA | 60 | AATNLAD | 61 | QHFWGTPLM | 62 |
|  | Heavy | SYWMH | 53 | EINPINGRTNYSEKFKK | 63 | GTRAYHY | 55 |
| 16G4 | Light | RASDNIYSNLA | 60 | AVTNLAD | 64 | QHFWGTPLT | 52 |
|  | Heavy | SYWMH | 53 | EINPSNGRTNYNETFKS | 65 | GTRAYHY | 55 |
| Consensus Class II Light CDRs |  | RAS(E/D)N(L/I)YSNLA | 66 | (D/A)(A/V)T(N/D)LAD | 67 | QHFWGTPL(T/M) | 68 |
| Consensus Class II Heavy CDRs |  | SYWMH | 53 | EINP(T/I/S)NGRTNY(I/N/S)E(K/N/T)FK(S/K) | 69 | GTRAYH(Y/F) | 70 |
| 16F6 | Light | RASKSISKYLA | 71 | SGSTLQS | 72 | QQHNEYPWT | 73 |
|  | Heavy | SEYAWN | 74 | YISYSGTTSYNPSLKS | 75 | YGYGNPATRYFDV | 76 |
| 7G7 | Light | RARQSVSTSSYSFMH | 77 | YASIQES | 78 | QHTWEIPFT | 79 |
|  | Heavy | SYWMH | 80 | NIYPGSGSTKYDERFKS | 81 | GGYDSRAWFAY | 82 |
| 4C2 | Light | RARQSVSTSSYSFMH | 77 | YASIQES | 78 | QHTWEIPFT | 79 |
|  | Heavy | SYWMH | 80 | NIYPGSGSTKYDEKFKS | 83 | GGYDSRAWFAH | 84 |
| 1B12 | Light | TTSSSVPSSYFH | 85 | STSNLAS | 86 | HQYHRSPFT | 87 |
|  | Heavy | DYYMY | 88 | SISNGGDNTYYPDTVKG | 89 | QGALYDGYYRGAMDY | 90 |
| 13D4 | Light | RAGQDITNYLN | 91 | YTSRLHS | 92 | QQANTLPYT | 93 |
|  | Heavy | NYWIE | 94 | EILPGSGSTKYNEKFKG | 95 | RGGYGYDEFAY | 96 |
| Consensus Class IV Light CDRs |  | (R/T)(A/T)(R/S/G)(Q/S)(S/-)(V/-)(S/-)(T/-)(S/V/D)(S/P/I)(Y/S/T)(S/N)(F/Y)(M/F/L)(H/N) | 97 | (Y/S)(A/T)S(I/N/R)(Q/L)(E/A/H)S | 98 | (Q/H)(H/Q)(T/Y/A)(W/H/N)(E/R/T)(I/S/L)P(F/Y)T | 99 |
| Consensus Class IV) Heavy CDRs |  | (S/D/N)Y(W/Y)(M/I)(H/Y/E) | 100 | (N/S/E)I(Y/S/L)(P/N)G(S/G)(G/D)(S/N)T(K/Y)Y(D/P/N)(E/D)(R/K/T)(F/V)K(S/G) | 101 | (G/Q/R)G(Y/A/G)(D/L/Y)(S/Y/G)(R/D/Y)(A/G/D)(W/Y/G)(F/Y/E)(R/F/-)(G/-)(A/-)(M/-)(A/D)(Y/H) | 102 |

Representative clones from each class, (15G11, 7A4, 16F6 and 7G7), are exemplified herein for humanization and further characterization. Humanization was achieved using HVR grafts along with the inclusion of select vernier positions as outlined below and FIGS. 4A-4E. 15G11 was humanized by grafting the HVRs into the IGKV1-NL1*01 and IGHV1-3*01 human variable domains. Combinations of different mouse vernier positions were included in the humanized variants as outlined in FIG. 4E. Humanized 15G11 variant 15G11.v5 contains selected vernier positions in VL (positions 43 and 48) and VH (positions 48, 67, 69, 71 and 73) as outlined in FIG. 4A. In addition, The N-terminus of VH was changed from Q to E. For humanization of 7A4, an HVR graft was made using the 7A4 heavy chain and 8A2 light chain HVRs (7A4 and 8A2 are related clones, FIG. 3A). HVRs were grafted into the IGKV4-1*01 and IGHV1-2*02 human variable domains. Combinations of different mouse vernier positions were included in the humanized variants as outlined in FIG. 4E. Humanized 7A4 variant, 7A4.v15 contains selected vernier positions in VL (position 68) and VH (positions 24 and 71) and the CDR-L3 change G94A, as outlined in FIG. 4B. 7G7 was humanized by grafting the HVRs into the kappa 4 and subgroup I human consensus variable domains along with selected vernier positions in VH (position 93) as outlined in FIG. 4C. This humanized variant is called 7G7.v1. 16F6 was humanized by grafting the HVRs into the IGKV1-9*01 and IGHV4-59*01 human variable domains. Combinations of different mouse vernier positions were included in the humanized variants as outlined in FIG. 4E. Humanized 16F6 variant 16F6.v4 contains 2 changes in VL (I48L and F71Y) as well as selected vernier positions in VL (positions 43 and 44) and VH (positions 71 and 78) as outlined in FIG. 4D.

TABLE 4

Light and Heavy Chain CDRs of Humanized Antibodies/Fabs

| Clone name | Heavy/ Light | CDR1 | SEQ ID # | CDR2 | SEQ ID # | CDR3 | SEQ ID # |
|---|---|---|---|---|---|---|---|
| 15G11.v5 | Light | RASDNLYSNLA | 50 | DATNLAD | 51 | QHFWGTPLT | 52 |
|  | Heavy | SYWMH | 53 | EINPTNGRTNYIEKFKS | 54 | GTRAYHY | 55 |
| 7A4.v15 | Light | RASESVDSYGNSFMH | 29 | RASNLES | 30 | QQSNEAPPT | 127 |
|  | Heavy | DYAMH | 32 | GISTYFGRTNYNQKFKG | 33 | GLSGNYVMDY | 34 |
| 7G7.v1 | Light | RARQSVSTSSYSFMH | 77 | YASIQES | 78 | QHTWEIPFT | 79 |
|  | Heavy | SYWMH | 80 | NIYPGSGSTKYDERFKS | 81 | GGYDSRAWFAY | 82 |
| 16F6.v4 | Light | RASKSISKYLA | 71 | SGSTLQS | 72 | QQHNEYPWT | 73 |
|  | Heavy | SEYAWN | 74 | YISYSGTTSYNPSLKS | 75 | YGYGNPATRYFDV | 76 |

The affinity of humanized variants for human and cyno TfR was determined by SPR as IgG (FIG. 4E). Selected clones were also analyzed by SPR as Fab to assess monovalent affinity (Table 7). In both cases, the SPR experiments were performed as described above.

TABLE 5

Biacore Binding Data for Selected Fab-Formatted Variants

| Sample | HuTfR | | | CynoTfR | | | Cy/hu ratio |
|---|---|---|---|---|---|---|---|
|  | Ka | Kd | KD | Ka | Kd | KD |  |
| Mu15G11.Fab | 1.38E+06 | 4.65E-03 | 3.37E-09 | 1.07E+06 | 6.23E-03 | 5.81E-09 | 1.72 |
| Mu15G11.Fab | 6.34E+05 | 1.52E-03 | 2.41E-09 | 4.85E+05 | 3.68E-03 | 7.57E-09 | 3.15 |
| Hu15G11.v1.Fab | 6.38E+05 | 0.006986 | 1.09E-08 | 5.05E+05 | 0.0373 | 7.39E-08 |  |
| Hu15G11.v3.Fab | 6.42E+05 | 0.004657 | 7.26E-09 | 4.83E+05 | 0.0201 | 1.09E-08 |  |
| Hu15G11.v5.Fab | 4.56E+05 | 0.004063 | 8.91E-09 |  |  |  |  |
| hu15G11.v5.Fab | 7.76E+05 | 0.003643 | 4.70E-09 | 1.41E+06 | 0.02184 | 1.56E-08 | 3.4 |
| Mu7A4.Fab | 1.65E+06 | 3.13E-04 | 1.90E-10 | 1.14E+06 | 8.45E-04 | 7.41E-10 | 3.9 |
| Hu7A4.v5.Fab | 2.24E+06 | 1.53E-03 | 6.86E-11 | 1.18E+06 | 6.41E-03 | 5.44E-09 |  |
| Hu7A4.v8.Fab | 9.28E+05 | 1.07E-03 | 1.15E-09 | 7.97E+05 | 6.81E-03 | 8.55E-09 |  |
| Hu7A4.v9.Fab | 1.71E+06 | 6.86E-04 | 4.01E-10 | 8.08E+05 | 3.42E-03 | 4.23E-09 |  |
| Hu7A4.v12.Fab | 3.32E+06 | 8.44E-04 | 2.55E-10 | 1.74E+06 | 3.31E-03 | 1.90E-09 |  |
| hu7A4.v15.Fab | 9.10E+05 | 3.17E-04 | 3.48E-10 | 3.78E+05 | 0.001618 | 4.28E-09 | 11 |
| Hu7G7.v1 Fab | 1.44E+05 | 0.006594 | 4.58E-08 | 3.84E+04 | 0.007231 | 1.88E-07 | 4.4 |
| Mu16F6.Fab | 6.07E+04 | 1.90E-04 | 3.13E-09 | 5.11E+04 | 1.37E-03 | 2.68E-08 | 8.56 |
| Hu16F6.v4.Fab | 1.31E+05 | 1.69E-04 | 1.29E-09 | 9.89E+04 | 2.44E-03 | 2.47E-08 | 19.1 |

The binding epitope of the antibodies were re-confirmed as follows. A Tf-TfR blocking ELISA was performed in maxisorp plates coated with 2 μg/ml of purified human TfR in PBS at 4° C. overnight. Plates were washed with PBS/ 0.05% Tween 20 and blocked using Superblock blocking buffer in PBS (Thermo Scientific, Hudson, N.H.). 50 μl of 12.5 μM human holo-Tf (R&D Systems, Minneapolis, Minn.) was added to the plates for 40 min. A 50 μl titration of hu7A4.v15, hu15G11.v5, Tf competing antibody, and hu7G7.v1 (beginning at 10 μg/ml, 1:3 serial dilution) was added to the plate and incubated for 20 min. Plates were washed with PBS/0.05% Tween 20 and 1:1000 diluted HRP-Goat-anti human Fcγ (Jackson ImmunoResearch) was added to the plate and incubated for 1 h at room temperature. Plates were washed with PBS/0.05% Tween 20 and detected using TMB substrate (BioFX Laboratories, Owings Mills). An HFE-TfR binding ELISA was performed in maxisorp plates coated with 1 μg/ml of HFE in PBS at 4° C. overnight. Plates were washed with PBS/0.05% Tween 20 and blocked using Superblock blocking buffer in PBS (Thermo Scientific, Hudson, N.H.). A titration of human TfR (start at 100 μg/ml, 1:3 serial dilution) was added to the plate and incubated for 1 h. 1 μg/ml of hu15G11.v5, hu7A4.v15 or hu7G7.v1 was then added to the plate for 1 h. Plates were washed with PBS/0.05% Tween 20 and 1:1000 diluted HRP-Goat-anti human Fcγ (Jackson ImmunoResearch) was added the plate and incubated for 1 h at room temperature. Plates were washed with PBS/0.05% Tween 20 and detected using TMB substrate (BioFX Laboratories, Owings Mills). An HFE-TfR blocking ELISA was performed in maxisorp plates coated with 1 μg/ml HFE in PBS at 4° C. overnight. Plates were washed with PBS/0.05% Tween 20 and blocked using Superblock blocking buffer in PBS (Thermo Scientific, Hudson, N.H.). In a NUNC™ plate, a titration of hu7A4.v15, hu15G11.v5, Tf competiting antibody, human holo-Tf and control IgG (400 μg for all antibody, 8000 μg/ml for holo transferrin, 1:3 serial dilution) was combined with 2 μg/ml of biotinylated human TfR and incubated for 1 h. The mixture was then added to the HFE coated plate for 1 h at room temperature. Plates were washed with PBS/0.05% Tween 20 and 1:1000 diluted HRP-streptavidin (Southern-Biotech, Birmingham) was added the plate and incubated for 1 hour at room temperature. Plates were washed with PBS/0.05% Tween 20 and biotinylated human TfR bound to the plate was detected using TMB substrate (BioFX Laboratories, Owings Mills).

Figure 5:
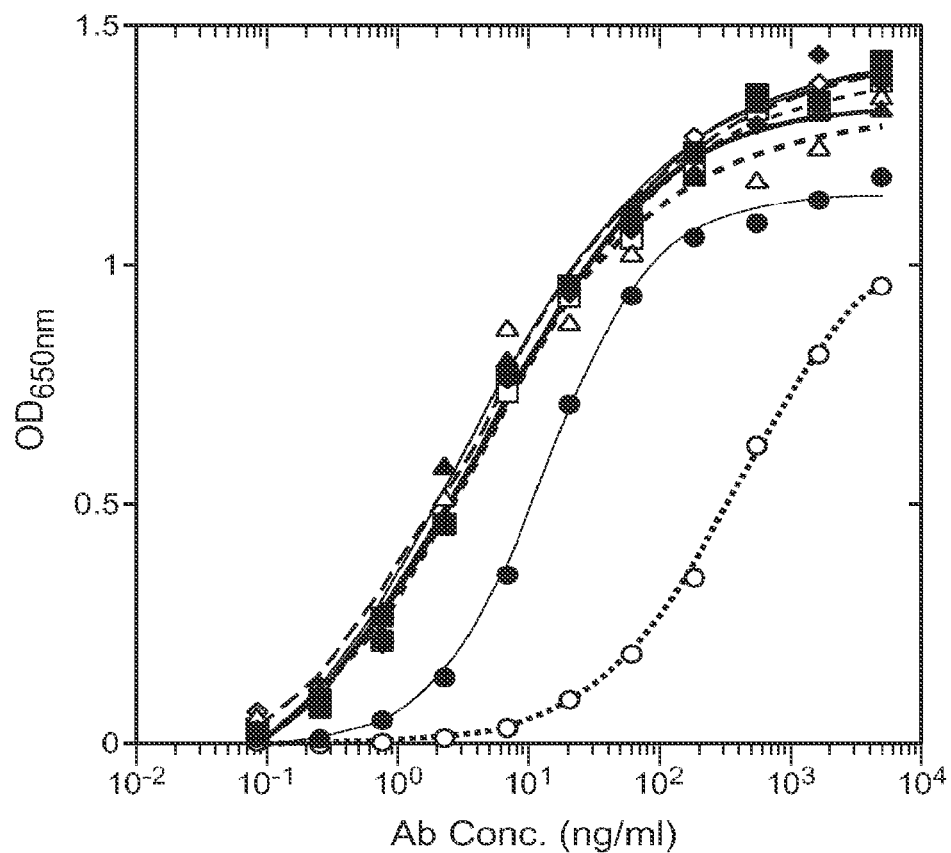
FIG. 5 depicts the binding of hu7A4.v15, hu15G11.v5 and hu7G7.v1 to huTfR in the presence of 6.3 µM holo-Tf. Antibody binding to immobilized huTfR is shown in the presence (open symbols and dashed lines) or absence (filled symbols and solid lines) of 6.3 µM holo-Tf.

Binding of these humanized variants to TfR was unaffected by the presence of 6.3 μM holo-Tf, whereas the binding of the Tf competing antibody that binds to the Tf binding site on TfR was inhibited (FIG. 5). Further, humanized 7A4.v15, 15G11.v5 and 7G7.v1 could still bind HFE captured huTfR, indicating that they did not affect binding of huTfR to immobilized HFE (FIG. 6A). In a related experiment, 7A4.v15 and 15G11.v5 did not block biotinylated TfR from binding to immobilized HFE. In contrast, this interaction was blocked by the Tf competing antibody and holo Tf (FIG. 6B). HFE and Tf are known to share a similar epitope on TfR (Bennet et al, Nature (2000) 403, 46-53).

Figure 25:
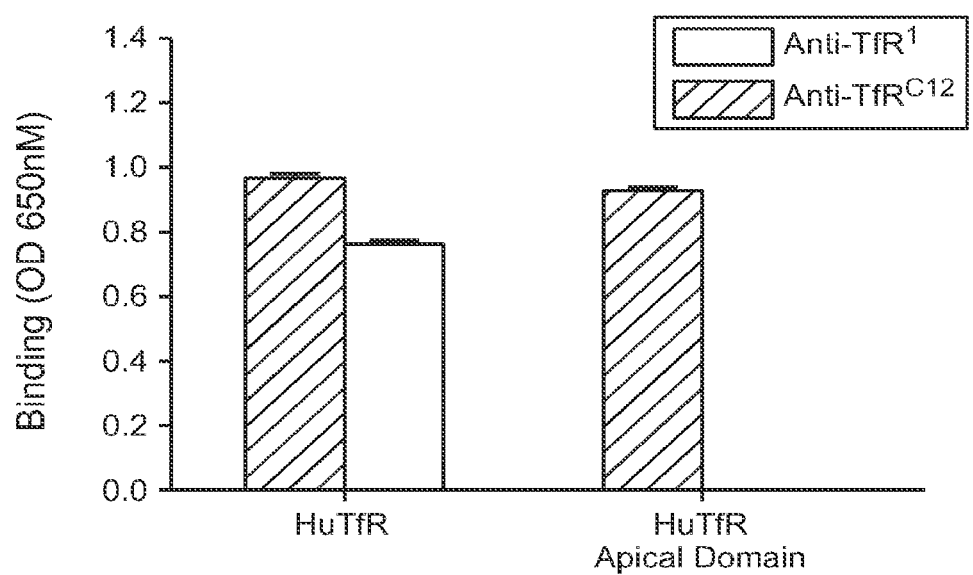
FIG. 25 depicts a competition assay between 15G11v.5 and anti-TfR$^{c12}$ as described in Example 1.

Immobilized 15G11v.5 and anti-TfR[C12] were evaluated for binding to biotinylated human TfR ECD or monovalent M13 phage displaying the human TfR apical domain. Anti-TfR[C12] was derived from a synthetic antibody phage library that was panned against human TfR ECD and binds to a site on the human TfR which competes with transferrin binding. Antibodies were coated at 1 μg/ml in PBS on Maxisorp plates. Bound biotinylated human TfR ECD or TfR-apical domain phage were detected with HRP-streptavidin (GE health care, RPN 4401V) or HRP-anti-M13 (GE health care, 27-9421-01), respectively. FIG. 25 shows that 15G11v.5 binds to human TfR apical domain. The 15G11v.5 binding site was mapped to the apical domain, a site distant from the TfR ligand binding sites.

Example 2: Affinity Engineering Human/Cyno Cross-Reactive Anti-TfR Antibodies

In addition to the humanized variants described above, additional affinity engineered variants were made. Exemplified herein is affinity engineering of 15G11.v5 and 7A4.v15. Affinity variants were generated by making individual alanine substitutions in CDR-L3 or CDR-H3 using standard techniques. These variants were screened as IgG by ELISA and SPR to identify positions important for binding to human and cyno TfR; the monovalent affinity of selected variants as Fab was also determined. Ala scan variant IgGs or Fab were expressed in 293 cells and binding to human or cyno TfR quantified by ELISA in maxisorp plates coated with 1.8 μg/ml of goat anti-human Fcγ (Jackson ImmunoResearch) in PBS at 4° C. overnight. Plates were washed with PBS/0.05% Tween 20 and blocked using Superblock blocking buffer in PBS (Thermo Scientific, Hudson, N.H.). Supernatants containing expressed IgG were diluted serially 1:5 and added to the plate for 1 h. Purified hu15G11.v5 or hu7A4.v15 were used as standards (diluted 1:5 beginning at 1 μg/ml). Plates were washed with PBS/0.05% Tween 20 and 1:1000 diluted HRP-Goat-anti kappa (Southern Biotech) was added the plate and incubated for 1 h at room temperature. Plates were washed with PBS/0.05% Tween 20 and detected using TMB substrate (BioFX Laboratories, Owings Mills). Binding was also assessed by SPR, as described above. The results are shown in FIGS. 7A (15G11.v5 variants) and 7B (7A4.v15 variants).

Further variants of 15G11.v5 with individual alanine substitutions at positions in CDR-L1, CDR-L2, CDR-H1 and CDR-H2 were also generated, expressed and first screened for binding to human and cyno TfR by ELISA (Table 6). The Hu/Cy binding ELISA was performed in maxisorp plates coated with 2 μg/ml of purified human or cyno TfR in PBS at 4° C. overnight. Plates were washed with PBS/0.05% Tween 20 and blocked using Superblock blocking buffer in PBS (Thermo Scientific, Hudson, N.H.). Cell culture supernatants containing the expressed Ala scan variant IgGs were serially diluted 1:5 and added to the wells for 1 h. Plates were washed with PBS/0.05% Tween 20 and 1:1000 diluted HRP-Goat-anti human Fcγ (Jackson ImmunoResearch) was added the plate and incubated for 1 hour at room temperature. Plates were washed with PBS/0.05% Tween 20 and detected using TMB substrate (BioFX Laboratories, Owings Mills).

TABLE 6

ELISA Analysis of hu15G11.v5 IgG Ala Variants

| | | CynoTfR EC50 (ng/ml) | HuTfR EC50 (ng/ml) |
|---|---|---|---|
| | 15G11.v5 | 1.8 | 0.8 |
| R- | G26A | 6.1 | 1.1 |
| | Y27A | 1467.1 | 21.1 |
| | T28A | 0.8 | 0.4 |
| | F29A | 12.5 | 1.5 |
| | T30A | 0.9 | 0.4 |
| | S31A | 0.1 | 0.05 |
| | Y32A | 1.4 | 0.4 |
| | W33A | 362.5 | 59.6 |
| | M34A | 1.1 | 0.4 |

TABLE 6-continued

ELISA Analysis of hu15G11.v5 IgG Ala Variants

|  |  | CynoTfR EC50 (ng/ml) | HuTfR EC50 (ng/ml) |
|---|---|---|---|
| HVR-H2 | G49A | 1.1 | 0.3 |
|  | E50A | 409.7 | 20.6 |
|  | I51A | 0.6 | 0.2 |
|  | N52A | 0.9 | 0.3 |
|  | P52aA | 8.1 | 3.9 |
|  | T53A | 0.7 | 0.3 |
|  | R56A | 5405.4 | 55.1 |
|  | N58A | 80.4 | 6.3 |
|  | Y59A | 0.7 | 0.3 |
|  | I60A | 0.7 | 0.3 |
|  | E61A | 0.6 | 0.2 |
|  | K62A | 0.7 | 0.3 |
|  | F63A | 0.6 | 0.4 |
|  | K64A | 0.6 | 0.3 |
|  | S65A | 0.7 | 0.2 |
| HVRL1 | R24A | 0.4 | 0.1 |
|  | S26A | 0.6 | 0.2 |
|  | D27A | 0.8 | 0.2 |
|  | N28A | 0.8 | 0.2 |
|  | L29A | 0.9 | 0.3 |
|  | Y30A | 1.0 | 0.3 |
|  | S31A | 0.7 | 0.3 |
|  | N32A | 4.0 | 1.6 |
|  | L33A | 0.1 | 0.05 |
| HVR-L2 | D50A | 0.5 | 0.2 |
|  | T52A | 0.3 | 0.2 |
|  | N53A | 0.6 | 0.3 |
|  | L54A | 0.5 | 0.4 |
|  | D56A | 0.5 | 0.3 |

Selected variants were then purified and their monovalent affinity for human or cyno TfR assessed by SPR (Table 7).

TABLE 7

Monovalent SPR Analysis of Select 15G11.v5 Fab Alanine Variants

|  | HuTfR | | | CynoTfR | | | Cy/hu ratio |
|---|---|---|---|---|---|---|---|
|  | Ka | Kd | KD | Ka | Kd | KD |  |
| Hu15G11.v5 Fab | 6.74E+05 | 4.74E−03 | 7.03E−09 | 4.51E+05 | 1.27E−02 | 2.82E−08 | 4.0 |
| Hu15G11.HC32A Fab | 2.38E+05 | 1.78E−03 | 7.47E−09 | 1.77E+05 | 8.51E−03 | 4.80E−08 | 6.4 |
| Hu15G11.HC34A Fab | 5.64E+05 | 4.03E−03 | 7.14E−09 | 3.04E+05 | 9.90E−03 | 3.26E−08 | 4.6 |
| Hu15G11.HC52A Fab | 5.30E+05 | 2.36E−02 | 4.44E−08 | 4.87E+05 | 5.67E−02 | 1.17E−07 | 2.6 |
| Hu15G11.HC52A Fab | 5.64E+05 | 1.96E−02 | 3.46E−08 | ND | ND | ND | ND |
| Hu15G11.HC51A Fab | 4.33E+05 | 1.04E−02 | 2.39E−08 | 3.13E+05 | 3.29E−02 | 1.05E−07 | 4.4 |
| Hu15G11.HC53A Fab | 8.90E+05 | 1.15E−02 | 1.29E−08 | 4.84E+05 | 2.50E−02 | 5.18E−08 | 4.0 |
| Hu15G11.HC54A Fab | 2.06E+05 | 8.71E−03 | 4.24E−08 | 2.80E+05 | 1.69E−02 | 6.02E−08 | 1.4 |

Example 3: Bispecific Anti-Human TfR Antibody Construction and IN VIVO Analysis

Certain of the foregoing antibody variants were reformatted as bispecific antibodies with a second arm specifically binding to BACE1. The anti-human TfR antibodies Hu15G11.v5, Hu15G11.LC92A, Hu15G11.HC52A and Hu15G11.HC53A were used to engineer the TfR binding arm of the bispecific using 'knob in hole' bispecific antibody construction technology (Carter, P. (2001) J. Immunol Methods 248, 7-15; Ridgway, J. B., Presta, L. G., and Carter, P. (1996) Protein Eng. 9, 617-621; Merchant, A. M., Zhu, Z., Yuan, J. Q., Goddard, A., Adams, C. W., Presta, L. G., and Carter, P. (1998) Nat. Biotechnol. 16, 677-681; Atwell, S., Ridgway, J. B., Wells, J. A., and Carter, P. (1997) J. Mol. Biol. 270, 26-35). In addition to the knob and hole mutations in the Fc for anti-TfR (hole) and anti-BACE1 (knob), all half-antibodies contained mutations in the Fc region that abrogated effector function (N297G) and Hu15G11.v5 and Hu15G11.LC92A contained an additional Fc mutation that abrogated effector function (D265A). The knob and hole half-antibodies were purified separately from *E. coli* and combined at a 1:1.1 ratio of anti-TfR to prevent formation of anti-TfR homodimers. Assembly of the bispecific antibody was completed by reductive annealing for at least three days at room temperature in a buffer containing reduced glutathione at a 100x ratio to antibody and 200 mM arginine pH 8.0. Following assembly, bispecific antibodies were purified by hydrophobic interaction chromatography. The assembly was confirmed by liquid chromatography mass spectroscopy and SDS-PAGE. The purified antibodies were confirmed to be homogeneous and monodisperse by size exclusion and multi angle laser light spectroscopy.

The resulting bispecific antibodies were called 15G11.v5 (anti-TfR[3]), 15G11.W92A (15G11.LC92A or anti-TfR[2]), Hu15G11.N52A (anti-TfR[5,2,4]) and Hu15G11.T53A (anti-TfR[5,3,4]). The monovalent affinity and kinetics for human and cyno TfR was determined for 115G11.v5 and 115G11.W92A by SPR, as above (see Table 9). Anti-TfR[1] and anti-TfR[2] possess similar monovalent binding affinities as anti-TfR[A] and anti-TfR[D] do for binding to mouse TfR (see Atwal et al., *Sci. Transl. Med.* 3, 84ra43 (2011); Yu et al., *Sci. Transl. Med.* 25 May 2011: Vol. 3, Issue 84, p. 84ra44).

TABLE 8

Monovalent SPR Analysis of 15G11.v5 (TfR[1]) and 15G11.W92A (LC92A, TfR[2])

|  | HuTfR | | | CynoTfR | | | Cyno/human ratio |
|---|---|---|---|---|---|---|---|
|  | Ka | Kd | KD | Ka | Kd | KD |  |
| Hu15G11.v5 Fab | 6.74E+05 | 4.74E−03 | 7.03E−09 | 4.51E+05 | 1.27E−02 | 2.82E−08 | 4.0 |
| Hu15G11.W92A Bispecific | 1.28E+05 | 3.77E−02 | 2.95E−07 | 8.36E+04 | 5.20E−02 | 6.22E−07 | 2.1 |

Additionally, the binding affinity of the anti-TfR[1], anti-TfR[2], Hu15G11.N52A and Hu15G11.T53A bispecific antibodies were measured against human and cyno TfR by SPR as previously described. As shown in Table 9 below, Anti-TfR[52.4] and anti-TfR[53.4] have binding affinities to human and cyno TfR between TfR1[h15G11.v5] and TfR2[LC92.4].

TABLE 9

Anti-cyno/human TfR antibodies (nM)

| | Human TfR | Cyno TfR |
|---|---|---|
| TfR1[h15G11.v5] | 10 | 37 |
| TfR2[LC92.4] | 270 | 810 |
| TfR[52.4] | 52 | 343 |
| TfR[53.4] | 24 | 143 |

Example 4: Impact of Effector-Containing and Effectorless Monospecific and Bispecific Antibodies on a Human Erythroleukemia Cell Line and Primary Bone Marrow Mononuclear Cells Prior studies in mice had determined that antibodies binding murine TfR with effector function and/or complement binding capabilities selectively depleted TfR-expressing reticulocytes. To ascertain whether the depletion observed in the mouse studies was unique to a murine system, further experiments were performed utilizing anti-TfR that bind to human TfR.

Figure 8A:
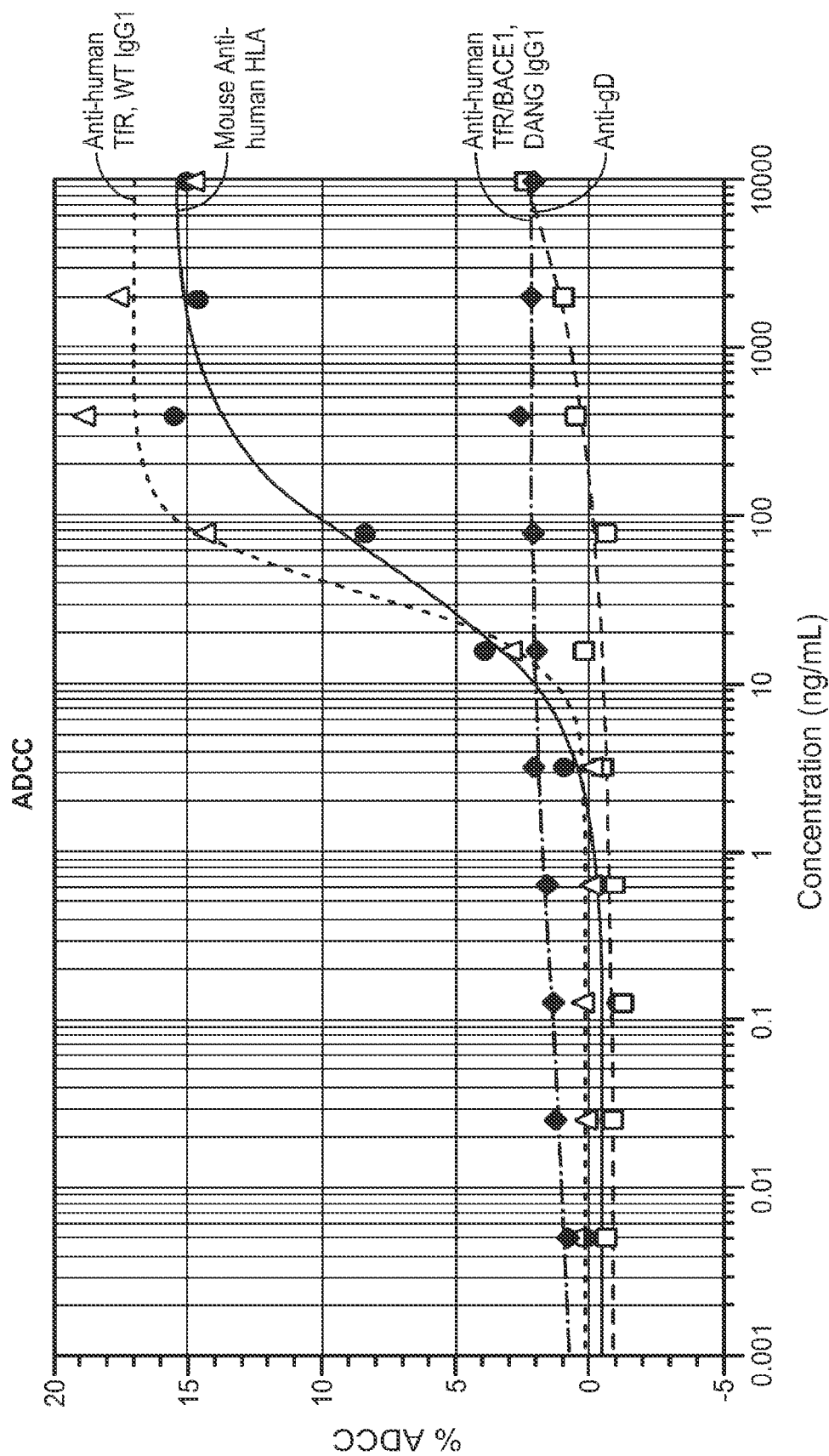
FIGS. 8A-B and FIGS. 9A-B depict the results of experiments assessing the impact of effector function status on ADCC activity of anti-human TfR ("anti-hTFR") antibodies in primary human bone marrow mononuclear cells or in a human erythroblast cell line, as described in Example 4.
Figure 8B:
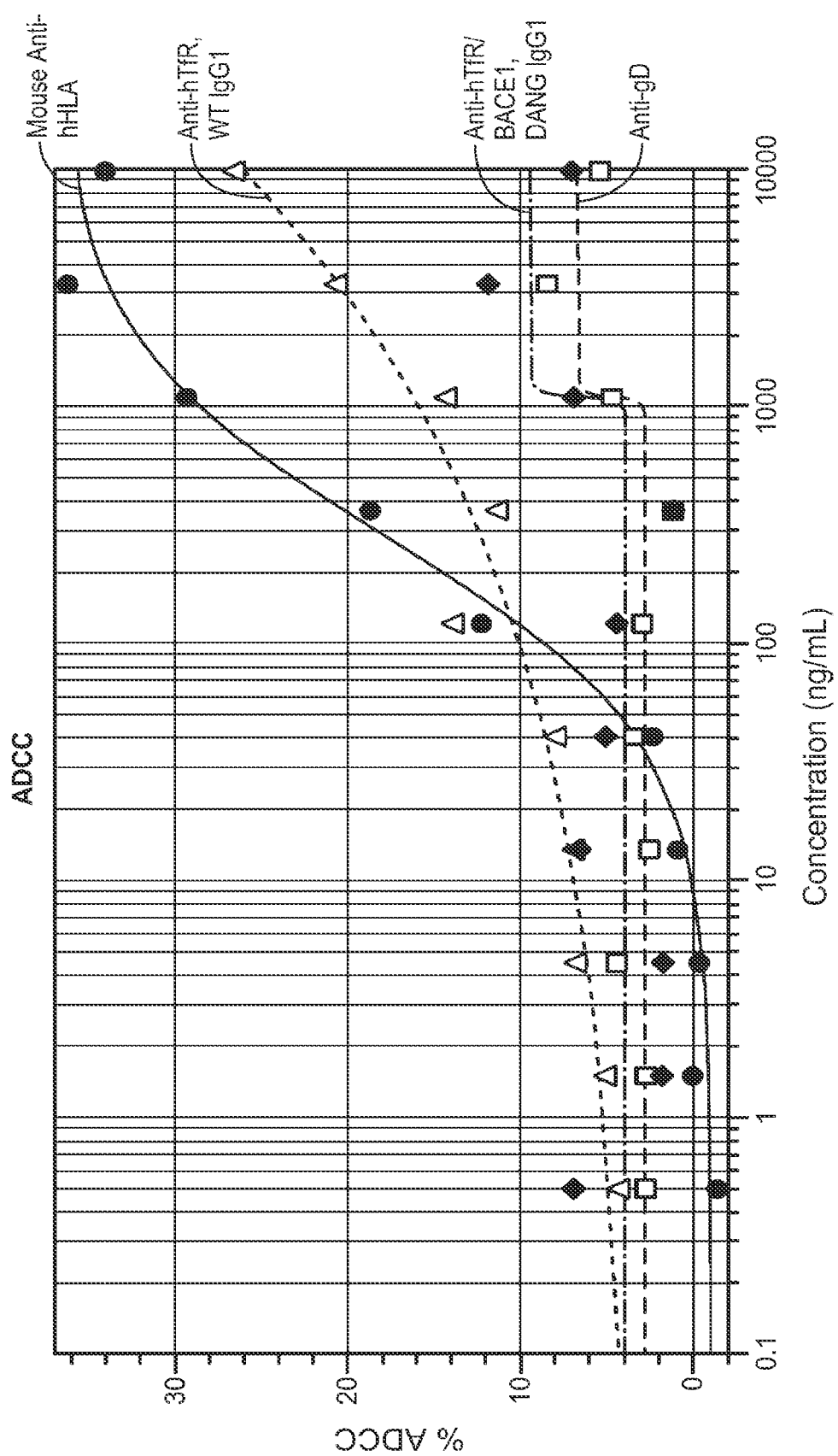

ADCC assays were carried out using peripheral blood mononuclear cells (PBMCs) from healthy human donors as effector cells. A human erythroleukemia cell line (HEL, ATCC) and primary human bone marrow mononuclear cells (AllCells, Inc.) were used as target cells. To minimize inter-donor variability which could potentially arise from allotypic differences at the residue 158 position in FcγRIIIA, blood donors were limited to those carrying the heterozygous RcγRIIIA genotype (F/V158) in the first set of experiments (FIG. 8A-B). For the second set of experiments (FIG. 9A-B), only HEL cells were used as the target cells, with PBMCs from healthy human donors carrying either the F/V158 genotype or the FcγRIIIA V/V158 genotype. The V/V158 genotype was also included in this assay due to the known association with increased NK cell-mediated ADCC activity as well as ability to bind IgG4 antibodies (Bowles and Weiner, 2005; Bruhns et al. 2008). Cells were counted and viability was determined by Vi-CELL® (Beckman Coulter; Fullerton, Calif.) following the manufacturer's instructions.

PBMCs were isolated by density gradient centrifugation using Uni-Sep™ blood separation tubes (Accurate Chemical & Scientific Corp.; Westbury, N.Y.). Target cells in 50 μL of assay medium (RPMI-1640 with 1% BSA and 100 units/mL penicillin and streptomycin) were seeded in a 96-well, round-bottom plate at 4×10⁴/well. Serial dilutions of test and control antibodies (50 μL/well) were added to the plates containing the target cells, followed by incubation at 37° C. with 5% $CO_2$ for 30 minutes to allow opsonization. The final concentrations of antibodies ranged from 0.0051 to 10,000 ng/mL following 5-fold serial dilutions for a total of 10 data points. After the incubation, 1.0×10⁶ PBMC effector cells in 100 μL of assay medium were added to each well to give a ratio of 25:1 effector: target cells, and the plates were incubated for an additional 4 hours. The plates were centrifuged at the end of incubation and the supernatants were tested for lactate dehydrogenase (LDH) activity using a Cytotoxicity Detection Kit™ (Roche Applied Scinece; Indianapolis, Ind.). The LDH reaction mixture was added to the supernatants and the plates were incubated at room temperature for 15 minutes with constant shaking. The reaction was terminated with 1 M $H_3PO_4$, and absorbance was measured at 490 nm (the background, measured at 650 nm was subtracted for each well) using a SpectraMax Plus microplate reader. Absorbance of wells containing only the target cells served as the control for the background (low control), whereas wells containing target cells lysed with Triton-X100 provided the maximum signal available (high control). Antibody-independent cellular cytotoxicity (AICC) was measured in wells containing target and effector cells without the addition of antibody. The extent of specific ADCC was calculated as follows:

$$\% \ ADCC = 100 \times \frac{A_{490} \ (\text{Sample}) - A_{490} \ (AICC)}{A_{490} \ (\text{High Control}) - A_{490} \ (\text{Low Control})}$$

ADCC values of sample dilutions were plotted against the antibody concentration, and the dose-response curves were fitted to a four-parameter model using SoftMax Pro.

In a first set of experiments, the ADCC activity of various anti-human TfR constructs were assessed using either a human erythroleukemia cell line (HEL cells) or primary human bone marrow mononuclear cells as the target cells. Bivalent IgG1 effector function-competent anti-human TfR1 antibody 15G11, and a bispecific form of this antibody with an anti-BACE1 arm in a human IgG1 format containing D265A and N297G mutations to abrogate effector function (see Example 3), were tested at various concentrations in the ADCC assay, using anti-gD WT IgG1 as a negative control and murine anti-human HLA (class I) as a positive control. The results are shown in FIGS. 8A and 8B. With either the HEL cells as targets (FIG. 8A) or the bone marrow mononuclear cells as targets (FIG. 8B), the monospecific, effector positive anti-human TfR antibody 15G11 elicited significant ADCC activity. This activity was similar to that of the positive control anti-human HLA antibodies on the HEL cells, and at a robust yet lower level relative to the positive control on the bone marrow mononuclear cells. The somewhat lower level observed in the bone marrow mononuclear cells experiment is likely due to the fact that only a portion of the heterogeneous mixture of myeloid and erythroid lineage PBMC cells used in the experiment express high levels of TfR, whereas the HEL cells have consistently high TfR expression throughout the clonal cell population. In sharp contrast, the bispecific effectorless anti-humanTfR/BACE1 antibody did not display any ADCC activity in either HEL or bone marrow mononuclear cells, similar to the negative control.

Figure 9A:
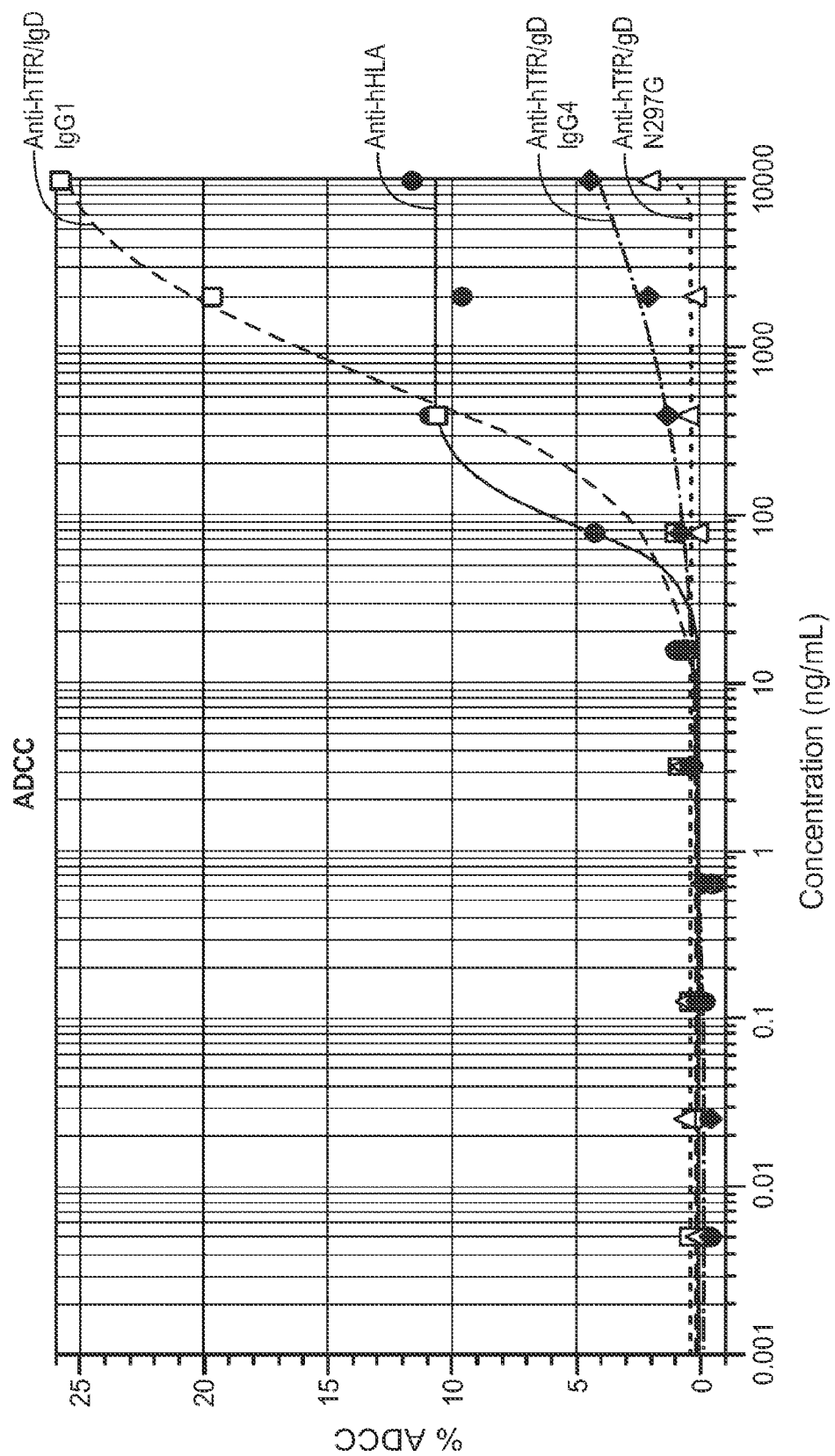
Figure 9B:
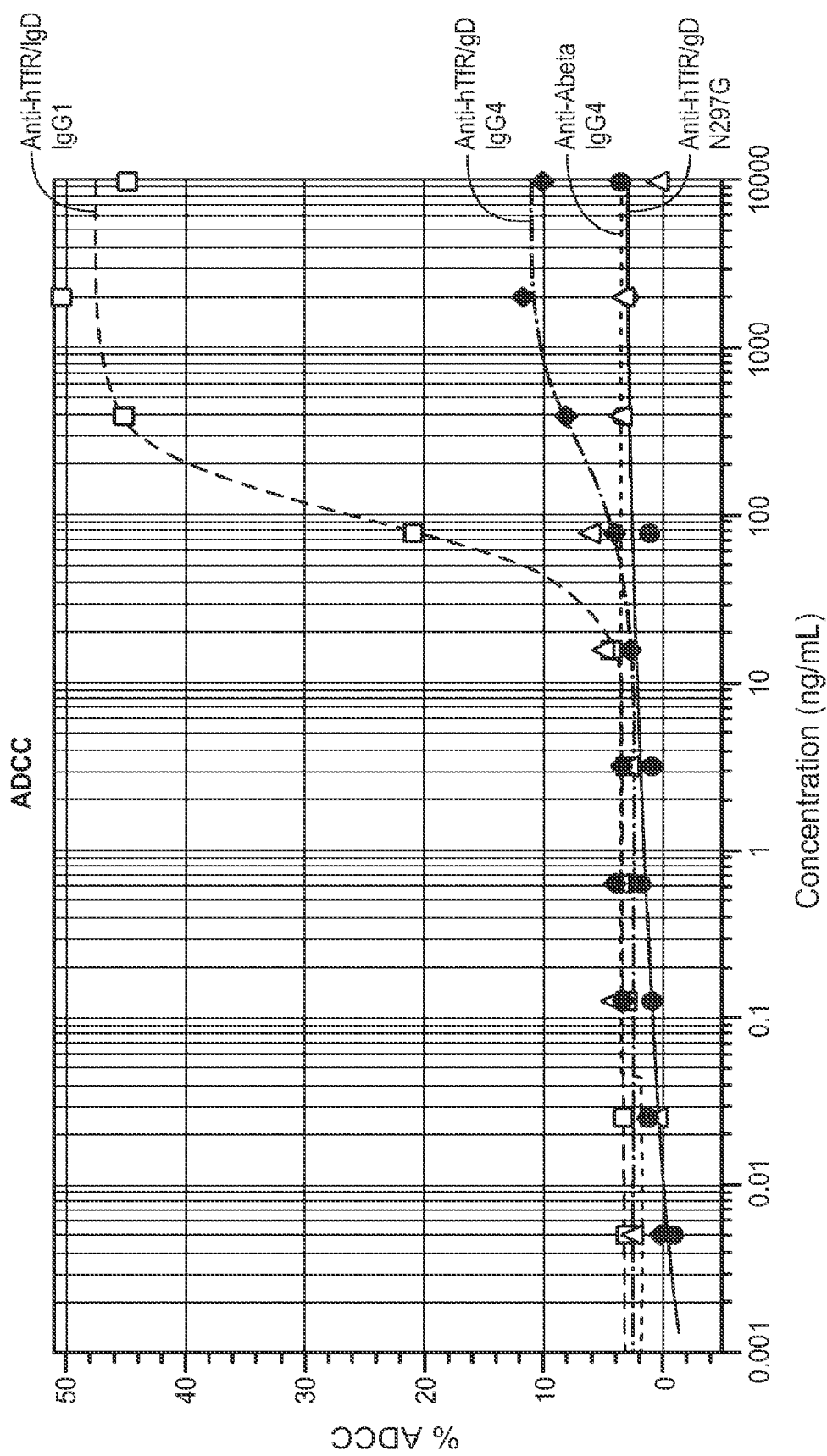

In a second set of experiments, the impact of switching the antibody isotype in this assay system was assessed. The ADCC assay procedure was identical to that described above, with the exception that all target cells were HEL cells, and the effector cells were PBMCs from healthy human donors either carrying the heterozygous FcγRIIIa-V/F158 genotype or the homozygous FcγRIIIa-V/V158 genotype. All anti-human TfR tested were bispecific with anti-gD, on three different Ig backbones: wild-type human IgG1, human IgG1 with the N297G mutation, and human IgG4. An anti-Abeta antibody with a human IgG4 backbone was also tested, and mouse anti-human HLA (class I) served as a positive control. The results are shown in FIGS. 9A and 9B. As anticipated based on the known association between effector cell activation and the V/V158 genotype (Bowles and Weiner 2005), ADCC activity was more robustly elicited by V/V158 donor PBMCs (~45% of target cells impacted) relative to F/V158 donors (~25% of target cells impacted) (compare FIG. 9A to FIG. 9B). Anti-TfR/gD with the wild-type IgG1 induced robust ADCC in HEL cells, while the anti-TfR/gD with the effectorless IgG1 did not show any ADCC activity in HEL cells, replicating the results from the first set of experiments. Notably, at concentrations of 100 ng/mL or higher, anti-TfR/gD of the IgG4 isotype showed a mild ADCC activity. This activity was not observed in the anti-Abeta IgG4 results, indicating that TfR binding was required for the ADCC activity. This finding correlates with previous reports that IgG4 has minimal, but measurable, effector function (Adolffson et al., J. Neurosci. 32(28):9677-9689 (2012); van der Zee et al. Clin Exp. Immunol 64: 415-422 (1986)); Tao et al., J. Exp. Med. 173:1025-1028 (1991)).

Figure 10:
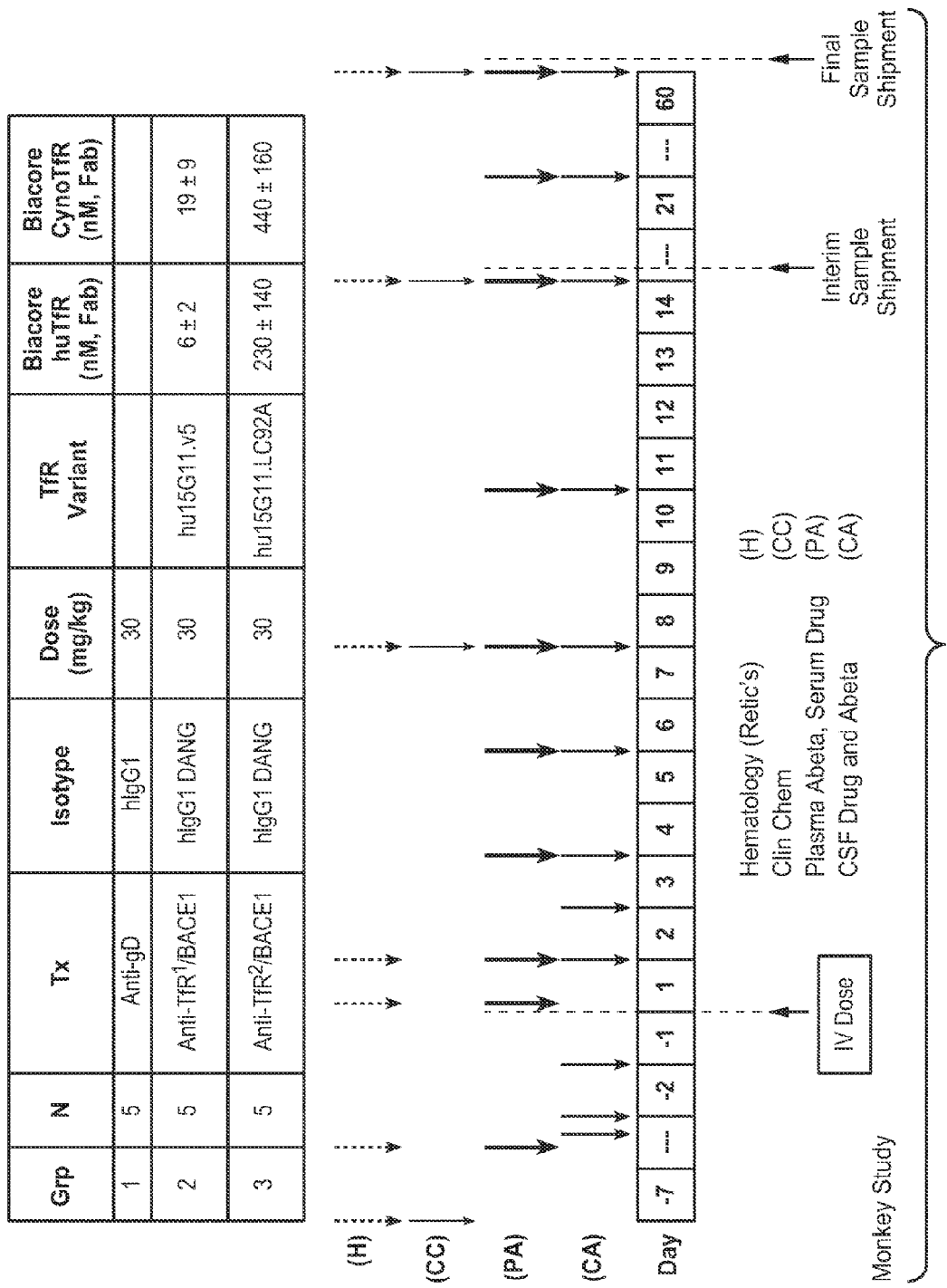
FIG. 10 depicts the dosing and sampling scheme for the primate study described in Example 5.

Example 5: Assessment of Bispecife Anti-Human TrR/BACE1 Bispecific Antibodies In Vivo A. Pharmacokinetic, Pharmacodynamic and Safety Study To evaluate the drug concentrations, pharmacodynamics effects, and safety of the bispecific anti-human TfR antibodies in vivo, cynomolgus monkeys (*Macaca fascicularis*) were dosed with bispecific antibodies using anti-TfR antibody clone 15G11 paired with the same anti-BACE1 arm used in prior examples (anti-TfR$^1$/BACE1), or clone 15G11.LC92A paired with the same anti-BACE1 arm used in prior examples (anti-TfR$^2$/BACE1) or Hu15G11.N52A (anti-TfR$^{52A}$/BACE1) and Hu15G11.T$^{53A}$ (anti-TfR$^{53A}$/BACE1). These bispecific antibodies were in a human IgG1 format with N297G or D265A and N297G mutations abrogating effector function, as described previously. As a control, an anti-gD molecule on human IgG1 was used. This study was performed in non-human primates because cross-reactivity of these anti-TfR antibodies is limited to non-human primates and humans. In addition, studies have shown that the mechanisms of drug transport between the cerebrospinal fluid (CSF) and plasma compartments may be similar between humans and primates (Poplack et al, 1977). The antibodies were administered by a single intravenous (IV) bolus injection into the saphenous vein at a dose of 30 mg/kg to conscious cynomolgus monkeys with indwelling cisterna magna catheters. At various timepoints up to 60 days post-dose, plasma, serum, and (CSF) were sampled. Sample analysis included hematology (whole blood), clinical chemistry (serum), antibody concentrations (serum and CSF), and pharmacodynamic response to the antibody (plasma and CSF). See FIG. 10 for a detailed sampling scheme.

The concentrations of the dosed antibodies in cynomolgus monkey serum and CSF were measured with an ELISA using a sheep anti-human IgG monkey absorbed antibody coat, followed by adding serum samples starting at a dilution of 1:100, and finished by adding a goat anti-human IgG antibody conjugated to horseradish peroxidase monkey adsorbed for detection. The assay had a standard curve range of 0.78-50 ng/mL and a limit of detection of 0.08 µg/mL. Results below this limit of detection were reported as less than reportable (LTR).

FIGS. 11A-B shows the results of the pharmacokinetic analysis for anti-TfR1/BACE1 and anti-TfR2/BACE1. The pharmacokinetic profile for anti-gD was as expected for a typical human IgG1 antibody in cynomolgus monkey with a mean clearance of 3.98 mL/day/kg. Both anti-TfR/BACE1 antibodies cleared faster than anti-gD, likely due to peripheral target-mediated clearance. Anti-TfR1/BACE1 had the fastest clearance, consistent with it having the highest binding affinity to TfR, whereas anti-TfR2/BACE1 showed an improved pharmacokinetic profile (ie, prolonged exposure in serum) as compared to anti-TfR1/BACE1, likely due to its reduced affinity for TfR. The clearance for anti-TfR1/BACE1 and anti-TfR2/BACE1 were 18.9 mL/day/kg and 8.14 mL/day/kg, respectively. All antibodies were detected in the CSF at approximately one one-thousandth of the serum concentration. However, there was high variability, and overall no detectable difference in the CSF antibody concentrations across the molecules.

TABLE 10

Mean (±SD) PK parameter estimates for all test antibodies following a single IV bolus dose administration at 30 mg/kg in cynomolgus monkeys (n = 5)

| Antibody | AUC$_{all}$ (day*µg/mL) | AUC$_{inf}$ (day*µg/mL) | C$_{max}$ (µg/mL) | CL (mL/day/kg) | V$_{ss}$ (mL/kg) |
|---|---|---|---|---|---|
| anti-gD | 7640 ± 1790 | 7930 ± 1910 | 912 ± 141 | 3.98 ± 1.05 | 51.3 ± 10.2 |
| anti-TfR$^1$/BACE1 | 1610 ± 240 | 1610 ± 237 | 809 ± 132 | 18.9 ± 2.54 | 41.0 ± 8.18 |
| anti-TfR$^2$/BACE1 | 3750 ± 528 | 3750 ± 530 | 850 ± 69.2 | 8.14 ± 1.21 | 41.2 ± 6.06 |

SD = standard deviation; IV = intravenous; AUC$_{all}$ = area under the concentration-time curve from time 0 to the time of last measurable concentration; AUC$_{inf}$ = area under the concentration-time curve extrapolated to infinity; C$_{max}$ = observed maximum serum concentration; CL = clearance; V$_{ss}$ = volume of distribution at steady state; Min = minimum; Max = maximum.

Figure 19:
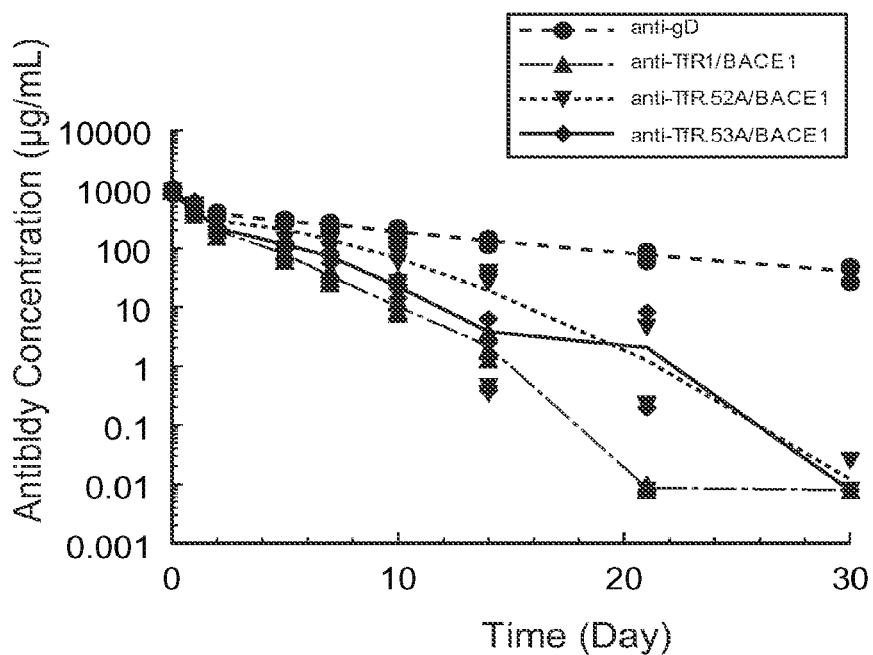
FIG. 19 depicts the pharmacokinetic properties of Anti-TfR$^1$/BACE1, Anti-Tfr$^{52A}$/BACE1 and Anti-TfR$^{53A}$/BACE1 as described in Example 5.

FIG. 19 shows the results of the pharmacokinetic analysis for anti-TfR$^1$/BACE1, anti-TfR$^{52A}$/BACE1 and anti-TfR$^{53A}$/BACE1. All anti-TfR/BACE1 antibodies cleared faster than anti-gD, likely due to peripheral target-mediated clearance. Anti-TfR$^1$/BACE1 had the fastest clearance, consistent with it having the highest binding affinity to TfR, whereas anti-TfR$^{52A}$/BACE1 and anti-TfR$^{53A}$/BACE1 showed an improved pharmacokinetic profile (ie, prolonged exposure in serum) as compared to anti-TfR$^1$/BACE1, likely due to the reduced affinity for TfR of anti-TfR$^{52A}$/BACE1 and anti-TfR$^{53A}$/BACE1.

To look at the pharmacodynamic effect in response to anti-TfR/BACE1 dosing, we measured Abeta$_{1-40}$ and sAPPα and sAPPβ levels in cynomolgus monkey plasma and CSF. Abeta$_{1-40}$ was measured with an ELISA using an anti-Abeta$_{1-40}$ specific polyclonal antibody coat, followed by adding samples, and finishing by adding a mouse anti-human Abeta$^{1-40}$ monoclonal antibody conjugated to horseradish peroxidase for detection. The assay has a limit of detection of 60 pg/mL for plasma and 140 pg/mL for CSF. Results below this concentration were reported as less than reportable (LTR). CSF concentrations of sAPPα and sAPPβ were determined using the sAPPα/sAPPβ Multi-spot assay (Mesoscale Discovery (Gaithersburg, Md.)). CSF was thawed on ice, then diluted 1:10 into 1% BSA in TBS-T (10 mM Tris buffer, pH 8.0, 150 mM NaCl, 0.1% Tween-20). The assay was performed as per the manufacturer's protocol. The assay had lower limit of quantification values of 0.05 ng/ml for sAPPα and 0.03 ng/mL for sAPPβ.

FIGS. 12A-E summarize the pharmacodynamics behavior of the antibodies. In the periphery, plasma Abeta$_{1-40}$ levels remained unchanged following anti-gD administration, but transiently decreased following anti-TfR/BACE1 administration. Both variants reduced plasma Abeta$_{1-40}$ levels, with a maximal inhibition of 50% achieved 1 day post-dosing. Plasma Abeta$_{1-40}$ levels gradually recovered, with animals given anti-TfR$^1$/BACE1 returning to baseline Abeta$_{1-40}$ levels around 14 days post-dose. Abeta$_{1-40}$ levels returned to baseline levels between 21 and 30 days post-dose in animals treated with anti-TfR$^2$/BACE1. Both anti-TfR/BACE1 antibodies reduced CSF Abeta$_{1-40}$ levels, with no change observed in anti-gD dosed animals. Anti-TrR$^1$/BACE1 administration resulted in a more significant decrease in CSF Abeta$_{1-40}$ levels (average maximal inhibition 50% of baseline) than that of anti-TfR$^2$/BACE1 (average maximal inhibition 20% of baseline). sAPPβ production was inhibited in anti-TfR/BACE1 treated animals, but not in animals who received anti-gD. Similar to results for Aβ40, anti-TfR$^1$/BACE1 had a stronger inhibitory effect on sAPPβ production than anti-TfR$^2$/BACE1. sAPPα production was stimulated during BACE1 inhibition by both anti-TfR$^1$/BACE1 and anti-TfR$^2$/BACE1, and the response correlated inversely with the level of inhibition observed for sAPPβ and Abeta$_{1-40}$. SAPPα and sAPPβ are the primary processing products of amyloid precursor protein (APP), and their levels are highly correlated. The ratio of sAPPβ/sAPPα normalizes the results to potential changes in basal APP expression or potential preanalytical differences in CSF collection and handling over the course of the study. The ratio of CSF sAPPβ/sAPPα with anti-TfR$^1$/BACE1 demonstrated a more robust PD effect than anti-TfR$^2$/BACE1. Thus, these results support target (i.e. BACE1) engagement by the anti-TfR/BACE1 antibodies.

The PD response for anti-TfR$^{52A}$/BACE1 and anti-TfR$^{53A}$/BACE1 also correlates with the duration of antibody exposure and a reduced affinity TfR arm shows increased reduction in Aβ$_{40}$ (data not shown). These data also support target engagement by these bispecific antibodies.

Overall, these results suggest that a bispecific anti-TfR/BACE1 antibody with an affinity for human TfR between that of anti-TfR$^1$/BACE1 and anti-TfR$^2$/BACE1 would likely have a desirable pharmacokinetic/pharmacodynamic balance.

No safety signals were observed in this study. There were no evident effects on any hematology or clinical chemistry parameters of monkeys given 30 mg/kg of any bispecific antibody administered up to 60 days post-dose. Importantly, reticulocyte levels were unaffected by treatment with either anti-TfR$^1$/BACE1 or anti-TfR$^2$/BACE1 (FIG. 13), as expected since these antibodies were effector-function-impaired and the overall level of circulating early reticulocytes with high TfR levels is very low in normal primates (see Example 4).

Figure 14:
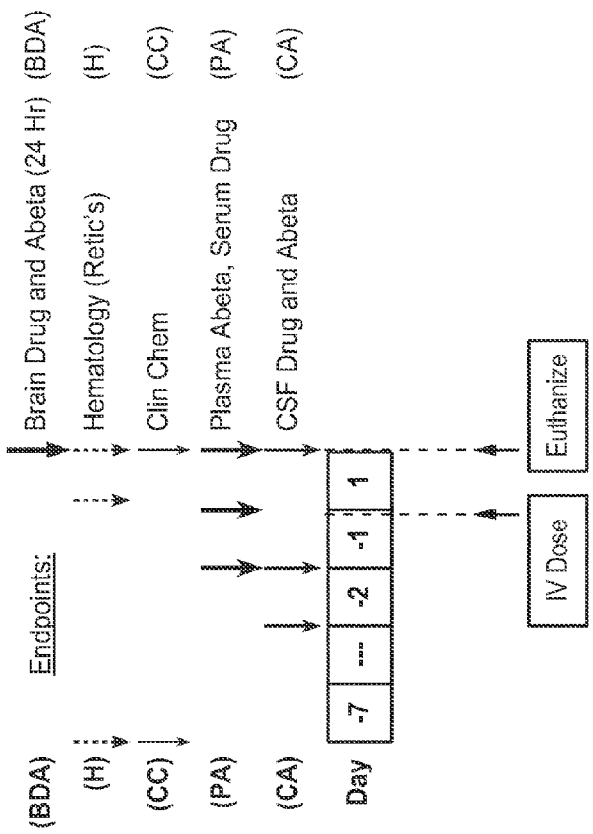
FIG. 14 depicts the dosing and sampling scheme for the primate study described in Example 6.
Figure 15A:
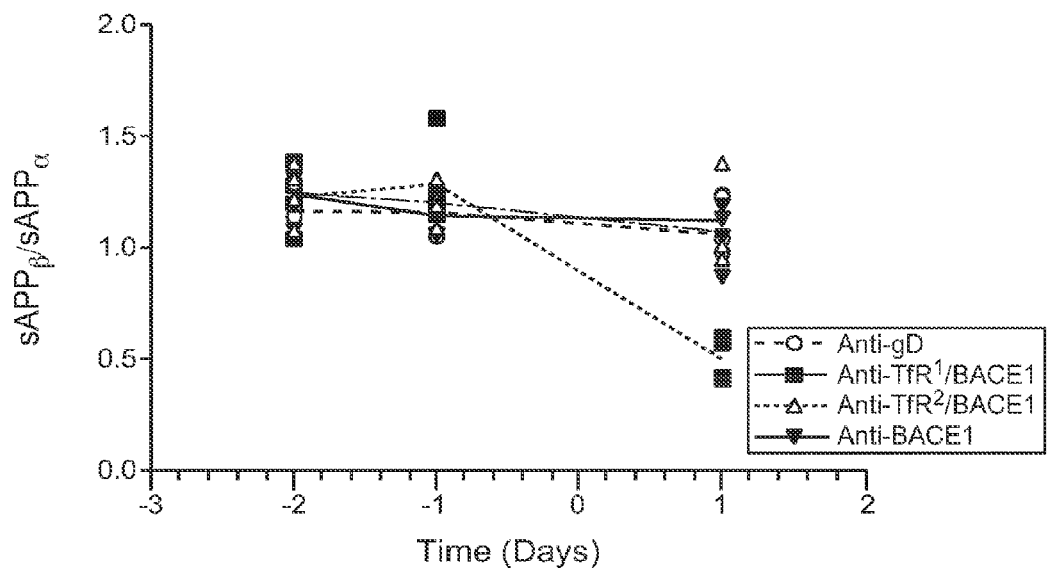
FIGS. 15A-15B depict the pharmacodynamic results (A) and brain antibody concentrations (B) of the experiments described in Example 6. Specifically.
Figure 15B:
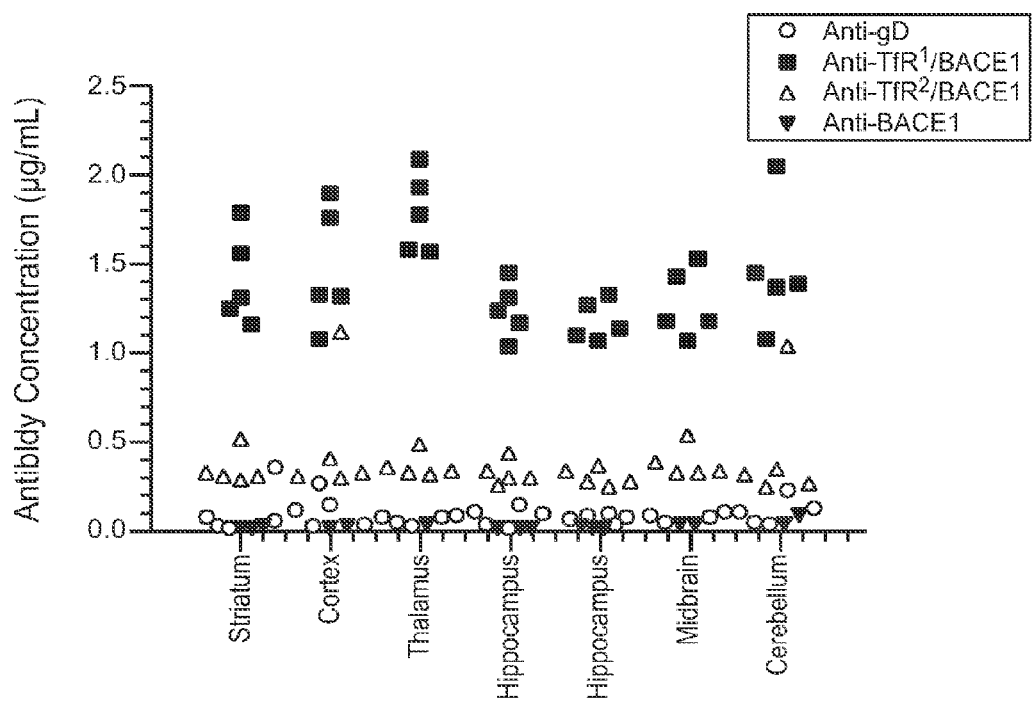

Example 6: Assessment of Bispecific Anti-Human TfR/BACE1 Bispecific Antibodies In Vivo To examine the relationship between antibody pharmacodynamics in CSF and pharmacokinetics in brain, cynomolgus monkeys (*Macaca fascicularis*) were dosed with bispecific antibodies anti-TfR$^1$/BACE1 or anti-TfR$^2$/BACE1, as in the previous example. These bispecific antibodies were in a human IgG1 format with D265A and N297G mutations abrogating effector function. As a control, an anti-gD molecule on human IgG1 was used. For comparison, we also dosed with a bivalent anti-BACE1 antibody, which is the same clone used for the bispecific antbibodies. The antibodies were administered by a single intravenous (IV) bolus injection into the saphenous vein at a dose of 30 mg/kg to conscious cynomolgus monkeys with indwelling cisterna magna catheters. Baseline CSF samples were collected 24 and 48 hours prior to dosing, and another CSF sample was collected 24 hours post-dose (as shown schematically in FIG. 14). Following CSF collection 24 hours post-dose, animals were perfused with saline and brains were harvested for analysis of antibody concentrations. Different brain regions were homogenized in 1% NP-40 (Cal-Biochem) in PBS containing Complete Mini EDTA-free protease inhibitor cocktail tablets (Roche Diagnostics). Homogenized brain samples were rotated at 4° C. for 1 hour before spinning at 14,000 rpm for 20 minutes. The supernatant was isolated for brain antibody measurement, using the ELISA method described in the previous example. Blood was also collected to confirm peripheral exposure and pharmacodynamics responses, which were similar to our observations in Example 5.

The pharmacodynamic effects of anti-TfR$^1$/BACE1 and anti-TfR$^2$/BACE1 as assessed in CSF were also similar to that observed in the previous example. FIG. 15 demonstrates that the ratio of CSF sAPPβ/sAPPα decreased robustly following dosing with anti-TfR$^1$/BACE1 Anti-TfR$^2$/BACE1 did not show an evident decrease at 24 hours post-dose in this study. Anti-BACE1 also showed no effect. Analysis of brain concentrations of antibody revealed that both the control IgG and the anti-BACE1 antibody had limited uptake into the brain, at levels that were just above detection in our assay (average ~670 pM). Anti-TfR$^2$/BACE1 had ~3-fold improved brain uptake over control IgG (average ~2 nM), and anti-TfR$^1$/BACE1 had the best brain uptake, ~15-fold greater than control IgG (average ~10 nM). The brain antibody concentrations for the different antibodies correlated with the pharmacodynamics response seen in CSF in our studies, with anti-TfR$^1$/BACE1 having the best brain uptake and most robust pharmacodynamics effect, and anti-TfR$^2$/BACE1 having less brain uptake and a more modest effect.

These results extend our previous findings to demonstrate that TfR-binding bispecific antibodies improve uptake in brain of non-human primates. In primates, as in mice, there is likely an optimum affinity to TfR that best balances brain uptake and TfR-mediated clearance. In our example, the higher affinity anti-TfR$^1$/BACE1 demonstrates good brain uptake, and is affected by peripheral target-mediated clearance. The reduced affinity TfR$^2$/BACE1 has improved clearance properties, but appears to have such low binding for TfR as to not be able to be efficiently transported by TfR (much in the same way that the lowest-affinity anti-TfR antibody TfR$^E$ in US2012/0171120 passes some affinity threshold beyond which the affinity is too low to permit sufficient interaction between the antibody and TfR such that the antibody would remain associated with TfR as TfR begins the translocation process). From the results of this experiment, an anti-human/cyno TfR/BACE1 bispecific antibody having affinity for TfR between that of TfR$^1$ and TfR$^2$ would be predicted to have improved uptake and clearance properties over either anti-TfR$^1$/BACE1 or anti-TfR$^2$/BACE1 in this system.

Example 7: Creation of Additional Effectorless Mutations in the Context of a Bispecific Transferrin Receptor Antibody Other mutations in the Fc region, which abrogate effector function in addition to N297G and D265A were tested for their ability to reduce or prevent depletion of TfR-expressing reticulocytes. Specifically, the Fc mutations L234A, L235A and P329G ("LALAPG") which are described in US Application Publication No 2012/0251531, which is incorporated herein by reference, were incorporated into the anti-TfR$^D$/BACE1 antibody (which is described in International Application Publication No. WO 2013/177062, and which is incorporated by reference herein in its entirety).

Pharmacokinetic analysis and reticulocyte count following a single antibody administration in mice were performed as follows. Wild type female C57B/6 mice ages 6-8 weeks were used for all studies. The animals' care was in accordance with institutional guidelines. Mice were dosed intravenously with a single 50 mg/kg dose of either an anti-gD antibody (murine IgG2a) with the LALAPG mutations, an anti-TfR$^D$/BACE1 antibody (rat/murine chimera) with the LALAPG mutations. Total injection volume did not exceed 250 µL and antibodies were diluted in D-PBS when necessary (Invitrogen). After 24 hours, whole blood was collected prior to perfusion in EDTA microtainer tubes (BD Diagnostics), and allowed to sit for 30 minutes at room temperature, and spun down at 5000× x g for 10 minutes. The top layer of plasma was transferred to new tubes for antibody measurements.

Total antibody concentrations in mouse plasma was measured using an anti-mouse IgG2a (allotype a)/anti-mouse IgG2a (allotype a) ELISA. NUNC 384-well Maxisorp immunoplates (Neptune, N.J.) were coated with mouse anti-mouse IgG2a allotype A, an allotype A specific antibody (BD/Phamigen San Jose, Calif.), overnight at 4° C. Plates were blocked with PBS, 0.5% BSA for 1 hour at 25° C. Each antibody (anti-gD and the anti-TtR/BACE1 bispecific variants) was used as a standard to quantify respective antibody concentrations. Plates were washed with PBS, 0.05% Tween-20 using a microplate washer (Bio-Tek instruments, Inc., Winooski, Vt.), and standards and samples diluted in PBS containing 0.5% BSA, 0.35 M NaCl, 0.25% CHAPS, 5 mM EDTA, 0.2% BgG, 0.05% Tween-20 and 15 ppm Proclin® (Sigma-Aldrich) were added for two hours at 25° C. Bound antibody was detected with biotin-conjugated mouse anti-mouse IgG2a allotype A, an allotype A specific antibody (BD/Pharmigen San Jose, Calif.). Bound biotin-conjugated antibody was detected with horseradish peroxidase-conjugated streptavidin (GE Helathcare Life Sciences, Pittsburgh, Pa.). Samples were developed using 3,3',5,5'-tetramethyl benzidine (TMB) (KPL, Inc., Gaithersburg, Md.) and absorbance measured at 450 nm on a Multiskan Ascent reader (Thermo Scientific, Hudson, N.H.). Concentrations were determined from the standard curve using a four-parameter non-linear regression program. The assay had lower limit of quantification (LLOQ) values of 78.13 ng/ml in plasma. Statistical analysis of differences between experimental groups was performed using a two-tailed unpaired t-test.

Figure 20:
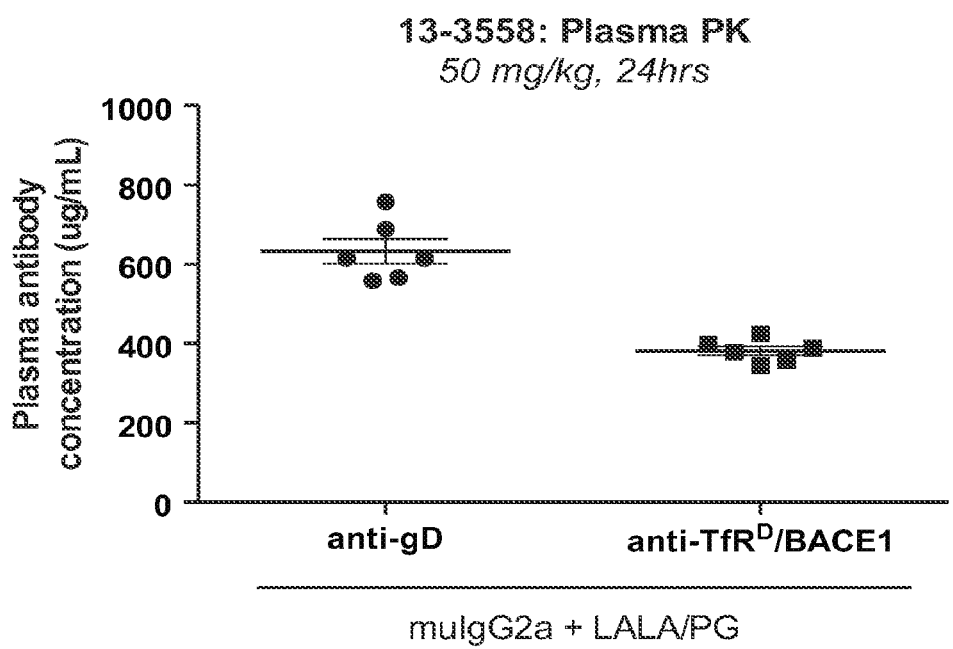
FIG. 20 depicts the pharmacokinetic properties of the murine IgG2a Anti-TfR$^D$/BACE1 and Anti-gD antibodies with the Fc effector function LALAPG mutations as described in Example 7.

Upon administration of the anti-TfR$^D$/BACE1 antibodies containing the Fc LALAPG mutations, the mice displayed no clinical symptoms as had been previously observed using antibodies with full effector function. See Couch et al., Sci. Trans. Med. 5:183ra57 (2013). FIG. 20 shows the results of the pharmacokinetic analysis.

Figure 21A:
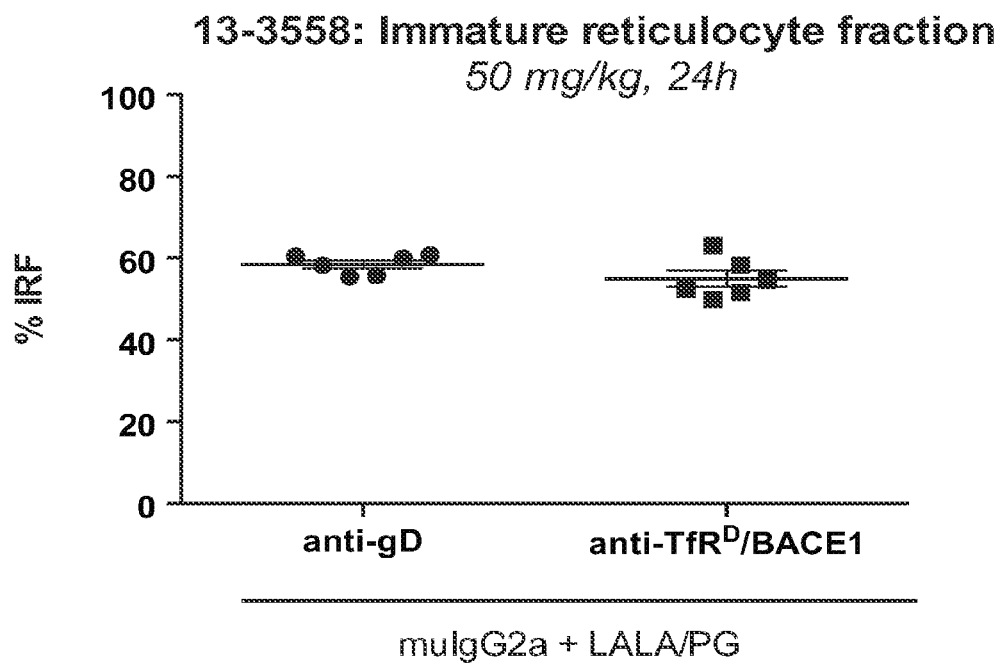
FIG. 21 depicts the total and immature reticulocyte count in mice 24 hours after administration of a 50 mg/kg dose of the murine IgG2a Anti-TfR$^D$/BACE1 and Anti-gD antibodies with the Fc effector function LALAPG mutations as described in Example 7.
Figure 21B:
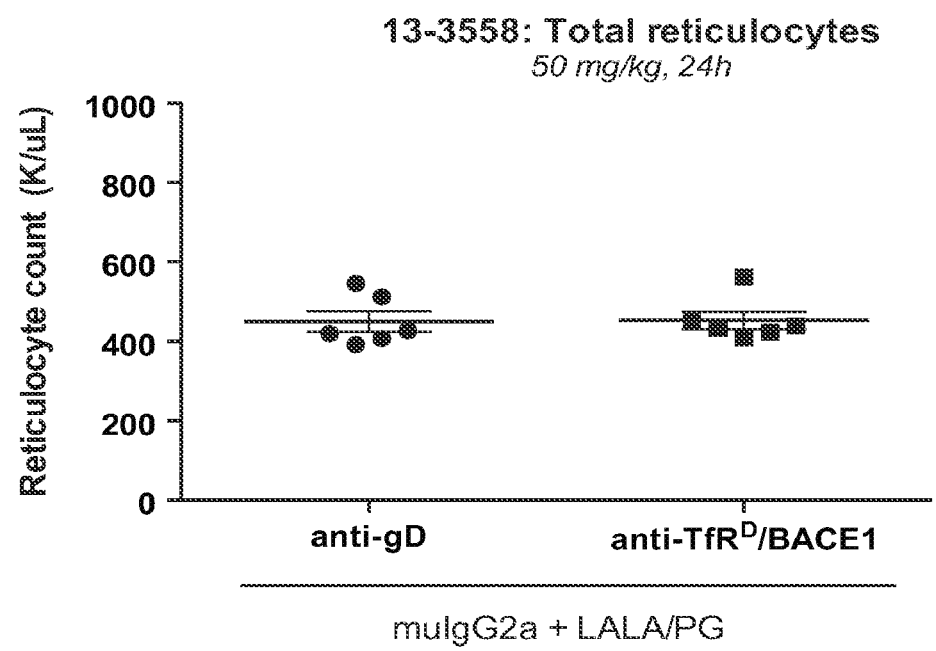

Additionally, immature and total reticulocyte counts were determined using the Sysmex XT2000iV (Sysmex, Kobe, Japan) according to manufacturer's instructions. At 24 hours post dose, there was no observed difference in the immature reticulocyte fraction or the total reticulocyte count with any antibody tested as seen in FIG. 21. These results suggest that the LALAPG mutation not only abrogates antibody effector function but also reduces complement binding and complement-mediated reticulocyte clearance seen even with an effectorless antibody framework (Couch et al. 2013). This is consistent with another report that incorporation of the LALA mutation on a human IgG1 can limit complement binding (Hessell et al. Nature 449:101-104 (2007)).

Example 8: Creation of FcRna$^{HIGH}$ Bispecific Variants

In order to increase the half-life of the bispecific antibodies, and thereby potentially increase the concentration of the antibody in the brain, bispecific variants were made containing mutations in the IgG constant domain and specifically in the Fc Receptor-neonate (FcRn) binding domain (FcRn$^{HIGH}$ mutations). The FcRn binding domain has been implicated in the maternal-fetal transfer of antibodies. See Story et al., J. Exp. Med., 180:2377 2381, 1994. The amino acid substitutions in the FcRn binding domain increase the affinity of the constant domain for the FcRn thereby increasing the half-life of the antibody.

FcRn binding domain mutations M252Y, S254T and T256E (YTE) have been described to increase FcRn binding and thus increase the half-life of antibodies. See U.S. Published Patent Application No. 2003/0190311 and Dall'Acqua et al., J. Biol. Chem. 281:23514-23524 (2006). Additionally, FcRn binding domain mutations N434A and Y436I (AI) have been described to also increase FcRn binding. See Yeung et al., J. Immunol. 182: 7663-7671 (2009). The YTE (M252Y/S254T/T256E) and AI (N434/Y436I) mutations were incorporated into both anti-TfR$^{524}$/BACE1 and anti-TfR$^2$/BACE1 bispecific antibodies containing either WT human IgG1 or effectorless LALAPG or N297G mutations. In addition, FcRn$^{HIGH}$ mutation were made in the anti-gD hIgG1 antibody as a control. Mutations were constructed using Kunkel mutatgenesis, antibodies were expressed transiently in CHO cells, and proteins were purified using protein A chromatography followed by size exclusion chromatography (SEC).

Binding of FcRn$^{HIGH}$ variant antibodies to FcRn was measured using BIAcore. Human and cynomolgus monkey FcRn proteins were expressed in CHO and purified using IgG affinity chromatography. Data were acquired on a BIAcore T200 instrument. A series S sensor chip CM5 (GE Healthcare, Cat. BR100530) was activated with EDC and NHS reagents according to the supplier's instructions, and anti-Fab antibody (Human Fab capture kit, GE Health care Bio-science. AB SE-75184, upsala, Sweden) was coupled to achieve approximately 10,000 response units (RU), followed by blocking un-reacted groups with 1 Methanolamine. For affinity measurements, antibodies were first injected at a 10 µl/min flow rate to capture approximately 1000 RU on 3 different flow cells (FC), except for FC1 (reference), and then 2-fold serial dilutions of human FcRn (or Cyno FcRn) in pH6 buffer (0.1M sodium phosphate), from low (1 nM) to high (25 µM) were injected (flow rate: 30 µl/min) one after the other in the same cycle with no regeneration between injections. Sensograms were recorded and subject to reference and buffer subtraction before evaluating by using BlAcore T200 Evaluation Software (version 2.0). Affinities were determined by analyzing the level of binding at steady state based on a 1:1 binding model. Binding affinities for LALAPG, N297G, LALAPG.YTE, and LALAPG.AI variants of anti-TfR$^{524}$/BACE1 are shown in Table 11 below. The data show that the FcRn$^{HIGH}$ variants enhance affinity at endosomal (pH 6) to both human and cyno FcRn.

TABLE 11

| Antibody | Effector Funcion | FcRn High | Human FcRn KD at pH 6 (uM) | Cyno FcRn KD at pH 6 (uM) |
|---|---|---|---|---|
| Anti-TfR.52A/BACE1.hIgG1 | WT | WT | | |
| Anti-TfR.52A/BACE1.hIgG1.N297G | N297G | WT | 1.3 | 2.1 |
| Anti-TfR.52A/BACE1.hIgG1.LALAPG | LALAPG | WT | 0.8 | 1.2 |
| Anti-TfR.52A/BACE1.hIgG1.N297G.YTE | N297G | YTE | | |
| Anti-TfR.52A/BACE1.hIgG1.LALAPG.YTE | LALAPG | YTE | 0.2 | 0.2 |
| Anti-TfR.52A/BACE1.hIgG1.N297G.AI | N297G | N434A/Y436I | | |
| Anti-TfR.52A/BACE1.hIgLALAPG.AI | LALAPG | N434A/Y436I | 0.6 | 0.4 |
| Anti-TfR.52A/BACE1.hIgG1.N297G.A | N297G | N434A | | |
| Anti-TfR2/BACE1.hIgG1.N297G | N297G | WT | 1.7 | 2.1 |
| Anti-TfR2/BACE1.hIgG1.LALAPG | LALAPG | WT | 1.1 | 1.2 |
| Anti-TfR2/BACE1.hIgG1.LALAPG.YTE | LALAPG | YTE | 0.3 | 0.2 |
| Anti-gD.hIgG1 | WT | WT | 0.7 | 0.9 |
| Anti-gD.hIgG1.YTE | WT | YTE | | |
| Anti-gD.hIgG1.AI | WT | N434A/Y436I | 0.3 | 0.4 |
| Anti-gD.hIgG1.A | WT | N434A | 0.1 | 0.7 |

Select FcRnHIGH variants will be tested in cynomologus monkeys to determine whether enhancement of FcRn affinity can increase improve the pharmacokinetic properties and/or increase the brain exposure of the anti-TfR/BACE1 antibodies.

To evaluate the safety of the effectorless and FcRn$^{HIGH}$ mutations, certain bispecific antibodies were administered to human transferrin receptor knock-in mice which express the human transferrin receptor. The huTfR knock-in mice were generated as follows. The construct for targeting human TFRC cDNA into the C57BL/6 Tfrc locus in ES cells was made using a combination of recombineering (Warming et al. Molecular and Cellular Biology vol. 26 (18) pp. 6913-22 2006; Liu et al Genome Research (2003) vol. 13 (3) pp. 476-84) and standard molecular cloning techniques.

Briefly, a cassette (human TFRC cDNA, SV40 pA, and frt-PGK-em7-Neo-BGHpA-frt) flanked by short homologies to the mouse Tfrc gene was used to modify a Tfrc C57BL/6J BAC (RP23 BAC library) by recombineering. The human TFRC cDNA cassette was inserted at the endogenous ATG and the remainder of Tfrc exon 2 plus the beginning of intron 2 was deleted. The targeted region in the BAC was then retrieved into pBlight-TK (Warming et al. Molecular and Cellular Biology vol. 26 (18) pp. 6913-22 2006) along with flanking genomic Tfrc sequences as homology arms for ES cell targeting. Specifically, the 2950 bp 5' homology arm corresponds to (assembly NCBI37/mm9): chr.16:32,610,333-32,613,282 and the 2599 bp 3' homology arm corresponds to chr.16:32,613,320-32,615,918. The final vector was confirmed by DNA sequencing.

The Tfrc/TFRC KI vector was linearized with NotI and C57BL/6N C2 ES cells were targeted using standard methods (G418 positive and gancyclovir negative selection). Positive clones were identified using PCR and taqman analysis, and confirmed by sequencing of the modified locus. Correctly targeted ES cells were transfected with a Flpe plasmid to remove Neo and ES cells were then injected into blastocysts using standard techniques. Germline transmission was obtained after crossing resulting chimaeras with C57BL/6N females.

Specifically, the antibodies listed in the table below were administered to huTfR knock-in mice in a single 50 mg/kg dose and 24 hours later blood was drawn and reticulocytes. huIg1, N297G

TABLE 12

| Antibody | Isotype | Number of Mice |
|---|---|---|
| Anti-gD | huIg1, N297G | 6 |
| anti-TfR$^{524}$/BACE1 | huIgG1, N297G | 6 |
| anti-TfR$^{524}$/BACE1 | huIgG1, LALAPG | 6 |
| anti-TfR$^{524}$/BACE1 | huIgG1, LALAPG/YTE | 6 |
| anti-TfR$^{524}$/BACE1 | huIgG1, LALAPG/AI | 6 |

Figure 22:
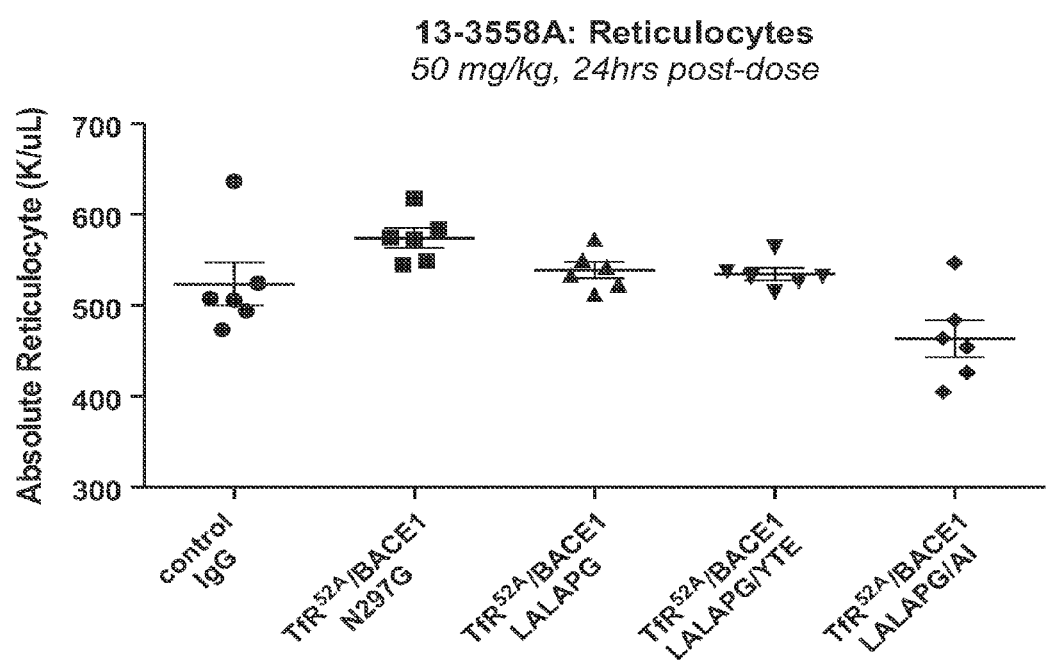
FIG. 22 depicts the total reticulocyte count in mice 24 hours after administration of a 50 mg/kg dose of the anti-TfR$^{52A}$/BACE1 (N297G), anti-TfR$^{52A}$/BACE1 (LALAPG), anti-TfR$^{52}$A/BACE1 (LALAPG/YTE), TfR$^{52}$A/BACE1 (LALAPG/AI) antibodies in human transferrin receptor knock-in mice as described in Example 8.

Following administration of the anti-TfR$^{524}$/BACE1 LALAPG, LALAPG/YTE or LALAPG/AI antibodies (Groups 3-5 in Table 12), human TfR knock-in mice displayed no clinical symptoms or reticulocyte loss (FIG. 22) as previously observed using anti-TfR antibodies with full effector function (Couch et al. 2013). These results indicate that incorporation of the LALAPG mutation on the human IgG1 framework also abrogates effector function, and further suggest that addition of either the YTE or AI FcRn$^{HIGH}$ mutations do not interfere with the desired properties of the LALAPG mutations to render the antibody effectorless.

ADCC assays were also carried out to confirm the effectorless status of LALAPG, LALAPG/YTE, and LALAPG/AI mutation combinations in a human-derived cell line. As previously, human erythroleukemia cell line (HEL, ATCC) was used as target cells with PBMCs from healthy human donors carrying either the F/V158 genotype or the FcγRIIIA V/V158 genotype. The V/V158 genotype was also included in this assay due to the known association with increased NK cell-mediated ADCC activity as well as ability to bind IgG4 antibodies (Bowles and Weiner, 2005; Bruhns et al. 2008). Cells were counted and viability was determined by Vi-CELL® (Beckman Coulter; Fullerton, Calif.) following the manufacturer's instructions.

PBMCs were isolated by density gradient centrifugation using Uni-Sep™ blood separation tubes (Accurate Chemical & Scientific Corp.; Westbury, N.Y.). Target cells in 50 μL of assay medium (RPMI-1640 with 1% BSA and 100 units/mL penicillin and streptomycin) were seeded in a 96-well, round-bottom plate at $4 \times 10^4$/well. Serial dilutions of test and control antibodies (50 μL/well) were added to the plates containing the target cells, followed by incubation at 37° C. with 5% $CO_2$ for 30 minutes to allow opsonization. The final concentrations of antibodies ranged from 0.0051 to 10,000 ng/mL following 5-fold serial dilutions for a total of 10 data points. After the incubation, $1.0 \times 10^6$ PBMC effector cells in 100 μL of assay medium were added to each well to give a ratio of 25:1 effector: target cells, and the plates were incubated for an additional 4 hours. The plates were centrifuged at the end of incubation and the supernatants were tested for lactate dehydrogenase (LDH) activity using a Cytotoxicity Detection Kit™ (Roche Applied Science; Indianapolis, Ind.). The LDH reaction mixture was added to the supernatants and the plates were incubated at room temperature for 15 minutes with constant shaking. The reaction was terminated with 1 M $H_3PO_4$, and absorbance was measured at 490 nm (the background, measured at 650 nm was subtracted for each well) using a SpectraMax Plus microplate reader. Absorbance of wells containing only the target cells served as the control for the background (low control), whereas wells containing target cells lysed with Triton-X100 provided the maximum signal available (high control). Antibody-independent cellular cytotoxicity (AICC) was measured in wells containing target and effector cells without the addition of antibody. The extent of specific ADCC was calculated as follows:

$$\% \; ADCC = 100 \times \frac{A_{490} \; (Sample) - A_{490} \; (AICC)}{A_{490} \; (High \; Control) - A_{490} \; (Low \; Control)}$$

ADCC values of sample dilutions were plotted against the antibody concentration, and the dose-response curves were fitted to a four-parameter model using SoftMax Pro.

Figure 23:
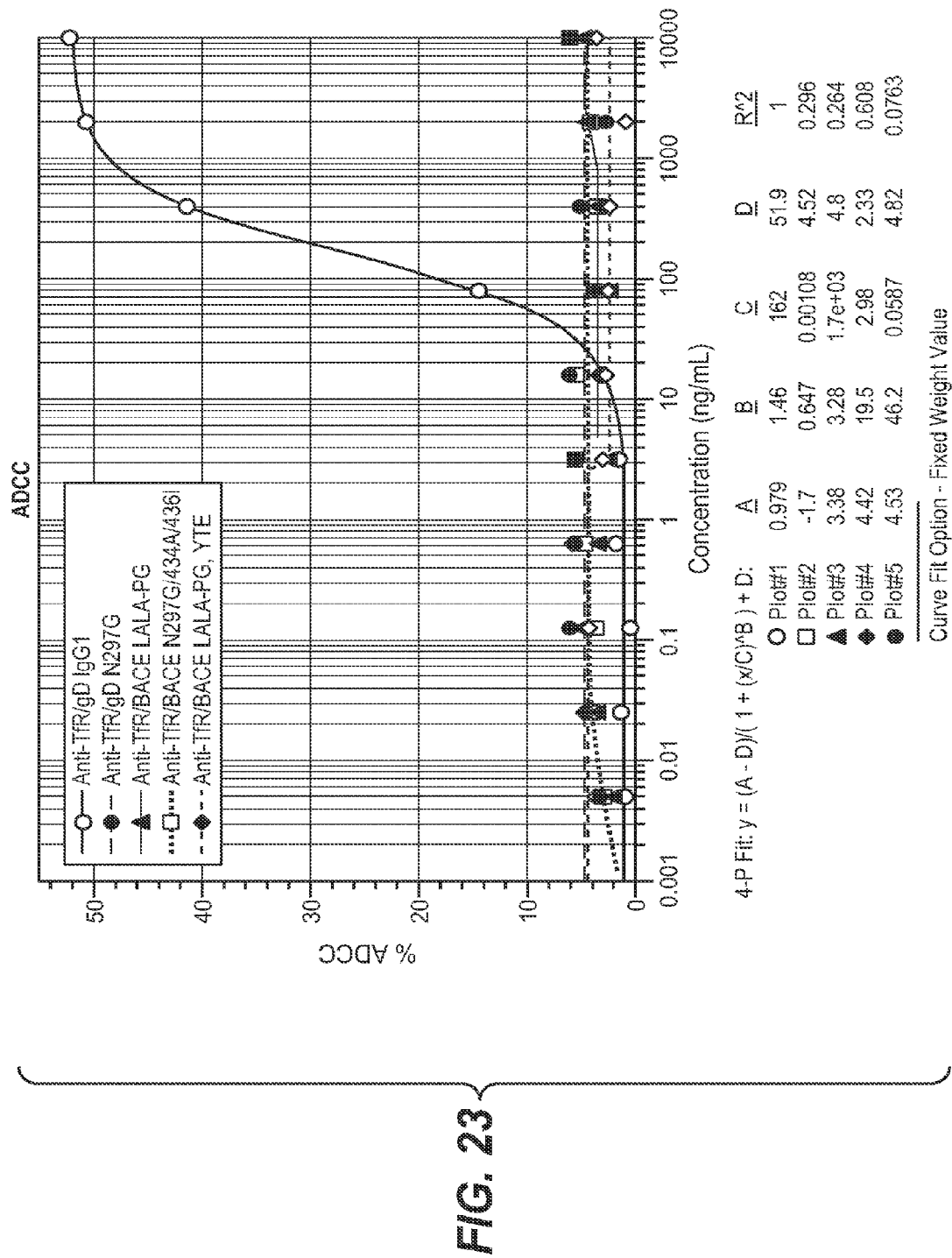
FIG. 23 depicts the results of experiments assessing the impact of effector function status on ADCC activity of anti-TfR/gD, anti-TfR/BACE1 (N297G), anti-TfR/BACE1 (LALAPG), anti-TfR-BACE1 (N297G/434A/436I) and anti-TfR/BACE1 (LALAPG/YTE) antibodies in primary human bone marrow mononuclear cells or in a human erythroblast cell line, as described in Example 8.

Results of the ADCC assay are shown in FIG. 23. As expected, the effector positive anti-human TfR antibody (anti-TfR[1]/gD IgG1 WT) elicited significant ADCC activity on the HEL cells. In contrast, the anti-TfR[524]/BACE1 antibody variants containing LALAPG, LALAPG/YTE, or LALAPG/AI mutations did not display any ADCC activity in HEL cells, similar to the negative control anti-TfR[524]/gD N297G antibody.

Example 9: Modification of Anti-TfR Bispecific Antibody Sequences

A mutation in heavy chain variable region FR4, methionine at position 108 changed to leucine (M108L), may be incorporated to promote stability of an anti-TfR antibody. Binding affinity of an anti-TfR Fab comprising the M108L mutation was similar to the unmodified Fab, as shown in Table 13.

TABLE 13

Binding affinity of anti-TfR Fab

| | ka (1/Ms) | kd (1/s) | KD (M) |
|---|---|---|---|
| antiTfR.52A.Fab | 3.71E+05 | 0.0204 | 5.50E−08 |
| antiTfR.52A.M108L.Fab | 3.20E+05 | 0.02312 | 7.22E−08 |

It is expected that a bispecific antibody comprising an anti-TfR arm comprising an anti-TfR[2].hIgG1.LALAPG.YTE heavy chain having an M108L mutation (SEQ ID NO: 160) will be more stable than the bispecific antibody comprising the same anti-TfR arm without the M108L heavy chain mutation, while also retaining binding affinity for TfR.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Table of Certain Sequences

| SEQ ID NO | Descripton | Sequence |
|---|---|---|
| 158 | Anti-TfR[524] M108L heavy chain variable region | EVQLVQSGAE VKKPGASVKV SCKASGYTFT SYWMHWVRQA PGQRLEWIGE IAPTNGRTNY IEKFKSRATL TVDKSASTAY MELSSLRSED TAVYYCARGT RAYHYWGQGT LVTVSS |
| 159 | Anti-TfR[2] M108L heavy chain variable region | EVQLVQSGAE VKKPGASVKV SCKASGYTFT SYWMHWVRQA PGQRLEWIGE INPTNGRTNY IEKFKSRATL TVDKSASTAY MELSSLRSED TAVYYCARGT RAYHYWGQGT LVTVSS |
| 160 | Anti-TfR[2]/Ag2.hIgG1.LALAPG.YTE. M108L bispecific antibody anti-TfR heavy chain Ag2 = antigen 2 | EVQLVQSGAE VKKPGASVKV SCKASGYTFT SYWMHWVRQA PGQRLEWIGE INPTNGRTNY IEKFKSRATL TVDKSASTAY MELSSLRSED TAVYYCARGT RAYHYWGQGT LVTVSSASTK GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD KTHTCPPCPA PEAAGGPSVF LFPPKPKDTL YITREPEVTC VVVDVSHEDP EVKFNWYVDG VEVHNAKTKP REEQYNSTYR VVSVLTVLHQ DWLNGKEYKC KVSNKALGAP IEKTISKAKG QPREPQVYTL PPSREEMTKN QVSLSCAVKG FYPSDIAVEW ESNGQPENNY KTTPPVLDSD GSFFLVSKLT VDKSRWQQGN VFSCSVMHEA LHNHYTQKSL SLSPGK |
| 161 | Anti-TfR[2]/Ag2.hIgG1.LALAPG.YTE bispecific antibody anti-TfR light chain | DIQMTQSPSS LSASVGDRVT ITCRASDNLY SNLAWYQQKP GKSPKLLVYD ATNLADGVPS RFSGSGSGTD YTLTISSLQP EDFATYYCQH FAGTPLTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |

Table of Certain Sequences

| SEQ ID NO | Descripton | Sequence |
|---|---|---|
| 162 | Anti-TfR$^{52.4}$ light chain variable region | DIQMTQSPSS LSASVGDRVT ITCRASDNLY SNLAWYQQKP GKSPKLLVYD ATNLADGVPS RFSGSGSGTD YTLTISSLQP EDFATYYCQH FWGTPLTFGQ GTKVEIK |
| 163 | Anti-TfR$^{2}$ light chain variable region | DIQMTQSPSS LSASVGDRVT ITCRASDNLY SNLAWYQQKP GKSPKLLVYD ATNLADGVPS RFSGSGSGTD YTLTISSLQP EDFATYYCQH FAGTPLTFGQ GTKVEIK |

What is claimed is:

1. An isolated antibody that binds to human transferrin receptor (TfR) and primate TfR, wherein the antibody comprises a heavy chain variable region amino acid sequence of SEQ ID NO: 158 or SEQ ID NO: 159, and a light chain variable region amino acid sequence of SEQ ID NO: 162 or SEQ ID NO: 163.

2. The isolated antibody of claim 1, wherein the antibody comprises a heavy chain variable region amino acid sequence of SEQ ID NO: 158 and a light chain variable region amino acid sequence of SEQ ID NO: 162, or a heavy chain variable region amino acid sequence of SEQ ID NO: 159 and a light chain variable region amino acid sequence of SEQ ID NO: 163.

3. The antibody of claim 1, which is a monoclonal antibody.

4. The antibody of claim 1, wherein the antibody comprises at least one mutation in the antibody Fc region, relative to a wild-type antibody Fc region of the same isotype, that reduces or eliminates the complement activation function of the antibody or the effector function of the antibody, or increases the half-life of the antibody.

5. The antibody of claim 4, wherein the at least one mutation reduces or eliminates the effector function or complement activation function relative to an antibody comprising a wild-type antibody Fc region of the same isotype.

6. The antibody of claim 4, wherein the at least one mutation reduces or eliminates the effector function relative to an antibody comprising a wild-type antibody Fc region of the same isotype.

7. The antibody of claim 4, wherein the at least one mutation increases the half-life of the antibody.

8. The antibody of claim 7, wherein the half-life is increased by at least one mutation in the FcRn binding domain of the antibody at a position selected from: 252, 254, 256, 434 and 436, wherein amino acid numbering is according to the EU numbering system.

9. The antibody of claim 8, wherein the FcRn binding domain comprises mutations at positions 252, 254 and 256.

10. The antibody of claim 9, wherein the FcRn binding domain comprises M252Y, S254T and T256E mutations.

11. The antibody of claim 8, wherein the FcRn binding domain comprise mutations at positions 434 and 436.

12. The antibody of claim 11, wherein the FcRn binding domains comprises N434A and Y436I mutations.

13. The antibody of claim 1, wherein the antibody is of an isotype that naturally has reduced or eliminated effector function.

14. The antibody of claim 1, wherein the glycosylation of the antibody is reduced by a method selected from: production of the antibody in an environment that does not permit wild-type glycosylation; removal of carbohydrate groups already present on the antibody; and mutation of a glycosylation site of the antibody such that wild-type glycosylation does not occur.

15. The antibody of claim 14, wherein the antibody is produced in a non-mammalian cell production system, or where the antibody is produced synthetically.

16. The antibody of claim 14, wherein the Fc region of the antibody comprises a mutation at position 297 such that the wild-type asparagine residue at that position is replaced with another amino acid that interferes with glycosylation at that position, wherein amino acid numbering is according to the EU numbering system.

17. The antibody of claim 1, wherein the effector function or complement activation function is reduced or eliminated by deletion of all or a portion of the Fc region.

18. The antibody of claim 1, wherein the antibody comprises at least one mutation is-selected from: a point mutation of the Fc region to impair binding to one or more Fc receptors selected from the following positions: 234, 235, 238, 239, 248, 249, 252, 254, 265, 268, 269, 270, 272, 278, 289, 292, 293, 294, 295, 296, 297, 298, 301, 303, 322, 324, 327, 329, 333, 335, 338, 340, 373, 376, 382, 388, 389, 414, 416, 419, 434, 435, 437, 438, and 439; a point mutation of the Fc region to impair binding to C1q selected from the following positions: 270, 322, 329, and 321; and a point mutation at position 132 of the CH1 domain, wherein amino acid numbering is according to the EU numbering system.

19. The antibody of claim 18, wherein the antibody comprises at least one point mutation of the Fc region to impair binding to one or more Fc receptors selected from 234, 235, 265, 297 and 329.

20. The antibody of claim 19, wherein the Fc region comprises a mutation at position 297 or at positions 265 and 297.

21. The antibody of claim 19, wherein the Fc region comprises mutations at positions 234, 235 and 329.

22. The antibody of claim 19, wherein the Fc region comprises a N297G mutation; D265A and N297A mutations; or D265A and N297G mutations.

23. The antibody of claim 19, wherein the Fc region comprises L234A, L235A, and P329G mutations.

24. The antibody of claim 1, wherein the antibody has a KD for TfR of about 20 nM to 100 nM.

25. The antibody of claim 1, wherein the antibody is coupled to a therapeutic compound.

26. The antibody of claim 25, wherein the antibody is a multispecific antibody and the therapeutic compound optionally forms one portion of the multispecific antibody.

27. The antibody of claim 26, wherein the multispecific antibody comprises a first antigen binding site which binds TfR and a second antigen binding site which binds a brain antigen.

28. The antibody of claim 27, wherein the multispecific antibody comprises a first heavy chain comprising the sequence of SEQ ID NO: 160 and a first light chain comprising the sequence of SEQ ID NO: 161.

29. The antibody of claim 27, wherein the brain antigen is selected from the group consisting of: beta-secretase 1 (BACE1), Abeta, epidermal growth factor receptor (EGFR), human epidermal growth factor receptor 2 (HER2), tau, apolipoprotein E (ApoE), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), and caspase 6.

30. The antibody of claim 27, wherein the multispecific antibody binds both TfR and BACE1.

31. The antibody of claim 27, wherein the multispecific antibody binds both TfR and Abeta.

32. The antibody of claim 25, wherein the therapeutic compound is a neurological disorder drug.

33. A method of transporting a compound across the blood-brain barrier (BBB) in a subject comprising exposing the BBB to an antibody of claim 25 such that the antibody transports the compound coupled thereto across the BBB.

34. A method of increasing exposure of the central nervous system CNS of a subject to a compound, comprising exposing the CNS to an antibody of claim 25 such that the antibody transports the compound coupled thereto to the CNS.

35. A method of increasing retention in the CNS of a compound administered to a subject, comprising exposing the CNS to an antibody of claim 25 such that the retention in the CNS of the compound is increased.

36. A pharmaceutical formulation comprising the antibody of claim 1 and a pharmaceutically acceptable carrier.

37. An isolated nucleic acid encoding the antibody of claim 1.

38. A host cell comprising the nucleic acid of claim 37.

39. A method of producing an antibody comprising culturing the host cell of claim 38 so that the antibody is produced and optionally further comprising recovering the antibody from the host cell.

40. An isolated antibody fragment that binds to human transferrin receptor (TfR) and primate TfR, wherein the antibody fragment comprises a heavy chain variable region amino acid sequence of SEQ ID NO: 158 or SEQ ID NO: 159, and a light chain variable region amino acid sequence of SEQ ID NO: 162 or SEQ ID NO: 163.

* * * * *

UNITED STATES PATENT AND TRADEMARK OFFICE
CERTIFICATE OF CORRECTION

PATENT NO. : 10,508,151 B2
APPLICATION NO. : 15/525832
DATED : December 17, 2019
INVENTOR(S) : Yin Zhang et al.

It is certified that error appears in the above-identified patent and that said Letters Patent is hereby corrected as shown below:

In the Claims

1. In Claim 18 at Column 203, Line 30, "is-selected" should be changed to --selected--.

Signed and Sealed this
Eleventh Day of February, 2020

Andrei Iancu
*Director of the United States Patent and Trademark Office*